United States Patent
Loso et al.

(10) Patent No.: US 9,944,664 B2
(45) Date of Patent: Apr. 17, 2018

(54) METALLOENZYME INHIBITOR COMPOUNDS AS FUNGICIDES

(71) Applicant: Dow AgroSciences LLC, Indianapolis, IN (US)

(72) Inventors: Michael R. Loso, Carmel, IN (US); Gary D. Gustafson, Zionsville, IN (US); Asako Kubota, Arlington, VA (US); Maurice C. Yap, Zionsville, IN (US); Zachary A. Buchan, Zionsville, IN (US); Kimberly M. Steward, Zionsville, IN (US); Michael T. Sullenberger, Westfield, IN (US); William J. Hoekstra, Durham, NC (US); Christopher M. Yates, Raleigh, NC (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/683,907

(22) Filed: Apr. 10, 2015

(65) Prior Publication Data
US 2015/0291632 A1 Oct. 15, 2015

Related U.S. Application Data

(60) Provisional application No. 62/047,368, filed on Sep. 8, 2014, provisional application No. 61/979,543, filed on Apr. 15, 2014.

(51) Int. Cl.
| | | |
|---|---|---|
| *C07D 401/06* | (2006.01) | |
| *C07D 401/14* | (2006.01) | |
| *C07D 405/14* | (2006.01) | |
| *C07D 409/14* | (2006.01) | |
| *C07D 417/06* | (2006.01) | |
| *A61K 45/06* | (2006.01) | |
| *A61K 31/444* | (2006.01) | |
| *A61K 31/506* | (2006.01) | |
| *A61K 31/695* | (2006.01) | |
| *A01N 43/54* | (2006.01) | |
| *A01N 43/78* | (2006.01) | |
| *A01N 43/713* | (2006.01) | |
| *A01N 47/02* | (2006.01) | |
| *A01N 55/00* | (2006.01) | |
| *C07F 7/08* | (2006.01) | |
| *A61K 31/4439* | (2006.01) | |
| *A01N 43/40* | (2006.01) | |

(52) U.S. Cl.
CPC ............ *C07F 7/0812* (2013.01); *A01N 43/40* (2013.01); *A01N 43/54* (2013.01); *A01N 43/713* (2013.01); *A01N 43/78* (2013.01); *A01N 55/00* (2013.01); *A61K 31/444* (2013.01); *A61K 31/4439* (2013.01); *A61K 31/506* (2013.01); *A61K 31/695* (2013.01); *A61K 45/06* (2013.01); *C07D 401/06* (2013.01); *C07D 401/14* (2013.01); *C07D 405/14* (2013.01); *C07D 409/14* (2013.01); *C07D 417/06* (2013.01)

(58) Field of Classification Search
CPC ... C07F 7/0812; C07D 401/06; C07D 401/14; C07D 405/14; C07D 409/14; C07D 417/06; A61K 31/444; A61K 31/506; A61K 31/695; A61K 31/4439; A01N 43/54; A01N 43/78; A01N 43/713; A01N 47/02; A01N 55/00
See application file for complete search history.

(56) References Cited

U.S. PATENT DOCUMENTS

| 5,023,258 A | 6/1991 | Gymer et al. | |
| 5,089,513 A * | 2/1992 | Bird ................... | C07D 417/06 514/252.05 |
| 2005/0101639 A1 | 5/2005 | Ammermann et al. | |
| 2008/0234313 A1 | 9/2008 | Ramsbeck et al. | |
| 2012/0190639 A1 | 7/2012 | Everett et al. | |
| 2013/0085148 A1 | 4/2013 | Smith et al. | |

FOREIGN PATENT DOCUMENTS

| EP | 0097014 | 12/1983 |
| EP | 0097480 | 1/1984 |
| EP | 0101212 | 2/1984 |
| EP | 0102727 | 3/1984 |
| JP | H04208268 A | 7/1992 |
| WO | WO1985000289 | 1/1985 |
| WO | WO2001096283 | 12/2001 |
| WO | WO2013049559 | 4/2013 |
| WO | WO2013110002 | 7/2013 |
| WO | WO2015057873 | 4/2015 |

OTHER PUBLICATIONS

Pubchem. CID 71544239. Jun. 11, 2013. pp. 1-3 (onlinel, [retrieved on Jun. 5, 2015]. 1-5,8-10 Retrieved from the Internet <URL: http://pubchem.ncbinm.nih.gov/summary/summary.cgi?from=compound&cid=71544239>: p. 1.

(Continued)

*Primary Examiner* — Timothy R Rozof
(74) *Attorney, Agent, or Firm* — Charles W. Arnett; Faegre Baker Daniels LLP

(57) ABSTRACT

The instant invention describes compounds of Formula I having metalloenzyme modulating activity, and methods of treating diseases, disorders or symptoms thereof mediated by such metalloenzymes.

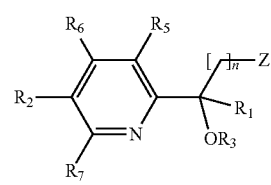

48 Claims, No Drawings

(56) References Cited

OTHER PUBLICATIONS

Pubchem. CID 21288486. Dec. 5, 2007, pp. 1-3 [online], [retrieved on Jun. 5, 2015]. 13-17,19 Retrieved from the Internet <URL: http;//pubchem.ncbl.nlm.nih.gov/summary/summary.cgi?frDm=compound&cid=21288486>; p. 1.
Pubchem. CID 21600769 Dec. 5, 2007, pp. 1-2 [online], [retrieved on Jun. 5, 2015}. Retrieved from the Internet <URL: http://pubchem.ncbi.nlm.nih.gov/summary/summary.cgi?from=compound8:cid=21600769>; p. 1.
Pubchem CID 56604428. Feb. 22, 2012, pp. 1-2 [online], [retrieved on Jun. 5, 2015]. Retrieved from the Internet <URL: hMp://pubchem.ncbi.nlm.nih.gov/summary/summary.cgi?from=compound&cid=56604428>; p. 1.
Pubchem. CID 23908064. Feb. 20, 2008, pp. 1-2 2 [online], {retrieved on Jun. 5, 2015]. Retrieved from (he Internet <URL; http://pubchem.ncbi.nlm.nih.gov/summary/summary.cgi?from=compound&cid=23908064>; p. 1.
Pubchem. CID 11287313. Oct. 26, 2006, pp. 1-2 [online], [retrieved on Jun. 5, 2015]. Retrieved from the Internet <URL: http://pubchem.ncbi.nlm.nih.gov/summary/summary.cgi?from=compound&cid=11287313>; p. 1.
Pubchem. CID 43506340. Jul. 21, 2009, pp. 1-2 [online], [retrieved on Jun. 5, 2015]. Retrieved from the Internet <URL: http://pubchem.ncbi.nlm.nih.gov/summary/summary.cgi?from=compound&cid=43506340>; p. 1.
Pubchem. CID 66825504. Nov. 30, 2012, pp. 1-3 [online], [retrieved on Jun. 5, 2015]. Retrieved from the Internet <URL: http://pubchem.ncbi.nlm.nih.gov/summary/summary.cgi?from=compound&cid=66825504>; p. 1.
Pubchem. CID 68431216, Dec. 1, 2012, pp. 1-3 [online], [retrieved on Jun. 5, 2015]. Retrieved from the Internet <URL: http://pubchem.ncbi.nlm.nih.gov/summary/summary.cgi?from=compound&cid=68431216>; p. 1.
Pubchem. CID 66825578. Nov. 30, 2012 pp. 1-3 [online], [retrieved on Jun. 5, 2015]. Retrieved from the Internet <URL: http://pubchem.ncbi.nlm.nih.gov/summary/summary.cgi?from=compound&cid=66825578>; p. 1.
Pubchem. CID 66825645. Nov. 30 2012, pp. 1-3 [online], [retrieved on Jun. 5, 2015]. Retrieved from the Internet <URL: http://pubchem.ncbi.nlm.nih.gov/summary/summary.cgi?from=compound&cid=66825645>; p. 1.
Pubchem. CID 59161937. Aug. 20, 2012, pp. 1-3 [online], [retrieved on Jun. 5, 2015]. Retrieved from the Internet <URL: http://pubchem.ncbi.nlm.nih.gov/summary/summary.cgi?from=compound&cid=59161937>; p. 1.
Powderly, WG et al. A Randomized Trial Comparing Fluconazole with Clotrimazole Troches for the Prevention of Fungal Infections in Patients with Advanced Human Immunodeficiency Virus Infection. The New England Journal of Medicine, vol. 332, No. 11, Mar. 16, 1995, pp. 700-705 [online], [retrieved on Jun. 5, 2015]. Retrieved from the Internet <URL:http://www.nejm.org/doilpdf/10.1056/NEJM199503163.321102>; p. 700, col. 1, paragraph 1.
Agrawal, A et al. Probing Chelation Motifs in HIV Integrase Inhibitors. Proc Natl Acad Sci U S A, vol. 109, No. 7, Feb. 14, 2012, pp. 2251-22556 [online] [retrieved on Jun. 5, 2015]. Retrieved from the Internet <URL: http://www.pnas.org/content/109/7/2251.full.pdf> <doi:10.1073/pnas.1112389109>; abstract.
Dawson, WAJM et al. Sensitivity of Fungi from Cereal Roots to Fluquinconazole and their Suppressiveness towards Take-all on Plants with or without Fluquinconazole Seed Treatment in a Controlled Environment. Plant Pathology, vol. 49, 2000, pp. 477-486 [online], [retrieved on Jun. 5, 2015]. Retrieved from the Internet <URL: http://onlinelibrary.wiley.com/doi/10.1046/j.1365-3059.2000.00479.x/epdf> abstract.
Ashauer, R et al. A Method to Predict and Understand Fish Survival Under Dynamic Chemical Stress Using Standard Ecotoxicity Data. Environmental Toxicology and Chemistry, vol. 32, No. 4, 2013, pp. 954-965 [online], [retrieved on Jun. 5, 2015]. Retrieved from the Internet <URL: http://onlinelibrary.wiley.com/doi/10.1002/etc.2144/epdf>; p. 955, col. 1, paragraph 3.
Richardson, MD. Changing patterns and trends in systemic fungal infections. Journal of Antimocrobial Chemotherapy, vol. 56, 2005, 51, pp. i5-i11 [online], [retrieved on Jun. 5, 2015]. Retrieved from the Internet <URL: http://jac.oxfordjournals.org/content/56/suppl_1/i5.full.pdf>; p. i7, col. 1, paragraphs 4-5.
European Patent Office, Application No. 15779821.6-1454/3131399, PCT/US2015025397, Communication Pursuant to Rule 164(1) EPC, Supplementary Partial European Search Report, and Provisional Opinion Accompanying the Partial Search Result, Feb. 10, 2017, 14 pages.
Patent Cooperation Treaty, PCT International Search Report, PCT/US2015/025397, Feb. 7, 2015, 6 pages.

* cited by examiner

METALLOENZYME INHIBITOR COMPOUNDS AS FUNGICIDES

CROSS REFERENCE TO RELATED APPLICATIONS

This application claims the benefit of U.S. Provisional Patent Application Ser. Nos. 61/979,543 filed Apr. 15, 2014 and 62/047,368 filed Sep. 8, 2014, which are expressly incorporated by reference herein.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to metalloenzyme inhibitors and their use as fungicides. The compounds of the present disclosure may offer protection against ascomycetes, basidiomycetes, deuteromycetes and oomycetes.

One embodiment of the present disclosure may include compounds of Formula I:

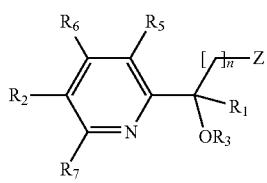

Where:
Z is optionally substituted 5-pyrimidinyl, optionally substituted 4-pyrimidinyl, optionally substituted thiazolyl, optionally substituted oxazolyl, optionally substituted 3-pyridinyl, or optionally substituted 4-pyridinyl;
n is 0 or 1;
$R_1$ is alkyl, haloalkyl, aryl, or heteroaryl, each optionally substituted with 0, 1, 2 or 3 independent $R_4$;
$R_2$ is aryl, heteroaryl aryloxy, heteroaryloxy, arylalkynyl, heteroarylalkynyl, arylalkyl, heteroarylalkyl, arylalkoxy, heteroarylalkoxy, aryloxyalkyl, or heteroaryloxyalkyl wherein each aryl or heteroaryl is optionally substituted with 0, 1, 2 or 3 independent $R_4$;
$R_3$ is independently H, alkyl, aryl, substituted aryl, heteroaryl, arylalkyl, or heteroarylalkyl, —C(O)alkyl, —C(O)aryl, —Si(alkyl)$_3$, each optionally substituted with 0, 1, 2 or 3 independent $R_4$;
$R_4$ is independently aryl, heteroaryl, alkyl, thioalkyl, cyano, cyanoalkyl, haloalkyl, hydroxy, alkoxy, halo, haloalkoxy, —C(O)alkyl, —C(O)OH, —C(O)Oalkyl, —SCF$_3$, —SF$_5$, —SCN, or SO$_2$(alkyl); and
$R_5$-$R_7$ are independently selected from the group consisting of H, alkyl, alkoxy, halo, and haloalkyl;
With the proviso that when n=1, Z is 1-tetrazolyl or 5-pyrimidinyl.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl and the like.

The term "aryl" or "Ar" refers to any aromatic ring, mono- or bi-cyclic, containing 0 heteroatoms.

The term "heterocycle" refers to any aromatic or non-aromatic ring, mono- or bi-cyclic, containing one or more heteroatoms.

The term "heteroaryl" or "Het" refers to any aromatic ring, mono- or bi-cyclic, containing one or more heteroatoms.

The term "alkoxy" refers to an —OR substituent.
The term "aryloxy" refers to an —OAr substituent.
The term "hetaryloxy" refers to an —OHet substituent.
The term "arylalkynyl" refers to an —≡— Ar substituent.
The term "heteroarylalkynyl" refers to an —≡— Het substituent.
The term "cyano" refers to a —C≡N substituent.
The term "hydroxyl" refers to an —OH substituent.
The term "amino" refers to a —NR$_2$ substituent.
The term "arylalkyl" refers to an -alkyl-Ar substituent.
The term "heteroarylalkyl" refers to an -alkyl-Het substituent.
The term "arylalkoxy" refers to —O(CH$_2$)$_n$Ar where n is an integer selected from the list 1, 2, 3, 4, 5, or 6.
The term "heteroarylalkoxy" refers to —O(CH$_2$)$_n$Het where n is an integer selected from the list 1, 2, 3, 4, 5, or 6.2
The term "haloalkoxy" refers to an —OR substituent, wherein R is substituted with Cl, F, Br, or I, or any combination of one or more halogen atoms.
The term "haloalkyl" refers to an alkyl, which is substituted with one or more halogen atoms.
The term "cyanoalkyl" refers to an alkyl, which is substituted with a cyano group.
The term "halogen" or "halo" refers to one or more halogen atoms, defined as F, Cl, Br, and I.
The term "nitro" refers to a —NO$_2$ substituent.
The term thioalkyl refers to an —SR substituent.

Throughout the disclosure, reference to the compounds of Formula I is read as also including diastereomers, enantiomers, and mixtures thereof. In another embodiment, Formula I is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, seeds, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the seeds, roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations may be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations may also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I may also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts may suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzyl-cocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination may generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzovindiflupyr, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, trifo-rine, triticonazole, validamycin, valifenalate, valiphenal, vinclozolin, zineb, ziram, zoxamide, *Candida oleophila*, *Fusarium oxysporum, Gliocladium* spp., *Phlebiopsis gigantea, Streptomyces griseoviridis, Trichoderma* spp., (RS)-N-(3,5-dichlorophenyl)-2-(methoxymethyl)-succinim-ide, 1,2-dichloropropane, 1,3-dichloro-1,1,3,3-tetrafluoro-acetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithiine 1,1,4,4-tetraoxide, 2-methoxyethylmercury acetate, 2-methoxyethylmercury chloride, 2-methoxyethylmercury silicate, 3-(4-chlorophe-nyl)-5-methylrhodanine, 4-(2-nitroprop-1-enyl)phenyl thio-cyanateme, ampropylfos, anilazine, azithiram, barium poly-sulfide, Bayer 32394, benodanil, benquinox, bentaluron, benzamacril; benzamacril-isobutyl, benzamorf, binapacryl, bis(methylmercury) sulfate, bis(tributyltin) oxide, buthio-bate, cadmium calcium copper zinc chromate sulfate, car-bamorph, CECA, chlobenthiazone, chloraniformethan, chlorfenazole, chlorquinox, climbazole, copper bis(3-phe-nylsalicylate), copper zinc chromate, cufraneb, cupric hydrazinium sulfate, cuprobam, cyclafuramid, cypendazole, cyprofuram, decafentin, dichlone, dichlozoline, diclobutra-zol, dimethirimol, dinocton, dinosulfon, dinoterbon, dipyri-thione, ditalimfos, dodicin, drazoxolon, EBP, ESBP, etacon-azole, etem, ethirim, fenaminosulf, fenapanil, fenitropan, fluotrimazole, furcarbanil, furconazole, furconazole-cis, fur-mecyclox, furophanate, glyodine, griseofulvin, halacrinate, Hercules 3944, hexylthiofos, ICIA0858, isopamphos, isovaledione, mebenil, mecarbinzid, metazoxolon, methfu-roxam, methylmercury dicyandiamide, metsulfovax, mil-neb, mucochloric anhydride, myclozolin, N-3,5-dichloro-phenyl-succinimide, N-3-nitrophenylitaconimide, natamycin, N-ethylmercurio-4-toluenesulfonanilide, nickel bis(dimethyldithiocarbamate), OCH, phenylmercury dim-ethyldithiocarbamate, phenylmercury nitrate, phosdiphen, prothiocarb; prothiocarb hydrochloride, pyracarbolid, pyri-dinitril, pyroxychlor, pyroxyfur, quinacetol; quinacetol sul-fate, quinazamid, quinconazole, rabenzazole, salicylanilide, SSF-109, sultropen, tecoram, thiadifluor, thicyofen, thio-chlorfenphim, thiophanate, thioquinox, tioxymid, tri-amiphos, triarimol, triazbutil, trichlamide, urbacid, zaril-amid, and any combinations thereof.

Additionally, the compounds described herein may be combined with other pesticides, including insecticides, nem-atocides, miticides, arthropodicides, bactericides or combi-nations thereof that are compatible with the compounds of the present disclosure in the medium selected for applica-tion, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropro-pane, abamectin, acephate, acetamiprid, acethion, aceto-prole, acrinathrin, acrylonitrile, alanycarb, aldicarb, aldoxy-carb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azin-phos-ethyl, azinphos-methyl, azothoate, barium hexafluoro-silicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bro-mophos, bromophos-ethyl, bufencarb, buprofezin, butacarb, butathiofos, butocarboxim, butonate, butoxycarboxim, cadusafos, calcium arsenate, calcium polysulfide, cam-phechlor, carbanolate, carbaryl, carbofuran, carbon disul-fide, carbon tetrachloride, carbophenothion, carbosulfan, cartap, cartap hydrochloride, chlorantraniliprole, chlorbicy-clen, chlordane, chlordecone, chlordimeform, chlordime-form hydrochloride, chlorethoxyfos, chlorfenapyr, chlorfen-vinphos, chlorfluazuron, chlormephos, chloroform, chloropicrin, chlorphoxim, chlorprazophos, chlorpyrifos, chlorpyrifos-methyl, chlorthiophos, chromafenozide, cin-erin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cyclo-prothrin, cyfluthrin, cyhalothrin, cypermethrin, cypheno-thrin, cyromazine, cythioate, DDT, decarbofuran, deltame-thrin, demephion, demephion-O, demephion-S, demeton, demeton-methyl, demeton-O, demeton-O-methyl, demeton-S, demeton-S-methyl, demeton-S-methylsulphon, diafenthi-uron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dime-tan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfo-ton, dithicrofos, d-limonene, DNOC, DNOC-ammonium, DNOC-potassium, DNOC-sodium, doramectin, ecdyster-one, emamectin, emamectin benzoate, EMPC, empenthrin, endosulfan, endothion, endrin, EPN, epofenonane, epri-nomectin, esdepallèthrine, esfenvalerate, etaphos, ethiofen-carb, ethion, ethiprole, ethoate-methyl, ethoprophos, ethyl formate, ethyl-DDD, ethylene dibromide, ethylene dichlo-ride, ethylene oxide, etofenprox, etrimfos, EXD, famphur, fenamiphos, fenazaflor, fenchlorphos, fenethacarb, fenflu-thrin, fenitrothion, fenobucarb, fenoxacrim, fenoxycarb, fenpirithrin, fenpropathrin, fensulfothion, fenthion, fen-thion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthi-etan, furathiocarb, furethrin, gamma-cyhalothrin, gamma-HCH, halfenprox, halofenozide, HCH, HEOD, heptachlor, heptenophos, heterophos, hexaflumuron, HHDN, hydram-ethylnon, hydrogen cyanide, hydroprene, hyquincarb, imi-dacloprid, imiprothrin, indoxacarb, iodomethane, IPSP, isa-zofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythida-thion, malathion, malonoben, mazidox, mecarbam, mecar-phon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bro-mide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoximmethyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, seeds, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Mycosphaerella graminicola*; impect stage: *Septoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f sp. *hordei*), powdery mildew of cucurbits (*Erysiphe cichoracearum*), anthracnose of cucurbits (*Glomerella lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating metalloenzyme inhibitor compounds of Formula (I). The following descriptions and examples are provided for illustrative purposes and should not be construed as limiting in terms of substituents or substitution patterns. It will be evident to one skilled in the art that many of the compounds of Formula I may be synthesized using more than one of the routes disclosed within the following schemes.

The compound of Formula 1.7, wherein $R_1$-$R_3$, $R_5$-$R_7$, and Z are as originally defined and n is 1, may be prepared according to the methods outlined in Scheme 1, steps c-e from the appropriately substituted precursors, such as compounds of Formulae 1.3 and 1.4, which may be prepared according to the methods outlined in Scheme 1, steps a-b. The compound of Formula 1.3 may be prepared via the condensation of the compound of Formula 1.0 with ethyl 2,2-difluoro-2-bromoacetate activated with copper (Cu(0)) in a polar, aprotic solvent such as dimethyl sulfoxide (DMSO), as shown in step a. Compound 1.4 may be prepared by treating the suitably electron deficient 4-fluorobenzonitrile of Formula 1.1 with a nucleophile, such as the phenoxide anion of the compound of Formula 1.2, generated by treating the phenol of Formula 1.2 with an alkali carbonate base, such as cesium carbonate ($Cs_2CO_3$), in a polar solvent like N,N-dimethylformamide (DMF) at an elevated temperature, for example 80-100° C., as shown in step b. The ketone of Formula 1.5 may be prepared via the condensation of the compound of Formula 1.3 with an appropriately substituted nucleophile, such as the the lithiated pyridine, generated by treating the bromopyridine of Formula 1.4 with n-butyllithium (n-BuLi) in an aprotic solvent, such as toluene, at a reduced temperature of about −78° C., as shown in step c. The epoxide of Formula 1.6 may be prepared by treating the ketone of Formula 1.5 with dimethyloxosulfonium methylide, generated by treating trimethylsulfoxonium iodide with a strong base, such as potassium tert-butoxide (KO$^t$Bu) or sodium hydride (NaH) in a mixture of polar, aprotic solvents, for example tetrahydrofuran (THF) and DMSO at a reduced temperature, for example between about −20° C. and 0° C., as shown in step d. The compound of Formula 1.7, wherein $R_1$-$R_3$, $R_5$-$R_7$, and Z are as originally defined and n is 1, may be prepared by treating an appropriately substituted epoxide, for example the epoxide of Formula 1.6, with a nucleophile, for example 1H-tetrazole, in the presence of an alkali carbonate base, such as potassium carbonate ($K_2CO_3$) in a polar solvent like DMF at an elevated temperature of about 60° C., as shown in step e.

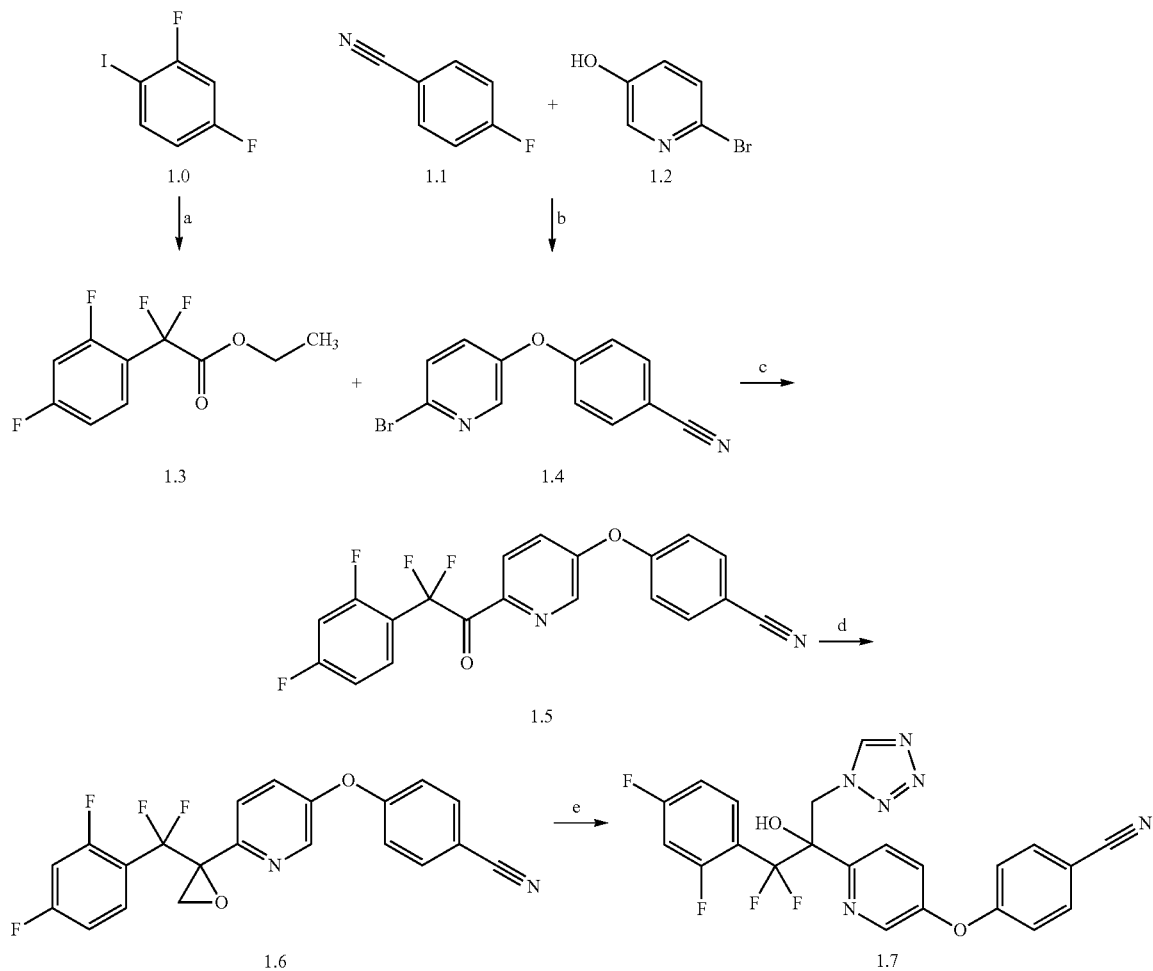

The compound of Formula 2.5, wherein $R_1$-$R_3$, $R_5$-$R_7$, and Z are as originally defined and n is 1, may be prepared according to the methods outlined in Scheme 2, steps b-d from the appropriately substituted precursors, such as compounds of Formulae 2.1 and 2.2, which may be prepared according to the methods outlined in Scheme 2, step a. The Weinreb amide of Formula 2.1 may be prepared from the propanaoic acid of Formula 2.0 using methodology reported by Trost et. al. (*J. Am. Chem. Soc.* 2010, 132, 8915-8917), as shown in step a. The ketone of Formula 2.3 may be prepared via the condensation of the Weinreb amide of Formula 2.1 with a nucleophile, such as a lithiated pyridine, generated via the treatment of an appropriately substituted bromopyridine, for example the bromopyridine of Formula 2.2, with n-BuLi in an aprotic solvent, such as diethyl ether ($Et_2O$), at a reduced temperature of about −78° C., as shown in step b. The epoxide of Formula 2.4 may be prepared from the ketone of Formula 2.3 using the methodology described in Scheme 1, step d, as shown in step c. The compound of Formula 2.5, wherein $R_1$-$R_3$, $R_5$-$R_7$, and Z are as originally defined and n is 1, may be prepared by treating an appropriately substituted epoxide, for example the epoxide of Formula 2.4, with a nucleophile, for example 1H-tetrazole, in the presence of an organic amine base, such as diisopropyl amine, in a polar, aprotic solvent such as DMSO at an elevated temperature of about 60° C., as shown in step d.

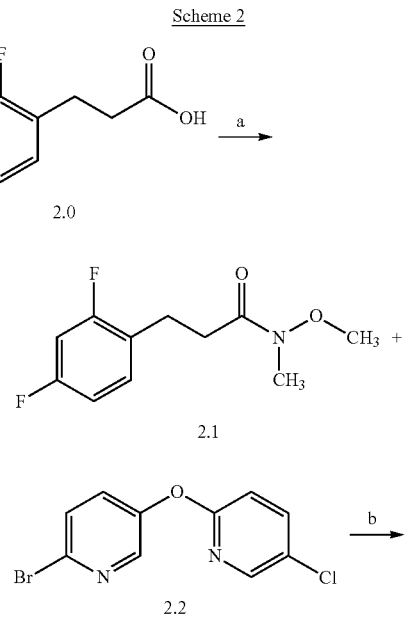

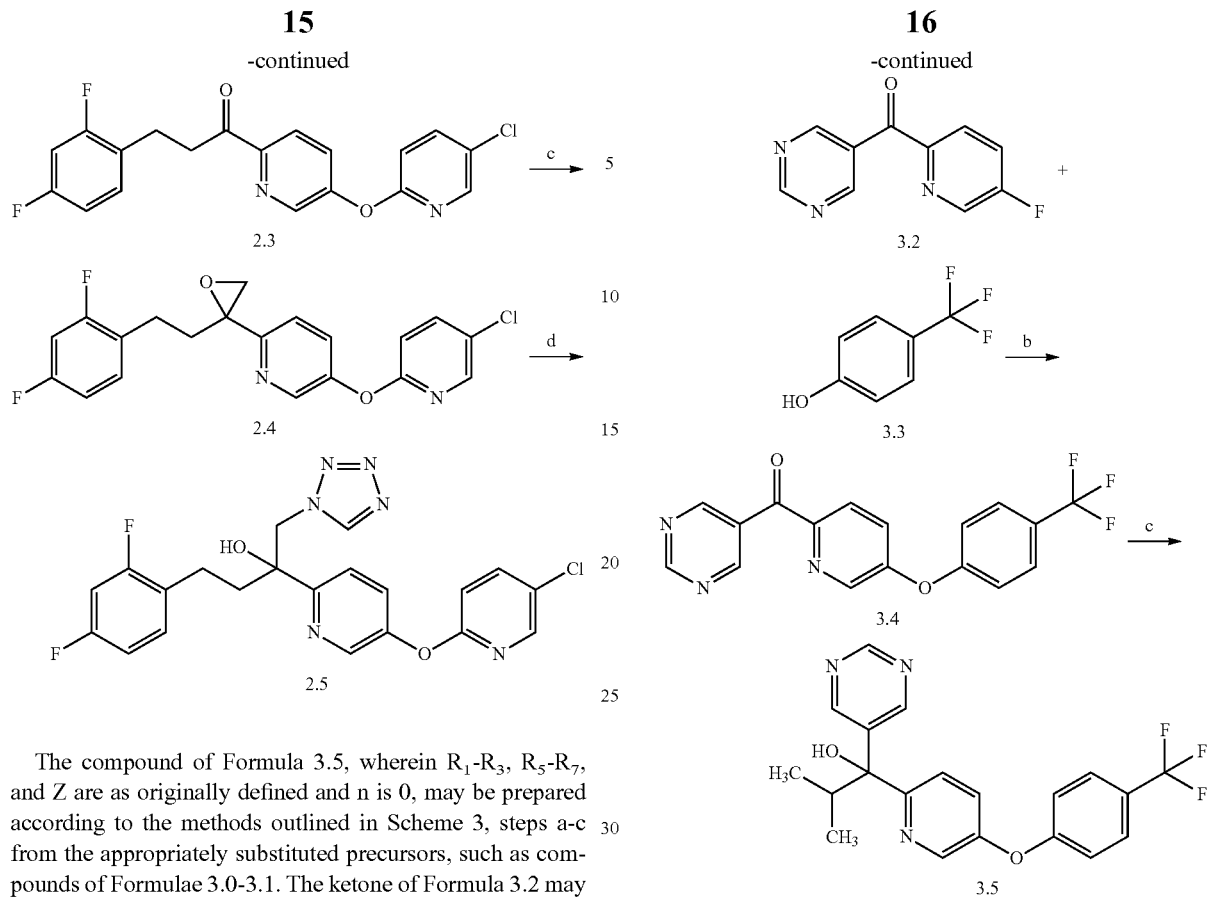

The compound of Formula 3.5, wherein $R_1$-$R_3$, $R_5$-$R_7$, and Z are as originally defined and n is 0, may be prepared according to the methods outlined in Scheme 3, steps a-c from the appropriately substituted precursors, such as compounds of Formulae 3.0-3.1. The ketone of Formula 3.2 may be prepared by treating the Weinreb amide of Formula 3.0 with a Grignard reagent, such as the Grignard prepared via transmetalation by treating the bromopyridine of Formula 3.2 with isopropylmagnesium chloride (i-PrMgCl) in an aprotic solvent like toluene at a temperature between about 0° C. and 23° C., as shown in step a. The 4-trifluoromethylphenyl ether of Formula 3.4 may be prepared from the ketone of Formula 3.2 via treatment with the phenol of Formula 3.3 in the presence of an alkali carbonate base, for example $Cs_2CO_3$, in a polar solvent such as DMF at an elevated temperature of about 110° C., as shown in step b. The compound of Formula 3.5, wherein $R_1$-$R_3$, $R_5$-$R_7$, and Z are as originally defined and n is 0, may be prepared by treating an appropriately substituted ketone, for example the ketone of Formula 3.4, with a nucleophile, for example a Grignard reagent such as i-PrMgCl in the presence of zinc chloride ($ZnCl_2$) and lithium chloride (LiCl), in a polar, aprotic solvent like THF at a reduced temperature of about 0° C., as described by Hatano et. al. (*J. Am. Chem. Soc.* 2006, 128, 9998-9999) and shown in step c.

The compound of Formula 4.5, wherein $R_1$-$R_3$, $R_5$-$R_7$, and Z are as originally defined and n is 1, may be prepared according to the methods outlined in Scheme 4, steps a-d from the appropriately substituted precursors, such as compounds of Formulae 4.0 and 3.2. The ketone of Formula 4.1 may be prepared by treating the Weinreb amide of Formula 4.0 and the bromopyridine of Formula 3.1 as described in Scheme 3, step a, as shown in step a. The ketone of Formula 4.3 may be prepared as described in Scheme 3, step b, from the ketone of Formula 4.1 and the phenol of Formula 4.2, as shown in step b. The epoxide of Formula 4.4 may be prepared from the ketone of Formula 4.3 using the methodology described in Scheme 1, step d, as shown in step c. The compound of Formula 4.5, wherein $R_1$-$R_3$, $R_5$-$R_7$, and Z are as originally defined and n is 1, may be prepared by treating an appropriately substituted epoxide, for example the epoxide of Formula 4.4, with a nucleophile, for example 1H-tetrazole, in the presence of an organic amine base, such as diisopropyl amine, in a polar, aprotic solvent such as DMF at an elevated temperature of about 70° C., as shown in step d.

Scheme 3

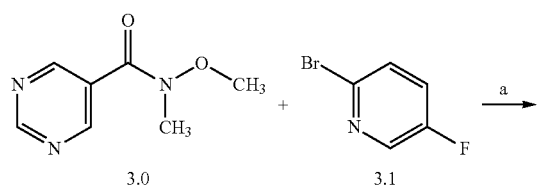

Scheme 4

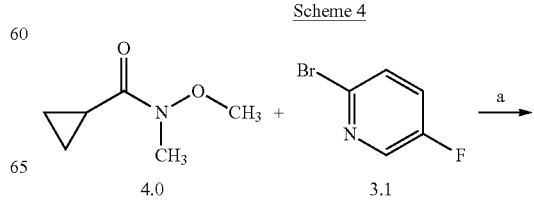

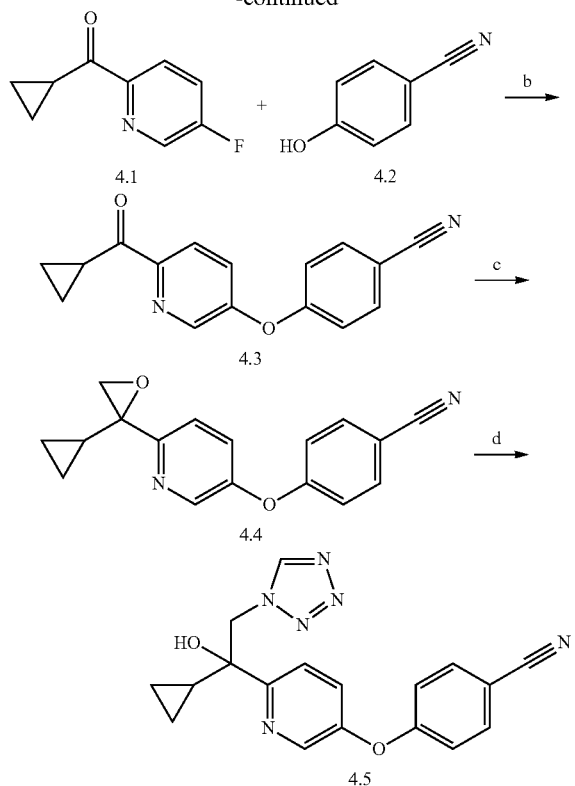

as shown in Scheme 6, steps c-d from the appropriately substituted precursors, such as compounds of Formulae 6.0-6.4, which may be prepared according to the methods outlined in Scheme 6, step a-b. The compound of Formula 6.5 may be prepared using methodology reported by Journet et. al. (*Tet. Lett.* 1998, 39, 1717-1720), which describes the preparation of the phosphonate compound of Formula 6.3 and its subsequent use in a Horner-Emmons condensation with the pyrimidine carbaldehyde of Formula 6.4, as shown in steps a and b. The compound of Formula 6.7 may be prepared via a Suzuki coupling between the bromopyridine of Formula 6.5 and an appropriately substituted boronic acid or boronate ester, for example the boronic acid of Formula 6.6, in the presence of an alkali carbonate base, such as sodium carbonate ($Na_2CO_3$), and a palladium catalyst, such as [1,1'-bis(diphenylphosphino)-ferrocene]palladium(II)dichloride [$PdCl_2(dppf)$], in a mixed solvent system, such as a polar, aprotic solvent, for example dioxane or acetonitrile ($CH_3CN$), mixed with water, wherein the ratio of organic solvent to water in the composition is about 3:1, at an elevated temperature of about 85° C., as shown in step c. The compound of Formula 6.8, wherein $R_1$-$R_3$, $R_5$-$R_7$, and Z are as originally defined and n is 1, may be prepared by treating an appropriately substituted ketone, for example the ketone of Formula 6.7, with a nucleophile, for example a Grignard reagent like methyl magnesium bromide (MeMgBr), in a polar, aprotic solvent such as THF at a reduced temperature of about −78° C., as shown in step d.

The compounds of Formula 5.1, wherein $R_1$-$R_3$, $R_5$-$R_7$, and Z are as originally defined and n is 0, may be prepared as shown in Scheme 5, step a by treating an appropriately substituted ketone, for example the ketone of Formula 5.0, with a nucleophile, for example an appropriately substituted Grignard reagent in a polar, aprotic solvent like THF at a reduced temperature of about 0° C. The Grignard reagent may be prepared from (chloromethyl)cyclopropane and magnesium (Mg) in the presence of catalytic iodine ($I_2$) in a polar, aprotic solvent like THF at an elevated temperature of about 65° C.

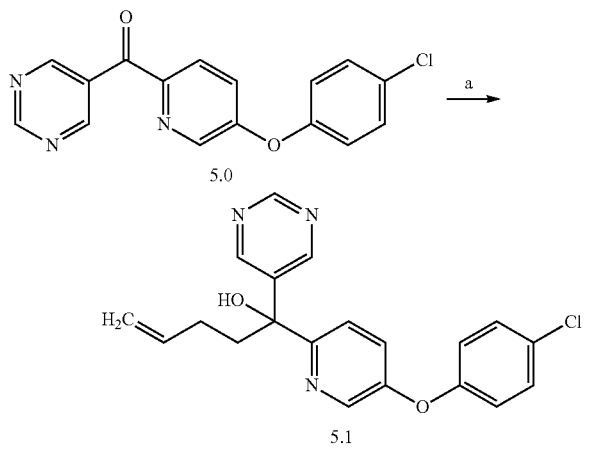

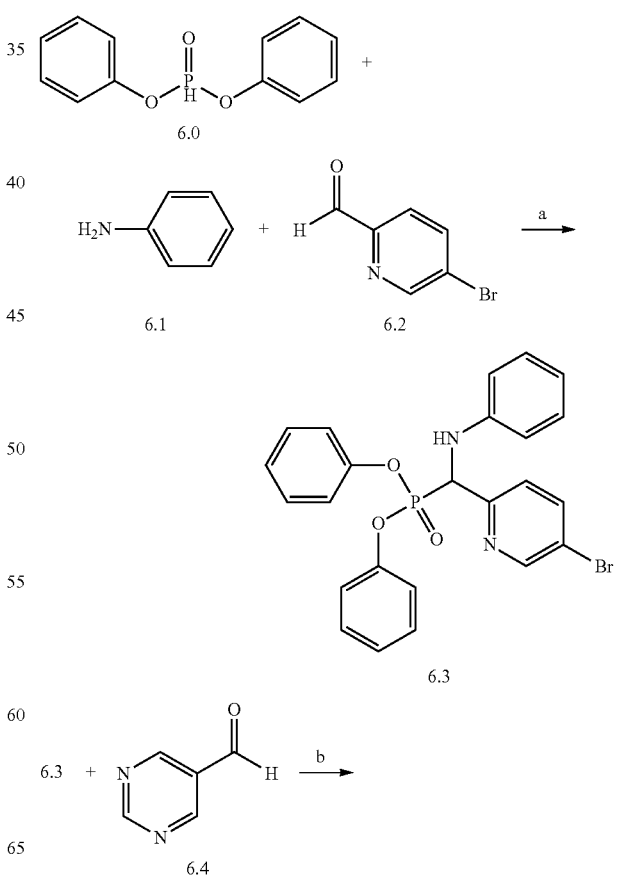

The compound of Formula 6.8, wherein $R_1$-$R_3$, $R_5$-$R_7$, and Z are as originally defined and n is 1, may be prepared

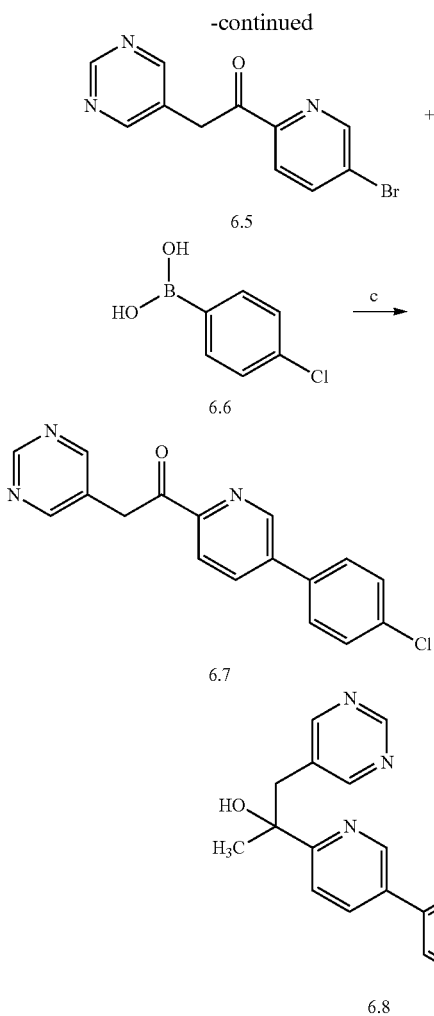

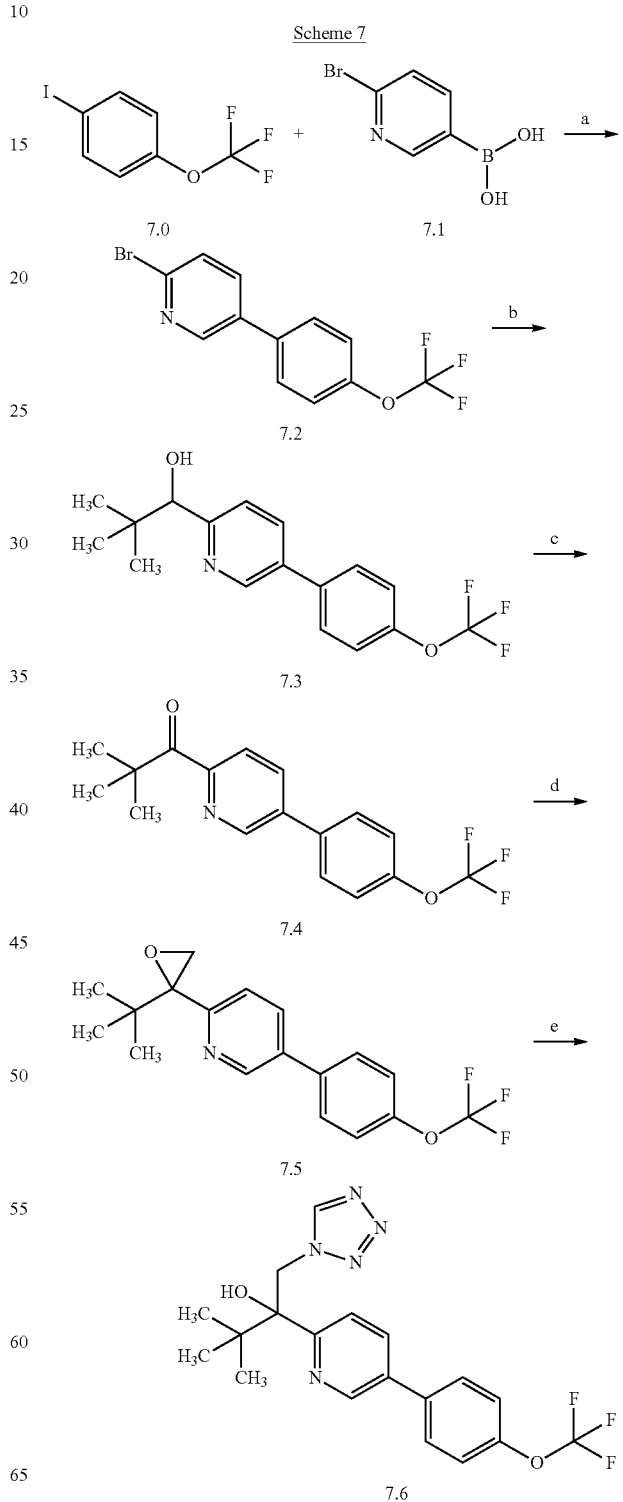

The compound of Formula 7.6, wherein $R_1$-$R_3$, $R_5$-$R_7$, and Z are as originally defined and n is 1, may be prepared as shown in Scheme 7, steps a-e. The bromopyridine of Formula 7.2 may be prepared via a Suzuki coupling between an appropriately substituted aryl halide, such as the iodobenzene of Formula 7.0 and a boronic acid or boronate ester, such as the pyridine boronic acid of Formula 7.1, in the presence of an alkali carbonate base, such as $K_2CO_3$, and a palladium catalyst, such as tetrakis(triphenylphosphine)palladium (0) [Pd(PPh$_3$)$_4$], in a polar solvent system, such as a polar, aprotic solvent, for example DMF, dioxane, or CH$_3$CN, mixed with water, wherein the ratio of organic solvent to water in the composition is about 4:1. The reaction is run at an elevated temperature of about 120° C., which may be achieved through conventional heating techniques or via microwave irradiation, as shown in step a. The secondary alcohol of Formula 7.3 may be prepared via metalation chemistry wherein a mixture of the bromopyridine of Formula 7.2 and excess pivaldehydeis treated with n-BuLi at a reduced temperature of about −78° C. in an aromatic hydrocarbon such as toluene, as shown in step b. The ketone of Formula 7.4 may be prepared by treating the secondary alcohol of Formula 7.3 with 1,1,1-triacetoxy-1,1-dihydro-1,2-benziodoxol-3(1H)-one (Dess-Martin periodinane) in a halogenated hydrocarbon, such as methylene chloride (CH$_2$Cl$_2$, DCM) at a reduced temperature of about 0° C., as shown in step c. The epoxide of Formula 7.5 may be prepared from the ketone of Formula 7.4 using the methodology described in Scheme 1, step d, as shown in step d. The compound of Formula 7.6, wherein $R_1$-$R_3$, $R_5$-$R_7$, and Z are as originally defined and n is 1, may be prepared by treating an appropriately substituted epoxide, for example the epoxide of Formula 7.5, with a nucleophile, for example 1H-tetrazole, in the presence of an alkali carbonate base, such as $K_2CO_3$, in a polar, aprotic solvent like DMSO at an elevated temperature of about 70° C., as shown in step e.

The compound of Formula 8.1, wherein $R_1$-$R_3$, $R_5$-$R_7$, and Z are as originally defined and n is 0, may be prepared as shown in Scheme 8, steps a-b. The ketone of Formula 8.0 may be prepared as described in Scheme 3, step a. The compound of Formula 8.1, wherein $R_1$-$R_3$, $R_5$-$R_7$, and Z are as originally defined and n is 0, may be prepared by treating an appropriately substituted ketone, for example the ketone of Formula 8.0, with a nucleophile, for example a Grignard reagent, such as tert-butylmagnesium chloride ($^t$BuMgCl), in the presence of $ZnCl_2$ and LiCl, in a polar, aprotic solvent like THF at a reduced temperature of about 0° C., as shown in step b.

Scheme 8

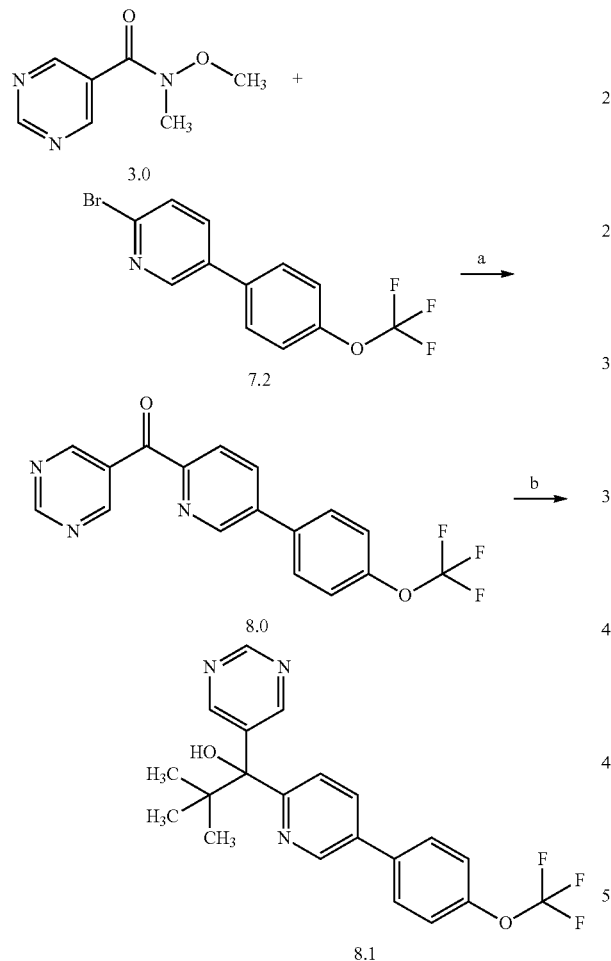

The compound of Formula 9.4, wherein $R_1$-$R_3$, $R_5$-$R_7$, and Z are as originally defined and n is 1, may be prepared as shown in Scheme 9, steps a-e. The pyridyl carbaldehyde of Formula 9.0 may be prepared via metalation chemistry, wherein a solution of the bromopyridine of Formula 7.2 in an aromatic hydrocarbon, such as toluene, is treated with n-BuLi at a reduced temperature of about −78° C. and the subsequent lithiopyridine is quenched with anhydrous DMF, as shown in step a. The secondary alcohol of Formula 9.1 may be prepared by treating a solution of the aldehyde of Formula 9.0 in an aprotic solvent like $Et_2O$ with a nucleophile, such as a Grignard reagent, which may be prepared by treating an appropriately substituted benzyl bromide, such as 4-chloro-2-fluorobenzyl bromide, with Mg powder in an aprotic solvent like $Et_2O$, as shown in step b. The ketone of Formula 9.2 may be prepared via the oxidation of the secondary alcohol of Formula 9.1 using Dess-Martin periodinane under the conditions described in Scheme 7, step c, as shown in step c. The epoxide of Formula 9.3 may be prepared from the ketone of Formula 9.2 using the methodology described in Scheme 1, step d, as shown in step d, but using an alcohol such as tert-butanol ($^t$BuOH) as the reaction solvent. The compound of Formula 9.4, wherein $R_1$-$R_3$, $R_5$-$R_7$, and Z are as originally defined and n is 1, may be prepared by treating an appropriately substituted epoxide, for example the epoxide of Formula 9.3, with a nucleophile, for example 1H-tetrazole, using the conditions described in Scheme 7, step e, as shown in step e.

Scheme 9

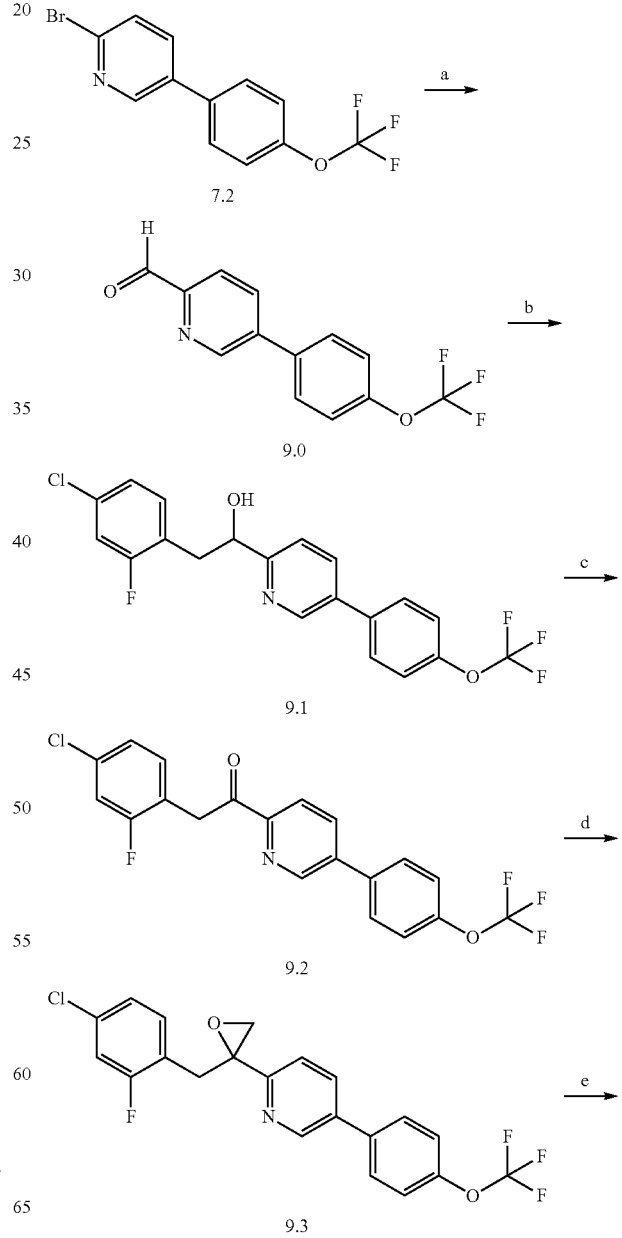

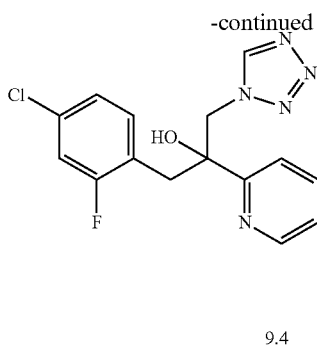

9.4

The compounds of Formulae 10.0 and 10.1, wherein $R_1$-$R_3$, $R_5$-$R_7$, and Z are as originally defined and n is 0, may be prepared as shown in Scheme 10, step a. The alkyne of Formula 10.0 may be prepared by treating a solution of an appropriately substituted ketone, such as the ketone of Formula 5.0, in a polar, aprotic solvent like THF, with an appropriately substituted nucleophile, such as an acetylide anion, at a reduced temperature of about 0° C. The acetylide anion may be prepared by treating an appropriately substituted terminal alkyne, such as 3,3-dimethylbut-1-yne with a Grignard reagent, for example ethylmagnesium bromide (EtMgBr), in a polar, aprotic solvent like THF at a temeprature of about 0° C. during the Grignard additon and about 40° C. following the addition. The compound of Formula 10.1 is simply the addition of residual Grignard, namely EtMgBr, into the ketone of Formula 5.0 as described in Scheme 5, step a.

Grignard reagent may be prepared by treating an appropriately substituted benzyl bromide, such as 1-(bromomethyl)-4-chloro-2-fluorobenzene, with Mg in an aprotic solvent like $Et_2O$ at a temperature of about 23° C. to about 35° C.

Scheme 11

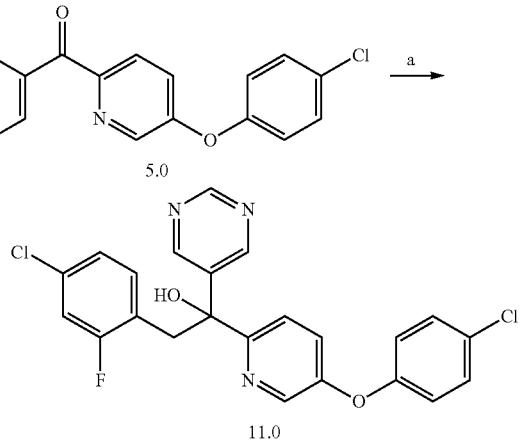

The compound of Formula 12.8, wherein $R_1$-$R_3$, $R_5$-$R_7$, and Z are as originally defined and n is 1, may be prepared according to the methods outlined in Scheme 12, steps c-f from the appropriately substituted precursors, such as compounds of Formulae 12.0-12.3, which may be prepared according to the methods outlined in Scheme 12, steps a-b.

Scheme 10

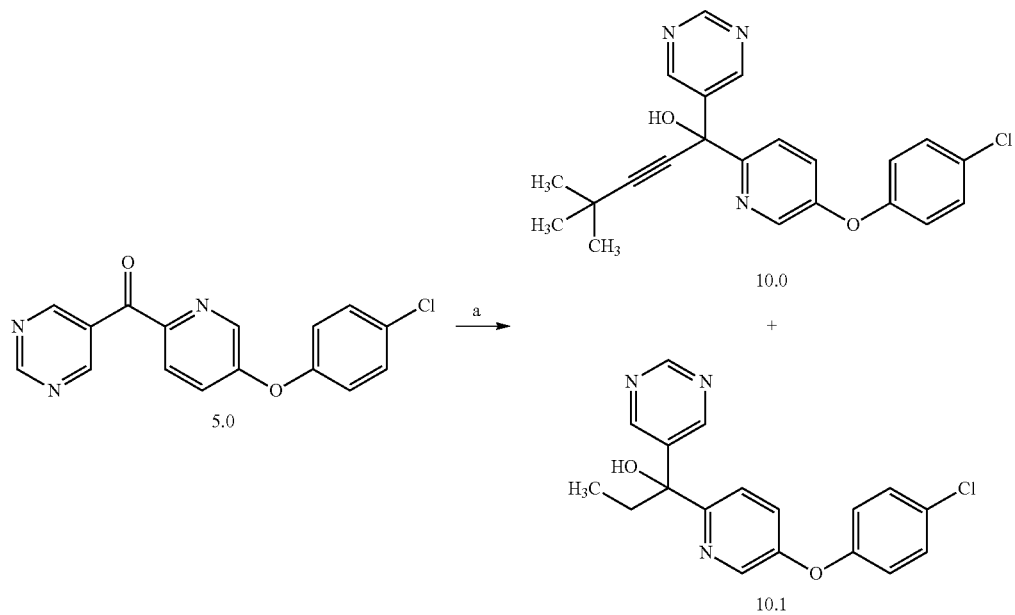

The compound of Formula 11.0, wherein $R_1$-$R_3$, $R_5$-$R_7$, and Z are as originally defined and n is 0, may be prepared as shown in Scheme 10, step a, by treating a solution of an appropriately substituted ketone, such as the ketone of Formula 5.0, in an aprotic solvent like $Et_2O$, with an appropriately substituted nucleophile, such as a Grignard Reagent, at a reduced temperature of about 0° C. The The ether of Formula 12.2 may be prepared by treating a mixture of the suitably electron deficient 4-fluorobenzonitrile of Formula 12.0 with an appropriately substituted phenol, such as the phenol of Formula 12.1, with an alkali carbonate base, such as $K_2CO_3$, in a polar, aprotic solvent such as DMSO at an elevated temperature of about 120° C., as shown in step a. The aldehyde of Formula 12.3 may be prepared by treating a solution of the nitrile of Formula 12.2 in a polar, aprotic solvent like THF with a reducing agent, for example diisobutylaluminum hydride (DIBAL-H), at a reduced temperature of about −78° C., as shown in step b. The secondary alcohol of formula 12.5 may be prepared by treating a solution of the aldehyde of Formula 12.3 in an aprotic solvent like Et$_2$O, with an appropriately substituted nucleophile, such as a Grignard reagent, at a reduced temperature of about 0° C., wherein the Grignard reagent may be prepared by treating an appropriately substituted benzyl bromide, such as 1-(bromomethyl)-4-chloro-2-fluorobenzene (Formula 12.4), with Mg in an aprotic solvent like Et$_2$O at a temperature of about 23° C. to about 35° C., as shown in step c. The ketone of Formula 12.6 may be prepared via the oxidation of the secondary alcohol of Formula 12.5 using Dess-Martin periodinane under the conditions described in Scheme 7, step c, as shown in step d. The epoxide of Formula 12.7 may be prepared by treating a solution of the ketone of Formula 12.6 in an aprotic solvent like Et$_2$O with diazomethane at a reduced temperature of about 0° C., as shown in step e. The compound of Formula 12.8, wherein R$_1$-R$_3$, R$_5$-R$_7$, and Z are as originally defined and n is 1, may be prepared as described in Scheme 7, step e, as shown in step f Scheme 12

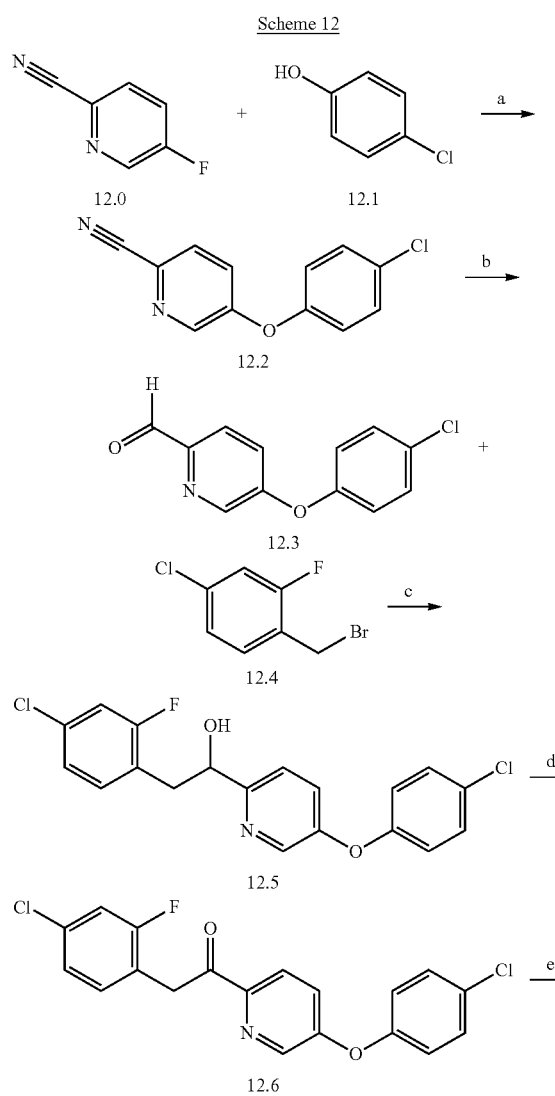

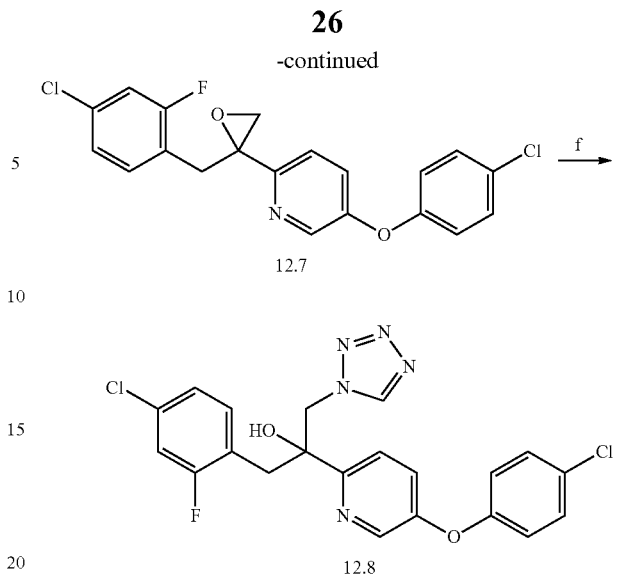

The compound of Formula 13.1, wherein R$_1$-R$_3$, R$_5$-R$_7$, and Z are as originally defined and n is 0, may be prepared via metallation chemistry as shown in Scheme 13, step a, by treating a mixture of a solution of an appropriately substituted ketone, such as the ketone of Formula 13.0, and an appropriately substituted aryl halide, such as 5-bromopyrimidine, in an aprotic solvent like THF with n-BuLi at a reduced temperature of about −78° C.

Scheme 13

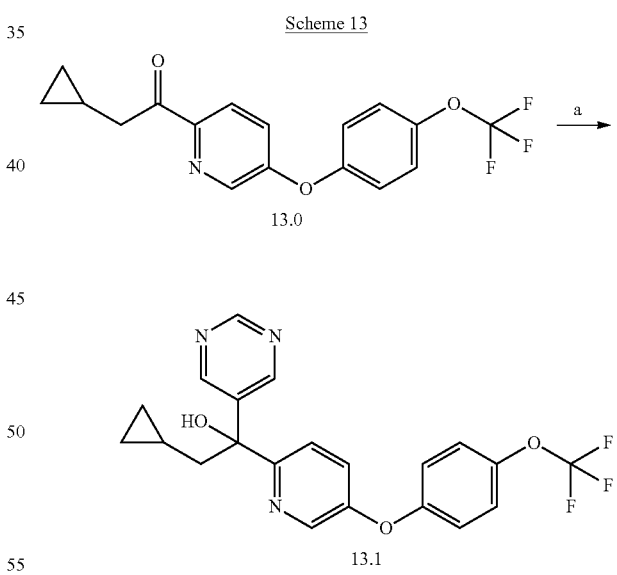

The compound of Formula 14.0, wherein R$_1$-R$_3$, R$_5$-R$_7$, and Z are as originally defined and n is 1, may be prepared as shown in Scheme 14, step a, by treating a mixture of a solution of an appropriately substituted ketone, such as the ketone of Formula 6.7, and trimethyl-(trifluoromethyl)silane, in an aprotic solvent like THF with a fluoride source, for example cesium fluoride (CsF), at a reduced temperature of about 0° C., followed by hydrolysis with a mineral acid, such as aqueous hydrogen chloride (HCl).

Scheme 14

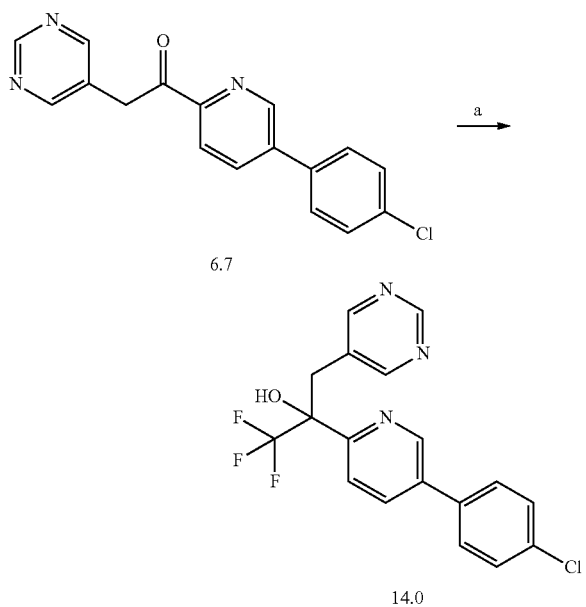

The compound of Formula 15.0, wherein $R_1$-$R_3$, $R_5$-$R_7$, and Z are as originally defined and n is 0, may be prepared via metallation chemistry as shown in Scheme 15, step a, by treating a solution of an appropriately substituted ketone, such as the ketone of Formula 8.0, in an aprotic solvent like $Et_2O$ at a reduced temperature of about −78° C. with an appropriately substituted nucleophile, such as the lithiobenzene prepared by treating a solution of an appropriately substituted aryl bromide, for example 1-bromo-2,4-difluorobenzene, in an aprotic solvent like $Et_2O$ with n-BuLi at a reduced temperature of about −78° C.

Scheme 15

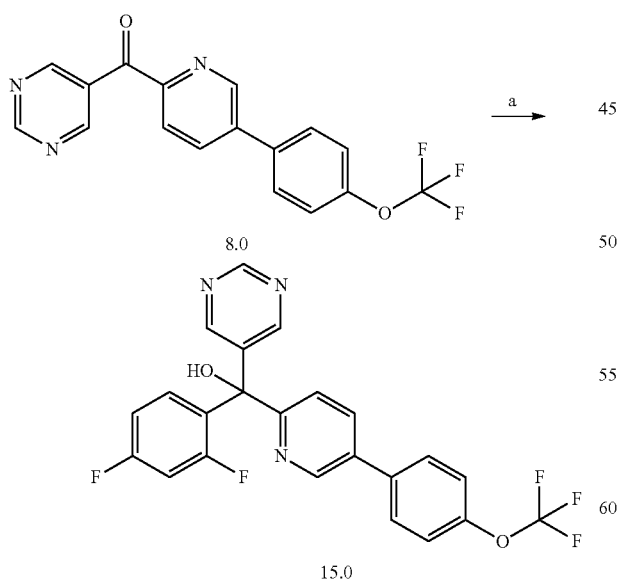

The compound of Formula 16.3 is representative of metalloenzyme inhibitors of Formula I, wherein $R_1$-$R_3$, $R_5$-$R_7$, and Z are as originally defined and n is 0, and can be prepared according to the methods outlined in Scheme 16, steps a-c. The ketone of Formula 16.1 can be prepared by treating the Weinreb amide of Formula 3.0 and the iodobromopyridine of Formula 16.0 as described in Scheme 3, step a at a temperature between about −40° C. and 23° C. in a polar, aprotic solvent like THF. The alcohol of Formula 16.2 can be prepared by treating a ketone of Formula 16.1 with a nucleophile, for example a Grignard reagent like tert-pentylmagnesium chloride, at a temperature between about −78° C. and 0° C. in a polar, aprotic solvent like THF as shown in step b. Alternatively, metallation chemistry utilizing alkyl- or aryllithium reagents can also be used to give alcohols represented by Formula 16.2, as described in Scheme 15, step a. The alcohol of Formula 16.3 can be prepared from the alcohol of Formula 16.2 and a boronic acid, a boronate ester, or an N-methyliminodiacetic acid (MIDA) boronate using the Suzuki coupling methodology described in Scheme 7, step a, or with a modified Suzuki coupling procedure as described in *Angew. Chem. Int. Ed.* 2012, 51, 2667, as shown in step c.

Scheme 16

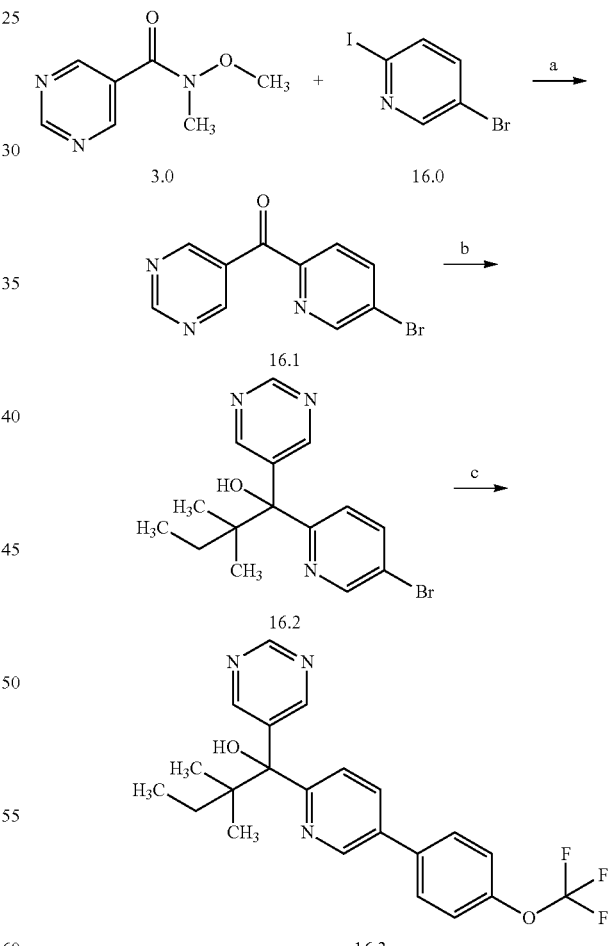

The compounds of Formulae 17.1 and 17.2 are representative of metalloenzyme inhibitors of Formula I, wherein $R_1$-$R_3$, $R_5$-$R_7$, and Z are as originally defined and n is 0, and can be prepared according to the methods outlined in Scheme 17, step a. The E and Z oxime isomers, compounds of Formulae 17.1 and 17.2 respectively, can be prepared by treating a ketone of Formula 17.0 with a base, such as sodium acetate (NaOAc), and an amine, such as O-methyl-hydroxylamine hydrochloride, in a polar, protic solvent like methanol (MeOH) at about 22° C., as shown in step a.

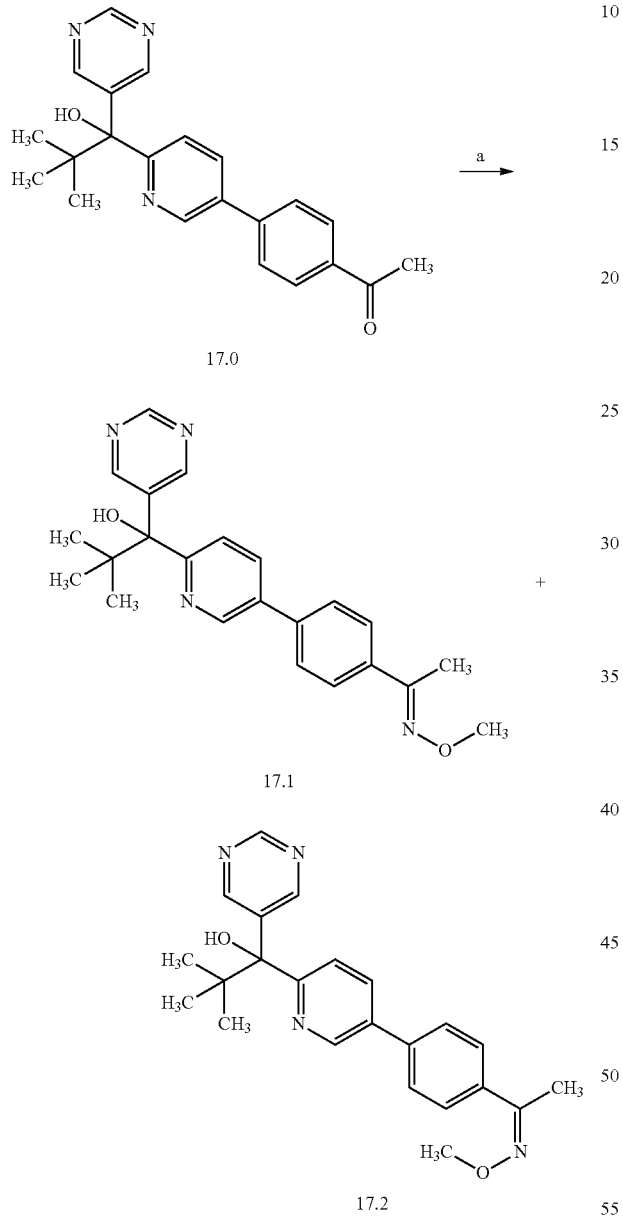

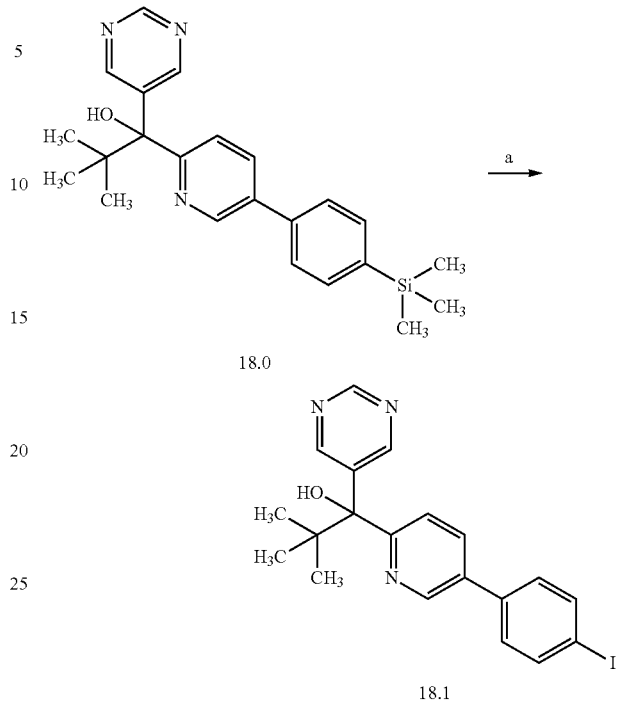

The compound of Formula 18.1 is representative of metalloenzyme inhibitors of Formula I, wherein $R_1$-$R_3$, $R_5$-$R_7$, and Z are as originally defined and n is 0, and can be prepared according to the methods outlined in Scheme 18. The compound of Formula 18.1 can be prepared by treating a compound of Formula 18.0 with an iodinating reagent, such as chloroiodomethane ($CH_2ClI$), in a halogenated hydrocarbon like DCM, at a temperature of about 23° C., as shown in step a.

EXAMPLES

Example 1

Preparation of 4-((6-(1-(2,4-difluorophenyl)-1,1-difluoro-2-hydroxy-3-(1H-tetrazol-1-yl)propan-2-yl)pyridin-3-yl)oxy)benzonitrile (1)

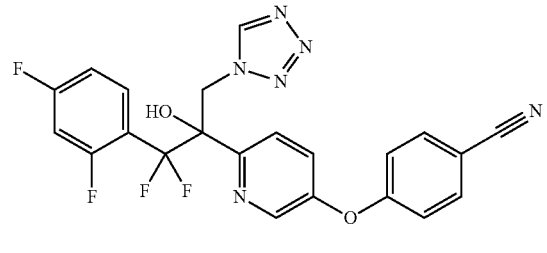 [SMILES: N#Cc1ccc(Oc2ccc(C(O)(Cn3cnnn3)C(F)(F)c3ccc(F)cc3F)nc2)cc1]

Step A1: Preparation of ethyl 2-(2,4-difluorophenyl)-2,2-difluoroacetate

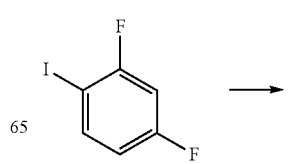

-continued

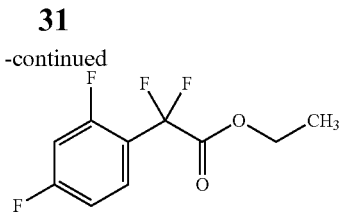

To a stirred suspension of copper metal (Cu, 10.59 grams (g), 166.6 millimole (mmol)) in anhydrous DMSO (80 milliliters (mL)) was added ethyl 2,2-difluoro-2-bromoacetate (16.9 g, 83.3 mmol) and the solution was stirred for 90 minutes (min) at room temperature. To this solution was added a solution of 2,4-difluoroiodobenzene (10.0 g, 41.7 mmol) in DMSO (10 mL) and the reaction mixture was stirred at room temperature for 48 hours (h). The reaction mixture was diluted with ethyl acetate (EtOAc, 800 mL), filtered through a pad of Celite®, and the filtrate was washed successively with 5% aqueous ammonium hydroxide (NH$_4$OH), saturated aqueous ammonium chloride (NH$_4$Cl) solution, and saturated aqueous sodium chloride (NaCl, brine) solution. The organic phase was dried over sodium sulfate (Na$_2$SO$_4$), filtered, and concentrated under reduced pressure to obtain the crude product which was purified by column chromatography (silica gel, SiO$_2$) to afford the title compound (7.9 g, 80%).

Step A2: Preparation of 4-(6-bromopyridin-3-yloxy)benzonitrile

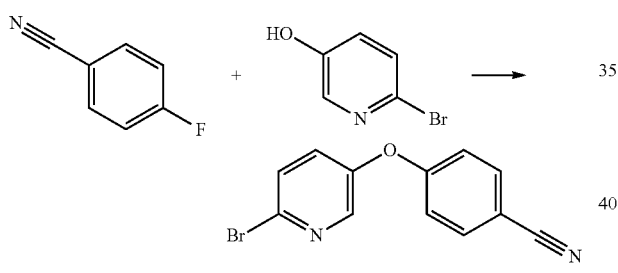

To a stirred suspension of 2-bromo-5-hydroxypyridine (10.0 g, 62.1 mmol) and 4-fluorobenzonitrile (11.21 g, 93.10 mmol) in DMF (125 mL) was added Cs$_2$CO$_3$ (40.44 g, 124.1 mmol) at room temperature under a nitrogen gas (N$_2$) atmosphere, and the reaction mixture was heated to 90° C. and stirred at 90° C. for 16 h. The reaction mixture was cooled to room temperature, diluted with ice water, and extracted with EtOAc. The combined organic extracts were washed with brine, dried over Na$_2$SO$_4$, filtered, and concentrated under reduced pressure to obtain the crude product which was purified by column chromatography (SiO$_2$) to afford the title compound (9.5 g, 55%).

Step B: Preparation of 4-(6-(2-(2,4-difluorophenyl)-2,2-difluoroacetyl)pyridin-3-yloxy)benzonitrile

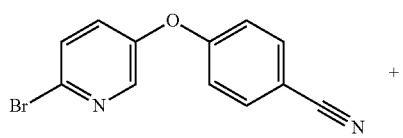

-continued

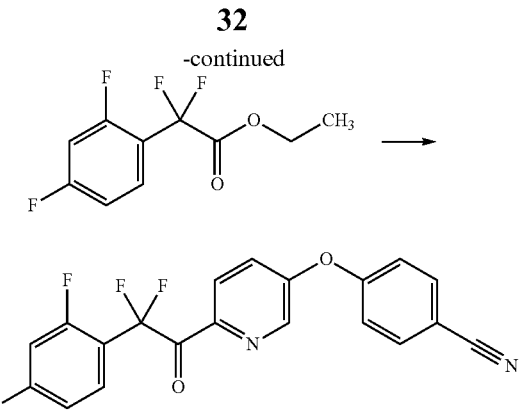

To a stirred suspension of 4-(6-bromopyridin-3-yloxy)benzonitrile (1 g, 3.63 mmol) in anhydrous toluene (10 mL) was added a solution of n-BuLi in hexane (2.5 Molar (M), 4.36 mL, 10.9 mmol) dropwise at −78° C. over a 10 min period and the mixture was stirred at −78° C. for 2 h. The reaction mixture was treated with a solution of ethyl 2-(2, 4-difluorophenyl)-2,2-difluoroacetate (1.71 g, 7.26 mmol) in toluene (10 mL), and the mixture was slowly warmed to room temperature and stirred for 16 h. The reaction mixture was quenched with 1 Normal (N) aqueous HCl solution and extracted with EtOAc. The organic extract was dried over Na$_2$SO$_4$, filtered, and concentrated under reduced pressure to obtain the title compound (1.75 g) which was used in the next step without further purification.

Step C: Preparation of 4-(6-(2-(2,4-difluorophenyl) difluoromethyl)oxiran-2-yl)pyridine-3-yloxy)benzonitrile

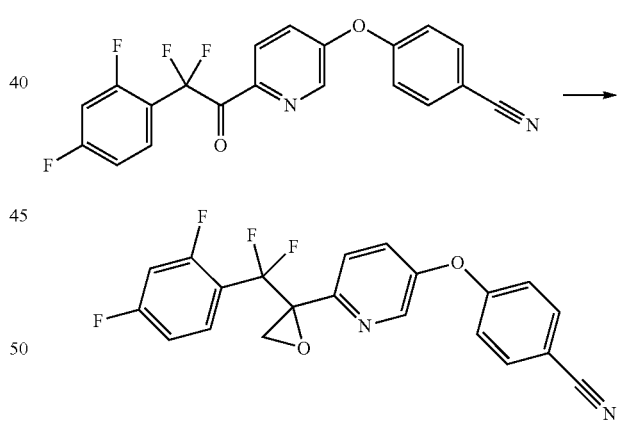

To a stirred suspension of trimethylsulfoxonium iodide (660 milligrams (mg), 3.02 mmol) in a mixture of anhydrous THF (10 mL) and DMSO (4 mL) at 0° C. was added potassium-tert-butoxide (KO$^t$Bu, 339 mg, 3.02 mmol) and the mixture was stirred for 90 min at 0° C. The reaction was cooled to −20° C. and a solution of 4-(6-(2-(2,4-difluorophenyl)-2,2-difluoroacetyl)pyridin-3-yloxy)benzonitrile (0.9 g, 2.32 mmol) in THF (19 mL) was added dropwise to the mixture over a 10 min period. The reaction mixture was warmed to 0° C., stirred at 0° C. for 30 min, and quenched with 1 N HCl solution followed by saturated aqueous sodium bicarbonate (NaHCO$_3$) solution. The mixture was extracted with EtOAc, and the organic phase was dried over Na$_2$SO$_4$, filtered, and concentrated under reduced pressure to obtain crude product which was purified by column chromatography (SiO$_2$) to afford the title compound (150 mg, 10%).

Step D: Preparation of 4-((6-(1-(2,4-difluorophenyl)-1,1-difluoro-2-hydroxy-3-(1H-tetrazol-1-yl)propan-2-yl)pyridin-3-yl)oxy)benzonitrile (1)

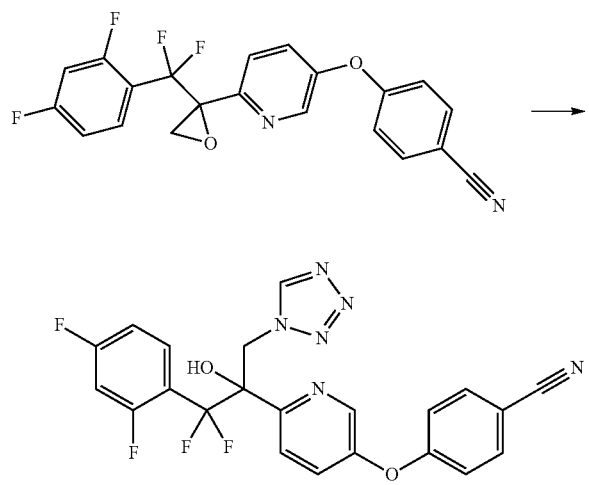 [SMILES: N#Cc1ccc(Oc2ccc(C3(C(F)(F)c4ccc(F)cc4F)CO3)nc2)cc1 ; N#Cc1ccc(Oc2ccc(C(O)(Cn3cnnn3)C(F)(F)c3ccc(F)cc3F)nc2)cc1]

To a stirred solution of 4-(6-(2-(2,4-difluorophenyl)difluoromethyl)oxiran-2-yl)pyridine-3-yloxy)benzonitrile (150 mg, 0.2 mmol) in DMF (2 mL) was added 1H-tetrazole (26 mg, 0.3 mmol) and K$_2$CO$_3$ (51 mg, 0.3 mmol) and the reaction mixture was stirred at 60° C. for 16 h. The reaction mixture was cooled to room temperature, quenched with ice water and extracted with EtOAc. The combined organic extracts were washed with brine, dried over Na$_2$SO$_4$, filtered, and concentrated under reduced pressure, and the resulting crude residue was purified by column chromatography (SiO$_2$) to give the title compound (35 mg, 20%) as pale-yellow semi-solid: See Table 2 for characterization data.

Example 2

Preparation of 2-(5-((5-chloropyridin-2-yl)oxy)pyridin-2-yl)-4-(2,4-difluorophenyl)-1-(1H-tetrazol-1-yl)butan-2-ol (2)

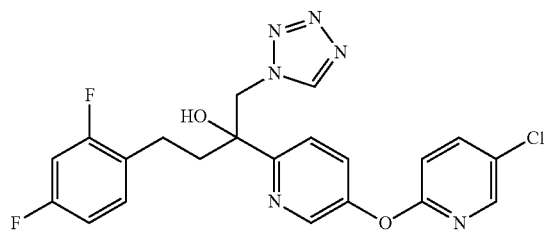 [SMILES: OC(CCc1ccc(F)cc1F)(Cn1cnnn1)c1ccc(Oc2ccc(Cl)cn2)cn1]

Step A: Preparation of 3-(2,4-difluorophenyl)-N-methoxy-N-methylpropanamide

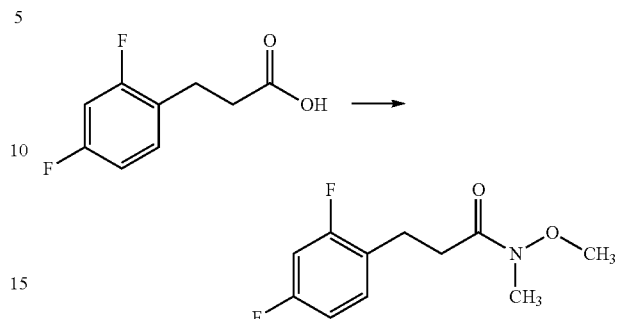

Followed an adapted procedure described by Trost, B. M. et. al. (Journal of the American Chemical Society (2010), 132(26), 8915-8917). To a magnetically stirred mixture of 3-(2,4-difluorophenyl)propanoic acid (1.0 g, 5.37 mmol), and two drops of DMF in anhydrous THF (10.8 mL) was added dropwise oxalyl chloride (0.564 mL, 6.45 mmol) under an inert atmosphere (N$_2$) at 0° C. The reaction mixture was stirred at 0° C. for 1 h and then the volatile components were removed by rotary evaporation under reduced pressure. The resulting oil was dissolved in CH$_2$Cl$_2$ and the volatile components were once again removed by rotary evaporation. In a separate 20 mL vial containing N,O-dimethylhydroxylamine hydrochloride (0.576 g, 5.91 mmol) suspended in CH$_2$Cl$_2$ (5.40 mL) was added pyridine (1.086 mL, 13.43 mmol), and the reaction mixture was cooled to 0° C. The freshly prepared acid chloride was dissolved in CH$_2$Cl$_2$ (5.40 mL) and the solution was added to the mixture dropwise over a 3 min period. A white precipitate formed immediately and the reaction was stirred while gradually warming to room temperature. After 2 h, the reaction mixture was diluted with EtOAc and washed successively with 2 N HCl, saturated aqueous NaHCO$_3$ (2×), and brine, and then dried by passing through a phase separator cartridge. The solvent and other volatile components were removed by rotary evaporation to give the title compound (1.195 g, 97%) as a light-yellow oil: $^1$H NMR (400 MHz, CDCl$_3$) δ 7.25-7.18 (m, 1H), 6.83-6.74 (m, 2H), 3.63 (s, 3H), 3.17 (s, 3H), 2.95 (t, J=7.7 Hz, 2H), 2.72 (t, J=7.6 Hz, 2H); $^{19}$F NMR (376 MHz, CDCl$_3$) δ −113.29, −114.40 (d, J=6.7 Hz); ESIMS m/z 230 [M+H]$^+$.

Step B: Preparation of 1-(5-((5-chloropyridin-2-yl)oxy)pyridin-2-yl)-3-(2,4-difluorophenyl)propan-1-one

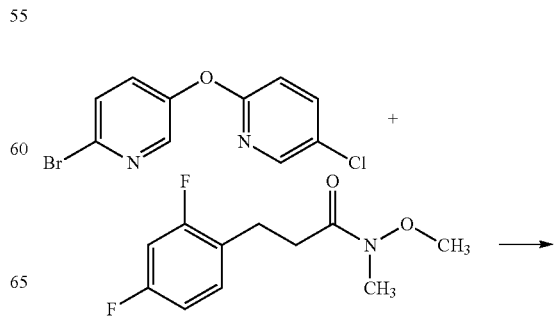

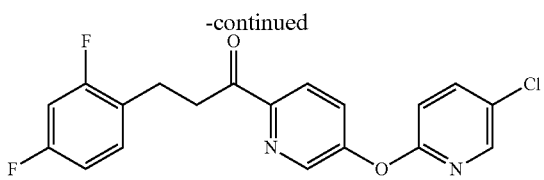

To a magnetically stirred mixture of 2-bromo-5-((5-chloropyridin-2-yl)oxy)pyridine (243 mg, 0.851 mmol) in anhydrous Et$_2$O (2908 microliters (μL)) at −78° C. was added a solution of n-BuLi in hexanes (2.0 M, 425 μL, 0.850 mmol) dropwise over a 1 min period. The reaction mixture was stirred at −78° C. for 40-60 min and then treated dropwise with a solution of 3-(2,4-difluorophenyl)-N-methoxy-N-methylpropanamide (150 mg, 0.654 mmol) in Et$_2$O (1454 μL). After 1 h, the reaction was quenched by the dropwise addition of 1 N HCl (5 mL) and then warmed to room temperature. The reaction was diluted with water (5 mL) and the phases were separated. The aqueous phase was extracted with additional Et$_2$O (2×), and the combined organics were dried by passing through a phase separator cartridge and concentrated under a gentle stream of N$_2$. The resulting residue was purified by column chromatography (SiO$_2$, 0→20% EtOAc in hexanes) to give the title compound (76 mg, 31.0%) as an off-white solid: $^1$H NMR (400 MHz, CDCl$_3$) δ 8.50 (dd, J=2.7, 0.5 Hz, 1H), 8.13-8.10 (m, 2H), 7.73 (dd, J=8.7, 2.7 Hz, 1H), 7.61 (dd, J=8.6, 2.7 Hz, 1H), 7.26-7.21 (m, 1H), 7.02 (dd, J=8.7, 0.6 Hz, 1H), 6.82-6.74 (m, 2H), 3.53 (t, J=7.5 Hz, 2H), 3.06 (t, J=7.5 Hz, 2H); $^{19}$F NMR (376 MHz, CDCl$_3$) δ −113.54 (d, J=6.8 Hz), −113.99 (d, J=6.8 Hz); ESIMS m/z 375 [M+H]$^+$.

Step C: Preparation of 5-chloro-2-((6-(2-(2,4-difluorophenethyl)oxiran-2-yl)pyridin-3-yl)oxy)pyridine

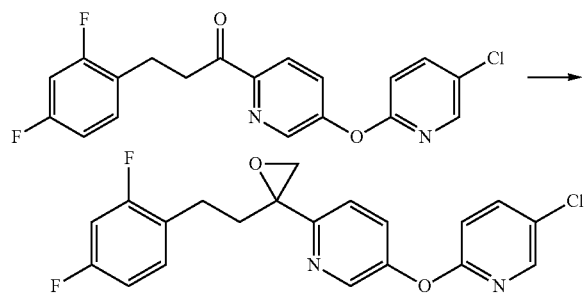

To a magnetically stirred mixture of trimethylsulfoxonium iodide (103 mg, 0.468 mmol) in THF (961 μL) was added NaH (18.73 mg, 0.468 mmol, 60% dispersion in mineral oil) under an N$_2$ atmosphere, and the mixture was stirred at room temperature for 1 h. The reaction mixture was cooled to 0° C. and treated dropwise with a solution of 1-(5-((5-chloropyridin-2-yl)oxy)pyridin-2-yl)-3-(2,4-difluorophenyl)propan-1-one (150 mg, 0.360 mmol) in THF (961 μL). After 2.5 h, the reaction was quenched by dropwise addition of saturated aqueous NH$_4$Cl, and the mixture was extracted with Et$_2$O (3×). The combined organic extracts were dried by passing through a phase separator cartridge and concentrated under a gentle stream of N$_2$. The resulting residue was purified by column chromatography (SiO$_2$, 0→30% EtOAc in hexanes) to give the title compound (56 mg, 40.0%) as a colorless oil: $^1$H NMR (400 MHz, CDCl$_3$) δ 8.44 (dd, J=2.7, 0.6 Hz, 1H), 8.10 (d, J=2.6 Hz, 1H), 7.72-7.67 (m, 1H), 7.48 (dd, J=8.6, 2.7 Hz, 1H), 7.39 (dd, J=8.6, 0.4 Hz, 1H), 7.18-7.10 (m, 1H), 6.97 (d, J=8.7 Hz, 1H), 6.80-6.70 (m, 2H), 3.06 (d, J=5.2 Hz, 1H), 2.85 (d, J=5.2 Hz, 1H), 2.83-2.75 (m, 2H), 2.71 (t, J=9.8 Hz, 1H), 2.14-2.07 (m, 1H); $^{19}$F NMR (376 MHz, CDCl$_3$) δ −113.69 (dd, J=6.6, 2.1 Hz), −114.18 (d, J=6.7 Hz); ESIMS m/z 389 [M+H]$^+$.

Step D: Preparation of 2-(5-((5-chloropyridin-2-yl)oxy)pyridin-2-yl)-4-(2,4-difluorophenyl)-1-(1H-tetrazol-1-yl)-butan-2-ol (2)

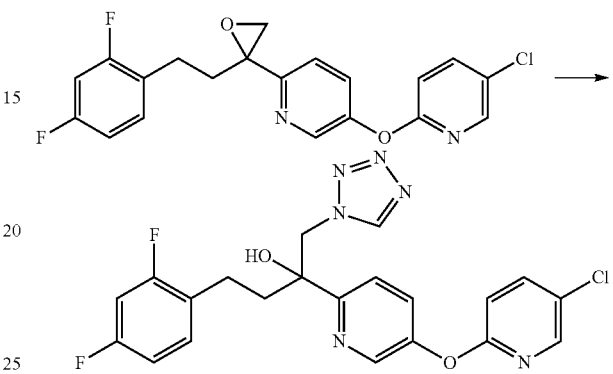

To a magnetically stirred mixture of 5-chloro-2-((6-(2-(2,4-difluorophenethyl)oxiran-2-yl)pyridin-3-yl)oxy)pyridine (56 mg, 0.144 mmol) in DMSO (480 μL) were added a mixture of diisopropylamine and 1H-tetrazole (1:1) (123 mg, 0.720 mmol), and the reaction mixture was warmed to 60° C. and stirred for 2-3 days (d) at 60° C. The reaction was quenched by the addition of water and extracted with CH$_2$Cl$_2$ (3×). The combined organic extracts were dried by passing through a phase separator cartridge and concentrated under a gentle stream of N$_2$. The resulting residue was purified by column chromatography (SiO$_2$, 20→60% EtOAc in hexanes) to yield two isomers of the product. Isolated the title compound (37.0 mg, 56%) as a white solid: See Table 2 for characterization data.

The 2H-isomer, 2-(5-((5-chloropyridin-2-yl)oxy)pyridin-2-yl)-4-(2,4-difluorophenyl)-1-(2H-tetra-zol-2-yl)butan-2-ol (19.0 mg, 28.7%) was isolated as a colorless oil: $^1$H NMR (400 MHz, CDCl$_3$) δ 8.43 (s, 1H), 8.37 (d, J=2.6 Hz, 1H), 8.11 (d, J=2.6 Hz, 1H), 7.71 (dd, J=8.7, 2.7 Hz, 1H), 7.55 (dd, J=8.6, 2.6 Hz, 1H), 7.42 (dd, J=8.6, 0.6 Hz, 1H), 7.04 (td, J=8.7, 6.6 Hz, 1H), 6.97 (d, J=8.7 Hz, 1H), 6.77-6.67 (m, 2H), 5.19 (s, 1H), 5.04 (s, 2H), 2.80-2.70 (m, 1H), 2.43-2.30 (m, 2H), 2.12 (ddd, J=13.4, 11.9, 4.9 Hz, 1H); $^{19}$F NMR (376 MHz, CDCl$_3$) δ −113.36 (d, J=6.7 Hz), −114.44 (d, J=6.7 Hz); ESIMS m/z 459 [M+H]$^+$.

Example 3

Preparation of 2-methyl-1-(pyrimidin-5-yl)-1-(5-(4-(trifluoromethyl)-phenoxy)pyridin-2-yl)propan-1-ol (3)

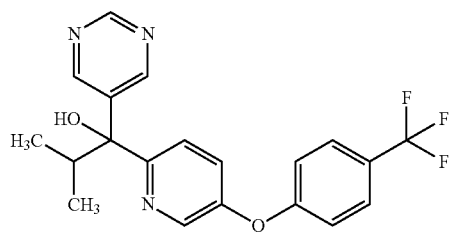 [SMILES: CC(C)C(O)(c1cncnc1)c1ccc(Oc2ccc(C(F)(F)F)cc2)cn1]

Step A: Preparation of (5-fluoropyridin-2-yl)(pyrimidin-5-yl)methanone

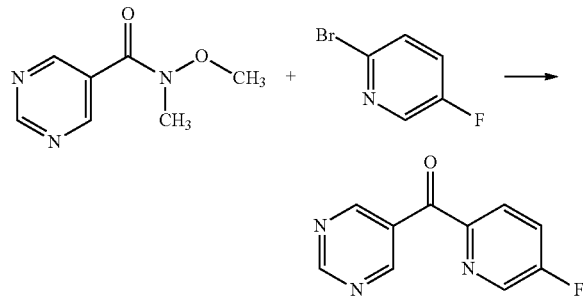

To a round bottomed flask equipped with a magnetic stir bar was added 2-bromo-5-fluoropyridine (2.063 g, 11.72 mmol) and the flask was purged with $N_2$. Anhydrous toluene (11.17 mL) was added and the reaction was cooled to 0° C. in an ice bath. The reaction was treated with a solution of i-PrMgCl in THF (2.0 M, 5.86 mL, 11.7 mmol) dropwise, and the mixture was stirred at 0° C. for 10 min, warmed to room temperature, and stirred at room temperature for 1.5 h. The resulting dark brown mixture was cooled to 0° C., treated with a solution of N-methoxy-N-methylpyrimidine-5-carboxamide (1.4 g, 8.37 mmol) in anhydrous toluene (5.58 mL), stirred at 0° C. for 3 h, and the resulting green-brown mixture was quenched with saturated aqueous $NH_4Cl$ solution (20 mL) while cold. The phases were separated and the aqueous phase was extracted with EtOAc (2×20 mL). The combined organics were dried over magnesium sulfate ($MgSO_4$), filtered, and concentrated. The residue was purified by column chromatography ($SiO_2$, 0→50% EtOAc in hexanes) to give the title compound (492 mg, 32%) as an off-white, fluffy solid: IR (Thin Film) 1678, 1577 $cm^{-1}$; $^1H$ NMR (400 MHz, $CDCl_3$) δ 9.50 (s, 2H), 9.38 (s, 1H), 8.59 (dd, J=2.8, 0.6 Hz, 1H), 8.32 (ddd, J=8.8, 4.6, 0.6 Hz, 1H), 7.66 (ddd, J=8.8, 7.9, 2.8 Hz, 1H); $^{19}F$ NMR (376 MHz, $CDCl_3$) δ -117.71; HRMS-ESI (m/z) $[M+H]^+$ calcd for $C_{10}H_7FN_3O$, 204.0568; found, 204.0567.

Step B: Preparation of pyrimidin-5-yl(5-(4-(trifluoromethyl)phenoxy)pyridin-2-yl)methanone

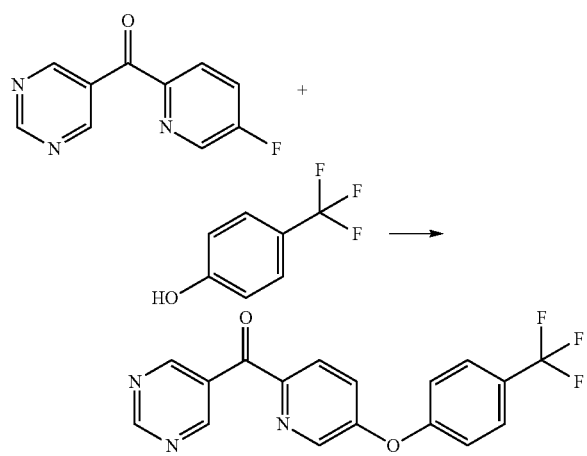

A magnetically stirred mixture of (5-fluoropyridin-2-yl)(pyrimidin-5-yl)methanone (200 mg, 0.984 mmol), 4-(trifluoromethyl)phenol (160 mg, 0.984 mmol), and $Cs_2CO_3$ (337 mg, 1.034 mmol) in DMF (1969 μL) was heated to 110° C. and stirred for 18 h. The reaction was cooled to room temperature, partitioned between water (3 mL) and EtOAc (3 mL), and the phases were separated. The aqueous phase was extracted with additional EtOAc (2×3 mL), and the combined organic extracts were washed with brine (2×3 mL), dried over $MgSO_4$, filtered, and concentrated. The residue was purified by column chromatography ($SiO_2$, 0→60% EtOAc in hexanes) to give the title compound (290 mg, 84%) as a slightly yellow solid: IR (Thin Film) 3383, 1667, 1573, 1319, 1234 $cm^{-1}$; $^1H$ NMR (400 MHz, $CDCl_3$) δ 9.51 (s, 2H), 9.37 (s, 1H), 8.50 (dd, J=2.8, 0.6 Hz, 1H), 8.28 (dd, J=8.7, 0.6 Hz, 1H), 7.78-7.68 (m, 2H), 7.49 (dd, J=8.7, 2.8 Hz, 1H), 7.25-7.19 (m, 2H); $^{19}F$ NMR (376 MHz, $CDCl_3$) δ -62.13; HRMS-ESI (m/z) $[M+H]^+$ calcd for $C_{17}H_{11}F_3N_3O_2$, 346.0798; found, 346.0780.

Step C: Preparation of 2-methyl-1-(pyrimidin-5-yl)-1-(5-(4-(trifluoromethyl)-phenoxy)pyridin-2-yl)propan-1-ol (3)

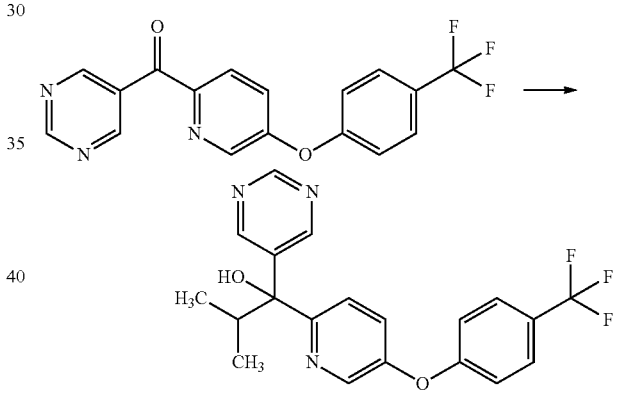

To a vial equipped with a magnetic stir bar were added $ZnCl_2$ (10.66 mg, 0.078 mmol) and LiCl (12.16 mg, 0.287 mmol) and the vial was capped and purged with $N_2$. A solution of i-PrMgCl in THF (2.0 M, 222 μL, 0.443 mmol) was added dropwise under $N_2$ and the reaction was stirred at room temperature for 1 h. The resulting homogeneous brown solution was cooled to 0° C. in an ice bath and a solution of pyrimidin-5-yl(5-(4-(trifluoromethyl)phenoxy)pyridin-2-yl)methanone (90 mg, 0.261 mmol) in anhydrous THF (2738 μL) was added slowly and the reaction was stirred at 0° C. for 4 h. The resulting red-brown reaction mixture was quenched while cold with saturated aqueous $NH_4Cl$ solution (3 mL) and the mixture was extracted with EtOAc (3×5 mL). The combined extracts were dried over $MgSO_4$, filtered, concentrated, and the residue was purified by column chromatography ($SiO_2$, 0→70% EtOAc in hexanes) to give the title compound (64 mg, 62%) as a slightly yellow, viscous oil: See Table 2 for characterization data.

Example 4

Preparation of 4-((6-(1-cyclopropyl-1-hydroxy-2-(1H-tetrazol-1-yl)ethyl)pyridin-3-yl)oxy)benzonitrile (19)

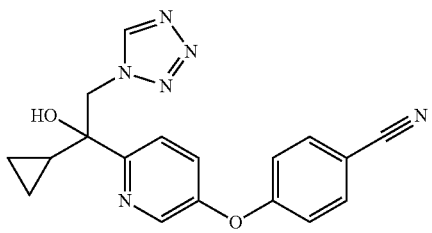 [SMILES: N#Cc1ccc(Oc2ccc(C(O)(Cn3cnnn3)C3CC3)nc2)cc1]

Step A: Preparation of cyclopropyl(5-fluoropyridin-2-yl)methanone

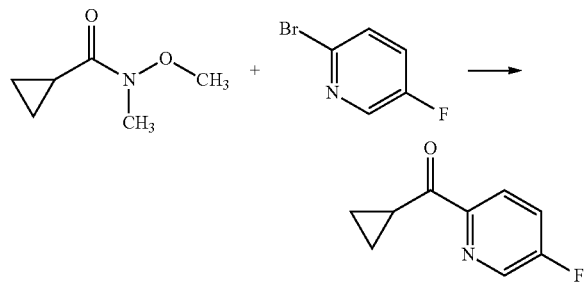

The title compound was prepared from 2-bromo-5-fluoropyridine and N-methoxy-N-methyl-cyclopropanecarboxamide according to the conditions described in Example 3A and was isolated as a yellow oil in 73% yield: IR (Thin Film) 1681, 1580, 1400, 1370 cm$^{-1}$; $^1$H NMR (400 MHz, CDCl$_3$) δ 8.55 (d, J=2.8 Hz, 1H), 8.10 (ddd, J=8.7, 4.7, 0.6 Hz, 1H), 7.52 (ddd, J=8.7, 8.0, 2.8 Hz, 1H), 3.55-3.39 (m, 1H), 1.28-1.22 (m, 2H), 1.15-1.08 (m, 2H); $^{19}$F NMR (376 MHz, CDCl$_3$) δ −120.55 (d, J=1.5 Hz); EIMS (m/z) 165.

Step B: Preparation of 4-((6-(cyclopropanecarbonyl)pyridin-3-yl)oxy)benzonitrile

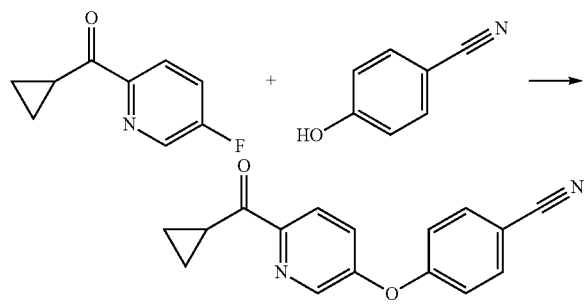

The title compound was prepared from cyclopropyl(5-fluoropyridin-2-yl)methanone and 4-hydroxybenzonitrile according to the conditions described in Example 3B. It was isolated as a light-yellow solid in 83% yield: IR (Thin Film) 2228, 1676, 1576, 1499, 1246 cm$^{-1}$; $^1$H NMR (400 MHz, CDCl$_3$) δ 8.50 (dd, J=2.7, 0.7 Hz, 1H), 8.10 (dd, J=8.6, 0.7 Hz, 1H), 7.75-7.67 (m, 2H), 7.45 (dd, J=8.6, 2.8 Hz, 1H), 7.16-7.10 (m, 2H), 3.47 (tt, J=7.9, 4.7 Hz, 1H), 1.30-1.21 (m, 2H), 1.15-1.09 (m, 2H); HRMS-ESI (m/z) [M+H]$^+$ calcd for C$_{16}$H$_{13}$N$_2$O$_2$, 265.0972; found, 265.0957.

Step C: Preparation of 4-((6-(cyclopropyl(hydroxy)(pyrimidin-5-yl)methyl)pyridin-3-yl)oxy)benzonitrile

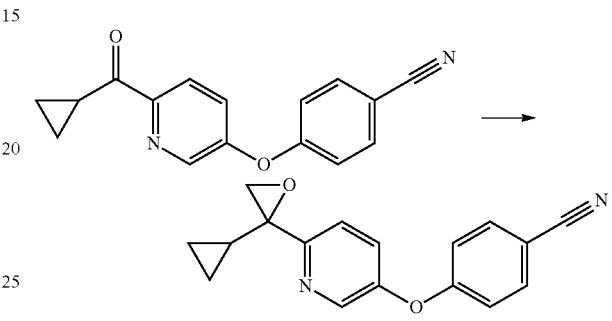

To a vial equipped with a magnetic stir bar were added trimethylsulfoxonium iodide (100 mg, 0.454 mmol), DMSO (841 μL), and anhydrous THF (841 μL). To the resulting mixture was added NaH (60% dispersion in mineral oil, 18.2 mg, 0.454 mmol) and the reaction was stirred at room temperature for 1 h. After gas evolution had ceased, the cloudy-white mixture was cooled to 0° C. and treated dropwise with a solution of 4-((6-(cyclopropanecarbonyl)pyridin-3-yl)oxy)-benzonitrile (100 mg, 0.378 mmol) in anhydrous THF (841 μL). The resulting cloudy, light-yellow mixture was slowly warmed to room temperature and the reaction was quenched with water (3 mL) and diluted with EtOAc (3 mL). The phases were separated and the aqueous layer was further extracted with EtOAc (3×3 mL). The combined organic extracts were dried over MgSO$_4$, filtered, concentrated, and the residue purified by column chromatography (SiO$_2$, 0→15% EtOAc in hexanes) to give the title compound (72 mg, 65%) as a light-yellow, viscous oil: IR (Thin Film) 2228, 1502, 1479, 1247 cm$^{-1}$; $^1$H NMR (400 MHz, CDCl$_3$) δ 8.43 (dd, J=2.8, 0.7 Hz, 1H), 7.68-7.61 (m, 2H), 7.54 (dd, J=8.6, 0.7 Hz, 1H), 7.38 (dd, J=8.6, 2.8 Hz, 1H), 7.08-7.01 (m, 2H), 3.00 (dd, J=5.8, 0.6 Hz, 1H), 2.95 (d, J=5.7 Hz, 1H), 1.85 (tt, J=8.4, 5.3 Hz, 1H), 0.67-0.58 (m, 1H), 0.58-0.49 (m, 1H), 0.49-0.38 (m, 2H); HRMS-ESI (m/z) [M+H]$^+$ calcd for C$_{17}$H$_{15}$N$_2$O$_2$, 279.1128; found, 279.1105.

Step D: 4-((6-(1-cyclopropyl-1-hydroxy-2-(1H-tetrazol-1-yl)ethyl)pyridin-3-yl)oxy)-benzonitrile (19)

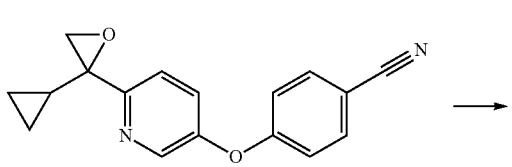

41
-continued

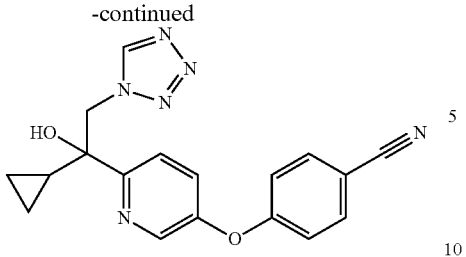

To a vial equipped with a magnetic stir bar were added 4-((6-(2-cyclopropyloxiran-2-yl)pyridin-3-yl)oxy)benzonitrile (69 mg, 0.248 mmol), diisopropylammonium tetrazol-1-ide (212 mg, 1.24 mmol), and DMF (1653 μL). The reaction mixture was warmed to 70° C., stirred at 70° C. for 13 h, cooled to room temperature, and partitioned between water (5 mL) and EtOAc (5 mL). The phases were separated and the aqueous phase was further extracted with EtOAc (3×3 mL). The combined organics were dried over MgSO4, filtered, concentrated, and purified by column chromatography (SiO$_2$, 0→75% EtOAc in hexanes) to give the title compound (11 mg, 12%) as an off-white, viscous semi-solid: See Table 2 for characterization data.

Example 5

Preparation of 1-(5-(4-chlorophenoxyl)pyridine-2-yl)-1-(pyrimidin-5-yl)pent-4-en-1-ol (21)

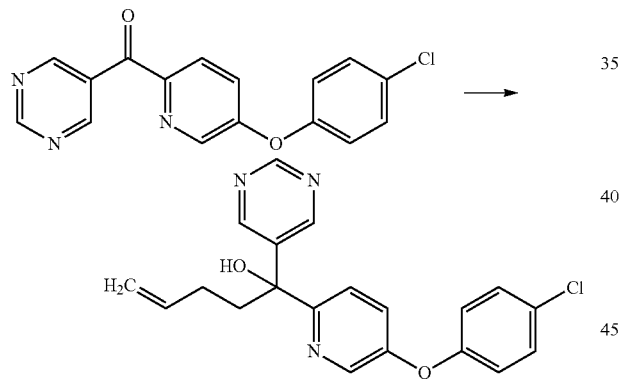

To an oven-dried vial equipped with a magnetic stir bar was added Mg (6.36 mg, 0.262 mmol) and the vial was evacuated and backfilled with N$_2$. Anhydrous THF (818 μL) was added followed by a crystal of I$_2$ and (chloromethyl)cyclopropane (22.68 μL, 0.245 mmol). The mixture was heated to reflux and stirred for 1.5 h under N$_2$. To a separate vial were added (5-(4-chlorophenoxyl)pyridin-2-yl)(pyrimidin-5-yl)methanone (51 mg, 0.164 mmol) and anhydrous THF (1 mL) and to the mixture was cooled to 0° C. To this solution was added the freshly prepared Grignard solution dropwise over an 8 min period, and the reaction mixture was stirred at 0° C. for 3 h, quenched while cold with saturated aqueous NH$_4$Cl solution (2 mL), and warmed to room temperature. The mixture was extracted with EtOAc (3×2 mL) and the combined extracts were dried over MgSO$_4$, filtered, concentrated, and the residue purified by column chromatography (SiO$_2$, 0→70% EtOAc in hexanes) to give the title compound (22 mg, 35%) as a light-yellow, viscous semi-solid: See Table 2 for characterization data.

42

Example 6

Preparation of 2-[5-(4-chlorophenyl)-2-pyridyl]-1-pyrimidin-5-yl-propan-2-ol (25)

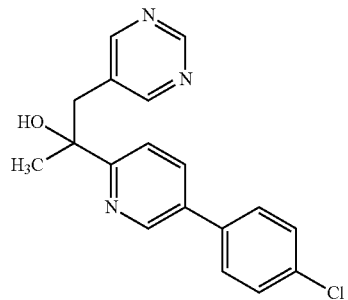 [SMILES: CC(O)(Cc1cncnc1)c1ccc(-c2ccc(Cl)cc2)cn1]

Step A: Preparation of diphenyl ((5-bromopyridin-2-yl)(phenylamino)methyl)-phosphonate

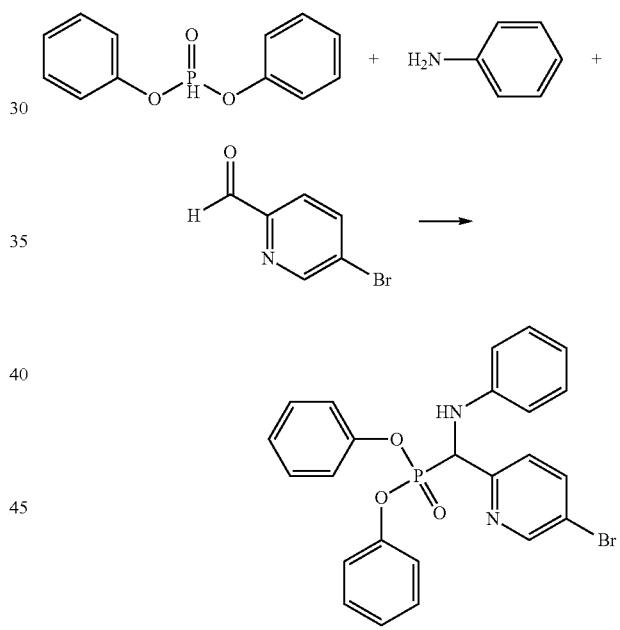

Followed an adapted procedure described by Journet, M., et. al. (Tetrandron Letters (1998), 39(13), 1717-1720). To a magnetically stirred mixture of 5-bromopicolinaldehyde (1 g, 5.38 mmol) in isopropyl alcohol (IPA, 13.44 mL) was added aniline (0.589 mL, 6.45 mmol) followed by diphenyl phosphite (1.665 mL, 8.60 mmol) and the reaction mixture was stirred at 25° C. Upon addition of the aniline to the partially dissolved aldehyde in IPA, the reaction formed a thick white precipitate which dissolved upon addition of the phosphite to give a homogeneous yellow solution which was stirred for 18 h. The stirrer was stopped and the reaction mixture was cooled in an ice bath. The resulting fine, white precipitate was isolated by vacuum filtration and washed several times with ice cold IPA. The solid was dried in a vacuum oven at room temperature for 4 h to give the title compound (2.501 g, 94%) as a white solid: mp 124-127° C.:

¹H NMR (400 MHz, CDCl₃) δ 8.65 (d, J=2.3 Hz, 1H), 7.76 (ddd, J=8.4, 2.3, 0.7 Hz, 1H), 7.48-7.45 (m, 1H), 7.30-7.22 (m, 4H), 7.19-7.11 (m, 4H), 7.09 (qd, J=2.5, 1.3 Hz, 2H), 7.06-7.01 (m, 2H), 6.80-6.74 (m, 1H), 6.71 (dd, J=8.6, 0.9 Hz, 2H), 5.35-5.23 (m, 2H); ¹³C NMR (101 MHz, CDCl₃) δ 153.41, 150.59, 150.56, 150.22, 150.14, 145.93, 145.80, 139.42, 139.40, 129.71, 129.33, 125.44, 125.32, 124.42, 124.38, 120.63, 120.58, 120.32, 120.28, 119.25, 114.31, 58.37, 56.83.

Step B: Preparation of 1-(5-bromopyridin-2-yl)-2-(pyrimidin-5-yl)ethanone

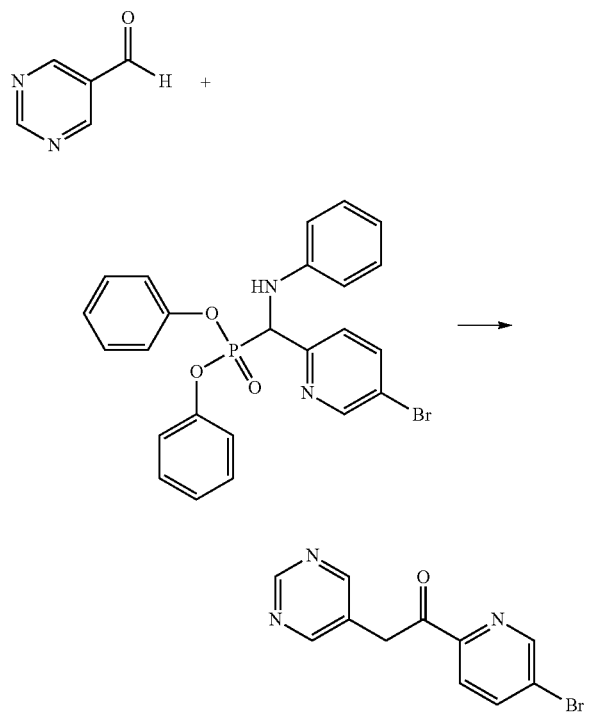 [SMILES: O=Cc1cncnc1 ; O=P(Oc1ccccc1)(Oc1ccccc1)C(Nc1ccccc1)c1ccc(Br)cn1 ; O=C(Cc1cncnc1)c1ccc(Br)cn1]

To a magnetically stirred mixture of diphenyl ((5-bromopyridin-2-yl)(phenylamino)-methyl)phosphonate (400 mg, 0.808 mmol), and pyrimidine-5-carbaldehyde (96 mg, 0.888 mmol) in a mixture of THF (1615 μL) and IPA (404 μL) was added Cs₂CO₃ (342 mg, 1.050 mmol) under an inert atmosphere (N₂). The reaction mixture was stirred at 25° C. for 16.5 h and then treated dropwise with 3 N HCl (0.81 mL, 2.42 mmol), which produced a gentle evolution of gas. After 2 h, the pH of the reaction mixture was adjusted to 9 by the addition of 5% w/v aqueous NaOH solution and extracted with EtOAc (3×). The combined organic extracts were dried by passing through a phase separator cartridge and the volatile components were evaporated under a gentle stream of N₂. The resulting residue was triturated with ice cold EtOAc to give the title compound (149 mg, 66.3%) as a light brown solid: ¹H NMR (400 MHz, CDCl₃) δ 9.14 (s, 1H), 8.79 (d, J=1.7 Hz, 1H), 8.72 (s, 2H), 8.02 (dd, J=8.4, 2.2 Hz, 1H), 7.96 (d, J=8.2 Hz, 1H), 4.52 (s, 2H); ¹³C NMR (101 MHz, CDCl₃) δ 196.19, 157.96, 157.40, 150.47, 150.37, 139.98, 128.33, 126.16, 123.66, 38.86; ESIMS m/z 278 [M+H]⁺, m/z 276 ([M−H]⁻).

Step C: Preparation of 1-(5-(4-chlorophenyl)pyridin-2-yl)-2-(pyrimidin-5-yl)ethanone

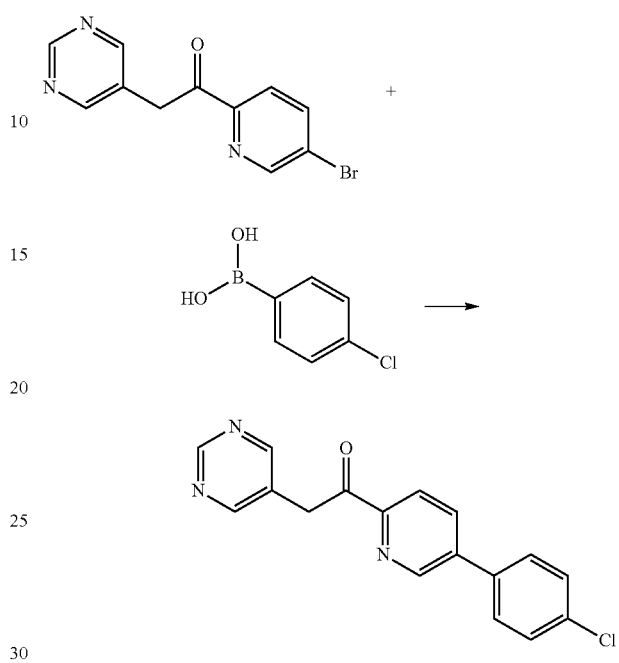

To a magnetically stirred mixture of 1-(5-bromopyridin-2-yl)-2-(pyrimidin-5-yl)ethanone (200 mg, 0.719 mmol), (4-chlorophenyl)boronic acid (141 mg, 0.899 mmol) and Na₂CO₃ (229 mg, 2.16 mmol) in a mixture of dioxane (2697 μL) and water (899 μL) was added [1,1'-bis(diphenylphosphino)ferrocene]palladium(II)dichloride (PdCl₂(dppf), 52.6 mg, 0.072 mmol) under an inert atmosphere (N₂). The reaction mixture was heated to and stirred at 85° C. for 17 h, cooled to room temperature, diluted with CH₃CN, filtered through a pad of Celite®, and the filtrate was evaporated under a gentle stream of N₂. The resulting residue was purified by column chromatography (SiO₂, 30→75% EtOAc in hexanes) to yield the title compound (116 mg, 52.1%) as an off-white solid: mp 150-155° C.; ¹H NMR (400 MHz, CDCl₃) δ 9.14 (s, 1H), 8.92 (dd, J=2.3, 0.8 Hz, 1H), 8.76 (s, 2H), 8.16 (dd, J=8.1, 0.8 Hz, 1H), 8.02 (dd, J=8.2, 2.3 Hz, 1H), 7.60-7.56 (m, 2H), 7.53-7.49 (m, 2H), 4.59 (s, 2H); ESIMS m/z 310 [M+H]⁺, m/z 308 ([M−H]⁻).

Step D: Preparation of 2-(5-(4-chlorophenyl)pyridin-2-yl)-1-(pyrimidin-5-yl)propan-2-ol (25)

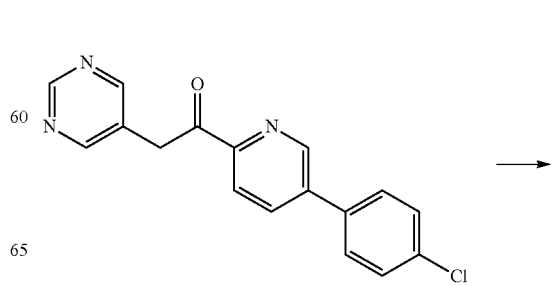

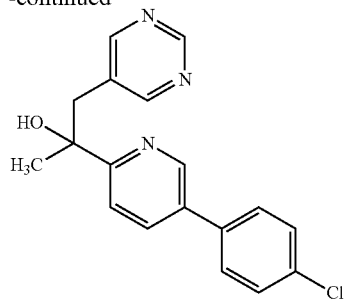

To a magnetically stirred mixture of 1-(5-(4-chlorophenyl)pyridin-2-yl)-2-(pyrimidin-5-yl)ethanone (50 mg, 0.161 mmol) in THF (1614 µL) cooled to −78° C. was added a solution of MeMgBr in Et$_2$O (3.0 M, 108 µL, 0.323 mmol) dropwise under an N$_2$ atmosphere. The reaction mixture was stirred at −78° C. for 105 min and quenched by the dropwise addition of saturated aqueous NH$_4$Cl (2 mL). The reaction mixture was removed from the cooling bath, warmed to room temperature, diluted with water and extracted with EtOAc (3×). The combined organic extracts were dried by passing through a phase separator cartridge and the volatile components were evaporated under a gentle stream of N$_2$. The resulting residue was adsorbed onto a pad of Celite® and purified by column chromatography (SiO$_2$, 50→80% EtOAc in hexanes) to yield recovered starting material (42%) and the title compound (19 mg, 36.1%) as a light-yellow solid: See Table 2 for characterization data.

Steps C and D may be conducted in either order to obtain desired product.

Example 7

Preparation of 3,3-dimethyl-1-(1H-tetrazol-1-yl)-2-[5-[4-(trifluoro-methoxy)phenyl]pyridine-2-yl]butan-2-ol (26)

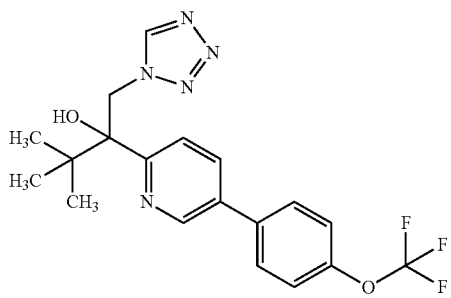 [SMILES: CC(C)(C)C(O)(Cn1cnnn1)c1ccc(-c2ccc(OC(F)(F)F)cc2)cn1]

Step A: Preparation of 2-bromo-5-(4-(trifluoromethoxy)phenyl)pyridine

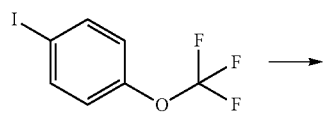

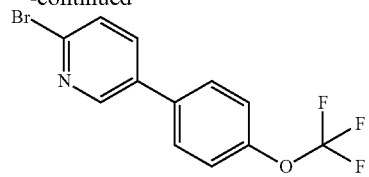

To a microwave vial equipped with a magnetic stir bar were added (6-bromopyridin-3-yl)boronic acid (1.37 g, 6.77 mmol), 1-iodo-4-(trifluoromethoxy)benzene (1.5 g, 5.21 mmol) and DMF (11.9 mL), followed by K$_2$CO$_3$ (2.52 g, 18.2 mmol) and water (2.98 mL). The reaction mixture was stirred under N$_2$ for 5 min and treated with Pd(PPh$_3$)$_4$ (16.05 mg, 0.014 mmol). The reaction vessel was capped, placed in a Biotage Initiator microwave reactor for 1 h at 120° C., with external IR-sensor temperature monitoring from the side of the vessel. The cooled reaction mixture was filtered through a pad of Celite® rinsing with EtOAc (100 mL), and the filtrate was washed successively with saturated aqueous NaHCO$_3$ (50 mL), water (3×50 mL), and brine (50 mL). The organic phase was dried over MgSO$_4$, filtered, and concentrated. The residue was purified by column chromatography (SiO$_2$, 0→10% EtOAc in hexanes) to give the title compound (1.07 g, 63%) as an off-white solid: IR (Thin Film) 3036, 1453, 1210, 1167 cm$^{-1}$; $^1$H NMR (400 MHz, CDCl$_3$) δ 8.57 (dd, J=2.6, 0.8 Hz, 1H), 7.71 (dd, J=8.2, 2.6 Hz, 1H), 7.63-7.54 (m, 3H), 7.38-7.29 (m, 2H); $^{19}$F NMR (376 MHz, CDCl$_3$) δ −57.83; HRMS-ESI (m/z) [M+H]$^+$ calcd for C$_{12}$H$_8$BrF$_3$NO, 317.9736; found, 317.9735.

Step B: Preparation of 2,2-dimethyl-1-(5-(4-(trifluoromethoxy)phenyl)pyridin-2-yl)propan-1-ol

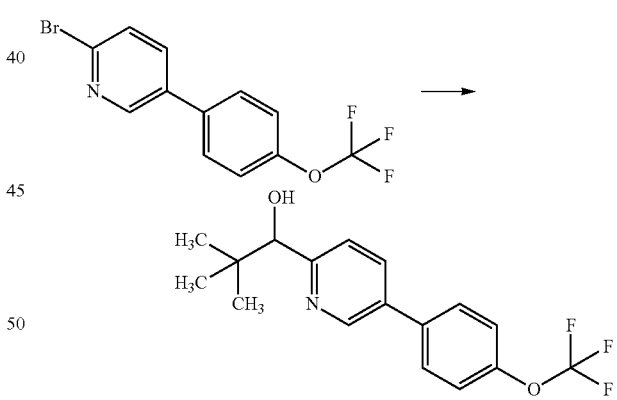

To a solution of 2-bromo-5-(4-(trifluoromethoxy)phenyl)pyridine (2 g, 6.32 mmol) and pivaldehyde (2 mL, 12.5 mmol) in toluene (20 mL) was added n-BuLi (10 mL, 15.8 mmol) at −78° C. and the mixture was stirred at the same temperature for 1 h. The reaction mixture was quenched with saturated aqueous NH$_4$Cl solution, warmed to room temperature, and extracted with EtOAc. The organic extract was washed with brine, dried over Na$_2$SO$_4$, filtered, and concentrated under reduced pressure. The residue was purified by column chromatography (SiO$_2$, 5→10% EtOAc in petroleum ether) to afford the title compound (3 g, 60% purity by LCMS) as yellow oil. The compound was used for the next step without further purification.

Step C: Preparation of 2,2-dimethyl-1-(5-(4-(trifluoromethoxy)phenyl)pyridin-2-yl)propan-1-one

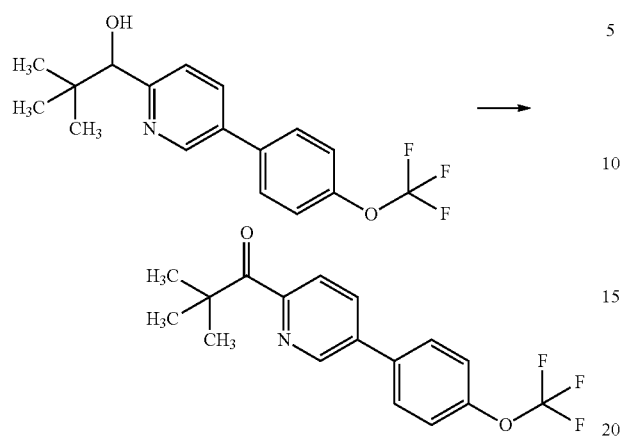

To a solution of 2,2-dimethyl-1-(5-(4-(trifluoromethoxy)phenyl)pyridin-2-yl)propan-1-ol (3 g, 5.6 mmol, 60% purity) in anhydrous $CH_2Cl_2$ (30 mL) was added Dess-Martin periodinane (7.8 g, 18.4 mmol) in portions at 0° C., and the reaction mixture was stirred at room temperature for 2 h. The reaction mixture was vacuum filtered, washing with $CH_2Cl_2$, and the filtrate was concentrated under reduced pressure. The residue was purified by column chromatography ($SiO_2$, 5→10% EtOAc in petroleum ether) to afford the title compound (500 mg, 25% over two steps) as an off-white solid.

Step D: Preparation of 2-(2-tert-butyloxiran-2-yl)-5-(4-(trifluoromethoxy)phenyl)pyridine

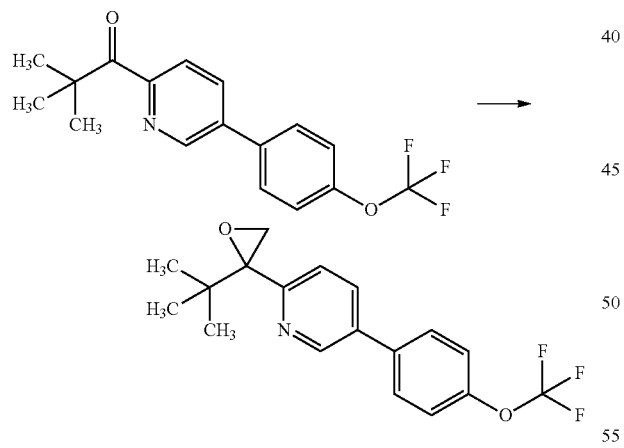

To a suspension of trimethylsulfoxonium iodide (613 mg, 2.78 mmol) in THF (5 mL) was added NaH (110 mg, 2.78 mmol, 60% dispersion in mineral oil) at 0° C. followed by DMSO (1 mL), and the reaction mixture was stirred for 1 h at 0° C. and then treated with a solution of 2,2-dimethyl-1-(5-(4-(trifluoromethoxy)phenyl)pyridin-2-yl)propan-1-one (600 mg, 1.85 mmol) in THF. The reaction mixture was warmed to room temperature, stirred for 15 h, poured into ice water, and extracted with EtOAc. The organic extract was washed with brine, dried over $Na_2SO_4$, filtered, and concentrated under reduced pressure. The residue was purified by column chromatography ($SiO_2$, 15→20% EtOAc in petroleum ether) to afford the title compound (150 mg, 24%) as yellow oil.

Step E: Preparation of 3,3-dimethyl-1-(1H-tetrazol-1-yl)-2-[5-[4-(trifluoromethoxy)phenyl]pyridine-2-yl]butan-2-ol (26)

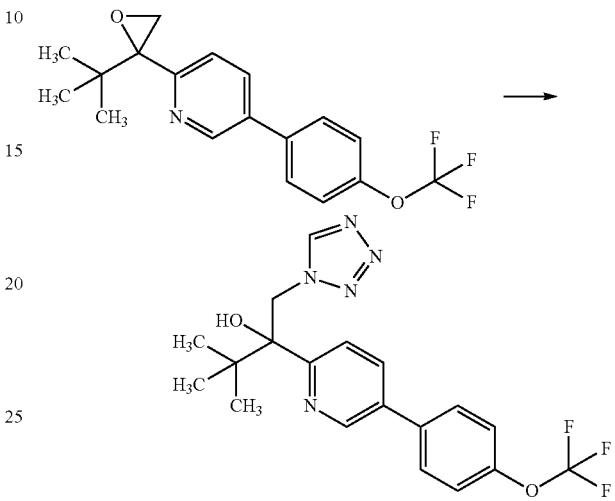

To a solution of 2-(2-tert-butyloxiran-2-yl)-5-(4-(trifluoromethoxy)phenyl)pyridine (450 mg, 1.33 mmol) in DMSO (5 mL) was added 1H-tetrazole (187 mg, 2.67 mmol) and $K_2CO_3$ (276 mg, 2.0 mmol) under an inert atmosphere. The reaction mixture was heated to and stirred at 70° C. for 48 h, cooled to room temperature, poured into water, and extracted with EtOAc. The organic extract was washed with brine, dried over $Na_2SO_4$, filtered, and concentrated under reduced pressure. The residue was purified by column chromatography ($SiO_2$, 5→10% EtOAc in petroleum ether) to afford the title compound (80 mg, 15%) as off-white solid: See Table 2 for characterization data.

The 2H regioisomer was also isolated (18 mg, 3%) as an off-white solid: $^1$H NMR (400 MHz, $CDCl_3$): δ 8.61 (d, J=2.4 Hz, 1H), 8.26 (s, 1H), 7.84 (dd, J=8.3, 2.4 Hz, 1H), 7.70 (d, J=8.3 Hz, 1H), 7.57 (d, J=8.4 Hz, 2H), 7.31 (d, J=8.4 Hz, 2H), 5.70 (d, J=13.4 Hz, 1H), 5.31 (brs, 1H), 5.09 (d, J=13.6 Hz, 1H), 1.09 (s, 9H); ESIMS m/z 408 [M+H]$^+$.

Example 8

Preparation of 2,2-dimethyl-1-(pyrimidin-5-yl)-1-(5-(4-(trifluoro-methoxy)phenyl)pyridin-2-yl)propan-1-ol (27)

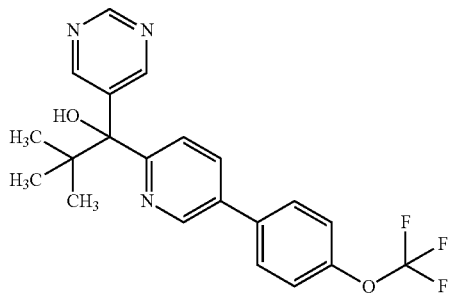 [SMILES: CC(C)(C)C(O)(c1cncnc1)c1ccc(-c2ccc(OC(F)(F)F)cc2)cn1]

Step A: Preparation of pyrimidin-5-yl(5-(4-(trifluoromethoxy)phenyl)pyridin-2-yl)methanone

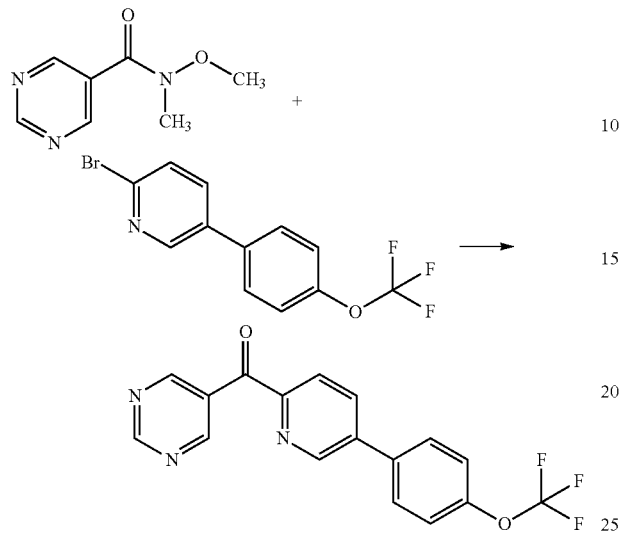

The title compound was prepared from 2-bromo-5-(4-(trifluoromethoxy)phenyl)-pyridine and N-methoxy-N-methylpyrimidine-5-carboxamide using the conditions described in Example 3A. Additional purification was required by reverse phase column chromatography (C$_{18}$, 10→100% CH$_3$CN in water) to give the title compound as an off-white solid in 31% yield: IR (Thin Film) 1663, 1316, 1163 cm$^{-1}$; $^1$H NMR (400 MHz, CDCl$_3$) δ 9.56 (s, 2H), 9.40 (s, 1H), 8.96 (dd, J=2.3, 0.8 Hz, 1H), 8.33 (dd, J=8.2, 0.8 Hz, 1H), 8.13 (dd, J=8.2, 2.3 Hz, 1H), 7.73-7.67 (m, 2H), 7.40 (m, 2H); $^{19}$F NMR (376 MHz, CDCl$_3$) δ −57.77; HRMS-ESI (m/z) [M+H]$^+$ calcd for C$_{17}$H$_{11}$F$_3$N$_3$O$_2$, 346.0798; found, 346.0803.

Step B: Preparation of 2,2-dimethyl-1-(pyridin-3-yl)-1-(5-(4-(trifluoromethoxy)-phenyl)pyridin-2-yl)propan-1-ol (27)

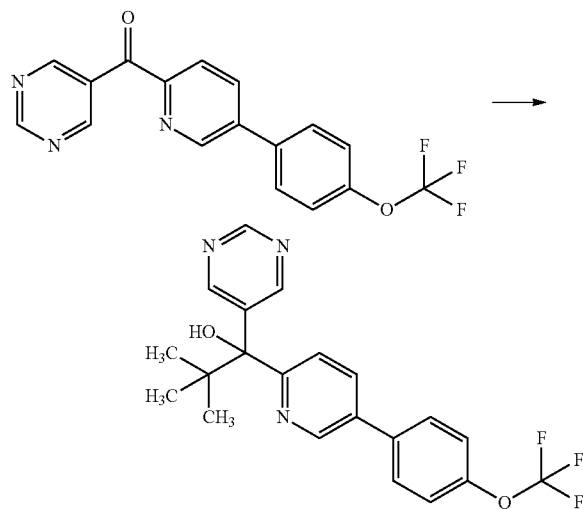

To a vial equipped with a magnetic stir bar were added ZnCl$_2$ (14.3 mg, 0.105 mmol) and LiCl (16.3 mg, 0.384 mmol) and the head space was purged with N$_2$. A 1 M solution of $^t$BuMgCl (593 μL, 0.593 mmol) in THF was added at room temperature and the reaction mixture was stirred for 1 h, cooled to 0° C., and treated with a solution of pyrimidin-5-yl(5-(4-(trifluoromethoxy)phenyl)pyridin-2-yl)methanone (114 mg, 0.33 mmol) in anhydrous THF (2327 μL). After 1 h at 0° C., additional $^t$BuMgCl solution (350 μL, 0.350 mmol) was added and stirring was continued at 0° C. for an additional 1 h and quenched while cold with saturated aqueous NH$_4$Cl solution (2 mL). The mixture was extracted with EtOAc (3×2 mL), and the combined extracts were dried over MgSO$_4$, filtered, and concentrated. The residue was purified by column chromatography (SiO$_2$, 0→45% EtOAc in hexanes to give the title compound (47.9 mg, 36%) as a bright-yellow semi-solid: See Table 2 for characterization data.

Example 9

Preparation of 1-(4-chloro-2-fluorophenyl)-3-(1H-tetrazol-1-yl)-2-(5-(4-(trifluoromethoxy)phenyl)pyridin-2-yl)propan-2-ol (28)

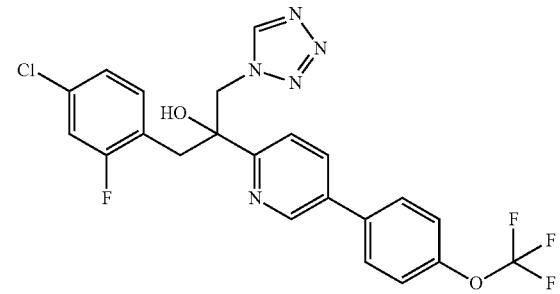 [SMILES: OC(Cc1ccc(Cl)cc1F)(Cn1cnnn1)c1ccc(-c2ccc(OC(F)(F)F)cc2)cn1]

Step A: Preparation of 5-(4-(trifluoromethoxy)phenyl)picolinaldehyde

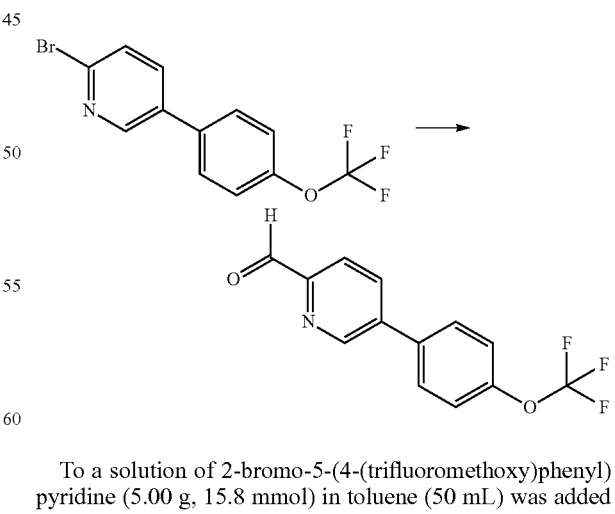

To a solution of 2-bromo-5-(4-(trifluoromethoxy)phenyl)pyridine (5.00 g, 15.8 mmol) in toluene (50 mL) was added n-BuLi (2.5 M in hexanes, 16 mL, 39.5 mmol) dropwise at −78° C. and the reaction mixture was stirred for 15 min, treated dropwise with anhydrous DMF (6 mL, 79.1 mmol), and stirred for 1 h at −78° C. The reaction mixture was quenched with saturated aqueous NH₄Cl solution, warmed to room temperature, and extracted with EtOAc. The extract was dried over Na₂SO₄, filtered, concentrated, and the residue was purified by column chromatography (SiO₂, 5→10% EtOAc in petroleum ether) to afford the title compound (1.2 g, 29%) as yellow solid.

Step B: Preparation of 2-(4-chloro-2-fluorophenyl)-1-(5-(4-(trifluoromethoxy)phenyl)pyridin-2-yl)ethanol

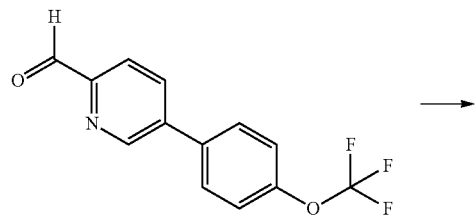

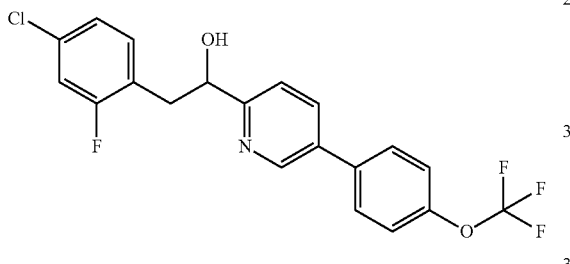

To a suspension of Mg powder (291 mg, 11.2 mmol) in anhydrous Et₂O (20 mL) was slowly added 1-(bromomethyl)-4-chloro-2-fluorobenzene (2.5 g, 11.2 mmol) and the reaction mixture was stirred vigorously for 15 min (vigorous reflux was observed). This Grignard solution was added dropwise to a solution of 5-(4-(trifluoromethoxy)phenyl) picolinaldehyde (1.2 g, 4.5 mmol) in Et₂O (10 mL) at 0° C. and the reaction mixture was warmed to room temperature and stirred for 1 h. The reaction mixture was quenched with ice water (100 mL) and extracted with EtOAc. The extract was dried over Na₂SO₄, filtered, concentrated, and the residue was purified by column chromatography (SiO₂, 5→10% EtOAc in petroleum ether) to afford the title compound as an off-white solid (1.1 g, 59%).

Step C: Preparation of 2-(4-chloro-2-fluorophenyl)-1-(5-(4-(trifluoromethoxy)phenyl)-pyridin-2-yl)ethanone

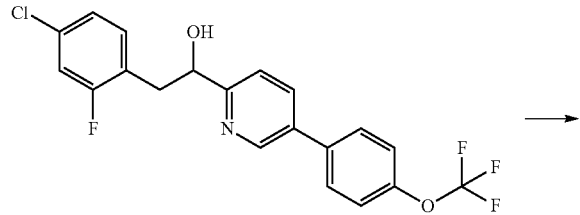

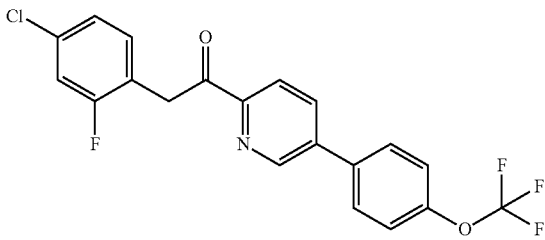

To a solution of 2-(4-chloro-2-fluorophenyl)-1-(5-(4-(trifluoromethoxy)phenyl)-pyridin-2-yl)ethanol (1.1 g, 2.67 mmol) in anhydrous CH₂Cl₂ (20 mL) was added Dess-Martin periodinane (2.3 g, 5.35 mmol) in portions at 0° C., and the reaction mixture was warmed to room temperature and stirred for 16 h. The reaction mixture was vacuum filtered, the cake washed with CH₂Cl₂, and the filtrate concentrated under reduced pressure. The residue was purified by column chromatography (SiO₂, 10→15% EtOAc in petroleum ether) to afford the title compound (900 mg, 83%) as an off-white solid.

Step D: Preparation of 2-(2-(4-chloro-2-fluorobenzyl)oxiran-2-yl)-5-(4-(trifluoro-methoxy)phenyl) pyridine

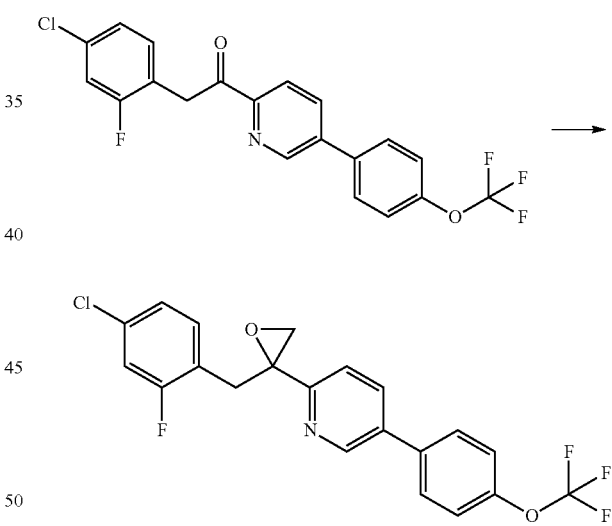

To a suspension of trimethylsulfoxonium iodide (320 mg, 1.45 mmol) in ᵗBuOH (5 mL) was added potassium tert-butoxide (KOᵗBu, 163 mg, 1.45 mmol) at 50° C., and the reaction mixture was stirred for 30 min, treated with a solution of 2-(4-chloro-2-fluorophenyl)-1-(5-(4-(trifluoromethoxy)-phenyl)pyridin-2-yl)ethanone (400 mg, 0.96 mmol) in ᵗBuOH (2 mL), and stirred for 16 h at 50° C. The reaction mixture was cooled to room temperature, poured into ice water, and extracted with EtOAc. The organic extract was washed with brine, dried over Na₂SO₄, filtered, concentrated under reduced pressure, and the residue purified by column chromatography (SiO₂, 5→10% EtOAc in petroleum ether) to afford the title compound (140 mg, 24%) as yellow oil.

Step E: Preparation of 1-(4-chloro-2-fluorophenyl)-3-(1H-tetrazol-1-yl)-2-(5-(4-(trifluoromethoxy)phenyl)pyridin-2-yl) propan-2-ol (28)

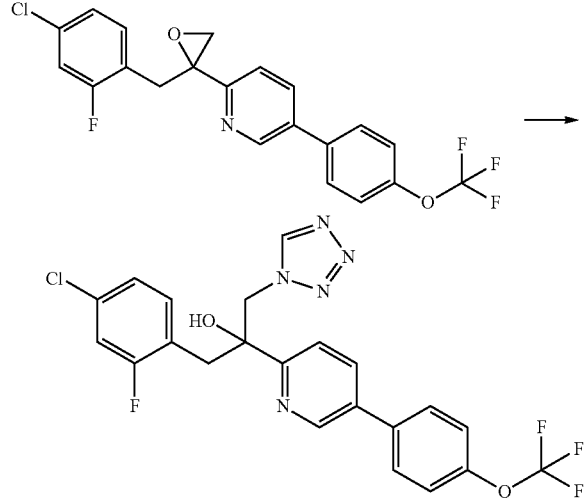

To a solution of 2-(2-(4-chloro-2-fluorobenzyl)oxiran-2-yl)-5-(4-(trifluoromethoxy)-phenyl)pyridine (130 mg, 0.3 mmol) in DMSO (5 mL) was added 1H-tetrazole (43 mg, 0.6 mmol) and K₂CO₃ (63 mg, 0.45 mmol) under an inert atmosphere. The reaction mixture was heated to 70° C. and stirred for 30 h. The reaction mixture was cooled to room temperature, poured into water, and extracted with EtOAc. The organic extract was washed with brine, dried over Na₂SO₄, filtered, and concentrated under reduced pressure. The residue was purified by column chromatography (SiO₂, 5→10% EtOAc in petroleum ether) to afford the title compound (23 mg, 15%) as off-white solid: See Table 2 for characterization data.

The 2H regioisomer (30 mg, 20%) was also obtained as an off white-solid: $^1$H NMR (300 MHz, CDCl₃): δ 8.63 (d, J=2.2 Hz, 1H), 8.40 (s, 1H), 7.84 (dd, J=8.2, 2.3 Hz, 1H), 7.58 (d, J=8.4 Hz, 2H), 7.48 (d, J=8.2 Hz, 1H), 7.32 (d, J=8.4 Hz, 2H), 7.16 (t, J=8.2 Hz, 1H), 7.04-6.92 (m, 2H), 5.32 (d, J=13.8 Hz, 1H), 5.10 (s, 1H), 5.06 (d, J=13.8 Hz, 1H), 3.35 (d, J=13.8 Hz, 1H), 3.26 (d, J=13.8 Hz, 1H); ESIMS m/z 494 [M+H]⁺.

Example 10

Preparation of 1-(5-(4-chlorophenoxyl)pyridin-2-yl)-4,4-dimethyl-1-(pyrimidin-5-yl)pent-2-yn-1-ol (29) and 1-(5-(4-chlorophenoxy)pyridin-2-yl)-1-(pyrimidin-5-yl)propan-1-ol (30)

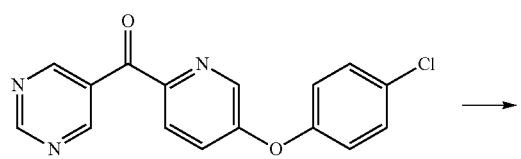

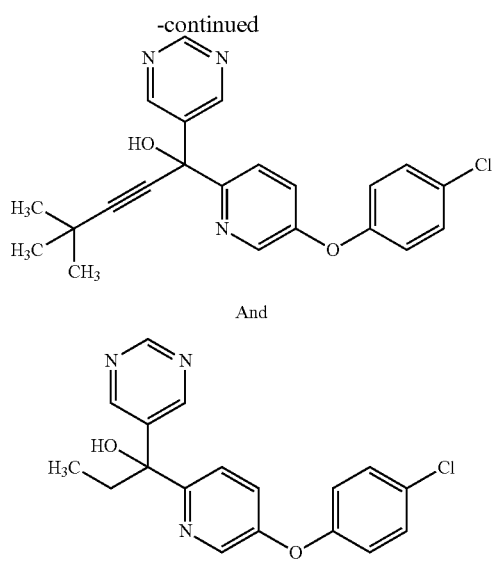

To a vial equipped with a magnetic stir bar was added 3,3-dimethylbut-1-yne (23.7 μL, 0.289 mmol) and the vial was purged with N₂. Anhydrous THF (0.2 mL) was added and reaction mixture was cooled to 0° C. The resulting solution was treated dropwise with a solution of EtMgBr (1.0 M, 289 μL, 0.289 mmol) in THF and the mixture was stirred at 0° C. for 15 min, warmed to and stirred at 40° C. for 2 h, and then cooled to room temperature. To a separate vial were added (5-(4-chlorophenoxyl)pyridin-2-yl)(pyrimidin-5-yl)methanone (30 mg, 0.096 mmol) and THF (481 μL), and the mixture was cooled to 0° C. The freshly prepared acetylide was added dropwise and the reaction was stirred at 0° C. for 4 h. The reaction was quenched while cold with saturated aqueous NH₄Cl solution (2 mL), extracted with EtOAc (3×2 mL), and the combined extracts were dried over MgSO₄, filtered, and concentrated. The residue was purified by column chromatography (SiO₂, 0→60% EtOAc in hexanes) to give the title compounds 29 and 30.

Compound 29 (17 mg, 45% yield) was isolated as a light-yellow, cloudy, viscous oil: See Table 2 for characterization data.

Compound 30 (3.6 mg, 11% yield) was isolated as a light-yellow, viscous oil: See Table 2 for characterization data.

Example 11

Preparation of 2-(4-chloro-2-fluorophenyl)-1-(5-(4-chlorophenoxy)-pyridin-2-yl)-1-(pyrimidin-5-yl) ethanol (41)

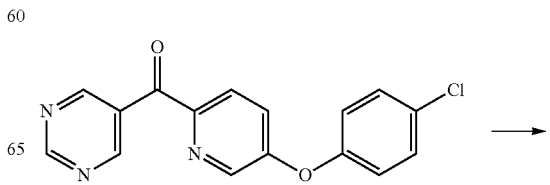

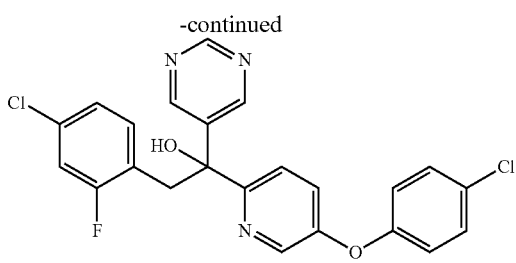

To a stirred suspension of Mg powder (0.012 g, 0.48 mmol) in Et$_2$O (2 mL) was slowly added 1-(bromomethyl)-4-chloro-2-fluorobenzene (0.076 g, 0.48 mmol) during which period refluxing solvent was observed. After complete addition the reaction mixture was stirred at room temperature for 30 min, and the freshly prepared Grignard reagent was added to a solution of (5-(4-chlorophenoxy) pyridin-2-yl) (pyrimidin-5-yl) methanone (from Example 3 using 4-chlorophenol in 3B; 0.1 g, 0.32 mmol) in Et$_2$O (3 mL) at 0° C. The reaction mixture was warmed to room temperature, stirred for 30 min, quenched carefully with saturated aqueous NH$_4$Cl solution, and extracted with EtOAc (2×20 mL). The combined organic extracts were dried over Na$_2$SO$_4$, filtered, concentrated under reduced pressure, and the residue purified by column chromatography (SiO$_2$) to give the title compound (10 mg, 7%) as a yellow liquid: See Table 2 for characterization data.

Example 12

Preparation of 1-(4-chloro-2-fluorophenyl)-2-(5-(4-chlorophenoxy)-pyridin-2-yl)-3-(1H-tetrazol-1-yl) propan-2-ol (42)

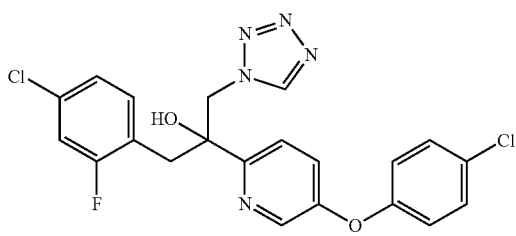 [SMILES: OC(Cc1ccc(Cl)cc1F)(Cn1cnnn1)c1ccc(Oc2ccc(Cl)cc2)cn1]

Step A: Preparation of 5-(4-chlorophenoxy)picolinonitrile

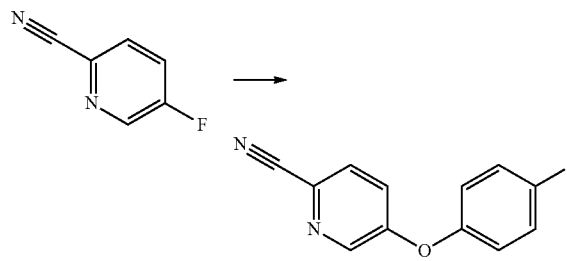

To an oven dried round bottomed flask equipped with a magnetic stir bar were added 2-cyano-5-fluoropyridine (10 g, 81.9 mmol), 4-chlorophenol (15.7 g, 122.9 mmol), and K$_2$CO$_3$ (22.1 g, 163.8 mmol) followed by DMSO (100 mL). The reaction mixture was heated to 120° C. and stirred at 120° C. for 3 h. The reaction was cooled to room temperature, diluted with water (200 mL), and the resulting solid was collected by filtration (Buchner funnel), air dried, and washed with pentane to afford a mixture of 5-(4-chlorophenoxy)picolinonitrile and 5-(4-chlorophenoxy)picolinamide. The solid (10 g) was dissolved in THF and the resulting solution was treated with triethylamine (Et$_3$N, 8.14 g, 80.6 mmol), cooled to 0° C., and treated dropwise with trifluoroacetic anhydride (TFAA, 16.9 g, 80.6 mmol) over a 30 min period. The reaction mixture was stirred for 10 min, quenched with water (100 mL), and extracted with EtOAc (500 mL). The organic extract was washed with water and brine, dried over Na$_2$SO$_4$, filtered, and concentrated under reduced pressure. The residue was purified by column chromatography (SiO$_2$) to afford the title compound (7 g, 48%).

Step B: Preparation of 5-(4-chlorophenoxy)picolinaldehyde

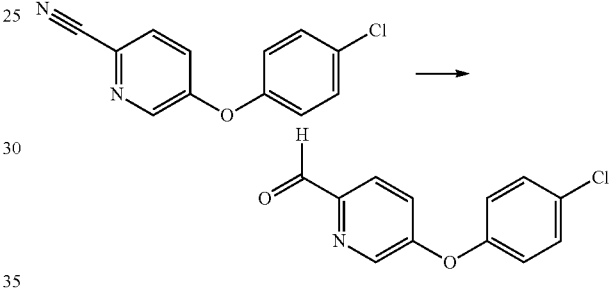

To a solution of 5-(4-chlorophenoxy)picolinonitrile (7 g, 30.4 mmol) in THF (70 mL) at −78° C. was added DIBAL-H (25% in toluene, 86.4 mL, 152 mmol) and the reaction mixture was stirred at −78° C. for 30 min. The reaction mixture was quenched with 2 N HCl at −78° C., warmed to room temperature, and extracted with EtOAc. The organic extract was washed with water and brine, dried over Na$_2$SO$_4$, filtered, and concentrated under reduced pressure. The residue was purified by column chromatography (SiO$_2$) to afford the title compound (5.4 g, 76%).

Step C: Preparation of 2-(4-chloro-2-fluorophenyl)-1-(5-(4-chlorophenoxyl)pyridin-2-yl)ethanol

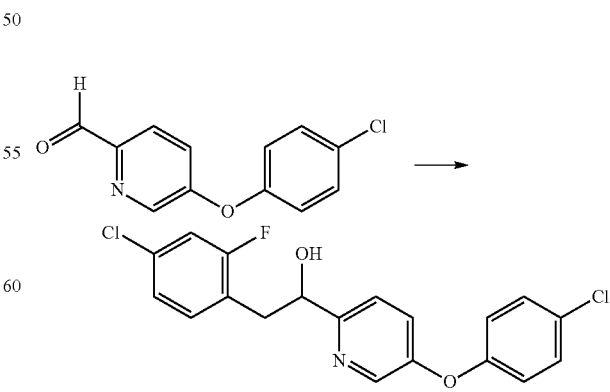

To a stirred suspension of Mg powder (1.12 g, 46.9 mmol) in Et$_2$O (60 mL) was slowly added 1-(bromomethyl)-4- chloro-2-fluorobenzene (0.615 g, 5.08 mmol) during which period refluxing of solvent was observed. After complete addition, the reaction mixture was stirred at room temperature for 30 min. The freshly prepared Grignard reagent was added to a solution of 5-(4-chlorophenoxy)picolinaldehyde (5.4 g, 23.4 mmol) in Et$_2$O (60 mL) at 0° C. and the mixture was warmed to room temperature, stirred for 30 min, quenched with saturated aqueous NH$_4$Cl solution, and extracted with EtOAc (2×200 mL). The combined organic extracts were dried over Na$_2$SO$_4$, filtered, and concentrated under reduced pressure to afford a residue which was purified by column chromatography (SiO$_2$) to give the title compound (4 g, 45%) as white solid.

Step D: Preparation of 2-(4-chloro-2-fluorophenyl)-1-(5-(4-chlorophenoxyl)pyridin-2-yl)ethanone

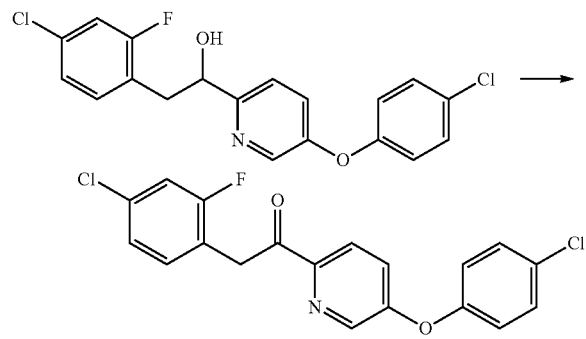

To a solution of 2-(4-chloro-2-fluorophenyl)-1-(5-(4-chlorophenoxy)-pyridin-2-yl)ethanol (4.00 g, 10.6 mmol) in CH$_2$Cl$_2$ (40 mL) at 0° C. was added Dess-Martin periodinane (8.99 g, 21.2 mmol) in portions, and the reaction mixture was stirred at room temperature for 16 h. The reaction mixture was filtered through Celite® rinsing with CH$_2$Cl$_2$ and the filtrate was concentrated under reduced pressure. The residue was purified by column chromatography (SiO$_2$) to afford the title compound (3.6 g, 92%).

Step E: Preparation of 2-(2-(4-chloro-2-fluorobenzyl)oxiran-2-yl)-5-(4-chlorophenoxyl)pyridine

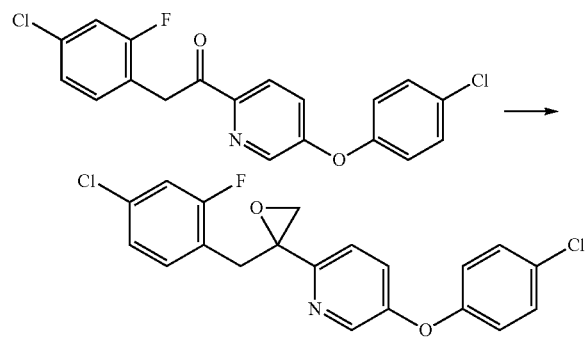

To a stirred suspension of 2-(4-chloro-2-fluorophenyl)-1-(5-(4-chlorophenoxyl)pyridin-2-yl)ethanone (1 g, 2.66 mmol) in Et$_2$O (10 mL) was slowly added diazomethane (50 mL, 0.5 M in Et$_2$O) at 0° C. and the mixture was stirred for 16 h at room temperature. The reaction mixture was quenched carefully with ice cold water and extracted with EtOAc. The organic extract was dried over Na$_2$SO$_4$, filtered, and concentrated under reduced pressure to give an oily residue which was purified by column chromatography (SiO$_2$) to afford the title compound (0.350 g, 36%).

Step F: Preparation of 1-(4-chloro-2-fluorophenyl)-2-(5-(4-chlorophenoxyl)pyridin-2-yl)-3-(1H-tetrazol-1-yl)propan-2-ol (42)

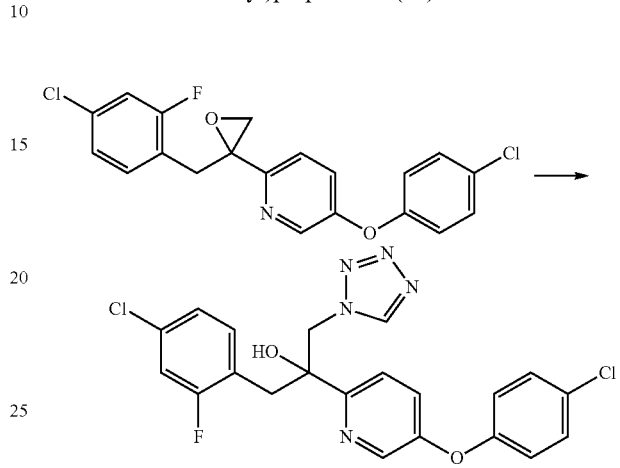

To a stirred solution of 2-(2-(4-chloro-2-fluorobenzyl)-oxiran-2-yl)-5-(4-chlorophenoxyl)pyridine (0.350 g, 8.99 mmol) in DMSO (3.5 mL) was added 1H-tetrazole (0.125 g, 17.98 mmol) followed by K$_2$CO$_3$ (0.186 g, 13.485 mmol) at room temperature under an inert atmosphere (N$_2$). The reaction mixture was warmed to and stirred at 60° C. for 16 h. The reaction mixture was cooled to room temperature, diluted with ice cold water (20 mL), and extracted with EtOAc (2×100 mL). The combined organic extracts were dried over anhydrous Na$_2$SO$_4$, filtered, concentrated under reduced pressure, and the residue was purified by column chromatography (SiO$_2$) to afford the title compound (140 mg, 34%) as an off white solid: See Table 2 for characterization data.

Example 13

Preparation of 2-cyclopropyl-1-(pyrimidin-5-yl)-1-(5-(4-(trifluoromethoxy)phenoxy)pyridin-2-yl)ethanol (45)

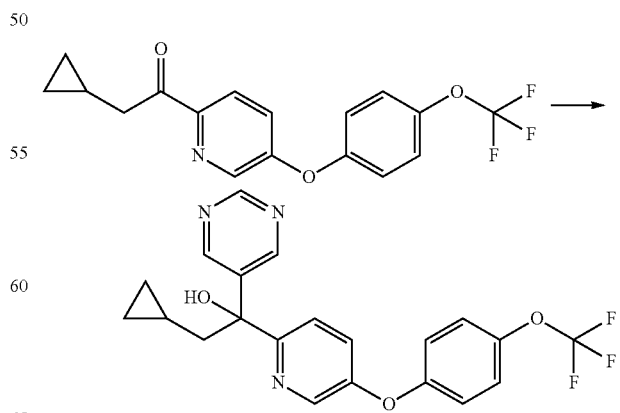

To a vial equipped with a magnetic stir bar were added 5-bromopyrimidine (33.9 mg, 0.213 mmol) and 2-cyclopropyl-1-(5-(4-(trifluoromethoxy)phenoxy)pyridin-2-yl)ethanone (prepared from 2-cyclopropyl-N-methoxy-N-methylacetamide using conditions described in Example 3, steps A and B; 40 mg, 0.119 mmol) followed by THF (593 μL), and the reaction mixture was cooled to −78° C. and treated with a 2.5 M solution of n-BuLi (95 μL, 0.237 mmol) in hexanes. The reaction mixture was stirred at −78° C. for 2 h, quenched with 0.5 mL of 1 M HCl, and partitioned between water (2 mL) and EtOAc (2 mL). The phases were separated and the aqueous phase was further extracted with EtOAc (2×2 mL). The combined organics were washed with brine (5 mL), dried over $Na_2SO_4$, filtered, and concentrated. The residue was purified by column chromatography ($SiO_2$, 0→100% EtOAc in hexanes) to give the title compound (4.1 mg, 8%) as a light-yellow, viscous oil: See Table 2 for characterization data.

Example 14

2-(5-(4-chlorophenyl)pyridin-2-yl)-1,1,1-trifluoro-3-(pyrimidin-5-yl)propan-2-ol (46)

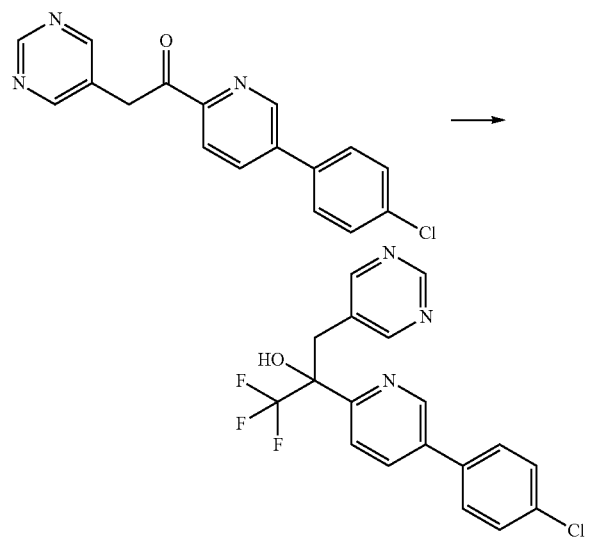

To a magnetically stirred mixture of 1-(5-(4-chlorophenyl)pyridin-2-yl)-2-(pyrimidin-5-yl)ethanone (50 mg, 0.161 mmol) and trimethyl(trifluoromethyl)silane (35.8 μL, 0.242 mmol) in THF (807 μL) was added CsF (4.90 mg, 0.032 mmol) at 0° C., and the reaction mixture was stirred for 85 min, quenched with 2 mL of 1 N HCl, stirred for 45 min, warmed to room temperature, diluted with water, and extracted with EtOAc (3×). The combined organic extracts were dried by passing through a phase separator cartridge. The solvents were evaporated and the resulting residue was purified by column chromatography ($SiO_2$, 30→60% acetone in hexanes) to yield the title compound and its corresponding TMS ether. The TMS ether was dissolved in THF (1.5 mL), treated with additional 1 N HCl (1 mL), and stirred at room temperature overnight, at which point LCMS showed complete conversion to the free hydroxy product. The reaction mixture was quenched by the addition of saturated aqueous $NaHCO_3$ (gas evolution observed), extracted with EtOAc (3×), and the combined organic extracts were dried by passing through a phase separator cartridge. The volatile components were removed under a gentle stream of $N_2$ to give the title compound (28 mg, 45.7%) as a brown oil: See Table 2 for characterization data.

Example 15

Preparation of (2,4-difluorophenyl)(pyrimidin-5-yl) (5-(4-(trifluoro-methoxy)phenyl)pyridin-2-yl)methanol (91)

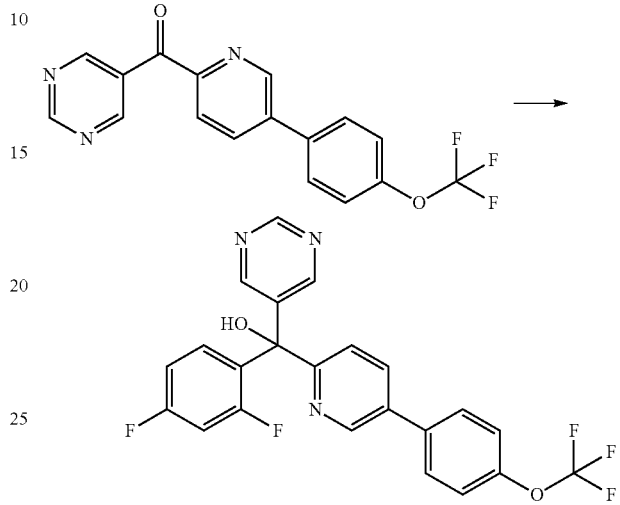

To a vial equipped with a magnetic stir bar was added 1-bromo-2,4-difluorobenzene (19.9 μL, 0.176 mmol) and the vial was purged with $N_2$. Anhydrous $Et_2O$ (306 μL) was added and the reaction mixture was cooled to −78° C. and treated with a solution of n-BuLi (2.5 M, 70.4 μL, 0.176 mmol) in hexane. The reaction mixture was stirred at −78° C. for 30 min and treated dropwise with a solution of pyrimidin-5-yl(5-(4-(trifluoromethoxy)phenyl)-pyridin-2-yl)methanone (Example 8A; 52.8 mg, 0.153 mmol) in anhydrous $Et_2O$ (306 μL), rinsing with additional $Et_2O$ (0.5 mL) and THF (1 mL). The resulting mixture was stirred at −78° C. for 2 h, warmed to and stirred at 0° C. for 1 h, and then quenched while cold with saturated aqueous $NH_4Cl$ solution (2 mL). The mixture was extracted with EtOAc (3×2 mL) and the combined extracts were dried over $MgSO_4$, filtered, and concentrated. The residue was purified by column chromatography ($SiO_2$, 0→40% EtOAc in hexanes) to give the title compound (27 mg, 37%) as an off-white, viscous semi-solid: See Table 2 for characterization data.

Example 16

Preparation of 2,2-dimethyl-1-pyrimidin-5-yl-1-[5-[4-(trifluoromethoxy)phenyl]-2-pyridyl]butan-1-ol (93)

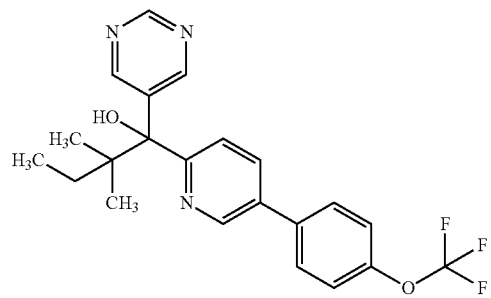 [SMILES: CCC(C)(C)C(O)(c1cncnc1)c1ccc(-c2ccc(OC(F)(F)F)cc2)cn1]

Step A: Preparation of (5-bromopyridin-2-yl)(pyrimidin-5-yl)methanone

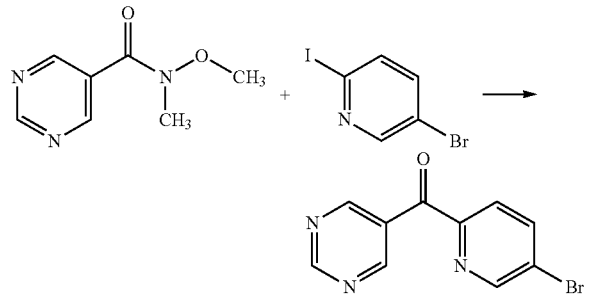

A round bottom flask equipped with a magnetic stir bar was charged with 5-bromo-2-iodopyridine (7.13 g, 25.1 mmol) and the flask was purged with $N_2$. Anhydrous THF (67 mL) was added and the reaction mixture was cooled to −40° C., treated with a 2.0 M solution of isopropylmagnesium chloride in THF (12.56 mL, 25.1 mmol) over 10 min period, and stirred at −40° C. for 1 h. The resulting cloudy, light-brown reaction mixture was treated with a solution of N-methoxy-N-methylpyrimidine-5-carboxamide (4.2 g, 25.1 mmol) in anhydrous THF (16.8 mL) over a 10 min period, stirred at −40° C. for 45 min, and warmed to room temperature. The reaction mixture was quenched with saturated (sat'd) aqueous (aq) ammonium chloride ($NH_4Cl$) solution (100 mL) and extracted with DCM (3×50 mL). The combined organic phases were dried over $Na_2SO_4$, filtered, concentrated, and the residue was purified by column chromatography ($SiO_2$, 0→20% EtOAc in DCM) to give the title compound (3.41 g, 50%) as a light yellow solid: IR (Thin Film) 1667, 1560, 1314 cm$^{-1}$; $^1$H NMR (400 MHz, CDCl$_3$) δ 9.50 (s, 2H), 9.39 (s, 1H), 8.81 (dd, J=2.0, 1.0 Hz, 1H), 8.18-8.06 (m, 2H); HRMS-ESI (m/z) [M+H]$^+$ calcd for $C_{10}H_7BrN_3O$, 263.9767; found, 263.9767.

Step B: Preparation of 1-(5-bromopyridin-2-yl)-2,2-dimethyl-1-(pyrimidin-5-yl)butan-1-ol

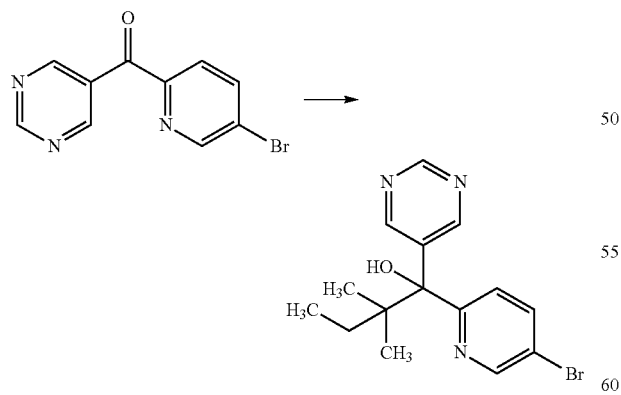

A vial equipped with a magnetic stir bar and fitted with a septum cap was purged with $N_2$ and charged with (5-bromopyridin-2-yl)(pyrimidin-5-yl)methanone (210 mg, 0.80 mmol) and anhydrous THF (2.6 mL). The reaction mixture was cooled to 0° C., treated dropwise with a 1 M solution of tert-pentylmagnesium chloride in Et$_2$O (1.19 mL, 1.193 mmol), stirred at 0° C. until complete, and quenched with sat'd aq $NH_4Cl$ solution (5 mL). The reaction mixture was warmed to room temperature, extracted with EtOAc (3×5 mL), and the combined organic extracts were dried over MgSO$_4$, filtered, concentrated, and purified by column chromatography (SiO$_2$, 0→50% EtOAc in hexanes) to give the title compound (134 mg, 49%) as a light-tan solid: IR (Thin Film) 3233, 1556, 1459, 1412, 1362 cm$^{-1}$; $^1$H NMR (400 MHz, CDCl$_3$) δ 9.18 (s, 2H), 9.07 (s, 1H), 8.64 (dd, J=2.4, 0.8 Hz, 1H), 7.88 (dd, J=8.6, 2.4 Hz, 1H), 7.67 (dd, J=8.6, 0.8 Hz, 1H), 5.42 (s, 1H), 1.54-1.40 (m, 1H), 1.39-1.28 (m, 1H), 0.99 (s, 6H), 0.80 (t, J=7.5 Hz, 3H); HRMS-ESI (m/z) [M+H]$^+$ calcd for $C_{15}H_{19}BrN_3O$, 336.0706; found, 336.0708.

Step C: Preparation of 2,2-dimethyl-1-(pyrimidin-5-yl)-1-(5-(4-(trifluoromethoxy)-phenyl)pyridin-2-yl)butan-1-ol

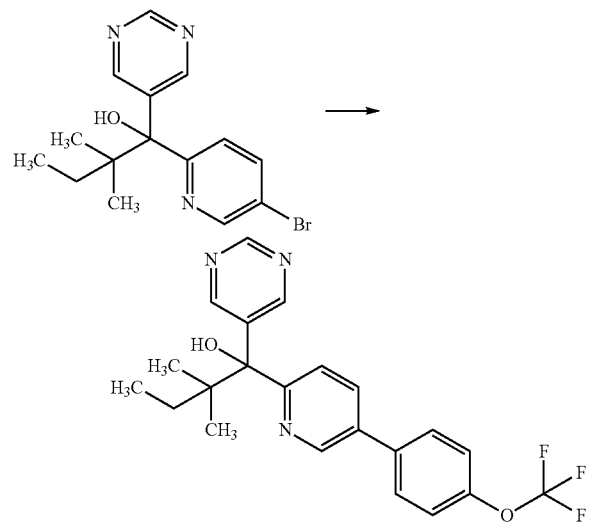

The title compound was prepared from 1-(5-bromopyridin-2-yl)-2,2-dimethyl-1-(pyrimidin-5-yl)butan-1-ol and (4-(trifluoromethoxy)phenyl)boronic acid according to the conditions described in Example 7A and was isolated as a light-yellow foam in 70% yield: See Table 2 for characterization data.

Example 17

Preparation of 1-(5-(2-fluoro-4-(trifluoromethoxy)phenyl)pyridin-2-yl)-2,2-dimethyl-1-(pyrimidin-5-yl)propan-1-ol (124)

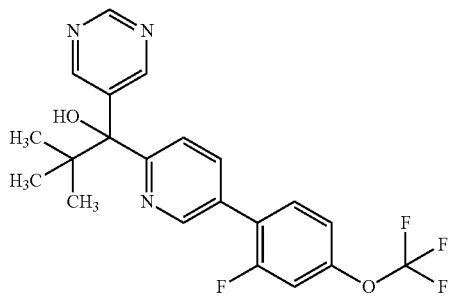 [SMILES: CC(C)(C)C(O)(c1cncnc1)c1ccc(-c2ccc(OC(F)(F)F)cc2F)cn1]

Step A: Preparation of 2-(2-fluoro-4-(trifluoromethoxy)phenyl)-4,4,5,5-tetramethyl-1,3,2-dioxaborolane

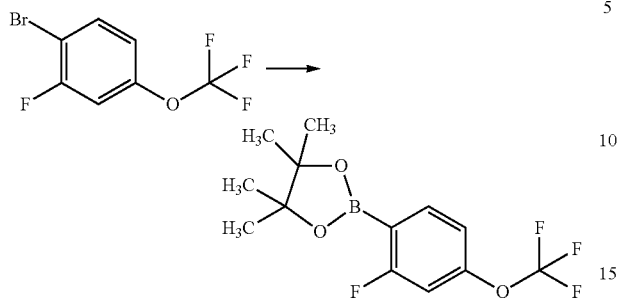

To a microwave vial equipped with a magnetic stir bar were added 4,4,4',4',5,5,5',5'-octamethyl-2,2'-bi(1,3,2-dioxaborolane) (294 mg, 1.16 mmol), potassium acetate (KOAc; 189 mg, 1.93 mmol) and Pd(dppf)Cl$_2$ (70.6 mg, 0.097 mmol) and the vial was purged with N$_2$. The resulting mixture was treated with a solution of 1-bromo-2-fluoro-4-(trifluoromethoxy)benzene (250 mg, 0.96 mmol) in 1,4-dioxane (3.9 mL). The reaction vessel was capped, placed in a Biotage Initiator microwave reactor for 2 h at 100° C., with external IR-sensor temperature monitoring from the side of the vessel. The cooled reaction mixture was filtered through a pad of Celite® rinsing with EtOAc, and the filtrate was washed with sat'd aq NaHCO$_3$ (15 mL) and brine (2×15 mL). The organic phase was dried over MgSO$_4$, filtered, and concentrated to a brown oil which was used without further purification: $^1$H NMR (400 MHz, CDCl$_3$) δ 7.77 (dd, J=8.3, 6.8 Hz, 1H), 7.01 (ddd, J=8.3, 2.3, 1.1 Hz, 1H), 6.92 (ddd, J=9.6, 2.2, 1.0 Hz, 1H), 1.36 (s, 12H); EIMS m/z 306.

Step B: Preparation of 1-(5-(2-fluoro-4-(trifluoromethoxy)phenyl)pyridin-2-yl)-2,2-dimethyl-1-(pyrimidin-5-yl)propan-1-ol

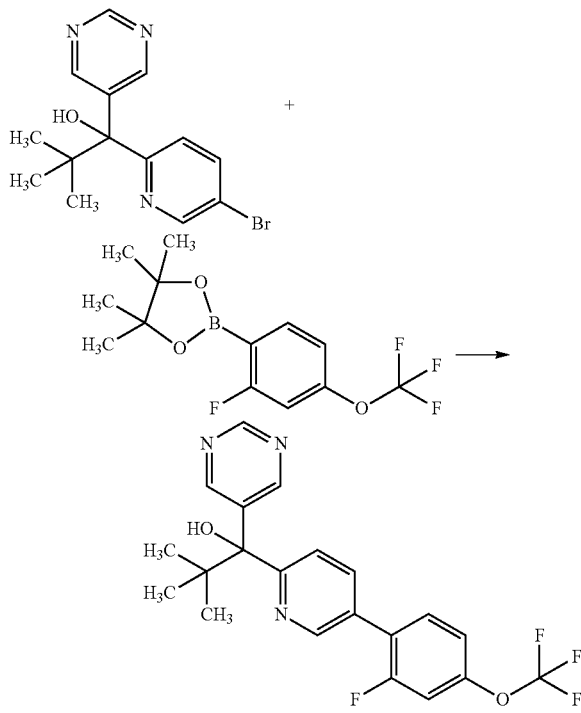

The title compound was prepared from 1-(5-bromopyridin-2-yl)-2,2-dimethyl-1-(pyrimidin-5-yl)propan-1-ol (prepared as described in Example 16A-16B with tBuMgCl at −78° C.) and 2-(2-fluoro-4-(trifluoromethoxy)phenyl)-4,4,5,5-tetramethyl-1,3,2-dioxaborolane according to the conditions described in Example 7A and was isolated as a white foam in 47% yield: See Table 2 for characterization data.

Example 18

Preparation of 1-(4-(6-(1-hydroxy-2,2-dimethyl-1-(pyrimidin-5-yl)propyl)pyridin-3-yl)phenyl)ethanone O-methyl oxime (130 and 132)

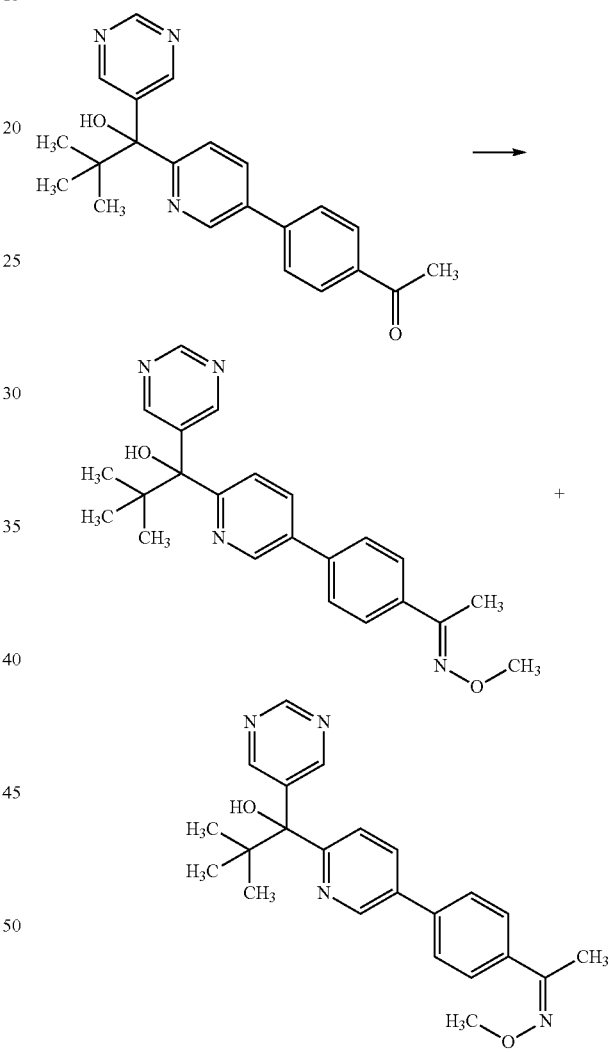

To a vial equipped with a magnetic stir bar were added 1-(4-(6-(1-hydroxy-2,2-dimethyl-1-(pyrimidin-5-yl)propyl)pyridin-3-yl)phenyl)ethanone (188 mg, 0.520 mmol), prepared as described in Example 16, NaOAc (51.2 mg, 0.624 mmol), O-methylhydroxylamine hydrochloride (52.1 mg, 0.624 mmol) and MeOH (3.5 mL) at room temperature, and the reaction mixture was stirred at room temperature for approximately 15 h. The reaction mixture was diluted with sat'd aq NaHCO$_3$ solution (10 mL), extracted with DCM (3×5 mL), and the combined organic extracts were washed with water (2×5 mL), dried over Na$_2$SO$_4$, filtered, and concentrated. The residue was purified by column chromatography (SiO$_2$, 0→40% EtOAc in hexanes) to give (E)-1-(4-(6-(1-hydroxy-2,2-dimethyl-1-(pyrimidin-5-yl)propyl)pyridin-3-yl)phenyl)ethanone O-methyl oxime (154 mg, 76%) as a white solid and (Z)-1-(4-(6-(1-hydroxy-2,2-dimethyl-1-(pyrimidin-5-yl)propyl)pyridin-3-yl)phenyl)ethanone O-methyl oxime (14 mg, 7%) as a white solid: See Table 2 for characterization data.

Example 19

Preparation of 5-(6-(1-hydroxy-2,2-dimethyl-1-(pyrimidin-5-yl)propyl)pyridin-3-yl)thiophene-2-carboxamide (133)

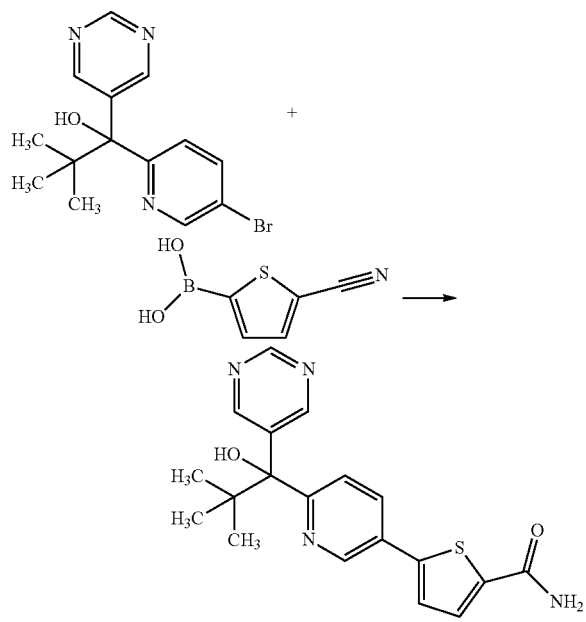

The title compound was prepared from 1-(5-bromopyridin-2-yl)-2,2-dimethyl-1-(pyrimidin-5-yl)propan-1-ol and 5-(4,4,5,5-tetramethyl-1,3,2-dioxaborolan-2-yl)thiophene-2-carbonitrile according to the conditions described in Example 7A and was isolated as a white solid in 10% yield: See Table 2 for characterization data.

Example 20

Preparation of 2-(3-fluorophenyl)-1-pyrimidin-5-yl-1-[5-[4-(trifluoromethoxy)-phenyl]-2-pyridyl]ethanol (139)

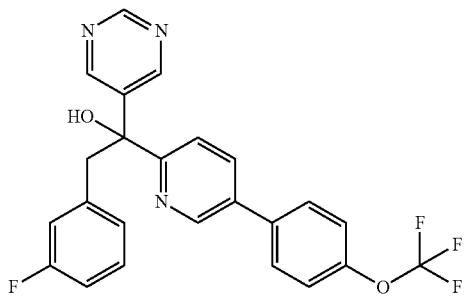 [SMILES: OC(Cc1cccc(F)c1)(c1cncnc1)c1ccc(-c2ccc(OC(F)(F)F)cc2)cn1]

Step A: Preparation of 1-(5-bromopyridin-2-yl)-2-(3-fluorophenyl)-1-(pyrimidin-5-yl)ethanol

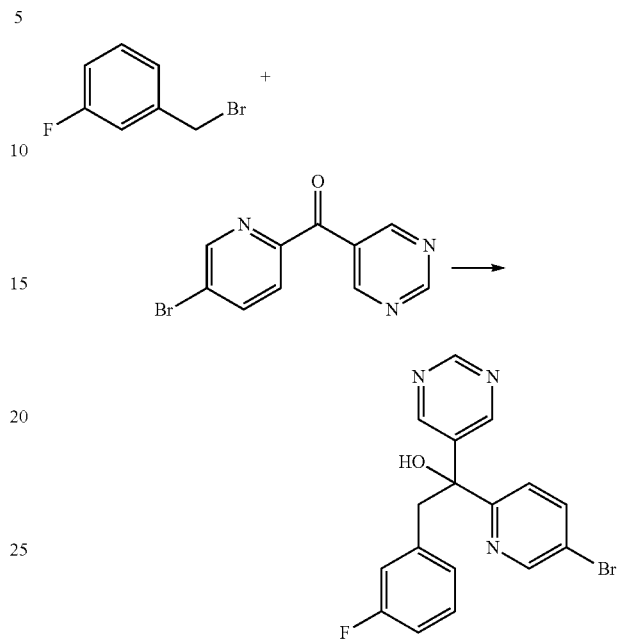

To an oven-dried vial equipped with a magnetic stir bar was added magnesium metal (Mg) which had been washed with 2 N HCl and dried (18.0 mg, 0.74 mmol) and the vial was purged with N$_2$. A crystal of I$_2$ was added and the mixture was diluted with anhydrous Et$_2$O (1.4 mL) and treated with 1-(bromomethyl)-3-fluorobenzene (91 µL, 0.74 mmol) at a rate such that no bubbling from the Mg was observed. The reaction vessel was periodically warmed allowing for gentle reflux until the I$_2$ color dissipated and most of the Mg was consumed. The reaction mixture was cooled to room temperature and stirred vigorously for 30. To a separate vial were added (5-bromopyridin-2-yl)(pyrimidin-5-yl)methanone (150 mg, 0.57 mmol) and anhydrous THF (2.8 mL). The resulting solution was cooled to 0° C., and the freshly prepared Grignard solution was slowly transferred to the flask containing the ketone, rinsing with additional anhydrous THF (1.4 mL). The mixture was stirred at 0° C. for 3 h and allowed to warm to room temperature as the ice melted. After 5 h, the reaction mixture was quenched with saturated aqueous (sat'd aq) NH$_4$Cl (5 mL), and extracted with EtOAc (3×3 mL). The combined extracts were dried over MgSO$_4$, filtered, and concentrated. The residue was purified by column chromatography (SiO$_2$, 0→60% EtOAc in hexanes) to afford the title compound (112 mg, 52%) as a light-yellow, viscous oil: $^1$H NMR (400 MHz, CDCl$_3$) δ 9.11 (s, 1H), 8.95 (s, 2H), 8.59 (dd, J=2.3, 0.8 Hz, 1H), 7.84 (dd, J=8.4, 2.3 Hz, 1H), 7.38 (dd, J=8.4, 0.8 Hz, 1H), 7.20-7.08 (m, 1H), 6.89 (tdd, J=8.4, 2.6, 1.0 Hz, 1H), 6.82-6.72 (m, 2H), 4.67 (s, 1H), 3.75 (d, J=13.6 Hz, 1H), 3.50 (d, J=13.6 Hz, 1H); $^{19}$F NMR (376 MHz, CDCl$_3$) δ −112.95; IR (Thin Film) 3217, 1411, 1092, 1007, 725 cm$^{-1}$; HRMS-ESI (m/z) [M+H]$^+$ calcd for C$_{17}$H$_{14}$BrFN$_3$O, 374.0299; found, 374.0299.

Step B: Preparation of 2-(3-fluorophenyl)-1-(pyrimidin-5-yl)-1-(5-(4-(trifluoromethoxy)phenyl)pyridin-2-yl)ethanol

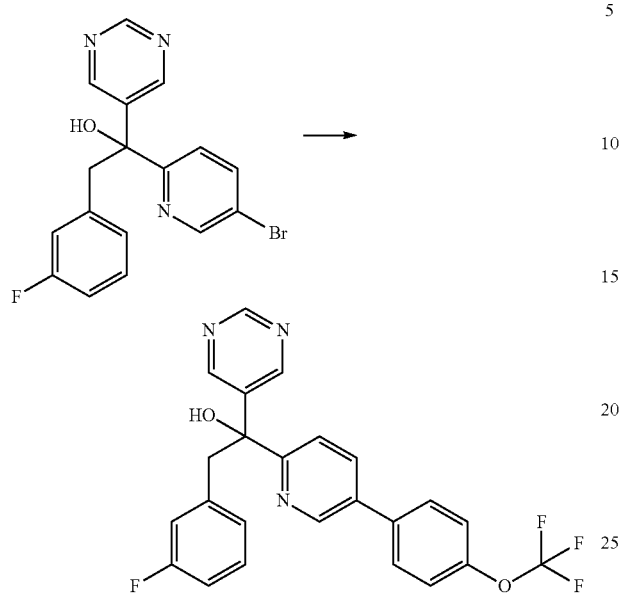

The title compound was prepared from 1-(5-bromopyridin-2-yl)-2-(3-fluorophenyl)-1-(pyrimidin-5-yl)ethanol and (4-(trifluoromethoxy)phenyl)boronic acid according to the conditions described in Example 7A and was isolated as a light-yellow, viscous, semi-solid in 64% yield: See Table 2 for characterization data.

Example 21

Preparation of 1-(5-(4-(1,1-difluoroethyl)phenyl)pyridin-2-yl)-2,2-dimethyl-1-(pyrimidin-5-yl)propan-1-ol (155)

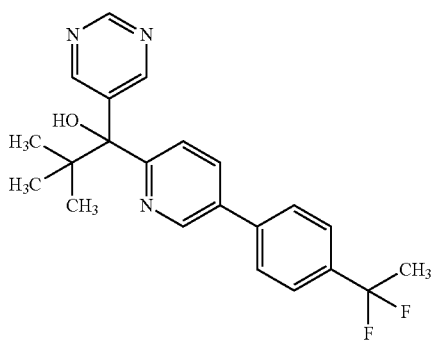 [SMILES: CC(F)(F)c1ccc(-c2ccc(C(O)(c3cncnc3)C(C)(C)C)nc2)cc1]

Step A: Preparation of 1-bromo-4-(1,1-difluoroethyl)benzene

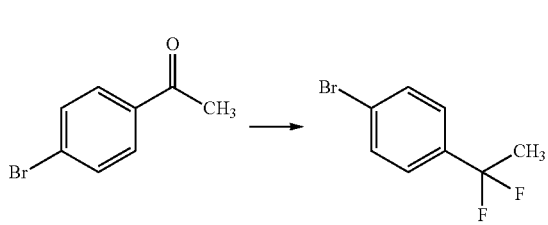

To a vial equipped with a magnetic stir bar were added a solution of 1-(4-bromophenyl)ethanone (295 mg, 1.48 mmol) in anhydrous DCM (3.0 mL) followed by a 50% solution of Deoxofluor® in toluene (1.6 mL, 4.45 mmol) at room temperature under $N_2$ and the vial was sealed. The reaction mixture was stirred for approximately 15 h at room temperature, but little conversion had taken place. The mixture was concentrated, treated with additional Deoxofluor® solution (0.66 mL, 1.79 mmol), and warmed to and stirred at 85° C. under $N_2$ for 5 h. The reaction mixture was cooled to 0° C. and carefully quenched by adding sat'd aq $NaHCO_3$ dropwise until gas evolution ceased. The bi-phasic mixture was extracted with DCM (2×5 mL), and the combined extracts were dried over $Na_2SO_4$, filtered, and concentrated. The residue was purified by column chromatography ($SiO_2$, 0→50% EtOAc in hexanes) to afford the title compound (83 mg, 25%) as a clear liquid: $^1$H NMR (400 MHz, $CDCl_3$) δ 7.58-7.53 (m, 2H), 7.41-7.35 (m, 2H), 1.90 (t, J=18.1 Hz, 3H); $^{19}$F NMR (376 MHz, $CDCl_3$) δ −87.86; IR (Thin Film) 1599, 1294, 1089 cm$^{-1}$; EIMS m/z 220/221.

Step B: Preparation of 2-(4-(1,1-difluoroethyl)phenyl)-4,4,5,5-tetramethyl-1,3,2-dioxaborolane

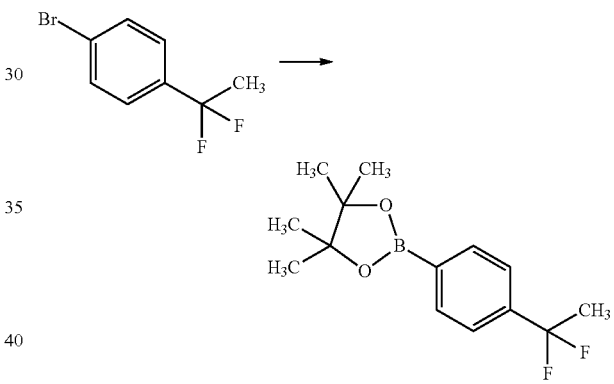

The title compound was prepared from 1-bromo-4-(1,1-difluoroethyl)benzene according to the conditions described in Example 17A and was isolated as a brown oil and used without further purification: $^1$H NMR (400 MHz, $CDCl_3$) δ 7.91-7.83 (m, 2H), 7.55-7.45 (m, 2H), 1.91 (t, J=18.2 Hz, 3H), 1.35 (s, 12H); $^{19}$F NMR (376 MHz, $CDCl_3$) δ −88.45; EIMS ink 268.

Step C: Preparation of 1-(5-(4-(1,1-difluoroethyl)phenyl)pyridin-2-yl)-2,2-dimethyl-1-(pyrimidin-5-yl)propan-1-ol

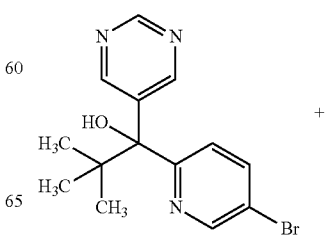
+

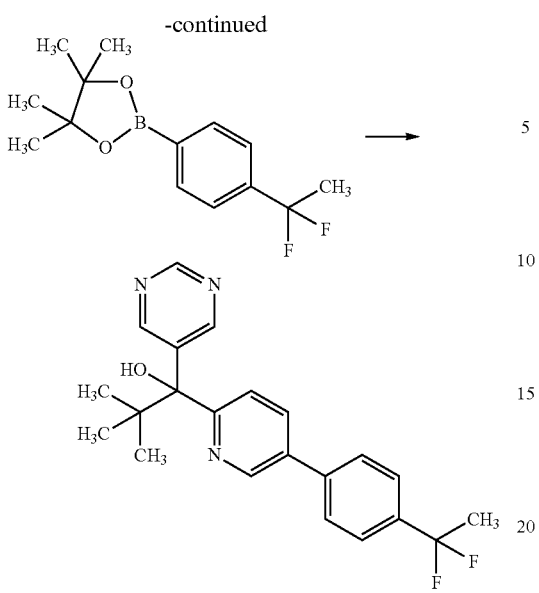

The title compound was prepared from 1-(5-bromopyridin-2-yl)-2,2-dimethyl-1-(pyrimidin-5-yl)propan-1-ol and 2-(4-(1,1-difluoroethyl)phenyl)-4,4,5,5-tetramethyl-1,3,2-dioxaborolane according to the conditions described in Example 7A and was isolated as a light brown solid in 65% yield: See Table 2 for characterization data.

Example 22

Preparation of 1-(5-(4-iodophenyl)pyridin-2-yl)-2,2-dimethyl-1-(pyrimidin-5-yl)propan-1-ol (165)

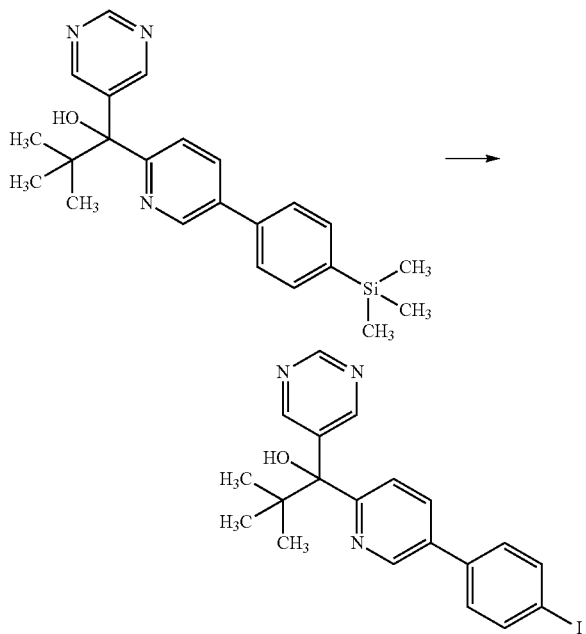

To a vial equipped with a magnetic stir bar were added a solution of 2,2-dimethyl-1-(pyrimidin-5-yl)-1-(5-(4-(trimethylsilyl)phenyl)pyridin-2-yl)propan-1-ol (59 mg, 0.15 mmol) in DCM (753 μL) followed by a solution of ICl (48.9 mg, 0.301 mmol) in DCM (0.5 mL) and the reaction mixture was stirred at room temperature. After approximately 23 h, the mixture was treated with additional ICl solution (48.9 mg, 0.301 mmol) in DCM (0.5 mL), stirred for 4 h, and quenched with sat'd aq sodium thiosulfate ($Na_2S_2O_3$; 2 mL). The mixture was diluted with DCM (2 mL) and the phases were separated. The organic phase was washed with water (3×2 mL), dried over $Na_2SO_4$, filtered, and concentrated. The residue was purified by column chromatography ($SiO_2$, 0→50% EtOAc in hexanes) to afford the title compound (32 mg, 47%) as an off-white solid: See Table 2 for characterization data.

Example 23

Preparation of 5-(1-methoxy-2,2-dimethyl-1-(5-(4-(trifluoromethoxy)phenyl)pyridin-2-yl)propyl)pyrimidine (277)

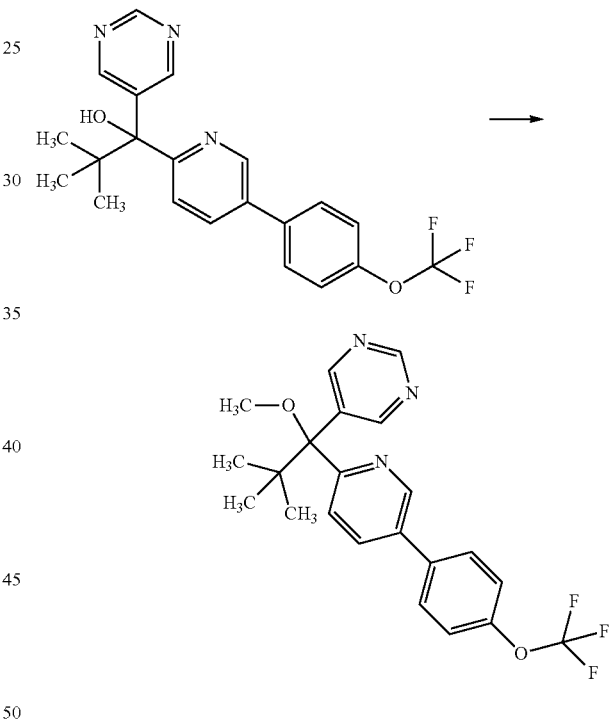

To a vial equipped with a magnetic stir bar was added 2,2-dimethyl-1-(pyrimidin-5-yl)-1-(5-(4-(trifluoromethoxy)phenyl)pyridin-2-yl)propan-1-ol (27) (150 mg, 0.372 mmol) and dry THF (2479 μl), and the head space was purged with $N_2$. To this was added sodium hydride (29.7 mg, 0.744 mmol). The reaction mixture was stirred at 0° C. for 5 min at which point methyl iodide (58.1 μl, 0.930 mmol) was added via syringe. The reaction gradually warmed to rt and then was quenched after 16 h by the addition of 1.5 mL sat. aq. $NH_4Cl$. The reaction mixture was diluted with water and extracted 3× with EtOAc. The combined organic layers were dried by passing through a phase separator and volatiles were removed under $N_2$. The residue was purified by column chromatography ($SiO_2$, 0→25% EtOAc in hexanes) to give the title compound (128 mg, 82%) as an oily yellow solid: See Table 2 for characterization data.

Example 24

Preparation of 1-(5-(4-iodophenyl)pyridin-2-yl)-2,2-dimethyl-1-(pyrimidin-5-yl)propan-1-ol (156)

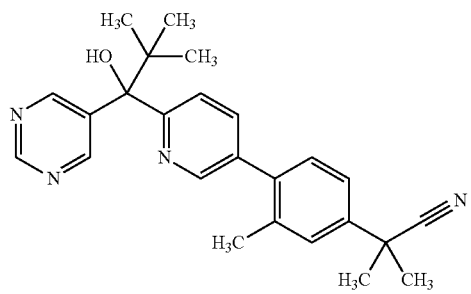 [SMILES: Cc1cc(C(C)(C)C#N)ccc1-c1ccc(C(O)(c2cncnc2)C(C)(C)C)nc1]

Step A: Preparation of 2-(4-bromo-3-methylphenyl)-2-methylpropanenitrile

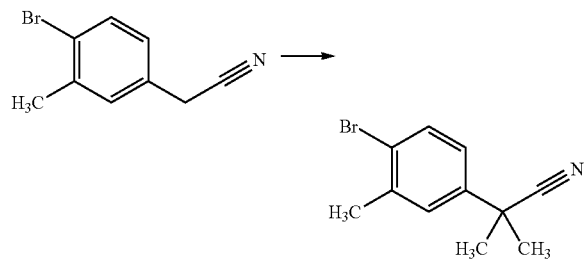

To a magnetically stirred mixture of 2-(4-bromo-3-methylphenyl)acetonitrile (1 g, 4.76 mmol) in dry THF (9.52 ml) at ice-bath temperatures was added NaH (0.571 g, 14.28 mmol) in a dry 100 mL round-bottomed flask under an argon atmosphere. The reaction mixture was stirred at ice-bath temperatures for 1 h, then iodomethane (0.893 ml, 14.28 mmol) was added dropwise and stirring was continued for 3 h. The reaction mixture was poured into crushed ice and water and extracted with ethyl acetate (3×). The combined organic extracts were dried over sodium sulfate, filtered, and evaporated to afford 1.1 g (92%) of the title compound as a brown oil, which was used without further purification. ¹H NMR (400 MHz, CDCl₃) δ 7.53 (d, J=8.4 Hz, 1H), 7.34 (d, J=2.4 Hz, 1H), 7.13 (dd, J=8.3, 2.5 Hz, 1H), 2.43 (s, 3H), 1.70 (s, 6H). GCMS m/z 237.

Step B: Preparation of 5-(2,2-dimethyl-1-((4,4,5,5-tetramethyl-1,3,2-dioxaborolan-2-yl)oxy)-1-(5-(4,4,5,5-tetramethyl-1,3,2-dioxaborolan-2-yl)pyridin-2-yl)propyl)pyrimidine

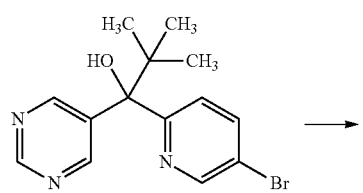

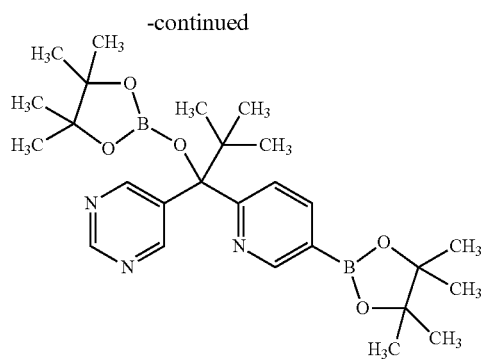

In a 4-neck 500 mL flask equipped with condenser, stir bar, temperature probe, and nitrogen inlet, 1-(5-bromopyridin-2-yl)-2,2-dimethyl-1-(pyrimidin-5-yl)propan-1-ol (9.74 g, 28.7 mmol) was stirred in dioxane (115 ml). Potassium acetate (3.70 g, 37.3 mmol) and 4,4,4',4',5,5,5',5'-octamethyl-2,2'-bi(1,3,2-dioxaborolane) (9.58 g, 37.3 mmol) were added. The mixture was sparged with nitrogen for 5 minutes. Pd(dppf)Cl₂(1.070 g, 1.436 mmol) was added. The mixture was heated to 85° C. for 2 h, then was allowed to cool. The reaction mixture was diluted with DCM (100 mL) and filtered through Celite. The filtrate was concentrated to dryness to provide a gummy solid. The solid was slurried in MTBE (30 mL) and heptane (100 mL). A solid was collected, washed with heptane and vacuum-dried at 35° C. to afford 13.6 g (86%) of the title compound as a gray solid, which was used as-is without further purification. ¹H NMR (500 MHz, CDCl₃) δ 9.11 (s, 2H), 9.05 (s, 1H), 8.90 (s, 1H), 8.45 (dd, J=8.1, 1.4 Hz, 1H), 8.06 (d, J=8.1 Hz, 1H), 1.43-1.23 (m, 24H), 1.02 (s, 9H).

Step C: Preparation of 2-(4-(6-(1-hydroxy-2,2-dimethyl-1-(pyrimidin-5-yl)propyl)pyridin-3-yl)-3-methylphenyl)-2-methylpropanenitrile

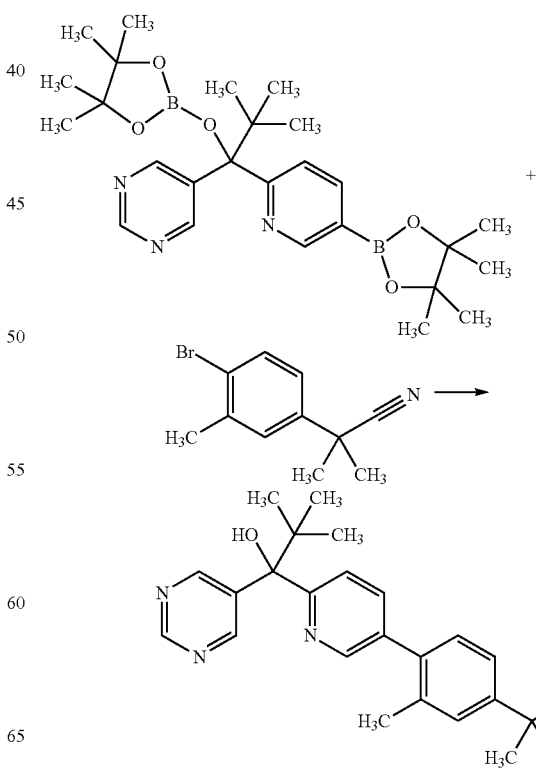

To a magnetically stirred mixture of 5-(2,2-dimethyl-1-((4,4,5,5-tetramethyl-1,3,2-dioxaborolan-2-yl)oxy)-1-(5-(4,4,5,5-tetramethyl-1,3,2-dioxaborolan-2-yl)pyridin-2-yl)propyl)pyrimidine (400 mg, 0.808 mmol) in toluene (2.423 mL) was added 2-(4-bromo-3-methylphenyl)-2-methylpropanenitrile (385 mg, 1.615 mmol), cesium fluoride (368 mg, 2.423 mmol), and tetrakis(triphenylphosphine)palladium(0) (140 mg, 0.121 mmol) in a dry 5 mL microwave vial under a $N_2$ atmosphere. Ethanol (0.808 mL) and water (0.808 mL) were added, and the reaction mixture was purged with argon for minute, then stirred at 110° C. for 30 minutes in the Biotage Initiator microwave. The reaction mixture was cooled to RT, diluted with DCM and sat'd aq. NH4Cl, and the entire mixture was filtered through a plug of cotton. The biphasic mixture was then separated on a phase sepator and the organic extracts were evaporated. The crude material was purified on silica (ISCO, 24 gram column, gradient from 10% to 50% EA/Hex over min) to afford partially purified product (254 mg). The material was triturated with benzene, then with petroleum ether to give a solid, which was washed with petroleum ether, but unable to be sufficiently purified away from a minor component. The mixture was repurified on silica (ISCO, 24 gram column, 30% isocratic EA/Hex) to afford 162 mg (48%) of the title compound as a white foam. See Table 2 for characterization data.

Example 25

5-(2-cyanopropan-2-yl)-2-(6-(1-hydroxy-2,2-dimethyl-1-(pyrimidin-5-yl)propyl)pyridin-3-yl)benzonitrile (175)

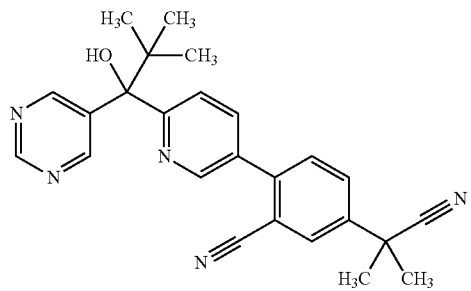

Step A: Preparation of 2-bromo-5-(hydroxymethyl)benzonitrile

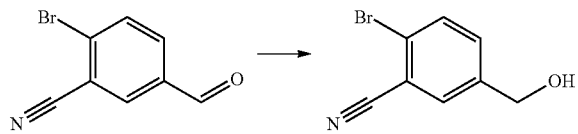 [SMILES: N#Cc1cc(C=O)ccc1Br ; N#Cc1cc(CO)ccc1Br]

To a magnetically stirred mixture of 2-bromo-5-formylbenzonitrile (1 g, 4.76 mmol) in dry EtOH (23.81 ml) at ice-bath temperatures was added $NaBH_4$ (0.216 g, 5.71 mmol) in a dry 100 mL round-bottomed flask under a $N_2$ atmosphere. The reaction mixture was stirred at reduced temperature and allowed to warm to rt overnight. The reaction mixture was evaporated to dryness, and the crude residue was diluted with sat'd aq. $NH_4Cl$ and stirred for 30 minutes. Then, 2N HCl was added with continued stirring until bubbling ceased. The resulting white precipitate was filtered with suction and air-dried to afford 688 mg (65%) of the title compound as a white solid. $^1H$ NMR (400 MHz, DMSO) δ 7.84 (d, J=5.1 Hz, 1H), 7.83 (s, 1H), 7.61-7.57 (m, 1H), 5.57 (s, 1H), 4.51 (s, 2H). $^{13}C$ NMR (101 MHz, DMSO) δ 143.50, 132.86, 132.85, 132.26, 122.08, 117.30, 113.98, 61.27. ESIMS m/z 212.0 $[M+H]^+$.

Step B: Preparation of 2-bromo-5-(chloromethyl)benzonitrile

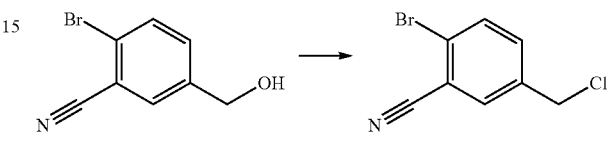

To a magnetically stirred mixture of 2-bromo-5-(hydroxymethyl)benzonitrile (0.5 g, 2.358 mmol) in dry DCM (11.79 ml) at ice-bath temperatures was added thionyl chloride (0.344 ml, 4.72 mmol) in a dry 50 mL round-bottomed flask. DMF (0.5 mL) was added to aid solubilization. The reaction mixture was stirred at reduced temperature for 15 min and then was allowed to warm to rt. After 1 h, GC-MS analysis indicated the reaction was complete. The reaction mixture was diluted with DCM and sat'd aq. $NaHCO_3$, then stirred vigorously for 30 min. The layers were separated, the aq layer was extracted again with DCM, and the combined DCM extracts were dried over sodium sulfate, and filtered through a phase separator. The DCM was evaporated to afford 485 mg (56%) of the title compound as a white wax. $^1H$ NMR (400 MHz, $CDCl_3$) δ 7.70 (d, J=3.8 Hz, 1H), 7.68 (d, J=2.1 Hz, 1H), 7.48 (dd, J=8.4, 2.3 Hz, 1H), 4.54 (s, 2H). 13C NMR (101 MHz, CDCl3) δ 137.70, 134.03, 133.82, 133.60, 125.14, 116.62, 116.36, 43.93. GC-MS m/z 231.

Step C: Preparation of 2-bromo-5-(cyanomethyl)benzonitrile

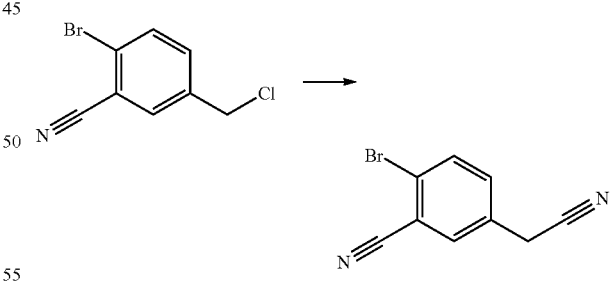

To a magnetically stirred mixture of 2-bromo-5-(chloromethyl)benzonitrile (0.485 g, 2.104 mmol) in dry DMSO (5.26 ml) was added sodium cyanide (0.155 g, 3.16 mmol) in a dry 25 mL vial under a $N_2$ atmosphere. The reaction mixture was stirred at rt overnight. GC-MS indicated the reaction was complete. The mixture was diluted with sat'd aq. $NaHCO_3$ and extracted with ether (3×). The combined ether extracts were dried over sodium sulfate, filtered, and evaporated. The crude material was purified on silica (ISCO, 40 gram column, gradient to 80% acetone/Hex over 20 min, monitor UV @ 220 nm) to afford 372 mg (72%) of the title compound as an orange wax. ¹H NMR (400 MHz, CDCl₃) δ 7.74 (d, J=8.4 Hz, 1H), 7.64 (d, J=2.3 Hz, 1H), 7.46 (dd, J=8.3, 2.3 Hz, 1H), 3.78 (s, 2H). 13C NMR (101 MHz, CDCl3) δ 134.06, 133.48, 133.29, 130.30, 125.27, 116.90, 116.32, 23.00. GC-MS m/z 220.

Step D: Preparation of 2-bromo-5-(2-cyanopropan-2-yl)benzonitrile

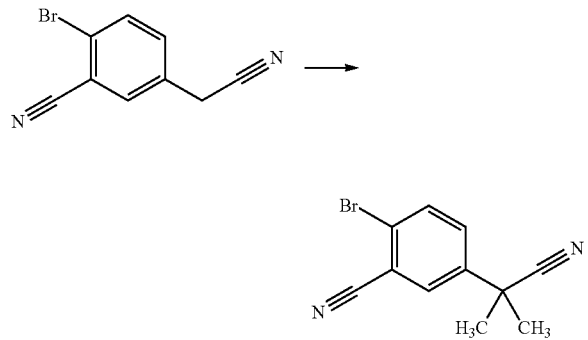

To a magnetically stirred mixture of 2-bromo-5-(cyanomethyl)benzonitrile (0.372 g, 1.683 mmol) in dry THF (8.41 ml) at ice-bath temperatures was added NaH (0.202 g, 5.05 mmol) in a dry 50 mL round-bottomed flask under a N₂ atmosphere. The reaction mixture was stirred at reduced temperature for 5 min, then iodomethane (0.316 ml, 5.05 mmol) was added, and the reaction mixture was allowed to warm to rt overnight. The reaction mixture was diluted with ether and sat'd aq. NH₄Cl, and the layers were separated. The aq layer was extracted again with ether, and the combined ether extracts were dried over sodium sulfate, filtered through a short pad of silica, and evaporated to afford 419 mg (95%) of the title compound as a yellow wax. ¹H NMR (400 MHz, CDCl₃) δ 7.74 (s, 1H), 7.73 (d, J=6.0 Hz, 1H), 7.60 (dd, J=8.5, 2.5 Hz, 1H), 1.74 (s, 6H). 13C NMR (101 MHz, CDCl3) δ 141.88, 133.86, 130.99, 130.88, 124.86, 122.87, 116.69, 116.60, 36.85, 28.82. GCMS m/z 248.

Step E: Preparation of 5-(2-cyanopropan-2-yl)-2-(6-(1-hydroxy-2,2-dimethyl-1-(pyrimidin-5-yl)propyl)pyridin-3-yl)benzonitrile

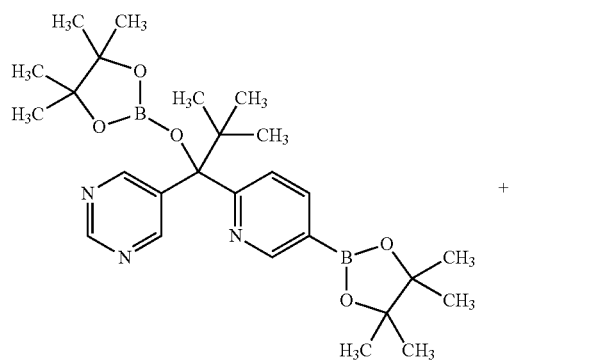

+

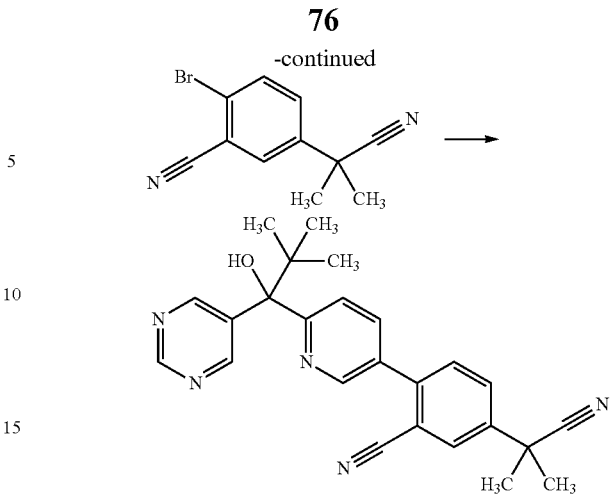

To a magnetically stirred mixture of 5-(2,2-dimethyl-1-((4,4,5,5-tetramethyl-1,3,2-dioxaborolan-2-yl)oxy)-1-(5-(4,4,5,5-tetramethyl-1,3,2-dioxaborolan-2-yl)pyridin-2-yl)propyl)pyrimidine (0.5 g, 1.010 mmol) in dry toluene (4.45 ml) and ethanol (0.297 ml) was added potassium phosphate (0.643 g, 3.03 mmol), 2-bromo-5-(2-cyanopropan-2-yl)benzonitrile (0.377 g, 1.514 mmol), tetrakis(triphenylphosphine)palladium(0) (0.117 g, 0.101 mmol), and water (0.297 ml) in a dry 10 mL microwave vial under an argon atmosphere. The reaction mixture was purged with argon for 1 min, then heated with stirring in the Biotage Initiator microwave at 110° C. for 30 min. The crude material was purified on silica (ISCO, gram column, gradient to 50% ether/DCM over 15 min) to afford 214 mg (49%) of the title compound as a white foam. ¹H NMR (400 MHz, CDCl₃) δ 9.24 (s, 2H), 9.10 (s, 1H), 8.75 (d, J=1.6 Hz, 1H), 8.02 (dd, J=8.3, 2.3 Hz, 1H), 7.95-7.91 (m, 1H), 7.90 (d, J=2.0 Hz, 1H), 7.86 (dd, J=8.3, 2.1 Hz, 1H), 7.58 (d, J=8.2 Hz, 1H), 5.81 (s, 1H), 1.80 (s, 6H), 1.10 (s, 9H). ¹³C NMR (126 MHz, CDCl₃) δ 161.16, 157.01, 156.41, 146.60, 142.76, 140.39, 136.75, 136.73, 132.24, 130.71, 130.63, 130.44, 123.12, 122.12, 122.08, 117.50, 112.30, 40.25, 36.95, 28.90, 26.30. ESIMS m/z 412.5 [M+H]⁺.

Example 26

Preparation of 2-(4-(6-(1-hydroxy-2,2-dimethyl-1-(pyrimidin-5-yl)propyl)pyridin-3-yl)-3-(methylthio)phenyl)-2-methylpropanenitrile (216)

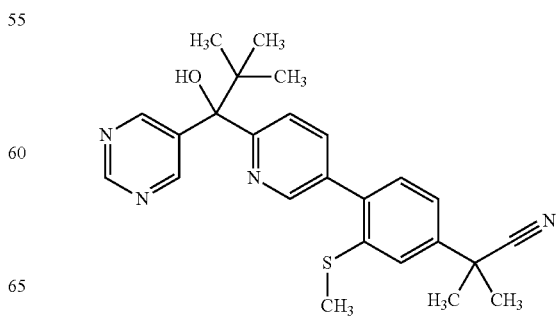

Step A: Preparation of 2-(3-fluoro-4-(6-(1-hydroxy-2,2-dimethyl-1-(pyrimidin-5-yl)propyl)pyridin-3-yl)phenyl)-2-methylpropanenitrile

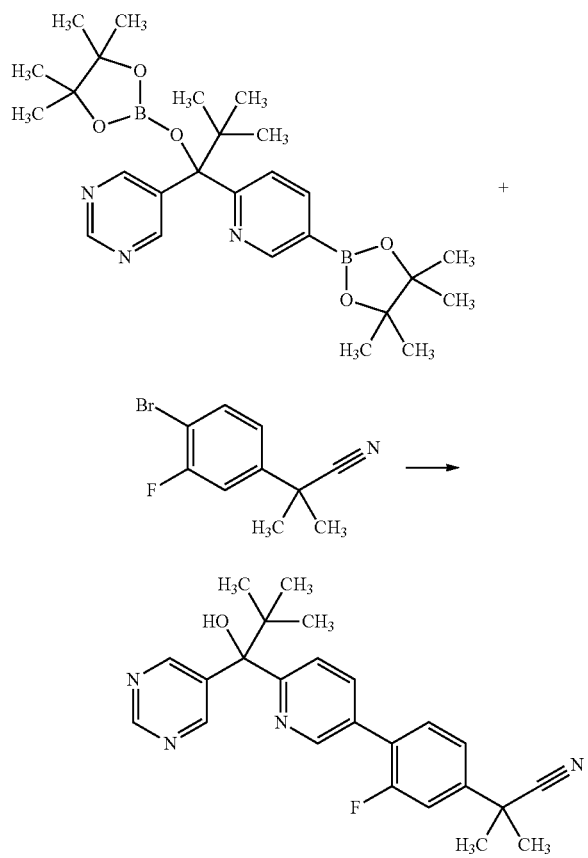

The title compound (159) was prepared from 5-(2,2-dimethyl-1-((4,4,5,5-tetramethyl-1,3,2-dioxaborolan-2-yl)oxy)-1-(5-(4,4,5,5-tetramethyl-1,3,2-dioxaborolan-2-yl)pyridin-2-yl)propyl)pyrimidine and 2-(4-bromo-3-fluorophenyl)-2-methylpropanenitrile according to the conditions described in Example 24C and was isolated in 43% as a brown oil. See Table 2 for characterization data.

Step B: Preparation of 2-(4-(6-(1-hydroxy-2,2-dimethyl-1-(pyrimidin-5-yl)propyl)pyridin-3-yl)-3-(methylthio)phenyl)-2-methylpropanenitrile

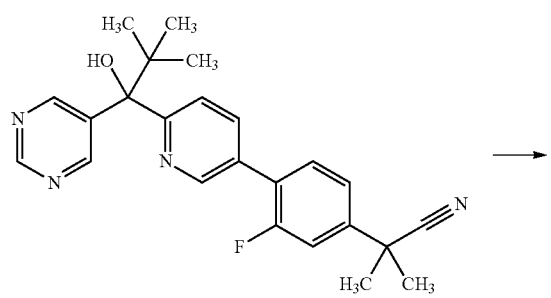

-continued

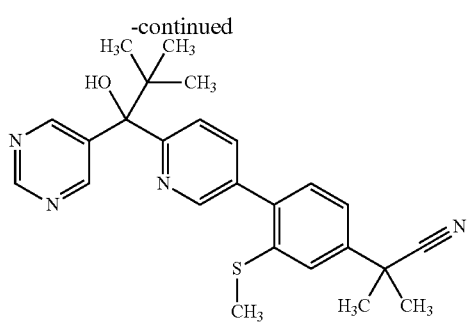

To a magnetically stirred mixture of 2-(3-fluoro-4-(6-(1-hydroxy-2,2-dimethyl-1-(pyrimidin-5-yl)propyl)pyridin-3-yl)phenyl)-2-methylpropanenitrile (50 mg, 0.124 mmol) in dry DMSO (1.648 mL) was added sodium thiomethoxide (43.3 mg, 0.618 mmol) in a dry 5 mL microwave vial under a $N_2$ atmosphere. The reaction mixture was stirred at 100° C. in the microwave for 45 min, then overnight at rt. UPLC-MS analysis indicated ~75% conversion. The reaction mixture was resubjected to heating in the microwave for 30 min at 100° C. The reaction mixture was cooled to rt and loaded directly onto silica. The crude material was purified on silica (ISCO, 24 gram column, stepwise gradient from 0% to 10% to 20% etc. to 60% ether/hexanes over 20 min) to afford only partially purified material. The product-containing fractions were combined and evaporated and the material was again purified on silica (ISCO, 24 gram column, gradient from 0 to 50% ether/DCM) to afford 45 mg (76%) of the title compound as a white foam. $^1$H NMR (300 MHz, CDCl$_3$) δ 9.23 (s, 2H), 9.09 (s, 1H), 8.59 (dd, J=2.0, 1.0 Hz, 1H), 7.86 (d, J=2.1 Hz, 1H), 7.84 (d, J=1.0 Hz, 1H), 7.44 (d, J=1.9 Hz, 1H), 7.31 (dd, J=8.0, 2.0 Hz, 1H), 7.22 (d, J=8.0 Hz, 1H), 6.30 (s, 1H), 2.42 (s, 3H), 1.79 (s, 6H), 1.09 (s, 9H). 13C NMR (126 MHz, CDCl3) δ 159.25, 158.68, 156.90, 156.43, 147.21, 142.40, 138.62, 137.54, 137.11, 135.79, 134.67, 130.58, 124.07, 122.80, 121.73, 121.49, 40.14, 37.26, 29.11, 26.35, 15.97. ESIMS m/z 433.5 [M+H]$^+$.

Example 27

Preparation of 1-(pyrimidin-5-yl)-1-(5-(4-(trifluoromethoxy)phenyl)pyridin-2-yl)but-2-yn-1-ol (199)

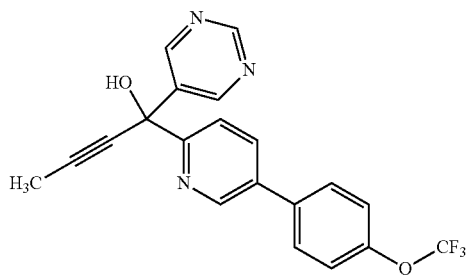 [SMILES: CC#CC(O)(c1cncnc1)c1ccc(-c2ccc(OC(F)(F)F)cc2)cn1]

Step A: Preparation of N-methoxy-N-methylpyrimidine-5-carboxamide

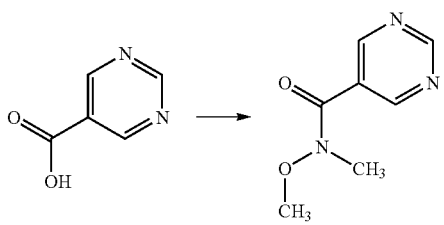

To a stirred mixture of pyrimidine-5-carboxylic acid (2.5 g, 20.15 mmol), and N,O-dimethyl hydroxylamine hydrochloride (2.49 g, 25.5 mmol) in DCM (50 mL), EDC.HCl (4.63 g, 24.17 mmol) and DMAP (3.69 g, 30.2 mmol) were added under a nitrogen atmosphere. The resulting reaction mixture was stirred at room temperature for 14 h. The reaction mixture was concentrated under reduced pressure; the obtained crude material was purified by flash column chromatography (100-200, SiO$_2$, 50-70% EA/Hexanes) to get N-methoxy-N-methylpyrimidine-5-carboxamide as a pale brown liquid. The product was confirmed by $^1$H NMR and LCMS. (2.8 g, 83%). $^1$H NMR (400 MHz, CDCl$_3$) δ 9.28 (s, 1H), 9.10 (s, 2H), 3.59 (s, 3H), 3.41 (s, 3H); ESIMS m/z 167.97 [M+H]$^+$.

Step B: Preparation of (5-bromopyridin-2-yl)(pyrimidin-5-yl)methanone

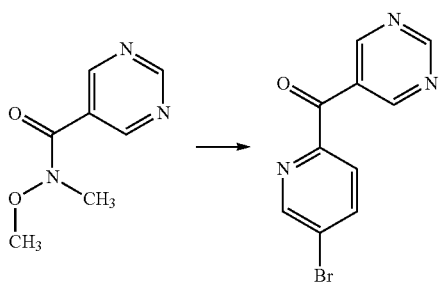

To a stirred solution of 5-bromo-2-iodopyridine (5 g, 17.60 mmol) in dry THF (50 mL), was added isopropyl magnesium chloride (2.0 M, 9.7 mL, 19.36 mmol) at 0° C. and the reaction mixture was stirred for 15 min at 0° C. before the addition of N-methoxy-N-methylpyrazine-2-carboxamide (3.2 g, 19.36 mmol) in dry THF (10 mL). The resulting reaction mixture was stirred for 2 h at RT. Then the reaction mixture was quenched with saturated NH$_4$Cl solution and was extracted with EtOAc. The organic layer was washed with brine, dried over Na$_2$SO$_4$, filtered and was concentrated under reduced pressure. The obtained crude product was purified by column chromatography (100-200 mesh silica) to afford (5-bromopyridin-2-yl) (pyrazin-2-yl) methanone (2) as a pale yellow solid (2 g, 43%). $^1$H NMR (300 MHz, CDCl$_3$) δ 9.49 (s, 2H), 9.38 (s, 1H), 8.82 (s, 1H), 8.12 (d, J=2.1 Hz, 2H); ESIMS m/z 264.10 [M+H]$^+$.

Step C: Preparation of pyrimidin-5-yl(5-(4-(trifluoromethoxy)phenyl)pyridin-2-yl)methanone

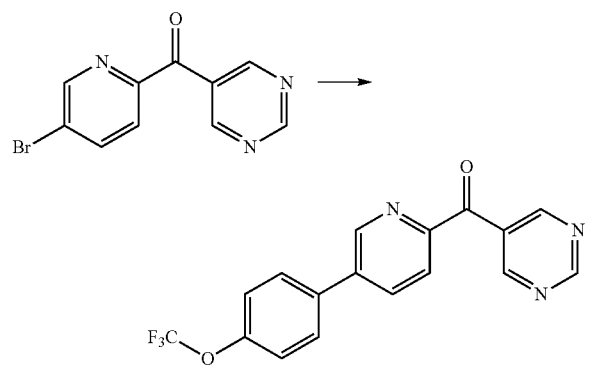

To a stirred solution of 5-bromopyridin-2-yl)(pyrimidin-5-yl)methanone (1.0 g, 3.816 mmol) in dry THF (25 mL) was added 4-(trifluoromethoxy)phenylboronic acid (0.930 g, 4.580 mmol) and K$_3$PO$_4$ (2.57 g, 11.450 mmol). The reaction mixture was then degassed with argon for 5 min, X-phos (70 mg, 4 mol %) and Pd(OAc)$_2$ (50 mg, 2 mol %) were added, and the reaction mixture was heated to 70-80° C. in a closed vessel for 5 h. The reaction mixture was cooled to room temperature, diluted with water and was extracted with ethyl acetate (3×20 mL). The combined organic layer was dried over anhydrous MgSO$_4$ and the volatiles were removed under reduced pressure. The resulting crude material was purified by column chromatography, eluting with 20-25% ethyl acetate in hexanes to afford pyrimidin-5-yl(5-(4-(trifluoromethoxy)phenyl)pyridin-2-yl)methanone (3) as a pale yellow solid (1.0 g, 63%); $^1$H NMR (400 MHz, CDCl$_3$) δ 9.55 (s, 2H), 9.39 (s, 1H), 8.84 (d, J=1.5 Hz, 1H), 8.33 (dd, J=2.4, 8.0 Hz, 1H), 8.16 (dd, J=2.4, 8.0 Hz, 1H), 7.70 (d, J=8.0 Hz, 2H), 7.40 (d, J=8.0 Hz, 2H); ESIMS m/z 346.47[M+H]$^+$.

Step D: Preparation of 1-(pyrimidin-5-yl)-1-(5-(4-(trifluoromethoxy)phenyl)pyridin-2-yl)but-2-yn-1-ol

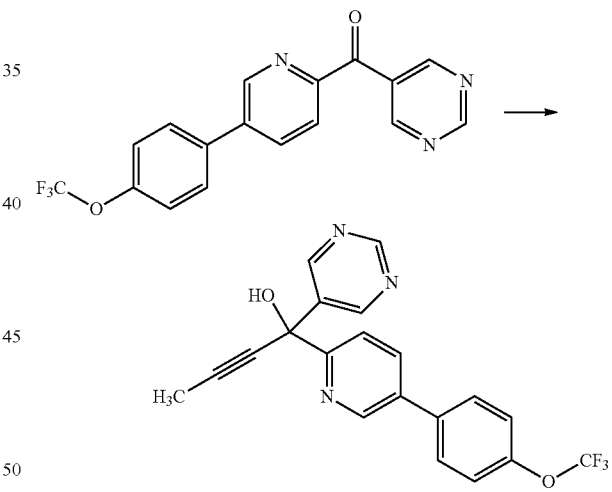

A stirred solution of pyrimidin-5-yl(5-(4-(trifluoromethoxy)phenyl)pyridin-2-yl)methanone (0.505 g, 1.464 mmol) in dry THF (17 mL) was cooled to −78° C., Prop-1-yn-1-ylmagnesium bromide (0.5 M, 8.78 mL, 4.39 mmol) was added and stirred for 1 h at −78° C. The reaction mixture was quenched with saturated aq. NH4Cl solution and was extracted with Ethyl acetate. The organic layer was washed with brine, dried over Na2SO4, filtered and concentrated under reduced pressure. The crude product was purified by column chromatography (100-200 mesh silica) to afford 350 mg (62%) of the title compound as a brown sticky liquid. See Table 2 for characterization data.

Example 28

Preparation of 2-(4-(6-(1-hydroxy-1-(4-methoxypyrimidin-5-yl)-2,2-dimethylpropyl)pyridin-3-yl)-3-methylphenyl)-2-methylpropanenitrile (129)

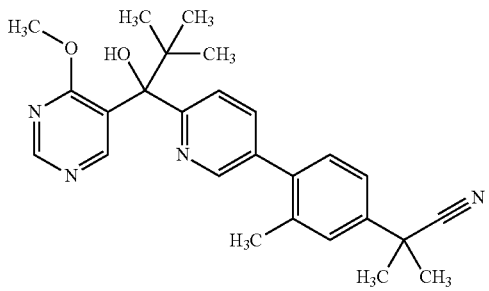 [SMILES: COc1ncncc1C(O)(c1ccc(-c2ccc(C(C)(C)C#N)cc2C)cn1)C(C)(C)C]

Step A: Preparation of N,4-dimethoxy-N-methylpyrimidine-5-carboxamide

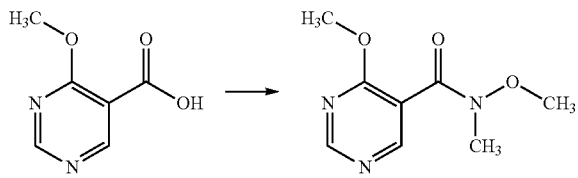

In a 500 mL single-neck flask equipped with a stir bar, 4-methoxypyrimidine-5-carboxylic acid (8.0 g, 33.2 mmol) and N,O-dimethylhydroxylamine hydrochloride (4.30 g, 43.2 mmol) were stirred in DCM (166 ml). DMAP (6.15 g, 49.8 mmol) and EDC hydrochloride (7.72 g, 39.9 mmol) were added. The mixture was stirred at 18° C. for 64 h, then silica (~50 g) was added to the reaction mixture. The yellow suspension was concentrated then loaded onto silica (~100 g). Chromatographed through a silica column (80 g) using EtOAc. The product fractions were concentrated to provide 2.4 g (36%) of the title compound a colorless oil which was used without further purification. $^1$H NMR (400 MHz, CDCl$_3$) δ 8.81 (s, 1H), 8.48 (s, 1H), 4.05 (d, J=0.7 Hz, 3H), 3.55 (s, 3H), 3.35 (s, 3H).

Step B: Preparation of (5-bromopyridin-2-yl)(4-methoxypyrimidin-5-yl)methanone

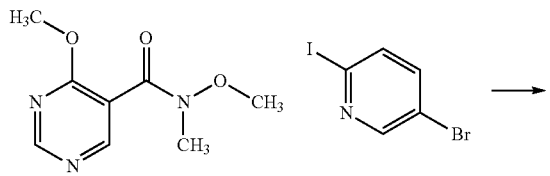

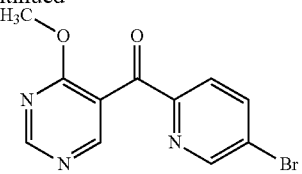

In a 3-neck 250 mL flask equipped with nitrogen inlet and temperature probe, 5-bromo-2-iodopyridine (5.02 g, 17.34 mmol) was stirred in THF (28.9 ml) at −15° C. Isopropylmagnesium chloride (2M, THF) (8.67 ml, 17.34 mmol) was added dropwise to maintain T<−10° C. The brown suspension was stirred for 1 h at −10° C. A solution of N,4-dimethoxy-N-methylpyrimidine-5-carboxamide (2.4 g, 11.56 mmol) in THF (20 mL) was added dropwise to maintain T=−10° C. After stirring at −10° C. for 30 min (solids dissolved), the cold bath was kept in place and the mixture was allowed to warm. After 3 h, the temperature had reached 5° C. 1N HCl (20 mL) was added to adjust the pH to ~7. The mixture was extracted with EtOAc (2×100 mL). The combined extracts were dried over Na$_2$SO$_4$, filtered and concentrated to provide a yellow oil. The crude material was loaded onto silica (25 g) using DCM and chromatographed on silica (80 g) using 40% EtOAc/hexanes to afford 2.19 g (61%) of the title compound as beige solid. $^1$H NMR (400 MHz, CDCl$_3$) δ 8.91 (d, J=1.7 Hz, 1H), 8.74-8.66 (m, 2H), 8.06 (dd, J=8.3, 2.1 Hz, 1H), 8.03-7.97 (m, 1H), 3.95 (d, J=1.7 Hz, 3H). HRMS-ESI (m/z) [M+H]+ calcd for C$_{11}$H$_9$BrN$_3$O$_2$, 293.9873; found, 293.9873.

Step C: Preparation of 1-(5-bromopyridin-2-yl)-1-(4-methoxypyrimidin-5-yl)-2,2-dimethylpropan-1-ol

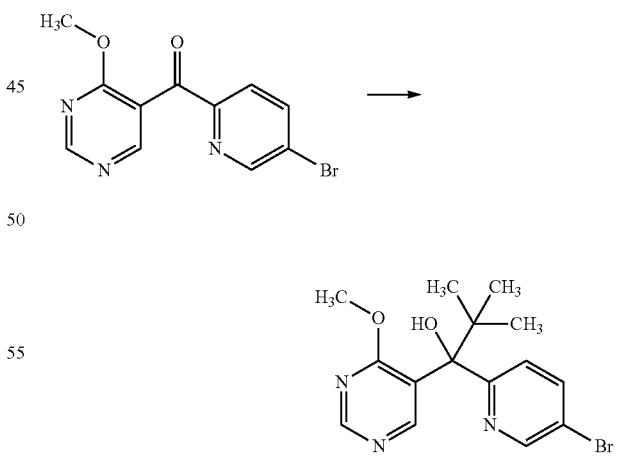

In a 200 mL single-neck flask equipped with stir bar, temperature probe and nitrogen inlet, (5-bromopyridin-2-yl)(4-methoxypyrimidin-5-yl)methanone (2.19 g, 7.07 mmol) was stirred in THF (60 mL). The solution was cooled to −75° C. Tert-Butylmagnesium chloride (2M, Et$_2$O) (4.24 mL, 8.49 mmol) was added dropwise by syringe maintaining T<-70° C. The orange mixture was stirred at -75° C. After 1 h, the cold bath was removed and the mixture was quickly but cautiously quenched with 0.5N HCl (17 mL) (final pH~7). The mixture was extracted with EtOAc (2×50 mL). The combined extracts were dried over Na$_2$SO$_4$, filtered and concentrated to provide an orange oil. The oil was dissolved in DCM and loaded onto silica (25 g). Purification via flash chromatography (silica, 25-40% EtOAc/Hexanes) afforded 1.38 g (50%) of the title compound as a yellow oil. $^1$H NMR (500 MHz, CDCl$_3$) δ 9.12 (s, 1H), 8.66 (s, 1H), 8.58 (dd, J=2.4, 0.5 Hz, 1H), 7.77 (dd, J=8.7, 2.4 Hz, 1H), 7.61 (dd, J=8.5, 0.6 Hz, 1H), 5.44 (s, 1H), 3.84 (s, 3H), 1.11 (s, 9H). HRMS-ESI (m/z) [M+H]+ calcd for C$_{15}$H$_{19}$BrN$_3$O$_2$, 352.0655; found, 352.0649.

Step D: Preparation of 5-(2,2-dimethyl-1-((4,4,5,5-tetramethyl-1,3,2-dioxaborolan-2-yl)oxy)-1-(5-(4,4,5,5-tetramethyl-1,3,2-dioxaborolan-2-yl)pyridin-2-yl)propyl)-4-methoxypyrimidine

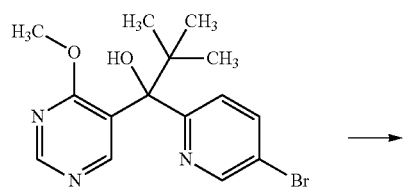

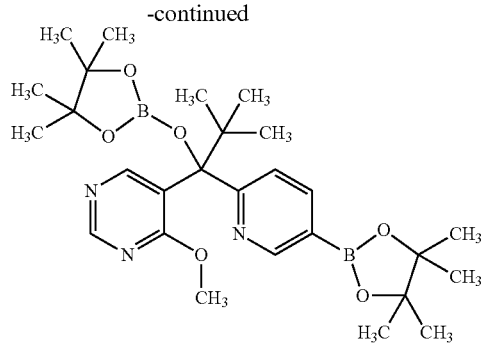

In a single-neck 200 mL flask equipped with stir bar, temperature probe and nitrogen inlet, 1-(5-bromopyridin-2-yl)-1-(4-methoxypyrimidin-5-yl)-2,2-dimethylpropan-1-ol (1.38 g, 3.53 mmol) was stirred in dioxane (35.3 ml). Potassium acetate (0.454 g, 4.58 mmol) and 4,4,4',4',5,5,5',5'-octamethyl-2,2'-bi(1,3,2-dioxaborolane) (0.904 g, 3.53 mmol) were added. The mixture was sparged with nitrogen for 5 min. Pd(dppf)Cl$_2$ (0.131 g, 0.176 mmol) was added. The mixture was heated to 85° C. After 3 h, no starting material was detected by UPLC. The mixture was allowed to cool to rt. The mixture was diluted with DCM (50 mL) and filtered through Celite. The filtrate was concentrated to dryness to provide a black foam. The crude foam was taken up in DMSO (~8 mL) and MeOH (~3 mL) and was purified via reverse phase chromatography (C18, 250 g, 30-70% ACN/water) to afford 750 mg (36%) of title compound as a white solid which was used as-is without further purification. $^1$H NMR (400 MHz, CDCl$_3$) δ 9.27 (s, 1H), 8.85 (s, 1H), 8.65 (s, 1H), 8.33 (q, J=8.1 Hz, 2H), 3.85 (s, 3H), 1.44-0.84 (m, 33H).

Step E: Preparation of 2-(4-(6-(1-hydroxy-1-(4-methoxypyrimidin-5-yl)-2,2-dimethylpropyl)pyridin-3-yl)-3-methylphenyl)-2-methylpropanenitrile

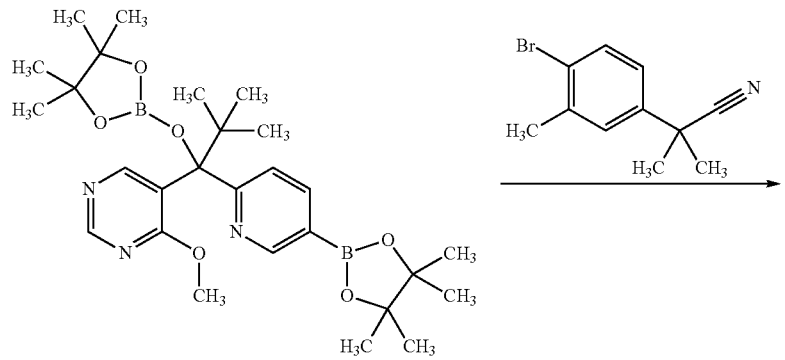

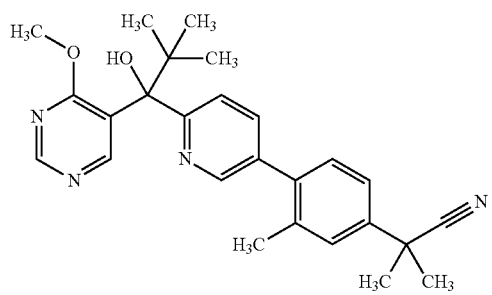

To a magnetically stirred mixture of 5-(2,2-dimethyl-1-((4,4,5,5-tetramethyl-1,3,2-dioxaborolan-2-yl)oxy)-1-(5-(4,4,5,5-tetramethyl-1,3,2-dioxaborolan-2-yl)pyridin-2-yl)propyl)-4-methoxypyrimidine (100 mg, 0.190 mmol) in dry toluene (2285 µl) was added 2-(4-bromo-3-methylphenyl)-2-methylpropanenitrile (54.4 mg, 0.228 mmol) (prepared as described in 24A), cesium fluoride (87 mg, 0.571 mmol), and tetrakis(triphenylphosphine)palladium (0) (22.00 mg, 0.019 mmol) in a dry 5 mL microwave vial under a N₂ atmosphere. EtOH (762 µl) and water (762 µl) were added, and the reaction mixture was purged with argon for 1 min. The reaction mixture was stirred at 110° C. for 30 min in a Biotage Initiator microwave, cooled to rt, and loaded onto a Celite dry-load cartridge. The crude material was purified on silica (ISCO, 24 gram column, gradient to 50% ether/DCM over 15 min) to afford 40 mg (46.4%) of the title compound as a clear viscous oil. See Table 2 for characterization data.

Example 29

Preparation of 2-(3-ethyl-4-(6-(1-hydroxy-2,2-dimethyl-1-(pyrimidin-5-yl)propyl)pyridin-3-yl)phenyl)-2-methylpropanenitrile (112)

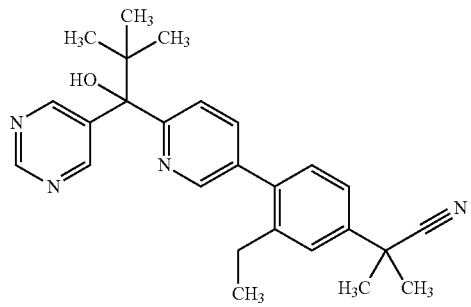

Step A: Preparation of 4-bromo-3-ethylbenzaldehyde

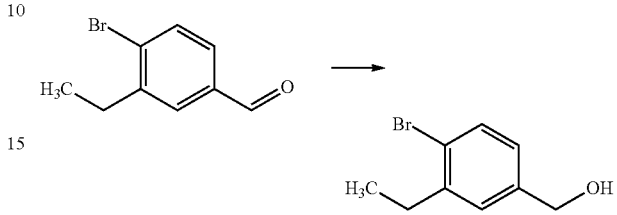

To a 200 mL round bottom flask was added 1-bromo-2-ethyl-4-iodobenzene (5.0 g, 16.08 mmol) and ethyl ether (161 mL). The reaction was placed under inert atmosphere and cooled in a dry ice/acetone bath. Then n-butyllithium (6.75 mL, 16.88 mmol) was added dropwise. The reaction was allowed to stir for 20 min. Then N,N-dimethylformamide (1.364 mL, 17.69 mmol) was added and the reaction was allowed to warm to rt as the ice bath melted. The reaction mixture was poured into brine solution and extracted with EtOAc (2×25 mL). The combined organics were dried over MgSO₄, filtered, and concentrated. The resulting residue was purified by flash chromatography (ISCO 24 g silica 0-30% EtOAc in Hex) to afford 2.95 g (85%) of the title compound as a yellow liquid. ¹H NMR (400 MHz, DMSO) δ 10.00 (s, 1H), 7.86 (t, J=2.2 Hz, 1H), 7.82 (dd, J=8.2, 3.1 Hz, 1H), 7.66 (dt, J=8.2, 2.1 Hz, 1H), 2.79 (qd, J=7.5, 2.5 Hz, 2H), 1.22 (td, J=7.5, 1.7 Hz, 3H). ¹³C NMR (101 MHz, DMSO) δ 192.25, 143.66, 135.68, 133.36, 130.37, 130.18, 128.31, 28.50, 13.74. EIMS m/z 213.

Step B: Preparation of (4-bromo-3-ethylphenyl)methanol

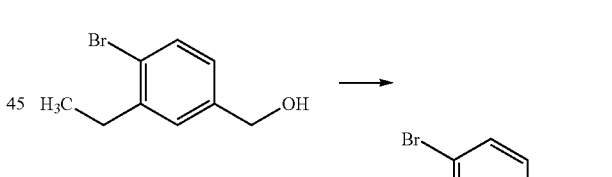

To a 200 mL round bottom flask charged with 4-bromo-3-ethylbenzaldehyde (2.954 g, 13.86 mmol) was added THF (100 mL) and sodium borohydride (0.551 g, 14.56 mmol). The reaction was allowed to stir overnight at rt. The reaction was quenched with water. The resulting solution was poured into brine solution and extracted with EtOAc (3×50 mL). The combined organics were dried over MgSO₄ filtered and concentrated. The resulting residue was purified by flash chromatography (ISCO 40 g silica 0-20% EtOAc in Hex) to afford 2.58 g (86%) of the title compound as light yellow liquid. ¹H NMR (400 MHz, DMSO) δ 7.50 (d, J=8.2 Hz, 1H), 7.28 (d, J=2.1 Hz, 1H), 7.08 (dd, J=8.2, 2.2 Hz, 1H), 5.25 (t, J=5.7 Hz, 1H), 4.46 (d, J=5.7 Hz, 2H), 2.69 (q, J=7.5 Hz, 2H), 1.16 (t, J=7.5 Hz, 3H). ¹³C NMR (126 MHz, DMSO) δ 142.97, 142.57, 132.49, 128.27, 126.43, 121.72, 62.67, 29.20, 14.77. EIMS m/z 215.

Step C: Preparation of 1-bromo-4-(chloromethyl)-2-ethylbenzene

To a 200 mL round bottom flask charged with (4-bromo-3-ethylphenyl)methanol (2.576 g, 11.98 mmol) was added dichloromethane (DCM) (100 mL), triethylamine (3.34 mL, 23.95 mmol), and methanesulfonyl chloride (1.120 mL, 14.37 mmol). The reaction was allowed to stir at room temperature for over the weekend. The reaction was poured into brine solution and extracted with additional DCM (3×30 mL). The combined organics were dried over MgSO4 filtered and concentrated. The resulting residue was purified by flash chromatography (ISCO 40 g Silica 0-50% EtOAc in Hex) to afford 1.9 g (67%) of the title compound as a clear liquid. ¹H NMR (400 MHz, DMSO) δ 7.57 (d, J=8.2 Hz, 1H), 7.41 (d, J=2.2 Hz, 1H), 7.21 (dd, J=8.2, 2.3 Hz, 1H), 4.73 (s, 2H), 2.70 (q, J=7.5 Hz, 2H), 1.17 (t, J=7.5 Hz, 3H). ¹³C NMR (126 MHz, DMSO) δ 143.36, 138.00, 133.15, 130.59, 128.75, 123.77, 45.80, 29.12, 14.55. EIMS m/z 233.

Step D: Preparation of 2-(4-bromo-3-ethylphenyl)acetonitrile

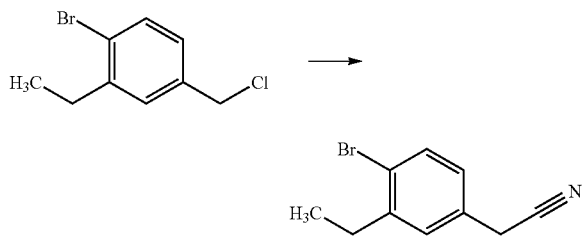

To a 200 mL round bottom flask, charged with 1-bromo-4-(chloromethyl)-2-ethylbenzene (1.9 g, 8.14 mmol) was added DMF (40.7 ml) and potassium cyanide (0.583 g, 8.95 mmol). The reaction was allowed to stir for 3 h. Analysis by GCMS showed ~50% completion. The reaction was allowed to stir overnight at rt. The reaction was poured into saturated $Na_2CO_3$ solution and extracted with EtOAc (3×40 mL). The combined organics were dried over $MgSO_4$ filtered and concentrated. The resulting residue was purified by flash chromatography (ISCO 40 g silica 0-40 EtOAc in Hex) to afford 1.152 g (63%) of the title compound as a clear liquid. $^1$H NMR (400 MHz, DMSO) δ 7.60 (d, J=8.2 Hz, 1H), 7.33 (d, J=2.3 Hz, 1H), 7.14 (dd, J=8.2, 2.4 Hz, 1H), 4.02 (s, 2H), 2.70 (q, J=7.5 Hz, 2H), 1.17 (t, J=7.5 Hz, 3H). $^{13}$C NMR (126 MHz, DMSO) δ 143.67, 133.39, 131.69, 129.98, 128.09, 123.02, 119.39, 29.13, 22.36, 14.58. EIMS m/z 224.

Step E: Preparation of 2-(4-bromo-3-ethylphenyl)-2-methylpropanenitrile

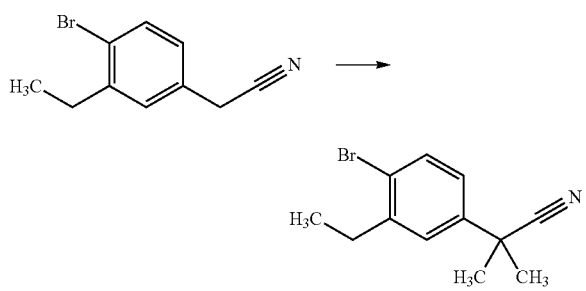

To a 20 mL vial charged with 2-(4-bromo-3-ethylphenyl)acetonitrile (1.052 g, 4.69 mmol) was added THF (45.0 mL). The reaction was cooled in a ice water bath, then potassium tert-butoxide (1.185 g, 10.56 mmol) was added. The reaction was allowed to stir for 20 min then iodomethane (0.646 mL, 10.33 mmol) was added. The reaction was allowed to stir for 4 h. The reaction was then poured into brine solution and extracted with EtOAc (2×30 mL). The combined organics were dried over $MgSO_4$, filtered and concentrated. The resulting residue was purified by flash chromatography (ISCO 40 g silica 0-30% EtOAc in Hex) to afford 1.05 g (88%) of the title compound as a semi-solid. $^1$H NMR (300 MHz, DMSO) δ 7.62 (d, J=8.4 Hz, 1H), 7.48 (d, J=2.5 Hz, 1H), 7.29 (dd, J=8.4, 2.6 Hz, 1H), 2.73 (q, J=7.5 Hz, 2H), 1.68 (s, 6H), 1.18 (t, J=7.5 Hz, 3H). $^{13}$C NMR (126 MHz, DMSO) δ 143.69, 141.88, 133.31, 127.21, 125.31, 124.79, 123.08, 36.89, 29.35, 28.64, 14.77. EIMS m/z 252.

Step F: Preparation of 2-(3-ethyl-4-(6-(1-hydroxy-2,2-dimethyl-1-(pyrimidin-5-yl)propyl)pyridin-3-yl)phenyl)-2-methylpropanenitrile

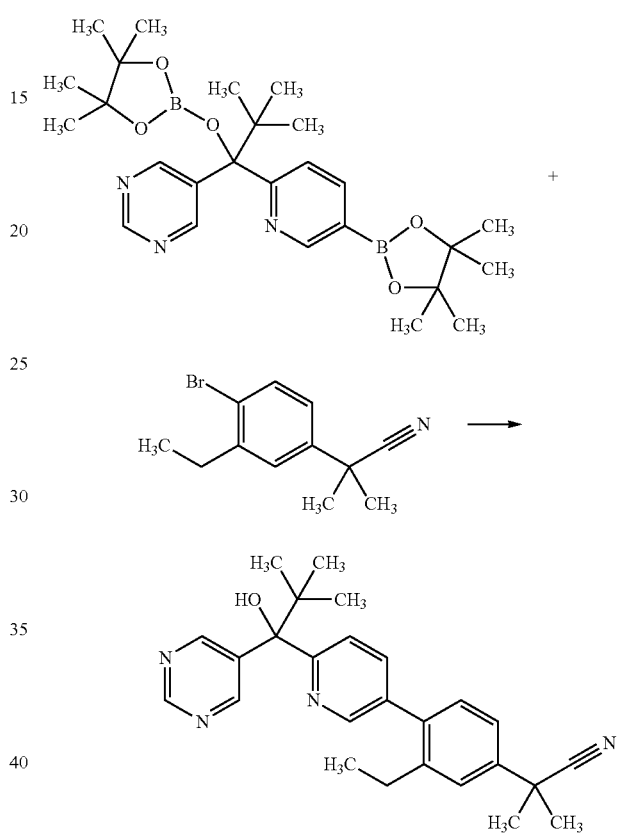

To a 20 mL microwave vessel 5-(2,2-dimethyl-1-((4,4,5,5-tetramethyl-1,3,2-dioxaborolan-2-yl)oxy)-1-(5-(4,4,5,5-tetramethyl-1,3,2-dioxaborolan-2-yl)pyridin-2-yl)propyl)pyrimidine (500 mg, 1.010 mmol), potassium phosphate (536 mg, 2.52 mmol) and bis(triphenylphosphine)palladium (II) chloride (35.4 mg, 0.050 mmol) were charged. The vessel was sealed and pumped and purged with $N_2$ gas (3×). Then a solution of 2-(4-bromo-3-ethylphenyl)-2-methylpropanenitrile (305 mg, 1.212 mmol) in Dioxane (5.0 mL) was added followed by water (1.250 mL). The reaction was pumped and purged with $N_2$ gas (3×). The reaction was heated to 100° C. for 1 h using microwave power. The reaction was poured into brine solution and extracted with EtOAc (2×25 mL). The combined organics were dried over $MgSO_4$ filtered and concentrated. The resulting residue was purified by flash chromatography (ISCO 40 g silica 0-70% EtOAc in Hexanes) and reverse phase chromatography (ISCO 100 g C18 5-100% ACN in $H_2O$) to afford 225 mg (53%) of the title compound as a white foam. See Table 2 for characterization data.

Example 30

Preparation of 1-(4-methoxypyrimidin-5-yl)-2,2-dimethyl-1-(5-(2,2,2-trifluoroethoxy)-[2,3'-bipyridin]-6'-yl)propan-1-ol (119)

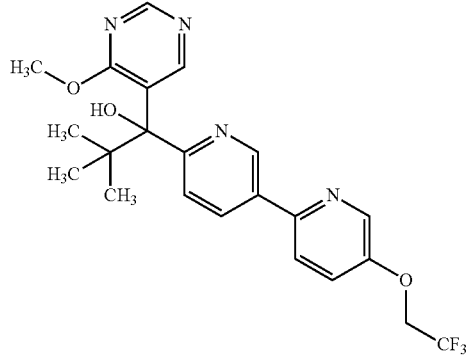 [SMILES: COc1ncncc1C(O)(c1ccc(-c2ccc(OCC(F)(F)F)cn2)cn1)C(C)(C)C]

Step A: Preparation of N,4-dimethoxy-N-methylpyrimidine-5-carboxamide

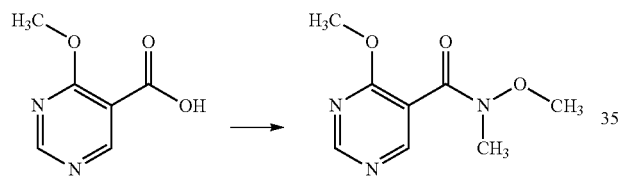

In a 500 mL single-neck flask equipped with a stir bar 4-methoxypyrimidine-5-carboxylic acid (8.0 g, 33.2 mmol) and N,O-dimethylhydroxylamine hydrochloride (4.30 g, 43.2 mmol) were stirred in DCM (166 ml). DMAP (6.15 g, 49.8 mmol) and EDC hydrochloride (7.72 g, 39.9 mmol) were added. The mixture was stirred at 18° C. for 64 h, then silica (~50 g) was added to the reaction mixture. The yellow suspension was concentrated then loaded onto silica (~100 g). Chromatographed through a silica column (80 g) using EtOAc. The product fractions were concentrated to provide 2.4 g (36%) of the title compound a colorless oil which was used without further purification. $^1$H NMR (400 MHz, CDCl$_3$) δ 8.81 (s, 1H), 8.48 (s, 1H), 4.05 (d, J=0.7 Hz, 3H), 3.55 (s, 3H), 3.35 (s, 3H).

Step B: Preparation of (5-bromopyridin-2-yl)(4-methoxypyrimidin-5-yl)methanone

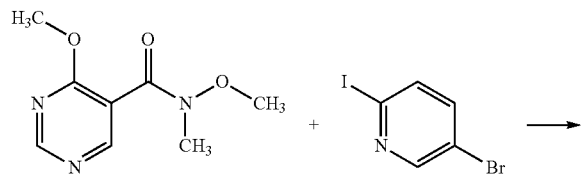

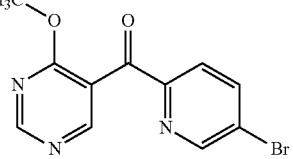

In a 3-neck 250 mL flask equipped with nitrogen inlet and temperature probe, 5-bromo-2-iodopyridine (5.02 g, 17.34 mmol) was stirred in THF (28.9 ml) at −15° C. Isopropylmagnesium chloride (2M, THF) (8.67 ml, 17.34 mmol) was added dropwise to maintain T<−10° C. The brown suspension was stirred for 1 h at −10° C. A solution of N,4-dimethoxy-N-methylpyrimidine-5-carboxamide (2.4 g, 11.56 mmol) in THF (20 mL) was added dropwise to maintain T=−10° C. After stirring at −10° C. for 30 min, the cold bath was kept in place and the mixture was allowed to warm. After 3 h, the temperature had reached 5° C. 1 N HCl (20 mL) was added to adjust the pH to ~7. The mixture was extracted with EtOAc (2×100 mL). The combined extracts were dried over Na$_2$SO$_4$, filtered and concentrated to provide a yellow oil. The crude material was loaded onto silica (25 g) using DCM and chromatographed on silica (80 g) using 40% EtOAc/hexanes to afford 2.19 g (61%) of the title compound as beige solid. $^1$H NMR (400 MHz, CDCl$_3$) δ 8.91 (d, J=1.7 Hz, 1H), 8.74-8.66 (m, 2H), 8.06 (dd, J=8.3, 2.1 Hz, 1H), 8.03-7.97 (m, 1H), 3.95 (d, J=1.7 Hz, 3H). HRMS-ESI (m/z) [M+H]$^+$ calcd for C$_{11}$H$_9$BrN$_3$O$_2$, 293.9873; found, 293.9873.

Step C: Preparation of 1-(5-bromopyridin-2-yl)-1-(4-methoxypyrimidin-5-yl)-2,2-dimethylpropan-1-ol

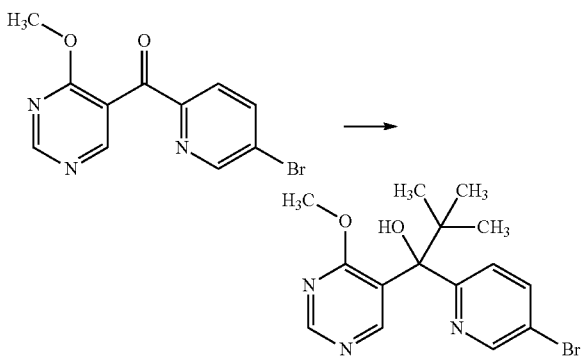

In a 200 mL single-neck flask equipped with stir bar, temperature probe and nitrogen inlet, (5-bromopyridin-2-yl)(4-methoxypyrimidin-5-yl)methanone (2.19 g, 7.07 mmol) was stirred in THF (60 nil). The solution was cooled to −75° C. tert-Butylmagnesium chloride (2M, Et2O) (4.24 ml, 8.49 mmol) was added dropwise by syringe maintaining T<−70° C. The orange mixture was stirred at −75° C. After 1 h, the cold bath was removed and the mixture was quickly but cautiously quenched with 0.5 N HCl (17 mL). (final pH~7). The mixture was extracted with EtOAc (2×50 mL). The combined extracts were dried over Na$_2$SO$_4$, filtered and concentrated to provide an orange oil. The oil was dissolved in DCM and loaded onto silica (25 g). Purification via flash chromatography on silica (80 g) using 25-40% EtOAc/hexanes afforded 1.38 g (50%) of the title compound as a yellow oil. $^1$H NMR (500 MHz, CDCl$_3$) δ 9.12 (s, 1H), 8.66 (s, 1H), 8.58 (dd, J=2.4, 0.5 Hz, 1H), 7.77 (dd, J=8.7, 2.4 Hz, 1H), 7.61 (dd, J=8.5, 0.6 Hz, 1H), 5.44 (s, 1H), 3.84 (s, 3H), 1.11 (s, 9H). HRMS-ESI (m/z) [M+H]$^+$ calcd for C$_{15}$H$_{19}$BrN$_3$O$_2$, 352.0655; found, 352.0649.

Step D: Preparation of 5-(2,2-dimethyl-1-((4,4,5,5-tetramethyl-1,3,2-dioxaborolan-2-yl)oxy)-1-(5-(4,4,5,5-tetramethyl-1,3,2-dioxaborolan-2-yl)pyridin-2-yl)propyl)-4-methoxypyrimidine

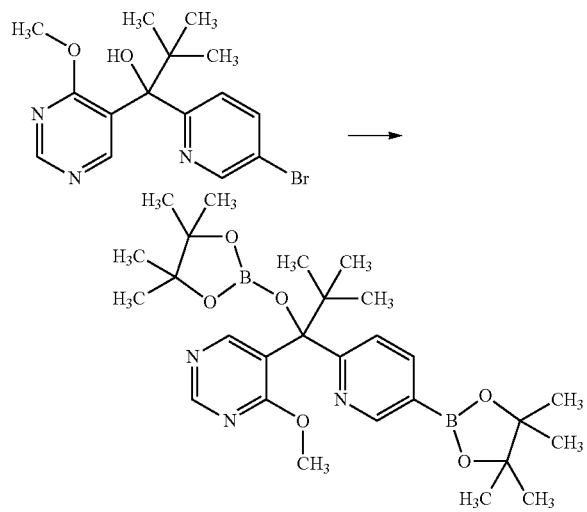

In a single-neck 200 mL flask equipped with stir bar, temperature probe and nitrogen inlet, 1-(5-bromopyridin-2-yl)-1-(4-methoxypyrimidin-5-yl)-2,2-dimethylpropan-1-ol (1.38 g, 3.53 mmol) was stirred in dioxane (35.3 ml). Potassium acetate (0.454 g, 4.58 mmol) and 4,4,4',4',5,5,5',5'-octamethyl-2,2'-bi(1,3,2-dioxaborolane) (0.904 g, 3.53 mmol) were added. The mixture was sparged with nitrogen for 5 min. Pd(dppf)Cl$_2$ (0.131 g, 0.176 mmol) was added. The mixture was heated to 85° C. After 3 h, no starting material was detected by UPLC. The mixture was allowed to cool. The mixture was diluted with DCM (50 mL) and filtered through Celite. The filtrate was concentrated to dryness to provide a black foam. The crude foam was taken up in DMSO (~8 mL) and MeOH (~3 mL) and chromatographed on C18 (250 g) using 30-70% ACN/water to afford 750 mg (36%) of title compound as a white solid which was used without further purification. $^1$H NMR (400 MHz, CDCl$_3$) δ 9.27 (s, 1H), 8.85 (s, 1H), 8.65 (s, 1H), 8.33 (q, J=8.1 Hz, 2H), 3.85 (s, 3H), 1.44-0.84 (m, 33H).

Step E: Preparation of 2-bromo-5-(2,2,2-trifluoroethoxyl)pyridine

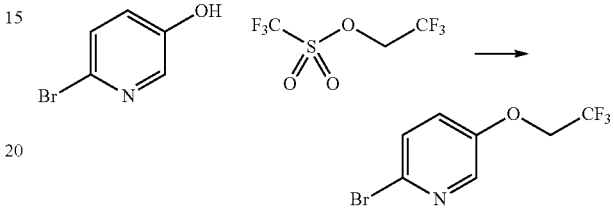

To a stirred solution of 6-bromopyridin-3-ol (1 g, 5.73 mmol) in acetone (20 ml) was added 2,2,2-trifluoroethyl triflouro methanesulfonate (2.01 g, 8.67 mmol) followed by K$_2$CO$_3$ (1.17 g, 8.67 mmol) at rt under an inert atmosphere. The reaction mixture was heated at 60° C. for 2 h. Then, the reaction mixture was diluted with ice cold water (20 mL) and extracted with EtOAc (2×50 mL). The combined organic layers were dried over anhydrous Na$_2$SO$_4$ and concentrated under reduced pressure. The obtained crude material was purified by column chromatography (SiO$_2$, 100-200 mesh) using 30% EtOAc in petroleum ether as an eluent afford the title compound (0.8 g, 54%). $^1$H NMR (400 MHz, CDCl$_3$) δ 8.12 (d, J=3.6 Hz, 1H), 7.43 (d, J=8.8, 1H), 7.20-7.15 (m, 1H) 4.39 (q, J=8.0 Hz, 2H); ESIMS m/z 256 [M+H]$^+$.

Step F: Preparation of 1-(4-methoxypyrimidin-5-yl)-2,2-dimethyl-1-(5-(2,2,2-trifluoroethoxy)-[2,3'-bipyridin]-6'-yl)propan-1-ol (119)

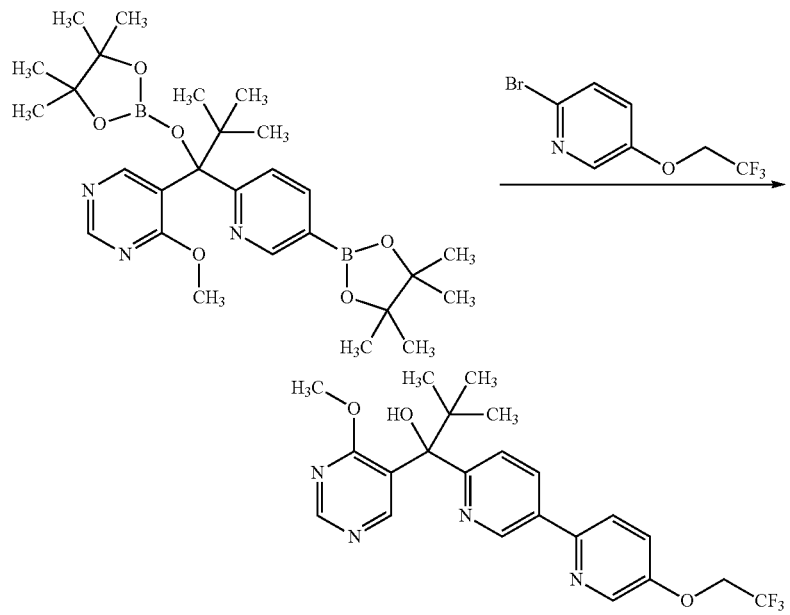

To a degassed solution of 15-(2,2-dimethyl-1-((4,4,5,5-tetramethyl-1,3,2-dioxaborolan-2-yl)oxy)-1-(5-(4,4,5,5-tetramethyl-1,3,2-dioxaborolan-2-yl)pyridin-2-yl)propyl)-4-methoxypyrimidine (0.43 g, 0.83 mmol), 2-bromo-5-(2,2,2-trifluoroethoxyl)pyridine (0.169 g, 0.66 mmol) and sodium carbonate (0.28 g, 2.64 mmol) in dioxane (6 mL) and water (2 mL) was added $PdCl_2(dppf)$ (0.054 g, 0.007 mmol) under a $N_2$ atmosphere. The reaction mixture was stirred at 85° C. for 16 h. The reaction mixture was quenched with ice cold water and extracted with EtOAc. The organic layer was washed with brine, dried over $Na_2SO_4$, filtered and concentrated under reduced pressure. The rude product was purified by column chromatography using 20% EtOAc/petroleum ether as an eluent to afford the title compound as a brown oil (99 mg, 33%). See Table 2 for characterization data.

BIOLOGY EXAMPLES

Example A

Evaluation of Fungicidal Activity: Leaf Blotch of Wheat (*Mycosphaerella graminicola*; Anamorph: *Septoria tritici*; Bayer Code SEPTTR)

For Type A assays, technical grades of the experimental fungicides in Table 4 below were dissolved in acetone, and then mixed with nine volumes of water containing 110 ppm Triton X-100. The fungicide solutions were applied onto wheat seedlings using an automated booth sprayer. For Type B assays, emulsifiable concentrate (EC) formulations of technical grades of the experimental fungicides in Table 4 below were prepared at 10% (w/v), and then mixed with 150 volumes of 0.1% Trycol 5941. These solutions were applied onto wheat seedlings using an automated track sprayer at 200 L/ha. All sprayed plants were allowed to air dry prior to further handling.

Wheat plants (variety Yuma) were grown from seed in a greenhouse in 50% mineral soil/50% soil-less Metro mix until the first leaf was fully emerged, with 7-10 seedlings per pot. Prior to or after application of experimental fungicides, plants were inoculated either with spores of a standard laboratory SEPTTR isolate (SI SEPTTR) or with spores from a SEPTTR field isolate collected from Wellsbourne, England in 2012 (FI SEPTTR). After inoculation the plants were kept for 3 days at 20° C. in 100% relative humidity (one day in a dark dew chamber followed by two days in a lighted dew chamber). Plants were then transferred to a 20° C. greenhouse for disease development. When disease symptoms were fully expressed on untreated plants, infection levels on treated plants were assessed on a scale of 0 to 100 percent disease severity. Percent disease control was calculated using the ratio of disease severity on treated plants relative to untreated plants. The results are shown below in Table 4.

TABLE 1

Structure and Preparation Method.

| Compound Number | Structure | Prepared According to Example |
|---|---|---|
| 1 | 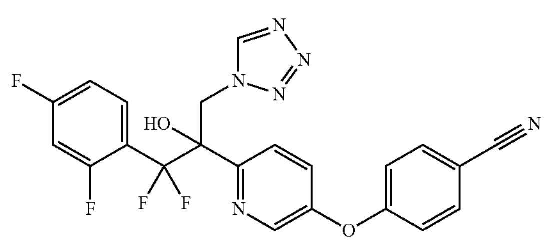 | Example 1 |
| 2 | 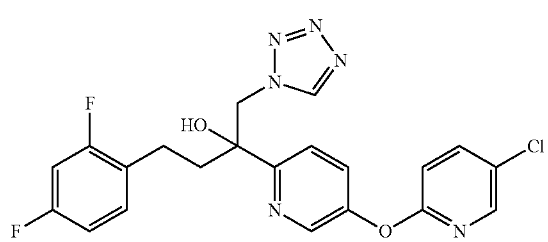 | Example 2 |
| 3 | 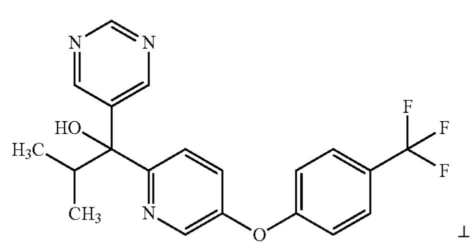 | Example 3 |

TABLE 1-continued

Structure and Preparation Method.

| Compound Number | Structure | Prepared According to Example |
|---|---|---|
| 4 | 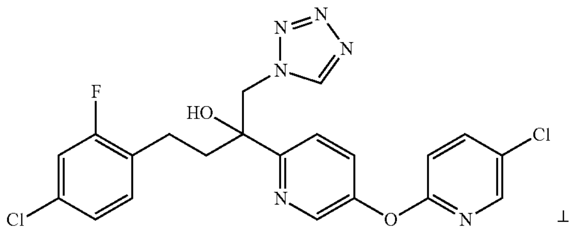 [SMILES: OC(CCc1ccc(Cl)cc1F)(Cn1cnnn1)c1ccc(Oc2ccc(Cl)cn2)cn1] | Prepared according to Example 2 using 3-(4-chloro-2-fluorophenyl)propanoic acid in 2A |
| 5 | 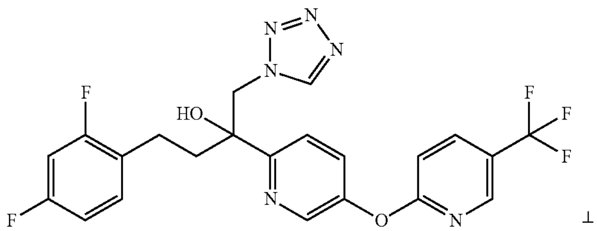 [SMILES: OC(CCc1ccc(F)cc1F)(Cn1cnnn1)c1ccc(Oc2ccc(C(F)(F)F)cn2)cn1] | Prepared according to Example 2 using 2-bromo-5-((5-(trifluoromethyl)pyridin-2-yl)oxy)pyridine in 2B |
| 6 | 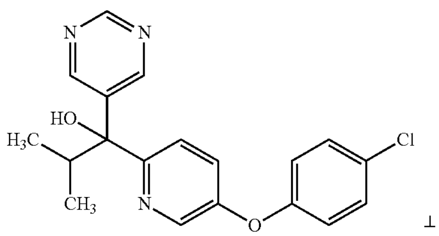 | Prepared according to Example 3 using 4-chlorophenol in 3B |
| 7 | 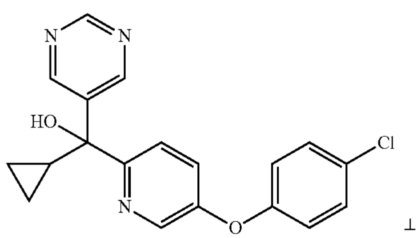 [SMILES: OC(c1cncnc1)(c1ccc(Oc2ccc(Cl)cc2)cn1)C1CC1] | Prepared according to Example 3 using 4-chlorophenol in 3B and cyclopropyl-magnesium bromide in 3C |
| 8 | 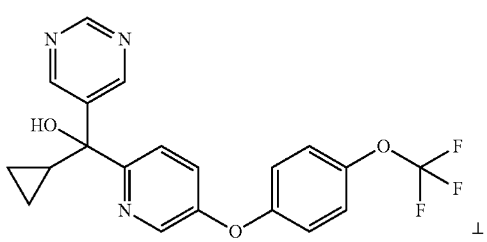 [SMILES: OC(c1cncnc1)(c1ccc(Oc2ccc(OC(F)(F)F)cc2)cn1)C1CC1] | Prepared according to Example 3 using 4-(trifluoromethoxy)phenol in 3B and cyclopropylmagnesium bromide in 3C |
| 9 | 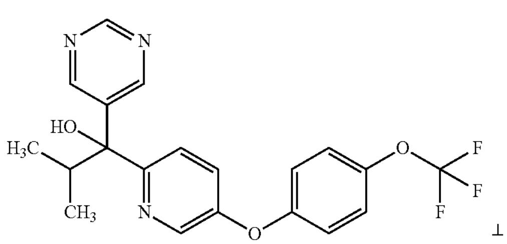 [SMILES: CC(C)C(O)(c1cncnc1)c1ccc(Oc2ccc(OC(F)(F)F)cc2)cn1] | Prepared according to Example 3 using 4-(trifluoromethoxy)phenol in 3B |

TABLE 1-continued

Structure and Preparation Method.

| Compound Number | Structure | Prepared According to Example |
|---|---|---|
| 10 | 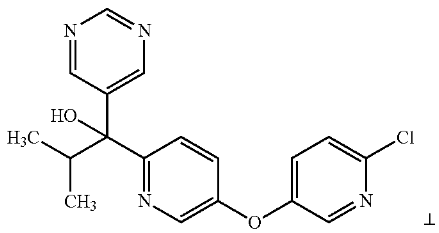 | Prepared according to Example 3 using 4-6-chloropyridin-3-ol in 3B |
| 11 | 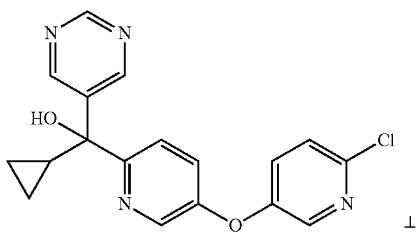 [SMILES: OC(c1cncnc1)(c1ccc(Oc2ccc(Cl)nc2)cn1)C1CC1] | Prepared according to Example 3 using 4-6-chloropyridin-3-ol in 3B and cyclopropylmagnesium bromide in 3C |
| 12 | 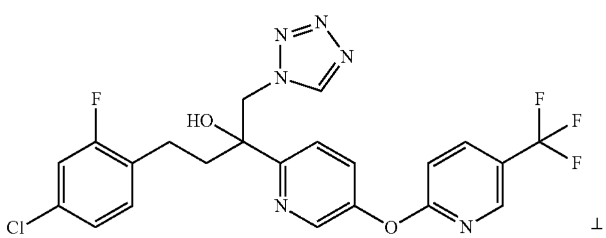 [SMILES: OC(CCc1ccc(Cl)cc1F)(Cn1cnnn1)c1ccc(Oc2ccc(C(F)(F)F)cn2)cn1] | Prepared according to Example 2 using 3-(4-chloro-2-fluorophenyl)propanoic acid in 3A and 2-bromo-5-((5-(trifluoromethyl)-pyridin-2-yl)oxy)pyridine in 3B |
| 13 | 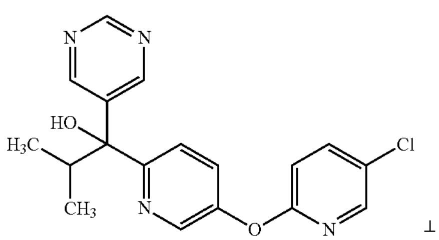 | Prepared according to Example 3 using 5-chloropyridin-2-ol in 3B |
| 14 | 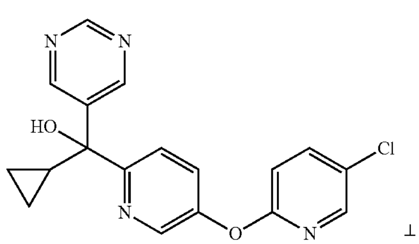 [SMILES: OC(c1cncnc1)(c1ccc(Oc2ccc(Cl)cn2)cn1)C1CC1] | Prepared according to Example 3 using 5-chloropyridin-2-ol in 3B and cyclopropylmagnesium bromide in 3C |
| 15 | 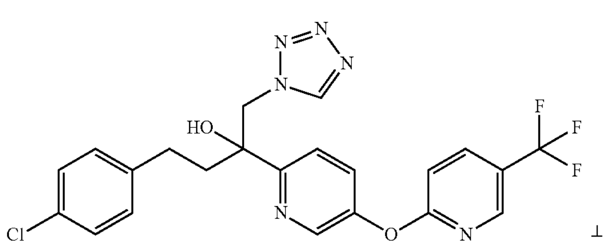 [SMILES: OC(CCc1ccc(Cl)cc1)(Cn1cnnn1)c1ccc(Oc2ccc(C(F)(F)F)cn2)cn1] | Prepared according to Example 2 using 3-(4-chloro)propanoic acid in 3A and 2-bromo-5-((5-(trifluoromethyl)-pyridin-2-yl)oxy)pyridine in 3B |

TABLE 1-continued

Structure and Preparation Method.

| Compound Number | Structure | Prepared According to Example |
|---|---|---|
| 16 | 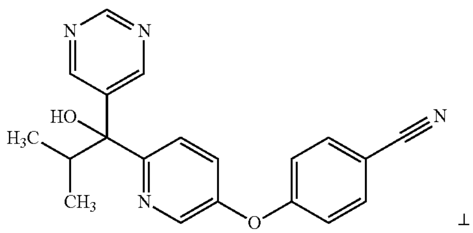 [SMILES: CC(C)C(O)(c1cncnc1)c1ccc(Oc2ccc(C#N)cc2)cn1] | Prepared according to Example 3 using 4-hydroxybenzonitrile in 3B |
| 17 | 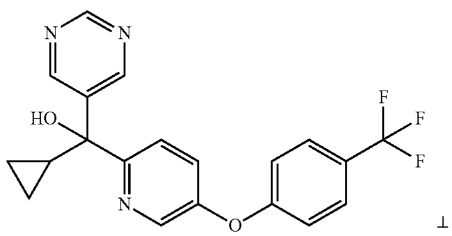 [SMILES: OC(c1cncnc1)(c1ccc(Oc2ccc(C(F)(F)F)cc2)cn1)C1CC1] | Prepared according to Example 3 using cyclopropylmagnesium bromide in 3C |
| 18 | 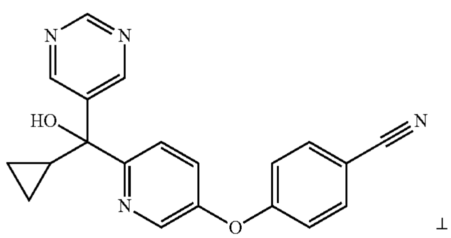 [SMILES: N#Cc1ccc(Oc2ccc(C(O)(c3cncnc3)C3CC3)nc2)cc1] | Prepared according to Example 3 using 4-hydroxybenzonitrile in 3B and cyclopropylmagnesium bromide in 3C |
| 19 | 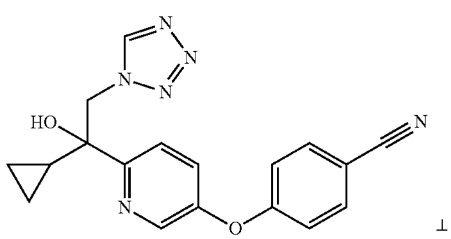 [SMILES: N#Cc1ccc(Oc2ccc(C(O)(Cn3cnnn3)C3CC3)nc2)cc1] | Example 4 |
| 20 | 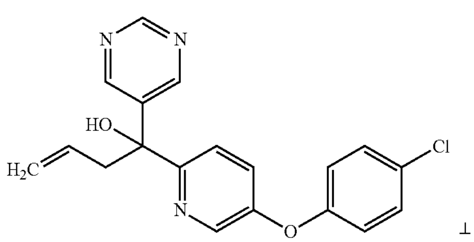 [SMILES: C=CCC(O)(c1cncnc1)c1ccc(Oc2ccc(Cl)cc2)cn1] | Prepared according to Example 3 using 4-chlorophenol in 3B and allylmagnesium bromide in 3C |
| 21 | 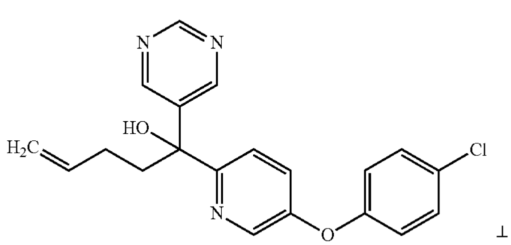 [SMILES: C=CCCC(O)(c1cncnc1)c1ccc(Oc2ccc(Cl)cc2)cn1] | Example 5 |

TABLE 1-continued

Structure and Preparation Method.

| Compound Number | Structure | Prepared According to Example |
|---|---|---|
| 22 | 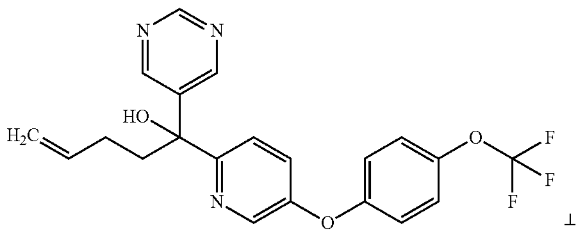 [SMILES: C=CCCC(O)(c1cncnc1)c1ccc(Oc2ccc(OC(F)(F)F)cc2)cn1] | Prepared according to Example 5 using pyrimidin-5-yl(5-(4-(trifluoromethoxy)-phenoxy)pyridin-2-yl)methanone |
| 23 | 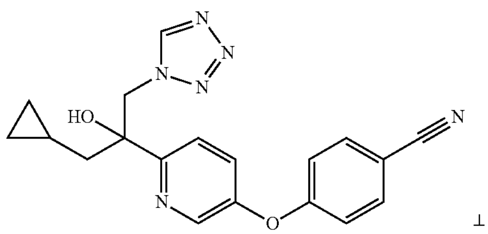 [SMILES: N#Cc1ccc(Oc2ccc(C(O)(CC3CC3)Cn3cnnn3)nc2)cc1] | Prepared according to Example 4 using 2-cyclopropyl-N-methoxy-N-methylacetamide in 4A |
| 24 | 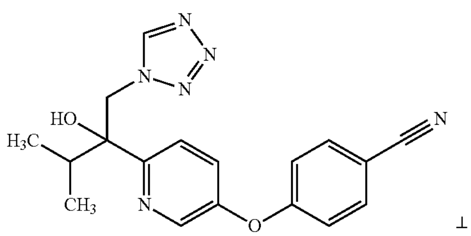 [SMILES: CC(C)C(O)(Cn1cnnn1)c1ccc(Oc2ccc(C#N)cc2)cn1] | Prepared according to Example 4 using N-methoxy-N-methylisobutyramide in 4A |
| 25 | 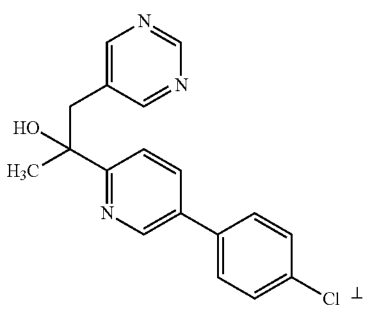 [SMILES: CC(O)(Cc1cncnc1)c1ccc(-c2ccc(Cl)cc2)cn1] | Example 6 |
| 26 | 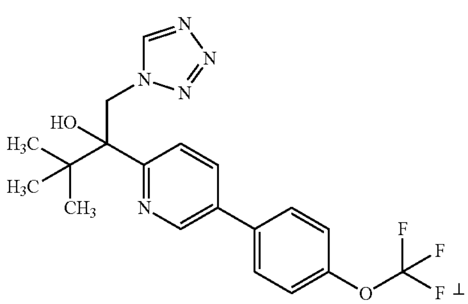 [SMILES: CC(C)(C)C(O)(Cn1cnnn1)c1ccc(-c2ccc(OC(F)(F)F)cc2)cn1] | Example 7 |

TABLE 1-continued

Structure and Preparation Method.

| Compound Number | Structure | Prepared According to Example |
|---|---|---|
| 27 | 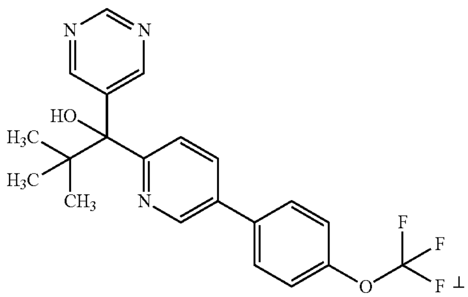 [SMILES: CC(C)(C)C(O)(c1cncnc1)c1ccc(-c2ccc(OC(F)(F)F)cc2)cn1] | Example 8 |
| 28 | 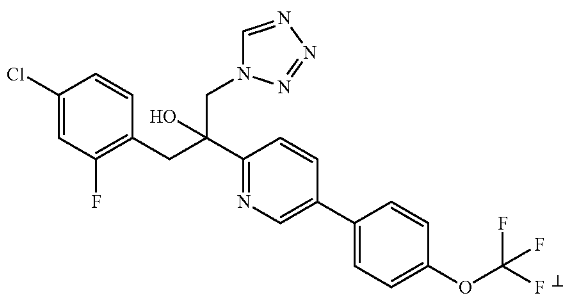 [SMILES: OC(Cc1ccc(Cl)cc1F)(Cn1cnnn1)c1ccc(-c2ccc(OC(F)(F)F)cc2)cn1] | Example 9 |
| 29 | 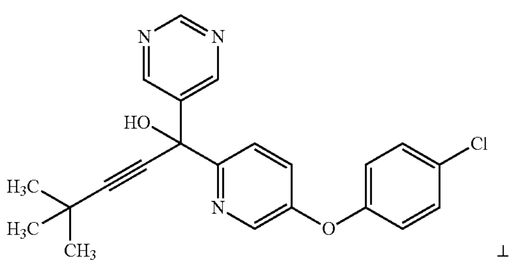 | Example 10 |
| 30 | 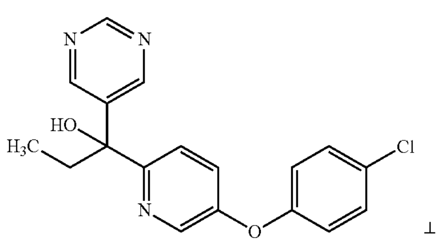 | Example 10 |
| 31 | 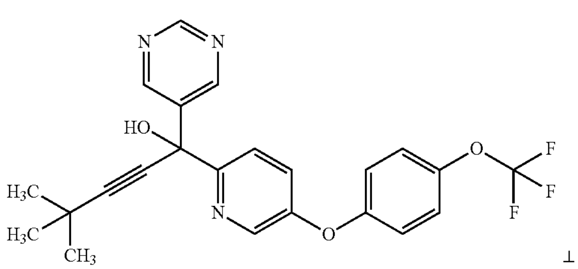 [SMILES: CC(C)(C)C#CC(O)(c1cncnc1)c1ccc(Oc2ccc(OC(F)(F)F)cc2)cn1] | Prepared according to Example 10 using pyrimidin-5-yl(5-(4-(trifluoromethoxy)-phenoxy)pyridin-2-yl)methanone (obtained from 4-(trifluoromethoxy)-phenol in 3B) |

TABLE 1-continued

Structure and Preparation Method.

| Compound Number | Structure | Prepared According to Example |
|---|---|---|
| 32 | 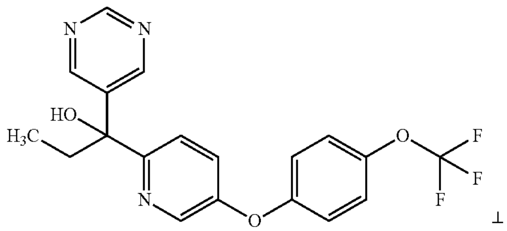 [SMILES: CCC(O)(c1cncnc1)c1ccc(Oc2ccc(OC(F)(F)F)cc2)cn1] | Prepared according to Example 10 using pyrimidin-5-yl(5-(4-(trifluoromethoxy)-phenoxy)pyridin-2-yl)methanone (obtained from 4-(trifluoromethoxy)-phenol in 3B) |
| 33 | 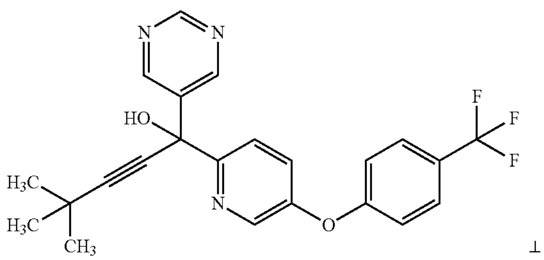 [SMILES: CC(C)(C)C#CC(O)(c1cncnc1)c1ccc(Oc2ccc(C(F)(F)F)cc2)cn1] | Prepared according to Example 10 using pyrimidin-5-yl(5-(4-(trifluoromethyl)-phenoxy)pyridin-2-yl)methanone (from 3B) |
| 34 | 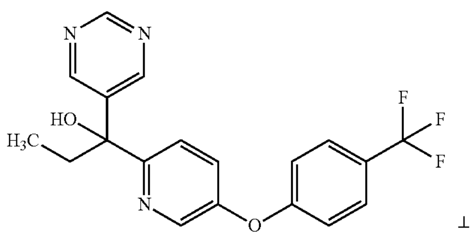 [SMILES: CCC(O)(c1cncnc1)c1ccc(Oc2ccc(C(F)(F)F)cc2)cn1] | Prepared according to Example 10 using pyrimidin-5-yl(5-(4-(trifluoromethyl)-phenoxy)pyridin-2-yl)methanone (from 3B) |
| 35 | 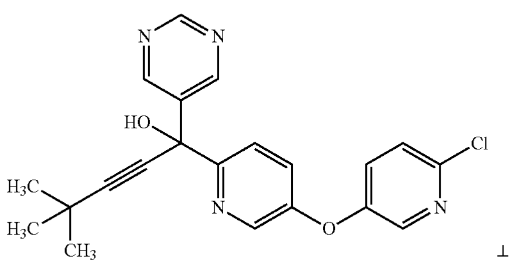 | Prepared according to Example 10 using (5-((6-chloropyridin-3-yl)oxy)pyridin-2-yl)(pyrimidin-5-yl)methanone (obtained from 6-chloropyridin-3-ol in 3B) |
| 36 | 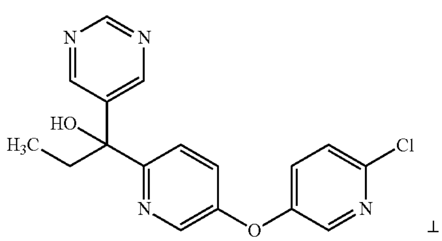 [SMILES: CCC(O)(c1cncnc1)c1ccc(Oc2ccc(Cl)nc2)cn1] | Prepared according to Example 10 using (5-((6-chloropyridin-3-yl)oxy)pyridin-2-yl)(pyrimidin-5-yl)methanone (obtained from 6-chloropyridin-3-ol in 3B) |
| 37 | 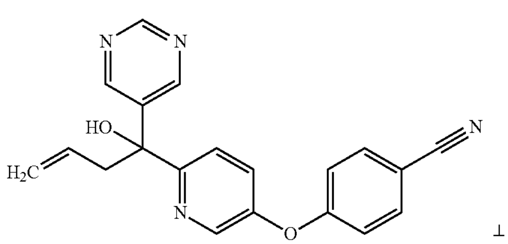 [SMILES: C=CCC(O)(c1cncnc1)c1ccc(Oc2ccc(C#N)cc2)cn1] | Prepared according to Example 3 using 4-hydroxybenzonitrile in 3B and allylmagnesium bromide in 3C |

TABLE 1-continued

Structure and Preparation Method.

| Compound Number | Structure | Prepared According to Example |
|---|---|---|
| 38 | 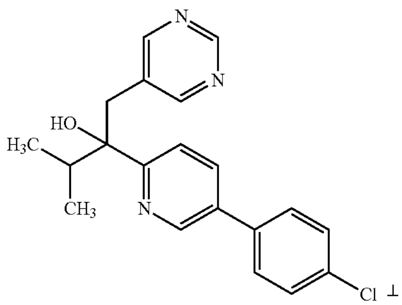 [SMILES: CC(C)C(O)(Cc1cncnc1)c1ccc(-c2ccc(Cl)cc2)cn1] | Prepared according to Example 6 using iso-propylmagnesium chloride in 6D |
| 39 | 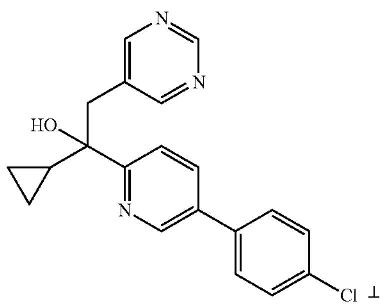 [SMILES: OC(Cc1cncnc1)(c1ccc(-c2ccc(Cl)cc2)cn1)C1CC1] | Prepared according to Example 6 using cyclopropylmagnesium bromide in 6D |
| 40 | 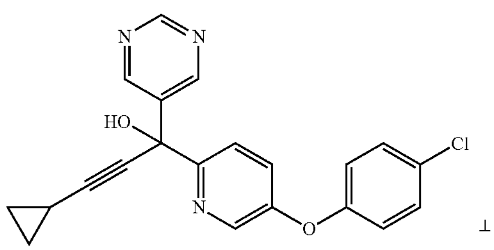 [SMILES: OC(C#CC1CC1)(c1cncnc1)c1ccc(Oc2ccc(Cl)cc2)cn1] | Prepared according to Example 10 using ethynylcyclopropane |
| 41 | 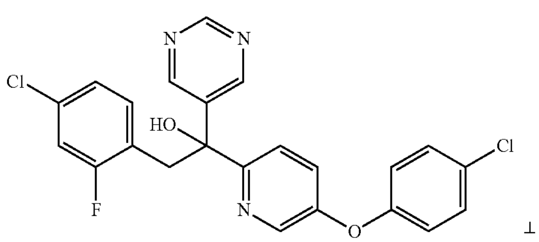 [SMILES: OC(Cc1ccc(Cl)cc1F)(c1cncnc1)c1ccc(Oc2ccc(Cl)cc2)cn1] | Example 11 |
| 42 | 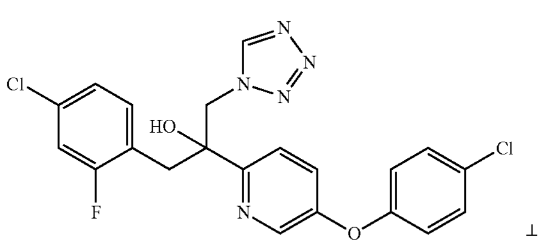 [SMILES: OC(Cc1ccc(Cl)cc1F)(Cn1cnnn1)c1ccc(Oc2ccc(Cl)cc2)cn1] | Example 12 |

TABLE 1-continued

Structure and Preparation Method.

| Compound Number | Structure | Prepared According to Example |
|---|---|---|
| 43 | 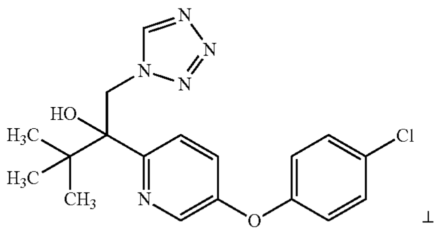 [SMILES: CC(C)(C)C(O)(Cn1cnnn1)c1ccc(Oc2ccc(Cl)cc2)cn1] | Prepared according to Example 4 using N-methoxy-N-methylpivalamide in 4A and 4-chlorophenol in 4B |
| 44 | 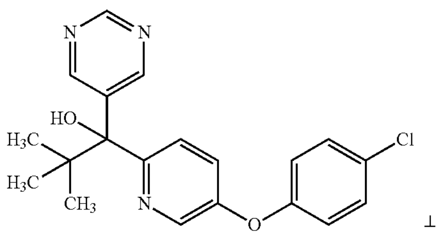 [SMILES: CC(C)(C)C(O)(c1cncnc1)c1ccc(Oc2ccc(Cl)cc2)cn1] | Prepared according to Example 3 using 4-chlorophenol in 3B and tert-butyllithium in 3C |
| 45 | 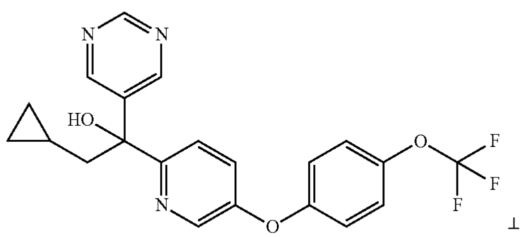 [SMILES: OC(CC1CC1)(c1cncnc1)c1ccc(Oc2ccc(OC(F)(F)F)cc2)cn1] | Example 13 |
| 46 | 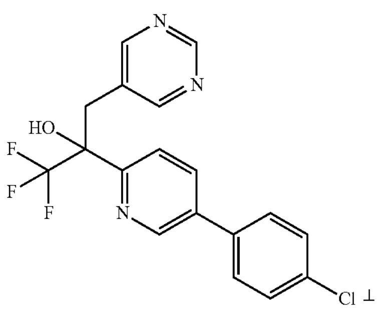 [SMILES: OC(Cc1cncnc1)(c1ccc(-c2ccc(Cl)cc2)cn1)C(F)(F)F] | Example 14 |
| 47 | 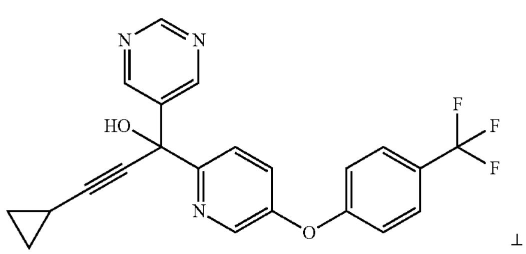 [SMILES: OC(C#CC1CC1)(c1cncnc1)c1ccc(Oc2ccc(C(F)(F)F)cc2)cn1] | Prepared according to Example 10 using ethynylcyclopropane and pyrimidin-5-yl(5-(4-(trifluoromethyl)-phenoxy)-pyridin-2-yl)methanone (from 3B) |
| 48 | 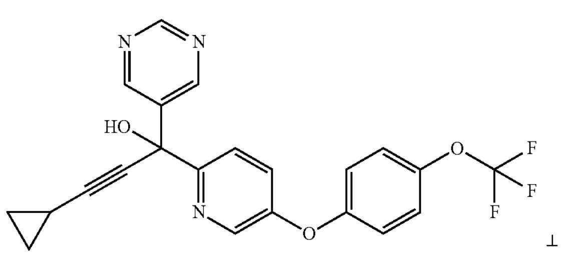 [SMILES: OC(C#CC1CC1)(c1cncnc1)c1ccc(Oc2ccc(OC(F)(F)F)cc2)cn1] | Prepared according to Example 10 using ethynylcyclopropane and pyrimidin-5-yl(5-(4-(trifluoromethoxy)-phenoxy)-pyridin-2-yl)methanone (from 3B) |

TABLE 1-continued

Structure and Preparation Method.

| Compound Number | Structure | Prepared According to Example |
|---|---|---|
| 49 | 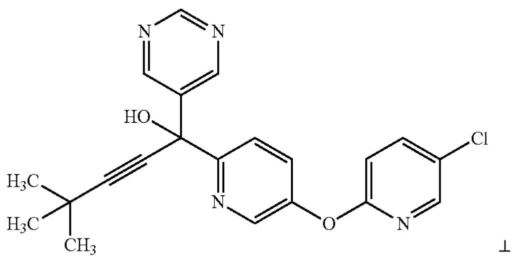 [SMILES: CC(C)(C)C#CC(O)(c1cncnc1)c1ccc(Oc2ccc(Cl)cn2)cn1] | Prepared according to Example 10 using (5-((5-chloropyridin-2-yl)oxy)pyridin-2-yl)(pyrimidin-5-yl)methanone (obtained from 5-chloropyridin-2-ol via 3B) |
| 50 | 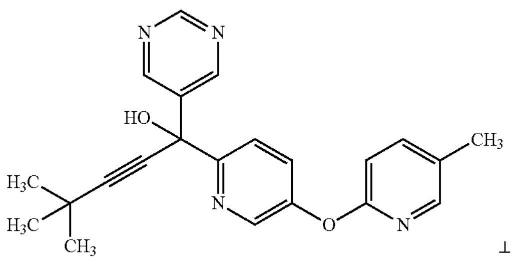 | Prepared according to Example 10 using (5-((5-methylpyridin-2-yl)oxy)pyridin-2-yl)(pyrimidin-5-yl)methanone (obtained from 5-methylpyridin-2-ol via 3B) |
| 51 | 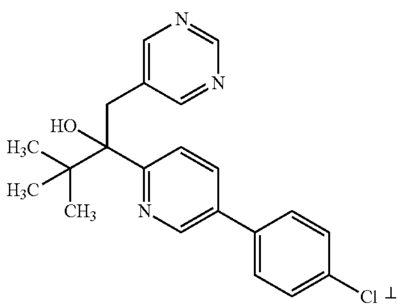 [SMILES: CC(C)(C)C(O)(Cc1cncnc1)c1ccc(-c2ccc(Cl)cc2)cn1] | Prepared according to Example 6 using tert-butylmagnesium bromide in 6D |
| 52 | 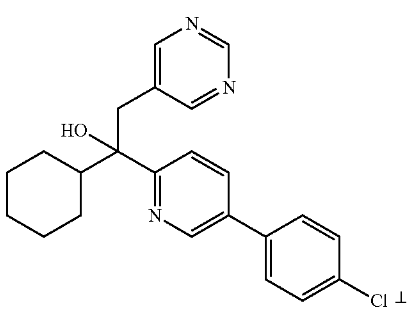 [SMILES: OC(Cc1cncnc1)(c1ccc(-c2ccc(Cl)cc2)cn1)C1CCCCC1] | Prepared according to Example 6 using cyclohexylmagnesium bromide in 6D |
| 53 | 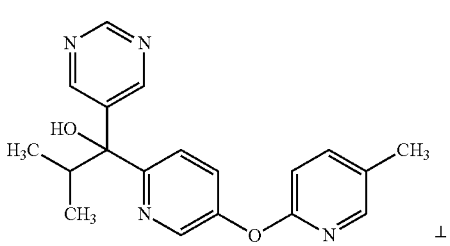 [SMILES: CCC(O)(c1cncnc1)c1ccc(Oc2ccc(C)cn2)cn1] | Prepared according to Example 3 using 5-methylpyridin-2-ol in 3B |

TABLE 1-continued

Structure and Preparation Method.

| Compound Number | Structure | Prepared According to Example |
|---|---|---|
| 54 | 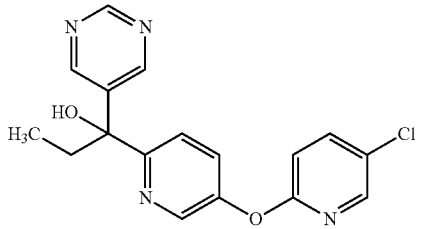 | Prepared according to Example 10 using (5-((5-chloropyridin-2-yl)oxy)pyridin-2-yl)(pyrimidin-5-yl)methanone (obtained from 5-chloropyridin-2-ol via 3B) |
| 55 | 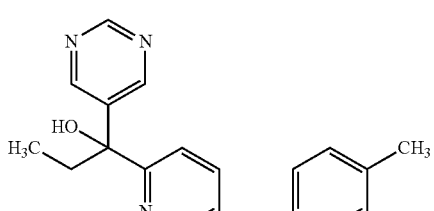 | Prepared according to Example 10 using (5-((5-methylpyridin-2-yl)oxy)pyridin-2-yl)(pyrimidin-5-yl)methanone (obtained from 5-methylpyridin-2-ol via 3B) |
| 56 | 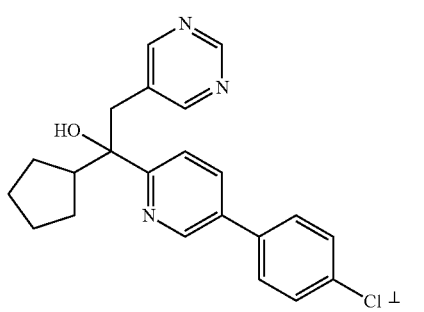 [SMILES: OC(Cc1cncnc1)(c1ccc(-c2ccc(Cl)cc2)cn1)C1CCCC1] | Prepared according to Example 6 using cyclopentylmagnesium bromide in 6D |
| 57 | 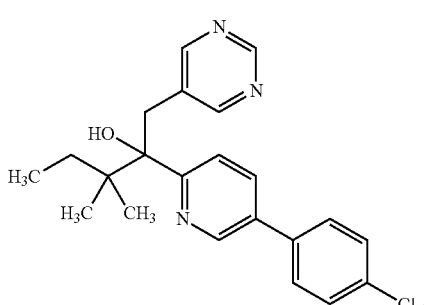 | Prepared according to Example 6 using tert-pentylmagnesium bromide in 6D |
| 58 | 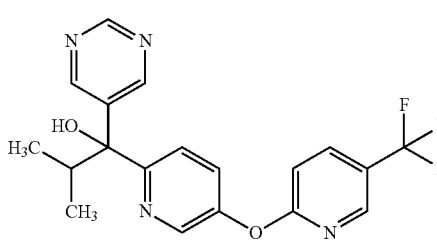 | Prepared according to Example 3 using 5-(trifluoromethyl)pyridin-2-ol in 3B |

TABLE 1-continued

Structure and Preparation Method.

| Compound Number | Structure | Prepared According to Example |
|---|---|---|
| 59 | 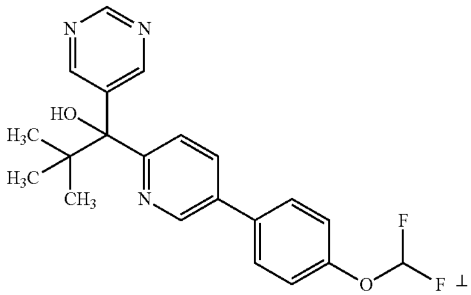 [SMILES: CC(C)(C)C(O)(c1cncnc1)c1ccc(-c2ccc(OC(F)F)cc2)cn1] | Prepared according to Example 8 using 2-bromo-5-(4-(difluoromethoxy)phenyl)-pyridine in 8A |
| 60 | 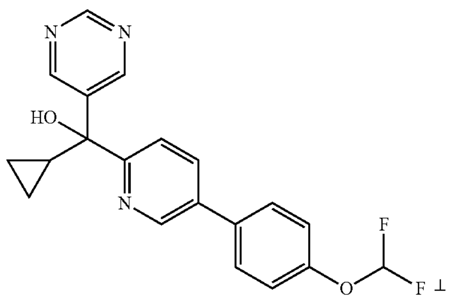 [SMILES: OC(c1cncnc1)(c1ccc(-c2ccc(OC(F)F)cc2)cn1)C1CC1] | Prepared according to Example 8 using 2-bromo-5-(4-(difluoromethoxy)phenyl)-pyridine in 8A and cyclopropylmagnesium bromide in 8B |
| 61 | 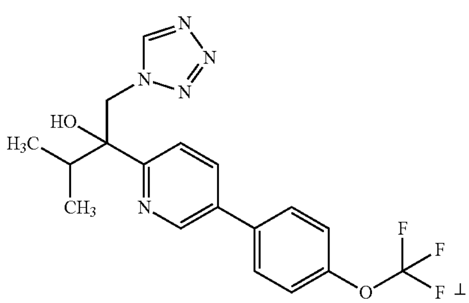 [SMILES: CC(C)C(O)(Cn1cnnn1)c1ccc(-c2ccc(OC(F)(F)F)cc2)cn1] | Prepared according to Example 7 using isobutyryl chloride in 7B |
| 62 | 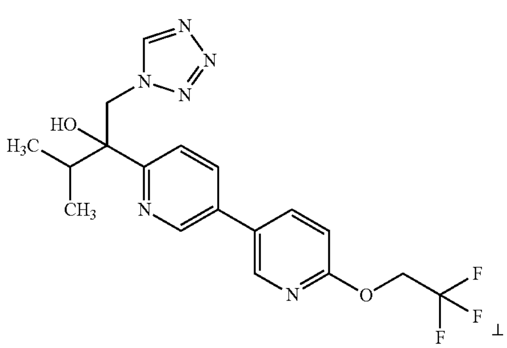 [SMILES: CC(C)C(O)(Cn1cnnn1)c1ccc(-c2ccc(OCC(F)(F)F)nc2)cn1] | Prepared according to Example 7 using (6-(2,2,2-trifluoroethoxy)pyridin-3-yl)boronic acid in 7A and isobutyryl chloride in 7B |

TABLE 1-continued

Structure and Preparation Method.

| Compound Number | Structure | Prepared According to Example |
|---|---|---|
| 63 | 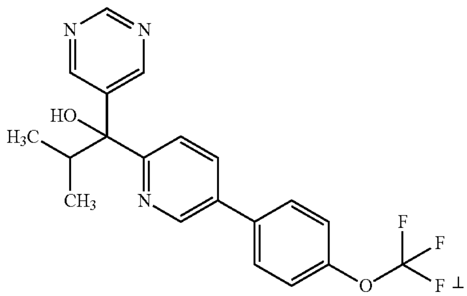 [SMILES: CC(C)C(O)(c1cncnc1)c1ccc(-c2ccc(OC(F)(F)F)cc2)cn1] | Prepared according to Example 8 using i-PrMgCl in 8B |
| 64 | 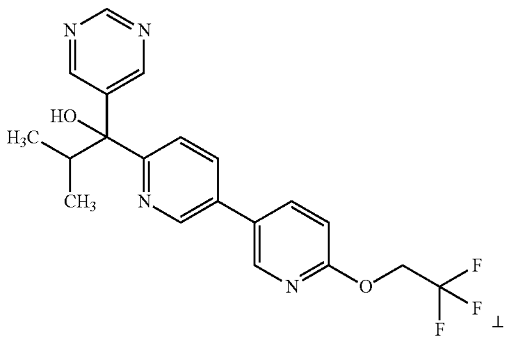 [SMILES: CC(C)C(O)(c1cncnc1)c1ccc(-c2ccc(OCC(F)(F)F)nc2)cn1] | Prepared according to Example 8 using 6-bromo-6'-(2,2,2-trifluoroethoxy)-3,3'-bipyridine in 8A and i-PrMgCl in 8B |
| 65 | 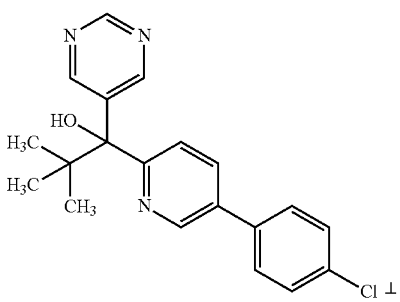 [SMILES: CC(C)(C)C(O)(c1cncnc1)c1ccc(-c2ccc(Cl)cc2)cn1] | Prepared according to Example 8 using 2-2-bromo-5-(4-chlorophenyl)pyridine in 8A |
| 66 | 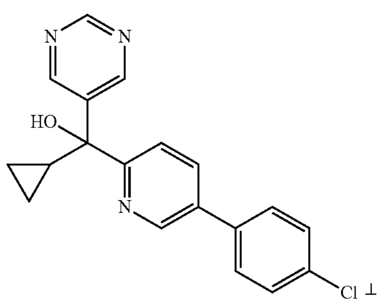 [SMILES: OC(c1cncnc1)(c1ccc(-c2ccc(Cl)cc2)cn1)C1CC1] | Prepared according to Example 8 using 2-2-bromo-5-(4-chlorophenyl)pyridine in 8A and cyclopropylmagnesium bromide in 8B |
| 67 | 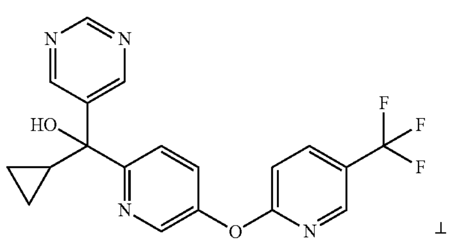 [SMILES: OC(c1cncnc1)(c1ccc(Oc2ccc(C(F)(F)F)cn2)cn1)C1CC1] | Prepared according to Example 3 using 5-(trifluoromethyl)pyridin-2-ol in 3B and cyclopropyl-magnesium bromide in 3C |

TABLE 1-continued

Structure and Preparation Method.

| Compound Number | Structure | Prepared According to Example |
|---|---|---|
| 68 | 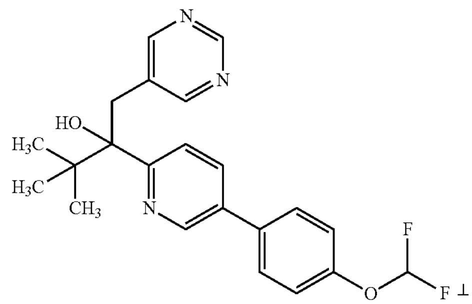 [SMILES: CC(C)(C)C(O)(Cc1cncnc1)c1ccc(-c2ccc(OC(F)F)cc2)cn1] | Prepared according to Example 6 using (4-(difluoromethoxy)phenyl)boronic acid in 6C and tert-butylmagnesium bromide in 6D |
| 69 | 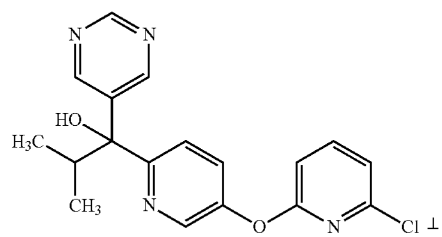 [SMILES: CC(C)C(O)(c1cncnc1)c1ccc(Oc2cccc(Cl)n2)cn1] | Prepared according to Example 3 using 6-chloropyridin-2-ol in 3B |
| 70 | 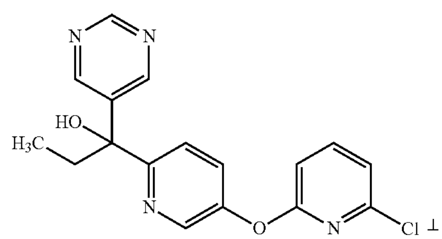 [SMILES: CCC(O)(c1cncnc1)c1ccc(Oc2cccc(Cl)n2)cn1] | Prepared according to Example 10 using (5-((6-chloropyridin-2-yl)oxy)pyridin-2-yl)(pyrimidin-5-yl)methanone (obtained from 6-chloropyridin-2-ol via 3B) |
| 71 | 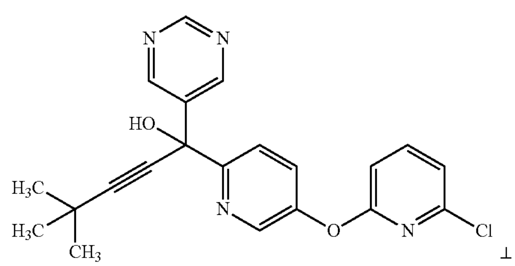 [SMILES: CC(C)(C)C#CC(O)(c1cncnc1)c1ccc(Oc2cccc(Cl)n2)cn1] | Prepared according to Example 10 using (5-((6-chloropyridin-2-yl)oxy)pyridin-2-yl)(pyrimidin-5-yl)methanone (obtained from 6-chloropyridin-2-ol via 3B) |
| 72 | 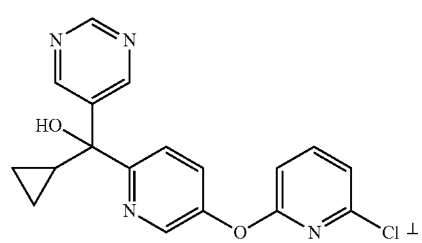 [SMILES: OC(c1cncnc1)(c1ccc(Oc2cccc(Cl)n2)cn1)C1CC1] | Prepared according to Example 3 using 6-chloropyridin-2-ol in 3B and cyclopropyl-magnesium bromide in 3C |

TABLE 1-continued

Structure and Preparation Method.

| Compound Number | Structure | Prepared According to Example |
|---|---|---|
| 73 | 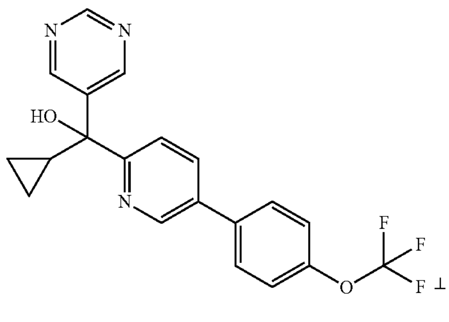 [SMILES: OC(c1cncnc1)(c1ccc(-c2ccc(OC(F)(F)F)cc2)cn1)C1CC1] | Prepared according to Example 8 using cyclopropylmagnesium bromide in 8B |
| 74 | 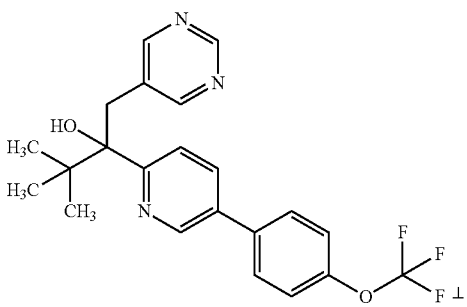 [SMILES: CC(C)(C)C(O)(Cc1cncnc1)c1ccc(-c2ccc(OC(F)(F)F)cc2)cn1] | Prepared according to Example 6 using (4-(trifluoromethoxy)phenyl)boronic acid in 6C and tert-butylmagnesium bromide in 6D |
| 75 | 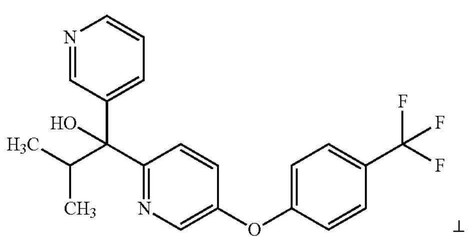 [SMILES: CC(C)C(O)(c1cccnc1)c1ccc(Oc2ccc(C(F)(F)F)cc2)cn1] | Prepared according to Example 3 using N-methoxy-N-methylnicotinamide in 3A |
| 76 | 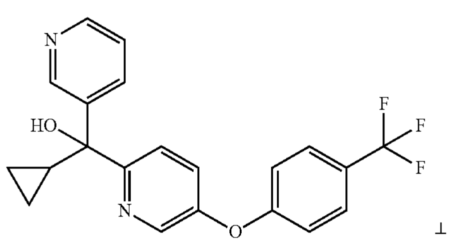 [SMILES: OC(c1cccnc1)(c1ccc(Oc2ccc(C(F)(F)F)cc2)cn1)C1CC1] | Prepared according to Example 3 using N-methoxy-N-methylnicotinamide in 3A and cyclopropylmagnesium bromide in 3C |
| 77 | 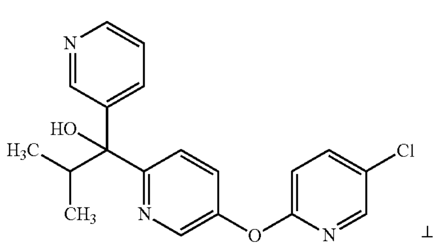 | Prepared according to Example 3 using N-methoxy-N-methylnicotinamide in 3A and 5-chloropyridin-2-ol in 3B |

TABLE 1-continued

Structure and Preparation Method.

| Compound Number | Structure | Prepared According to Example |
|---|---|---|
| 78 | 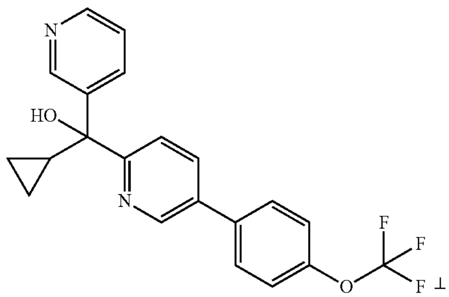 [SMILES: OC(c1cccnc1)(c1ccc(-c2ccc(OC(F)(F)F)cc2)cn1)C1CC1] | Prepared according to Example 8 using N-methoxy-N-methylnicotinamide in 8A and cyclopropylmagnesium bromide in 8B |
| 79 | 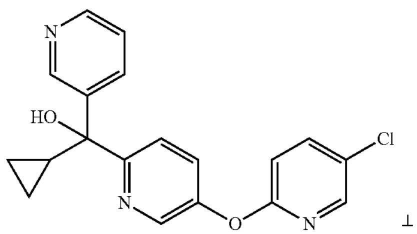 [SMILES: OC(c1cccnc1)(c1ccc(Oc2ccc(Cl)cn2)cn1)C1CC1] | Prepared according to Example 3 using N-methoxy-N-methylnicotinamide in 3A, 5-chloropyridin-2-ol in 3B, and cyclopropylmagnesium bromide in 3C |
| 80 | 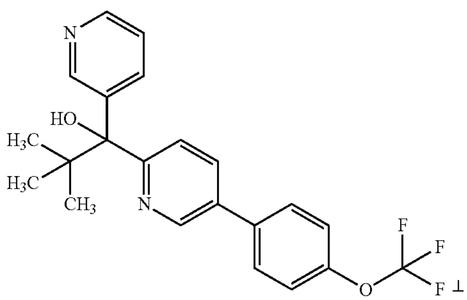 [SMILES: CC(C)(C)C(O)(c1cccnc1)c1ccc(-c2ccc(OC(F)(F)F)cc2)cn1] | Prepared according to Example 8 using N-methoxy-N-methylnicotinamide in 8A |
| 81 | 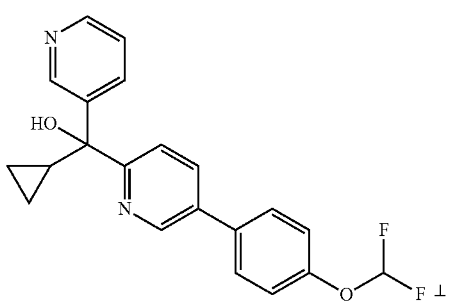 | Prepared according to Example 8 using N-methoxy-N-methylnicotinamide and 2-bromo-5-(4-(difluoromethoxy)phenyl)-pyridine in 8A and cyclopropylmagnesium bromide in 8B |
| 82 | 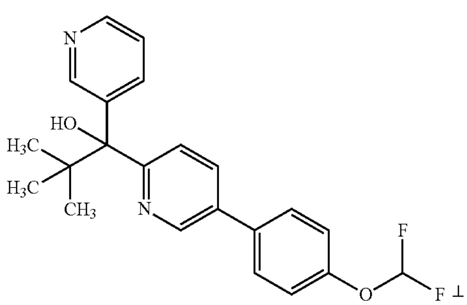 [SMILES: CC(C)(C)C(O)(c1cccnc1)c1ccc(-c2ccc(OC(F)F)cc2)cn1] | Prepared according to Example 8 using N-methoxy-N-methylnicotinamide and 2-bromo-5-(4-(difluoromethoxy)phenyl)-pyridine in 8A |

TABLE 1-continued

Structure and Preparation Method.

| Compound Number | Structure | Prepared According to Example |
|---|---|---|
| 83 | 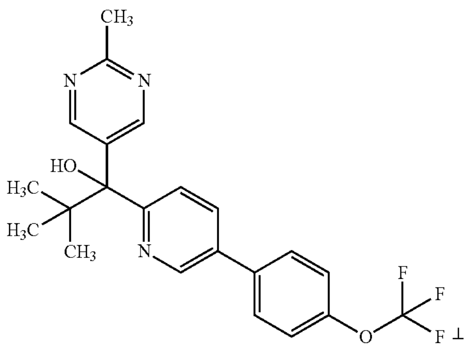 [SMILES: Cc1ncc(C(O)(c2ccc(-c3ccc(OC(F)(F)F)cc3)cn2)C(C)(C)C)cn1] | Prepared according to Example 8 using N-methoxy-N,2-dimethylpyrimidine-5-carboxamide in 8A |
| 84 | 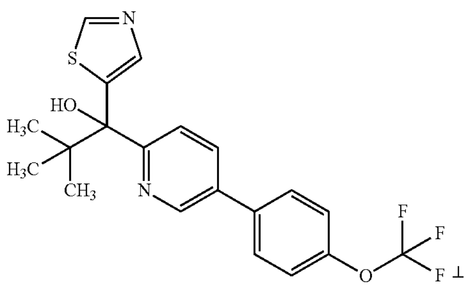 [SMILES: CC(C)(C)C(O)(c1ccc(-c2ccc(OC(F)(F)F)cc2)cn1)c1cncs1] | Prepared according to Example 8 using N-methoxy-N-methylthiazole-5-carboxamide in 8A |
| 85 | 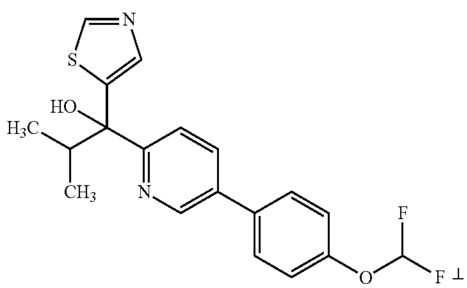 [SMILES: CC(C)C(O)(c1ccc(-c2ccc(OC(F)F)cc2)cn1)c1cncs1] | Prepared according to Example 8 using N-methoxy-N-methylthiazole-5-carboxamide and 2-Bromo-5-(4-(difluoromethoxy)phenyl)-pyridine in 8A and i-PrMgCl in 8B |
| 86 | 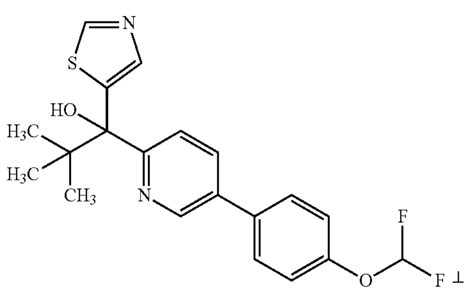 [SMILES: CC(C)(C)C(O)(c1ccc(-c2ccc(OC(F)F)cc2)cn1)c1cncs1] | Prepared according to Example 8 using N-methoxy-N-methylthiazole-5-carboxamide and 2-Bromo-5-(4-(difluoromethoxy)phenyl)-pyridine in 8A |
| 87 | 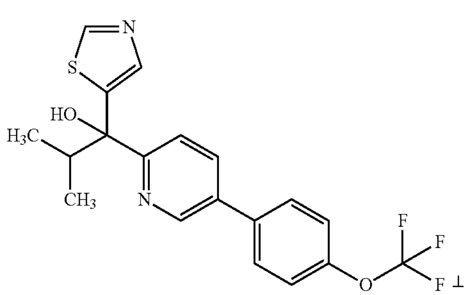 [SMILES: CC(C)C(O)(c1ccc(-c2ccc(OC(F)(F)F)cc2)cn1)c1cncs1] | Prepared according to Example 8 using N-methoxy-N-methylthiazole-5-carboxamide in 8A and i-PrMgCl in 8B |

TABLE 1-continued

Structure and Preparation Method.

| Compound Number | Structure | Prepared According to Example |
|---|---|---|
| 88 | 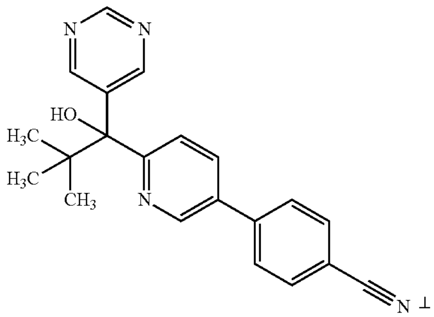 [SMILES: CC(C)(C)C(O)(c1cncnc1)c1ccc(-c2ccc(C#N)cc2)cn1] | Prepared according to Example 8 using 4-(6-bromopyridin-3-yl)benzonitrile in 8A |
| 89 | 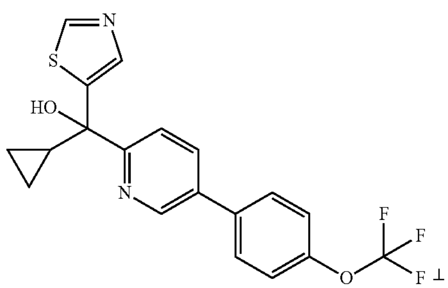 [SMILES: OC(c1ccc(-c2ccc(OC(F)(F)F)cc2)cn1)(c1cncs1)C1CC1] | Prepared according to Example 8 using N-methoxy-N-methylthiazole-5-carboxamide in 8A and cyclopropylmagnesium bromide in 8B |
| 90 | 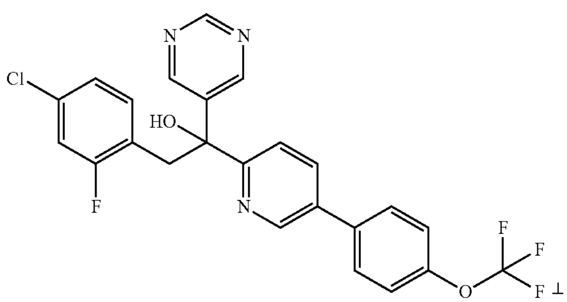 [SMILES: OC(Cc1ccc(Cl)cc1F)(c1cncnc1)c1ccc(-c2ccc(OC(F)(F)F)cc2)cn1] | Prepared according to Example 8 using (4-chloro-2-fluorobenzyl)magnesium bromide in 8B |
| 91 | 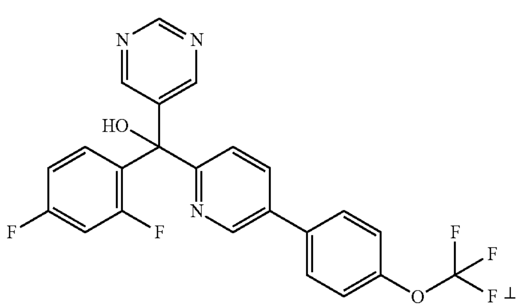 [SMILES: OC(c1cncnc1)(c1ccc(-c2ccc(OC(F)(F)F)cc2)cn1)c1ccc(F)cc1F] | Example 15 |

TABLE 1-continued

Structure and Preparation Method.

| Compound Number | Structure | Prepared According to Example |
|---|---|---|
| 92 | 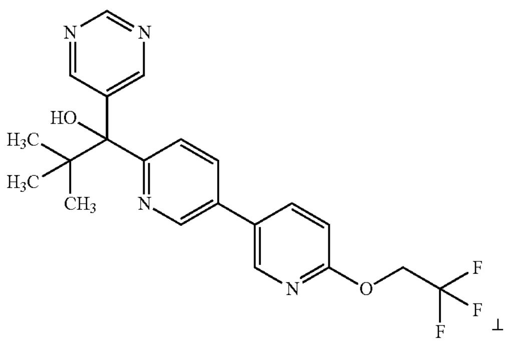 [SMILES: CC(C)(C)C(O)(c1cncnc1)c1ccc(-c2ccc(OCC(F)(F)F)nc2)cn1] | Prepared according to Example 8 using 6-bromo-6'-(2,2,2-trifluoroethoxy)-3,3'-bipyridine in 8A |
| 93 | 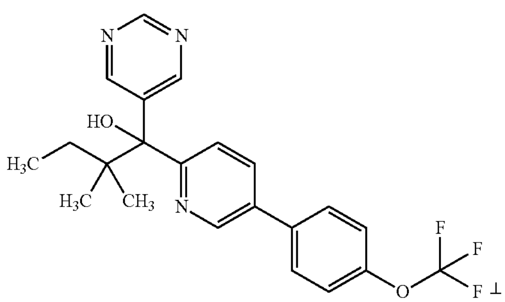 [SMILES: CCC(C)(C)C(O)(c1cncnc1)c1ccc(-c2ccc(OC(F)(F)F)cc2)cn1] | Example 16 |
| 94 | 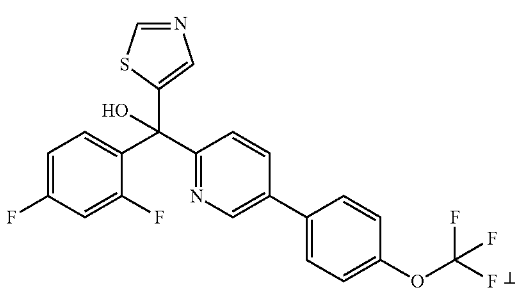 [SMILES: OC(c1ccc(-c2ccc(OC(F)(F)F)cc2)cn1)(c1cncs1)c1ccc(F)cc1F] | Prepared according to Example 16A, 15, and 16C, using N-methoxy-N-methylthiazole-5-carboxamide (prepared from thiazole-5-carboxylic acid) in 16A and (4-(trifluoromethoxy)-phenyl)boronic acid in 16C |
| 95 | 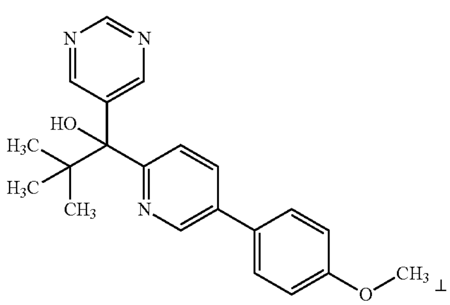 | Prepared according to Example 16A-16C, using tert-butylmagnesium chloride in 16B and (4-methoxyphenyl)boronic acid in 16C |

TABLE 1-continued

Structure and Preparation Method.

| Compound Number | Structure | Prepared According to Example |
|---|---|---|
| 96 | 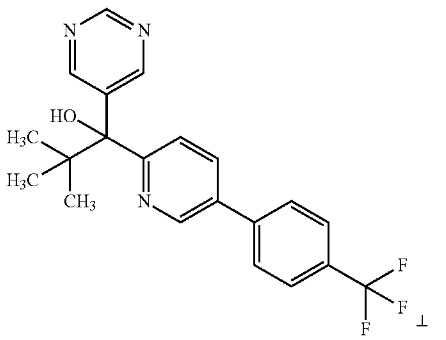 [SMILES: CC(C)(C)C(O)(c1cncnc1)c1ccc(-c2ccc(C(F)(F)F)cc2)cn1] | Prepared according to Example 16A-16C, using tert-butylmagnesium chloride in 16B and (4-(trifluoromethyphenyl)boronic acid in 16C |
| 97 | 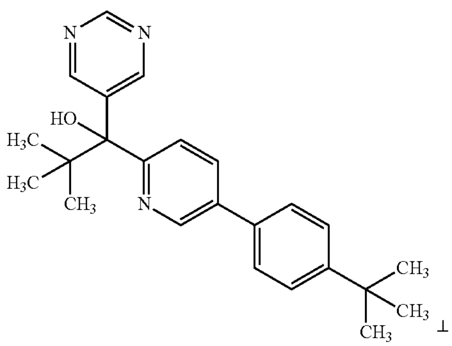 [SMILES: CC(C)(C)c1ccc(-c2ccc(C(O)(c3cncnc3)C(C)(C)C)nc2)cc1] | Prepared according to Example 16A-16C, using tert-butylmagnesium chloride in 16B and (4-(tert-butyl)phenyl)boronic acid in 16C |
| 98 | 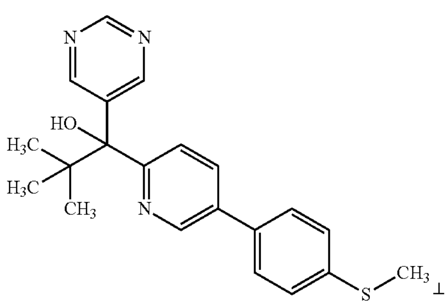 | Prepared according to Example 16A-16C, using tert-butylmagnesium chloride in 16B and (4-(methylthio)phenyl)boronic acid in 16C |
| 99 | 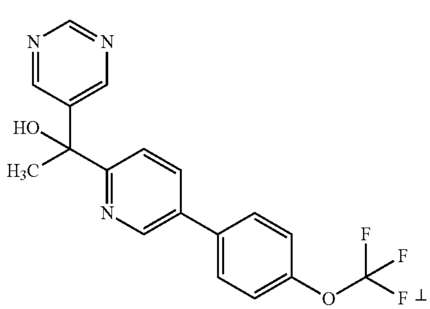 [SMILES: CC(O)(c1cncnc1)c1ccc(-c2ccc(OC(F)(F)F)cc2)cn1] | Prepared according to Example 16A-16C, using methylmagnesium bromide in 16B and (4-(trifluoromethoxy)phenyl)boronic acid in 16C |

TABLE 1-continued

Structure and Preparation Method.

| Compound Number | Structure | Prepared According to Example |
|---|---|---|
| 100 | 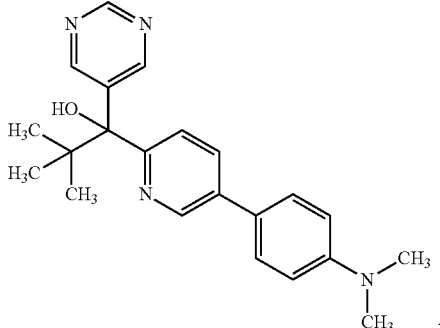 | Prepared according to Example 16A-16C, using tert-butylmagnesium chloride in 16B and (4-(dimethylamino)-phenyl)boronic acid in 16C |
| 101 | 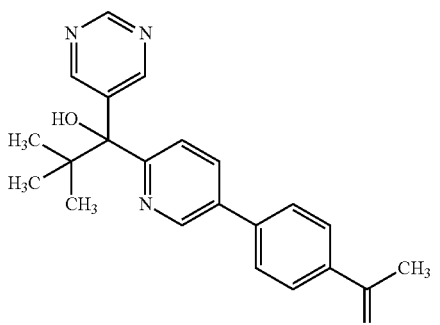 | Prepared according to Example 16A-16C, using tert-butylmagnesium chloride in 16B and (4-acetylphenyl)boronic acid in 16C |
| 102 | 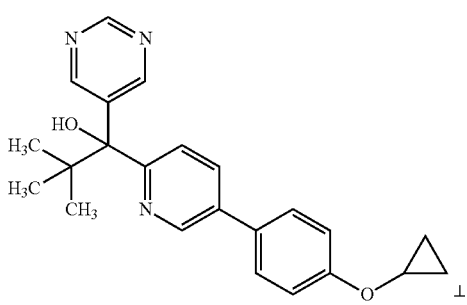 [SMILES: CC(C)(C)C(O)(c1cncnc1)c1ccc(-c2ccc(OC3CC3)cc2)cn1] | Prepared according to Example 16A-16C, using tert-butylmagnesium chloride in 16B and (4-cyclopropoxyphenyl)boronic acid in 16C |
| 103 | 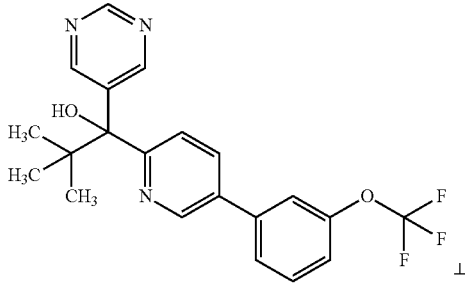 [SMILES: CC(C)(C)C(O)(c1cncnc1)c1ccc(-c2cccc(OC(F)(F)F)c2)cn1] | Prepared according to Example 16A-16C, using tert-butylmagnesium chloride in 16B and (3-(trifluoromethoxy)-phenyl)boronic acid in 16C |

TABLE 1-continued

Structure and Preparation Method.

| Compound Number | Structure | Prepared According to Example |
|---|---|---|
| 104 | 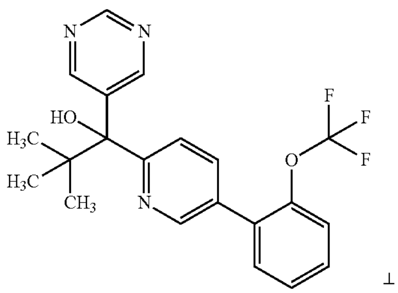 [SMILES: CC(C)(C)C(O)(c1cncnc1)c1ccc(-c2ccccc2OC(F)(F)F)cn1] | Prepared according to Example 16A-16C, using tert-butylmagnesium chloride in 16B and (2-(trifluoromethoxy)-phenyl)boronic acid in 16C |
| 105 | 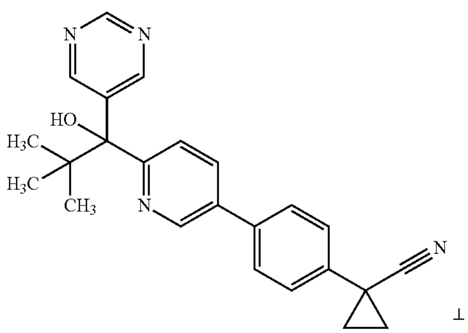 | Prepared according to Example 16A-16C, using tert-butylmagnesium chloride in 16B and (4-(1-cyanocyclopropyl)-phenyl)boronic acid in 16C |
| 106 | 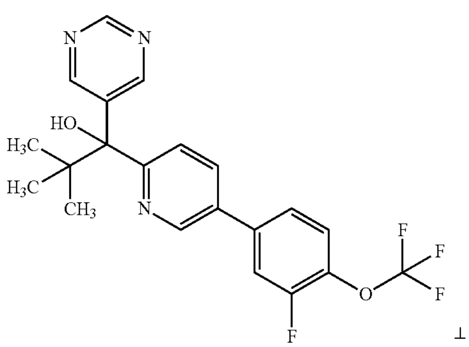 [SMILES: CC(C)(C)C(O)(c1cncnc1)c1ccc(-c2ccc(OC(F)(F)F)c(F)c2)cn1] | Prepared according to Example 16A-16C, using tert-butylmagnesium chloride in 16B and (3-fluoro-4-(trifluoromethoxy)-phenyl)boronic acid in 16C |
| 107 | 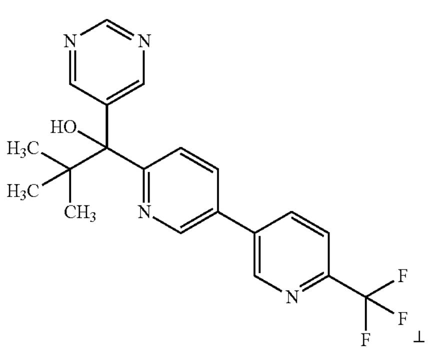 [SMILES: CC(C)(C)C(O)(c1cncnc1)c1ccc(-c2ccc(C(F)(F)F)nc2)cn1] | Prepared according to Example 16A-16C, using tert-butylmagnesium chloride in 16B and (6-(trifluoromethyl)pyridin-3-yl)boronic acid in 16C |

TABLE 1-continued

Structure and Preparation Method.

| Compound Number | Structure | Prepared According to Example |
|---|---|---|
| 108 | 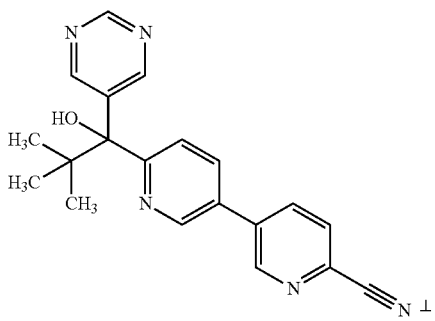 [SMILES: CC(C)(C)C(O)(c1cncnc1)c1ccc(-c2ccc(C#N)nc2)cn1] | Prepared according to Example 16A-16C, using tert-butylmagnesium chloride in 16B and (6-cyanopyridin-3-yl)boronic acid in 16C |
| 109 | 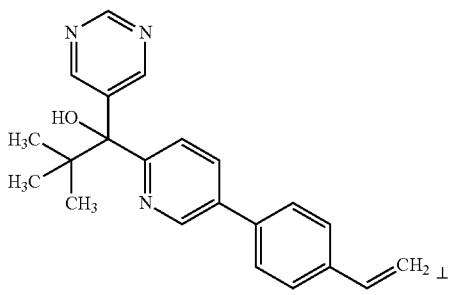 [SMILES: C=Cc1ccc(-c2ccc(C(O)(c3cncnc3)C(C)(C)C)nc2)cc1] | Prepared according to Example 16A-16C, using tert-butylmagnesium chloride in 16B and (4-vinylphenyl)boronic acid in 16C |
| 110 | 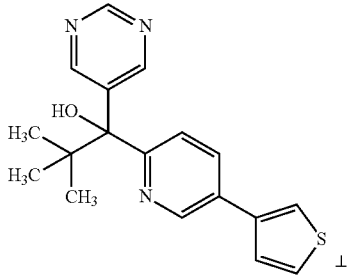 [SMILES: CC(C)(C)C(O)(c1cncnc1)c1ccc(-c2ccsc2)cn1] | Prepared according to Example 16A-16C, using tert-butylmagnesium chloride in 16B and thiophen-3-ylboronic acid in 16C |
| 111 | 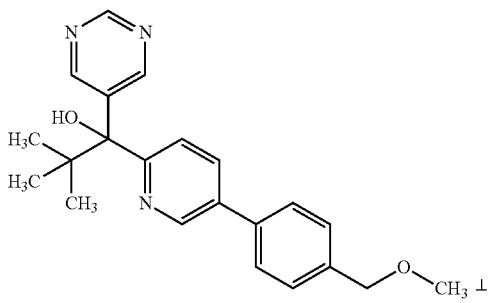 [SMILES: COCc1ccc(-c2ccc(C(O)(c3cncnc3)C(C)(C)C)nc2)cc1] | Prepared according to Example 16A-16C, using tert-butylmagnesium chloride in 16B and (4-(methoxymethyl)-phenyl)boronic acid in 16C |
| 112 | 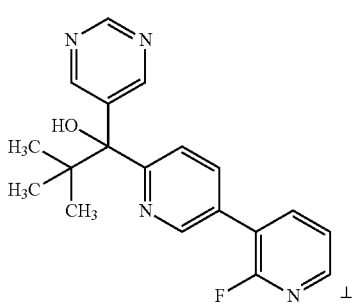 | Prepared according to Example 16A-16C, using tert-butylmagnesium chloride in 16B and (2-fluoropyridin-3-yl)boronic acid in 16C |

TABLE 1-continued

Structure and Preparation Method.

| Compound Number | Structure | Prepared According to Example |
|---|---|---|
| 113 | 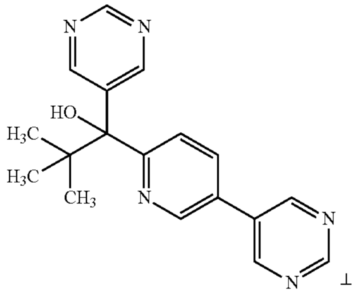 [SMILES: CC(C)(C)C(O)(c1cncnc1)c1ccc(-c2cncnc2)cn1] | Prepared according to Example 16A-16C, using tert-butylmagnesium chloride in 16B and pyrimidin-5-ylboronic acid in 16C |
| 114 | 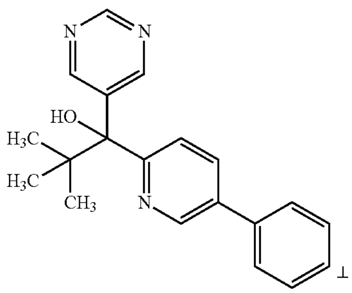 [SMILES: CC(C)(C)C(O)(c1cncnc1)c1ccc(-c2ccccc2)cn1] | Prepared according to Example 16A-16C, using tert-butylmagnesium chloride in 16B and phenylboronic acid in 16C |
| 115 | 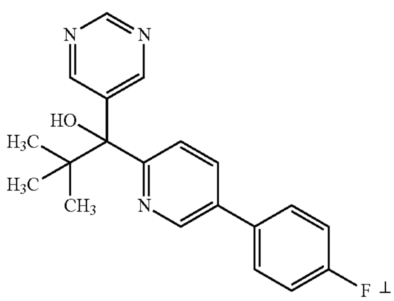 [SMILES: CC(C)(C)C(O)(c1cncnc1)c1ccc(-c2ccc(F)cc2)cn1] | Prepared according to Example 16A-16C, using tert-butylmagnesium chloride in 16B and (4-fluorophenyl)boronic acid in 16C |
| 116 | 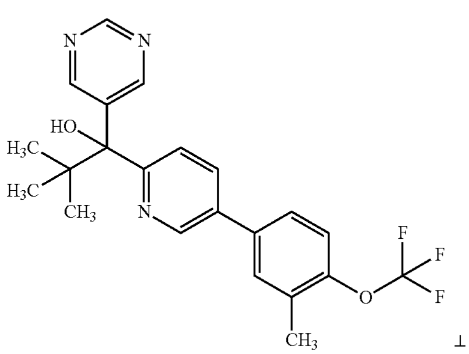 [SMILES: Cc1cc(-c2ccc(C(O)(c3cncnc3)C(C)(C)C)nc2)ccc1OC(F)(F)F] | Prepared according to Example 16A-16C, using tert-butylmagnesium chloride in 16B and (3-methyl-4-(trifluoromethoxy)phenyl)-boronic acid in 16C |

TABLE 1-continued

Structure and Preparation Method.

| Compound Number | Structure | Prepared According to Example |
|---|---|---|
| 117 | 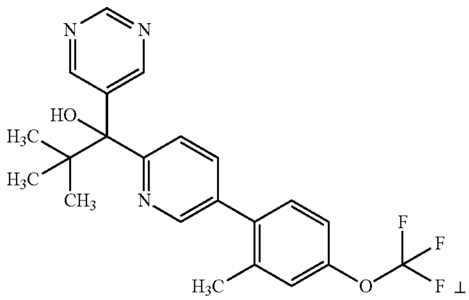 [SMILES: Cc1cc(OC(F)(F)F)ccc1-c1ccc(C(O)(c2cncnc2)C(C)(C)C)nc1] | Prepared according to Example 16A-16C, using tert-butylmagnesium chloride in 16B and (2-methyl-4-(trifluoromethoxy)phenyl)-boronic acid in 16C |
| 118 | 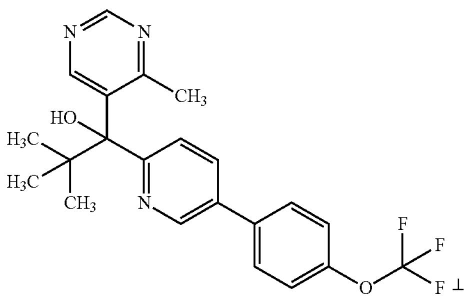 [SMILES: Cc1ncncc1C(O)(c1ccc(-c2ccc(OC(F)(F)F)cc2)cn1)C(C)(C)C] | Prepared according to Example 16A-16C, using N-methoxy-N,4-dimethylpyrimidine-5-carboxamide (prepared from 4-methylpyrimidine-5-carboxylic acid) in 16A, tert-butylmagnesium chloride in 16B, and (4-(trifluoromethoxy)-phenyl)boronic acid in 16C |
| 119 | 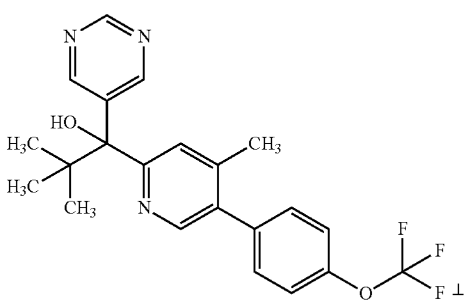 [SMILES: Cc1cc(C(O)(c2cncnc2)C(C)(C)C)ncc1-c1ccc(OC(F)(F)F)cc1] | Prepared according to Example 16A-16C, using 5-bromo-2-iodo-4-methyl-pyridine in 16A, tert-butylmagnesium chloride in 16B, and (4-(trifluoromethoxy)-phenyl)boronic acid in 16C |
| 120 | 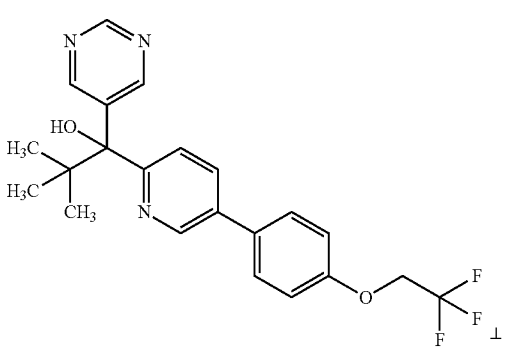 | Prepared according to Example 16A-16C, using tert-butylmagnesium chloride in 16B and (4-(2,2,2-trifluoroethoxy)-phenyl)boronic acid in 16C |

TABLE 1-continued

Structure and Preparation Method.

| Compound Number | Structure | Prepared According to Example |
|---|---|---|
| 121 | 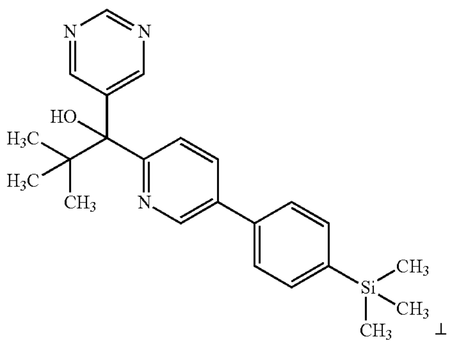 | Prepared according to Example 16A-16C, using tert-butylmagnesium chloride in 16B and (4-(trimethylsilyl)-phenyl)boronic acid in 16C |
| 122 | 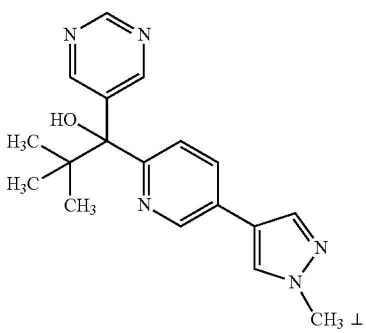 [SMILES: Cn1cc(-c2ccc(C(O)(c3cncnc3)C(C)(C)C)nc2)cn1] | Prepared according to Example 16A-16C, using tert-butylmagnesium chloride in 16B and (1-methyl-4-(4,4,5,5-tetramethyl-1,3,2-dioxaborolan-2-yl)-1H-pyrazole in 16C |
| 123 | 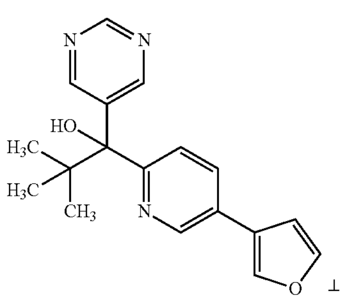 [SMILES: CC(C)(C)C(O)(c1cncnc1)c1ccc(-c2ccoc2)cn1] | Prepared according to Example 16A-16C, using tert-butylmagnesium chloride in 16B and 2-(furan-3-yl)-4,4,5,5-tetramethyl-1,3,2-dioxaborolane in 16C |
| 124 | 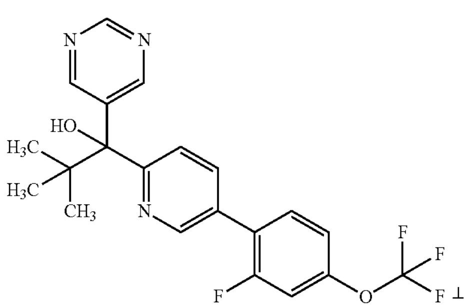 | Prepared according to Example 16A-16C, using tert-butylmagnesium chloride in 16B and 2-(2-fluoro-4-(trifluoromethoxy)phenyl)-4,4,5,5-tetramethyl-1,3,2-dioxaborolane (prepared from 1-bromo-2-fluoro-4-(trifluoromethoxy)benzene) in 16C |

TABLE 1-continued

Structure and Preparation Method.

| Compound Number | Structure | Prepared According to Example |
|---|---|---|
| 125 | 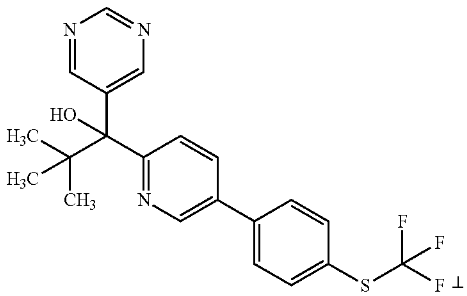 | Prepared according to Example 16A-16C, using tert-butylmagnesium chloride in 16B and 4,4,5,5-tetramethyl-2-(4-((trifluoromethypthio)phenyl)-1,3,2-dioxaborolane in 16C |
| 126 | 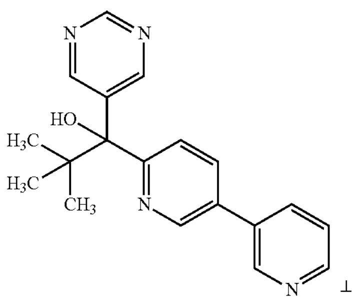 [SMILES: CC(C)(C)C(O)(c1cncnc1)c1ccc(-c2cccnc2)cn1] | Prepared according to Example 16A-16C, using tert-butylmagnesium chloride in 16B and pyridin-3-ylboronic acid in 16C |
| 127 | 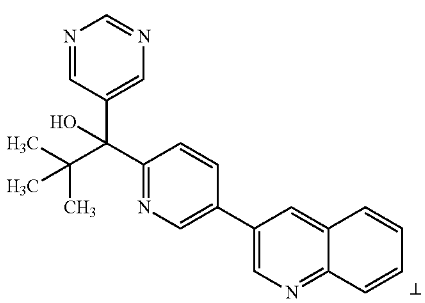 [SMILES: CC(C)(C)C(O)(c1cncnc1)c1ccc(-c2cnc3ccccc3c2)cn1] | Prepared according to Example 16A-16C, using tert-butylmagnesium chloride in 16B and quinolin-3-ylboronic acid in 16C |
| 128 | 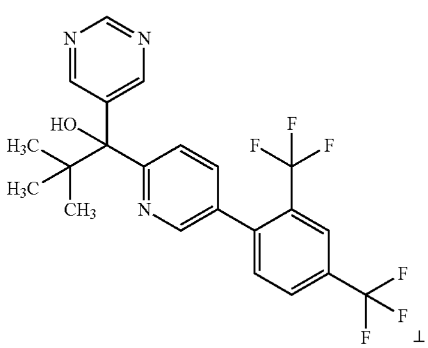 [SMILES: CC(C)(C)C(O)(c1cncnc1)c1ccc(-c2ccc(C(F)(F)F)cc2C(F)(F)F)cn1] | Prepared according to Example 16A-16C, using tert-butylmagnesium chloride in 16B and (2,4-bis(trifluoromethyl)-phenyl)boronic acid in 16C |

TABLE 1-continued

Structure and Preparation Method.

| Compound Number | Structure | Prepared According to Example |
|---|---|---|
| 130 | 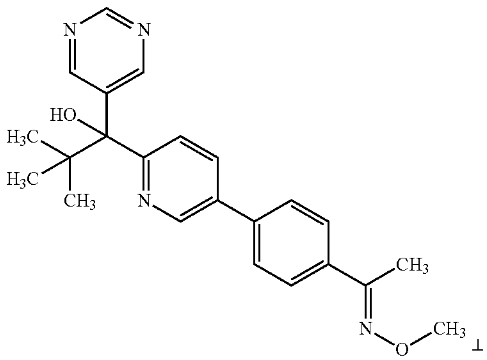 [SMILES: CO/N=C(\C)c1ccc(-c2ccc(C(O)(c3cncnc3)C(C)(C)C)nc2)cc1] | Example 18 |
| 131 | 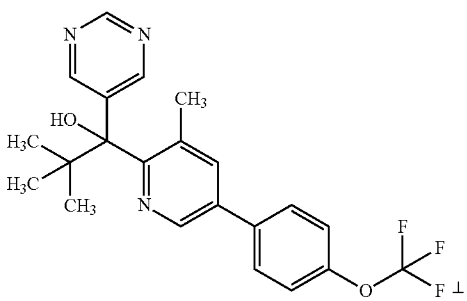 [SMILES: Cc1cc(-c2ccc(OC(F)(F)F)cc2)cnc1C(O)(c1cncnc1)C(C)(C)C] | Prepared according to Example 16A-16C, using 5-bromo-2-iodo-3-methyl-pyridine in 16A, tert-butylmagnesium chloride in 16B, and (4-(trifluoromethoxy)-phenyl)boronic acid in 16C |
| 132 | 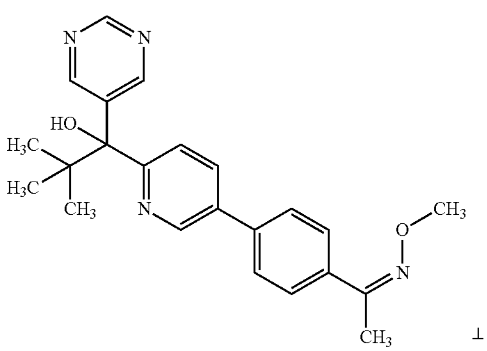 [SMILES: CO/N=C(/C)c1ccc(-c2ccc(C(O)(c3cncnc3)C(C)(C)C)nc2)cc1] | Example 18 |
| 133 | 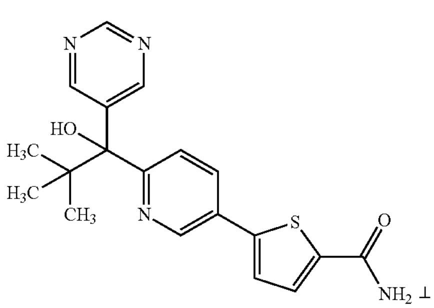 [SMILES: CC(C)(C)C(O)(c1cncnc1)c1ccc(-c2ccc(C(N)=O)s2)cn1] | Example 19 |

TABLE 1-continued

Structure and Preparation Method.

| Compound Number | Structure | Prepared According to Example |
|---|---|---|
| 134 | 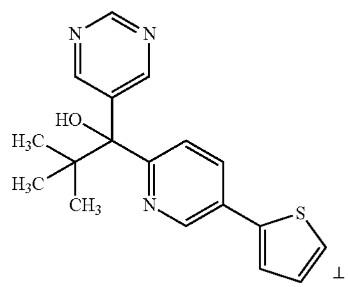 [SMILES: CC(C)(C)C(O)(c1cncnc1)c1ccc(-c2cccs2)cn1] | Prepared according to Example 16A-16C, using tert-butylmagnesium chloride in 16B and 4,4,5,5-tetramethyl-2-(thiophen-2-yl)-1,3,2-dioxaborolane in 16C |
| 135 | 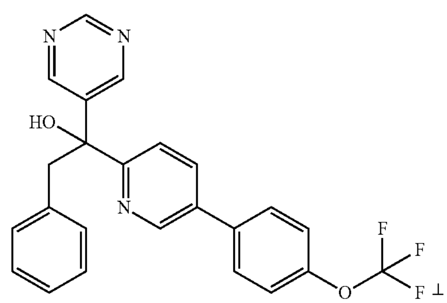 [SMILES: OC(Cc1ccccc1)(c1cncnc1)c1ccc(-c2ccc(OC(F)(F)F)cc2)cn1] | Prepared according to Example 20A-20B, using benzyl bromide in 20A |
| 136 | 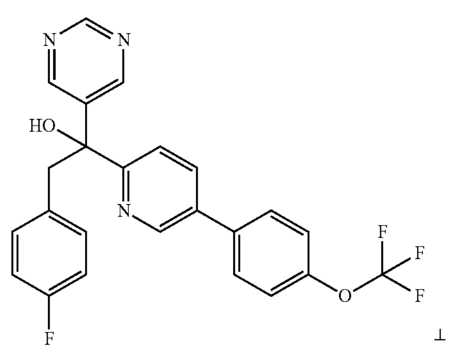 [SMILES: OC(Cc1ccc(F)cc1)(c1cncnc1)c1ccc(-c2ccc(OC(F)(F)F)cc2)cn1] | Prepared according to Example 20A-20B, using 4-fluorobenzyl bromide in 20A |
| 137 | 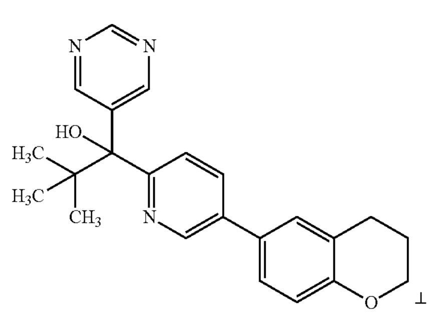 [SMILES: CC(C)(C)C(O)(c1cncnc1)c1ccc(-c2ccc3c(c2)CCCO3)cn1] | Prepared according to Example 16A-16C, using tert-butylmagnesium chloride in 16B and 2-(chroman-6-yl)-4,4,5,5-tetramethyl-1,3,2-dioxaborolane in 16C |

TABLE 1-continued

Structure and Preparation Method.

| Compound Number | Structure | Prepared According to Example |
|---|---|---|
| 138 | 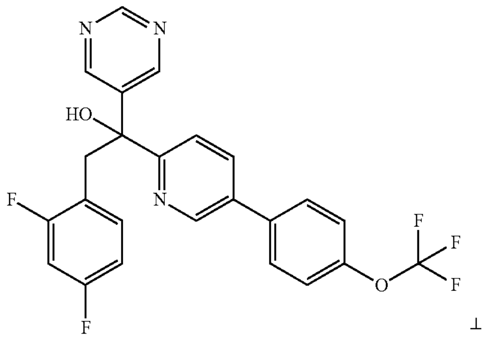 [SMILES: OC(Cc1ccc(F)cc1F)(c1cncnc1)c1ccc(-c2ccc(OC(F)(F)F)cc2)cn1] | Prepared according to Example 20A-20B, using 2,4-difluorobenzyl bromide in 20A |
| 139 | 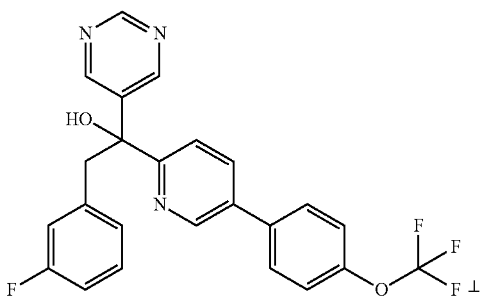 [SMILES: OC(Cc1cccc(F)c1)(c1cncnc1)c1ccc(-c2ccc(OC(F)(F)F)cc2)cn1] | Example 20 |
| 140 | 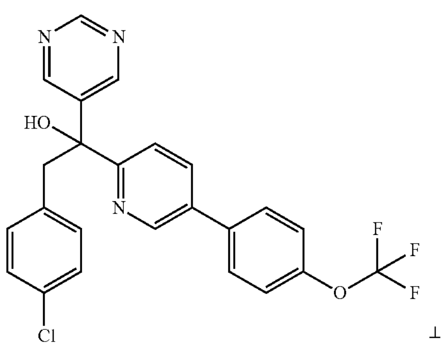 [SMILES: OC(Cc1ccc(Cl)cc1)(c1cncnc1)c1ccc(-c2ccc(OC(F)(F)F)cc2)cn1] | Prepared according to Example 20A-20B, using 4-chlorobenzyl bromide in 20A |
| 141 | 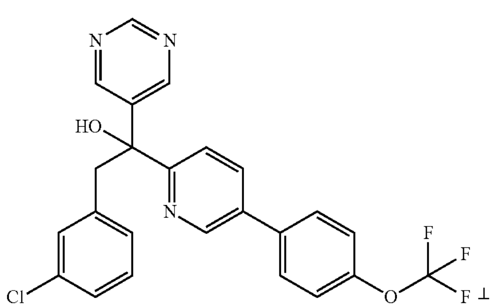 [SMILES: OC(Cc1cccc(Cl)c1)(c1cncnc1)c1ccc(-c2ccc(OC(F)(F)F)cc2)cn1] | Prepared according to Example 20A-20B, using 3-chlorobenzyl bromide in 20A |

TABLE 1-continued

Structure and Preparation Method.

| Compound Number | Structure | Prepared According to Example |
|---|---|---|
| 142 | 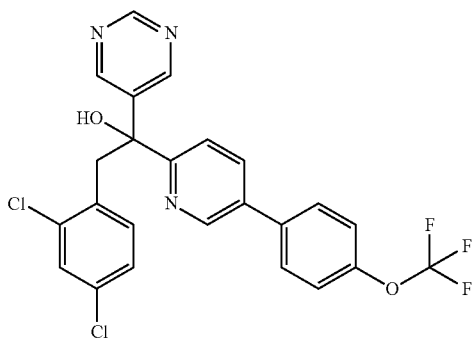 | Prepared according to Example 20A-20B, using 2,4-dichlorobenzyl bromide in 20A |
| 143 | 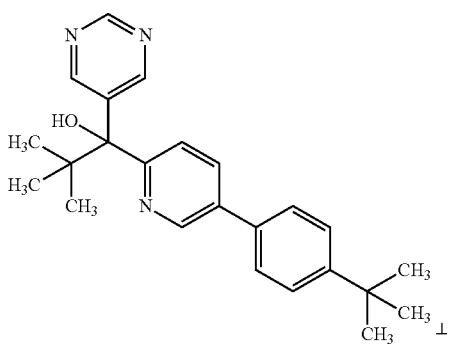 [SMILES: CC(C)(C)c1ccc(-c2ccc(C(O)(c3cncnc3)C(C)(C)C)nc2)cc1] | Prepared according to Example 16A-16C, using N-methoxy-N-methylnicotinamide (prepared from nicotinic acid) in 16A, tert-butylmagnesium chloride in 16B and 4-(tert-butylphenyl)boronic acid in 16C |
| 144 | 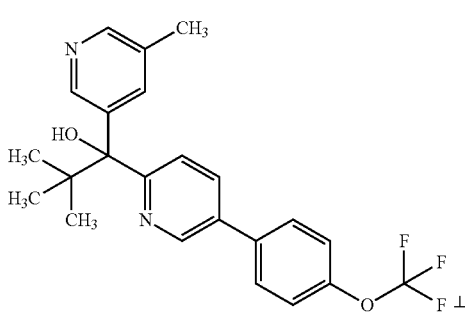 [SMILES: Cc1cncc(C(O)(c2ccc(-c3ccc(OC(F)(F)F)cc3)cn2)C(C)(C)C)c1] | Prepared according to Example 16A-16C, using N-methoxy-N,5-dimethylnicotinamide (prepared from 5-methylnicotinic acid) in 16A, tert-butylmagnesium chloride in 16B, and (4-(trifluoromethoxy)-phenyl)boronic acid in 16C |
| 145 | 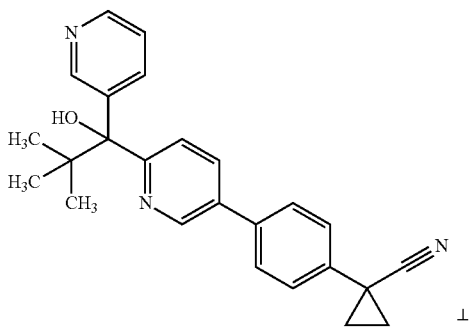 [SMILES: CC(C)(C)C(O)(c1cccnc1)c1ccc(-c2ccc(C3(C#N)CC3)cc2)cn1] | Prepared according to Example 16A-16C, using N-methoxy-N-methylnicotinamide (prepared from nicotinic acid) in 16A, tert-butylmagnesium chloride in 16B and 4-(1-cyanocyclopropyl)-phenyl)boronic acid in 16C |

TABLE 1-continued

Structure and Preparation Method.

| Compound Number | Structure | Prepared According to Example |
|---|---|---|
| 146 | 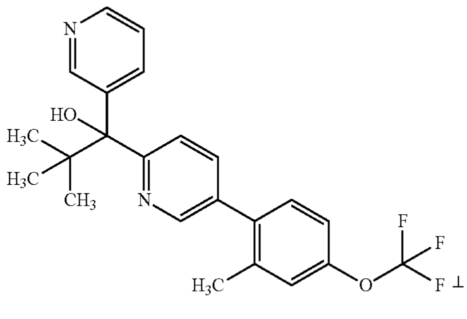 [SMILES: Cc1cc(OC(F)(F)F)ccc1-c1ccc(C(O)(c2cccnc2)C(C)(C)C)nc1] | Prepared according to Example 16A-16C, using N-methoxy-N-methylnicotinamide (prepared from nicotinic acid) in 16A, tert-butylmagnesium chloride in 16B and 2-methyl-4-(trifluoromethoxy)-phenylboronic acid in 16C |
| 147 | 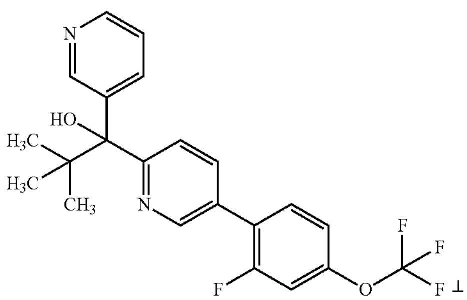 [SMILES: CC(C)(C)C(O)(c1cccnc1)c1ccc(-c2ccc(OC(F)(F)F)cc2F)cn1] | Prepared according to Example 16A-16C, using N-methoxy-N-methylnicotinamide (prepared from nicotinic acid) in 16A, tert-butylmagnesium chloride in 16B and 2-(2-fluoro-4-(trifluoromethoxy)phenyl)-4,4,5,5-tetramethyl-1,3,2-dioxaborolane (prepared from 1-bromo-2-fluoro-4-(trifluoromethoxy)-benzene) in 16C |
| 148 | 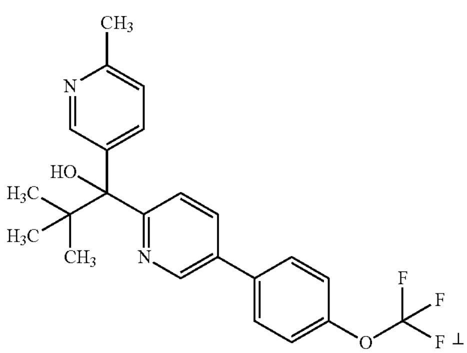 [SMILES: Cc1ccc(C(O)(c2ccc(-c3ccc(OC(F)(F)F)cc3)cn2)C(C)(C)C)cn1] | Prepared according to Example 16A-16C, using N-methoxy-N,6-dimethylnicotinamide (prepared from 6-methylnicotinic acid) in 16A, tert-butylmagnesium chloride in 16B and 4-(trifluoromethoxy)-phenylboronic acid in 16C |
| 149 | 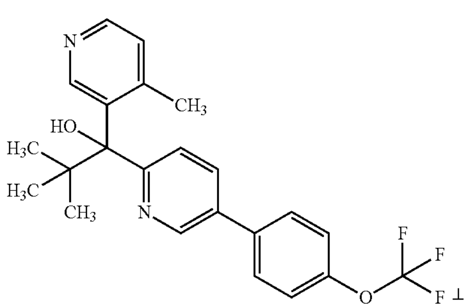 [SMILES: Cc1ccncc1C(O)(c1ccc(-c2ccc(OC(F)(F)F)cc2)cn1)C(C)(C)C] | Prepared according to Example 16A-16C, using N-methoxy-N,4-dimethylnicotinamide (prepared from 4-methylnicotinic acid) in 16A, tert-butylmagnesium chloride in 16B and 4-(trifluoromethoxy)-phenylboronic acid in 16C |

TABLE 1-continued

Structure and Preparation Method.

| Compound Number | Structure | Prepared According to Example |
|---|---|---|
| 150 | 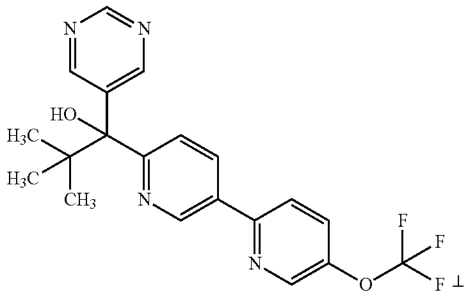 | Prepared according to Example 16A-16C, using tert-butylmagnesium chloride in 16B and 4-methyl-2,6-dioxo-8-(5-(trifluoromethoxy)pyridin-2-yl)hexahydro-[1,3,2]oxaza-borolo[2,3-b][1,3,2]oxazaborol-4-ium-8-uide in 16C |
| 151 | 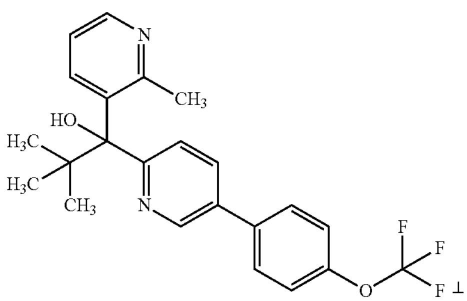 | Prepared according to Example 16A-16C, using N-methoxy-N,2-dimethylnicotinamide (prepared from 2-methylnicotinic acid) in 16A, tert-butylmagnesium chloride in 16B and 4-(trifluoromethoxy)-phenylboronic acid in 16C |
| 152 | 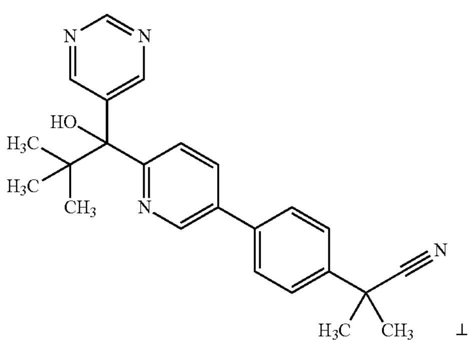 [SMILES: CC(C)(C#N)c1ccc(-c2ccc(C(O)(c3cncnc3)C(C)(C)C)nc2)cc1] | Prepared according to Example 16A-16C, using tert-butylmagnesium chloride in 16B and (4-(2-cyanopropan-2-yl)phenyl)boronic acid in 16C |
| 153 | 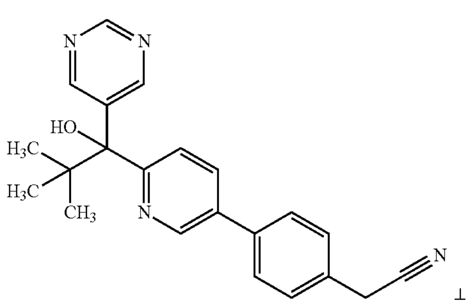 [SMILES: CC(C)(C)C(O)(c1cncnc1)c1ccc(-c2ccc(CC#N)cc2)cn1] | Prepared according to Example 16A-16C, using tert-butylmagnesium chloride in 16B and (4-(cyanomethyl)phenyl)boronic acid in 16C |

TABLE 1-continued

Structure and Preparation Method.

| Compound Number | Structure | Prepared According to Example |
|---|---|---|
| 154 | 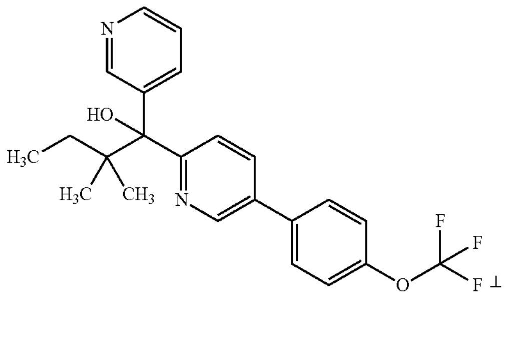 [SMILES: CCC(C)(C)C(O)(c1cccnc1)c1ccc(-c2ccc(OC(F)(F)F)cc2)cn1] | Prepared according to Example 16, using N-methoxy-N-methylnicotinamide (prepared from nicotinic acid) in 16A |
| 155 | 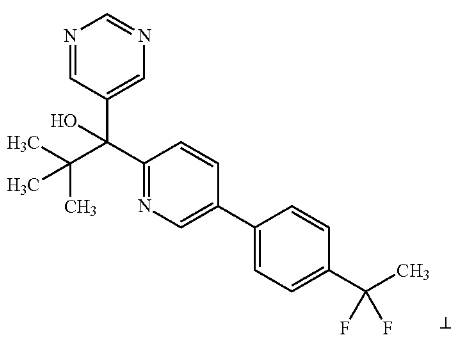 [SMILES: CC(F)(F)c1ccc(-c2ccc(C(O)(c3cncnc3)C(C)(C)C)nc2)cc1] | Example 21 |
| 156 | 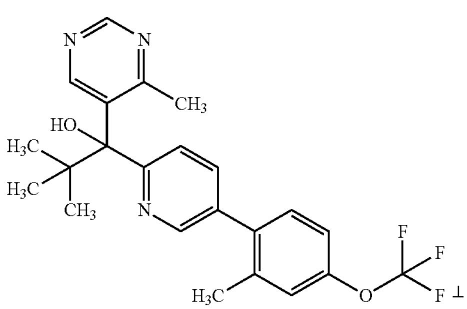 [SMILES: Cc1cc(OC(F)(F)F)ccc1-c1ccc(C(O)(c2cncnc2C)C(C)(C)C)nc1] | Prepared according to Example 16A-16C, using N-methoxy-N,4-dimethylpyrimidine-5-carboxamide (prepared from 4-methylpyrimidine-5-carboxylic acid) in 16A, tert-butylmagnesium chloride in 16B, and (2-methyl-4-(trifluoromethoxy)-phenyl)boronic acid in 16C |
| 157 | 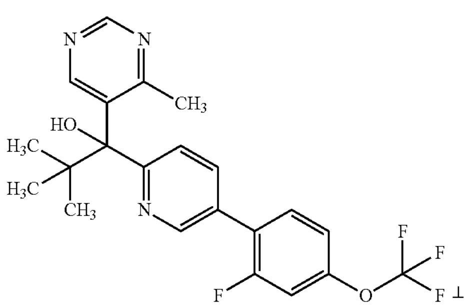 [SMILES: Cc1ncncc1C(O)(c1ccc(-c2ccc(OC(F)(F)F)cc2F)cn1)C(C)(C)C] | Prepared according to Example 16A-16C, using N-methoxy-N,4-dimethylpyrimidine-5-carboxamide (prepared from 4-methylpyrimidine-5-carboxylic acid) in 16A, tert-butylmagnesium chloride in 16B, and 2-(2-fluoro-4-(trifluoromethoxy)phenyl)-4,4,5,5-tetramethyl-1,3,2-dioxaborolane in 16C |

TABLE 1-continued

Structure and Preparation Method.

| Compound Number | Structure | Prepared According to Example |
|---|---|---|
| 158 | 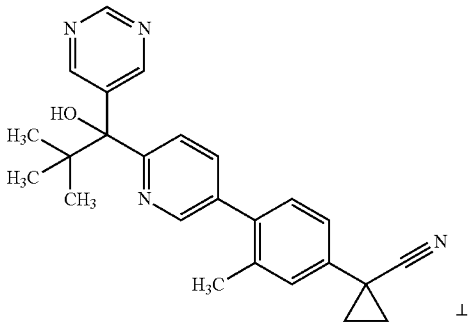 [SMILES: Cc1cc(C2(C#N)CC2)ccc1-c1ccc(C(O)(c2cncnc2)C(C)(C)C)nc1] | Prepared according to Example 16A-16C, using tert-butylmagnesium chloride in 16B and 1-(3-methyl-4-(4,4,5,5-tetramethyl-1,3,2-dioxaborolan-2-yl)phenyl)cyclopropane-carbonitrile in 16C |
| 159 | 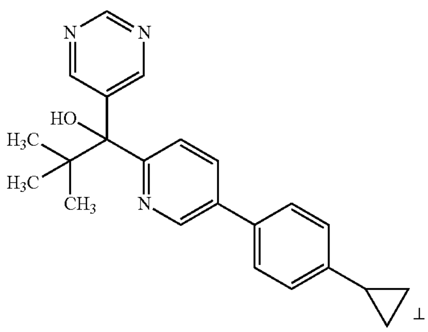 [SMILES: CC(C)(C)C(O)(c1cncnc1)c1ccc(-c2ccc(C3CC3)cc2)cn1] | Prepared according to Example 16A-16C, using tert-butylmagnesium chloride in 16B and 2-(4-cyclopropylphenyl)-4,4,5,5-tetramethyl-1,3,2-dioxaborolane in 16C |
| 160 | 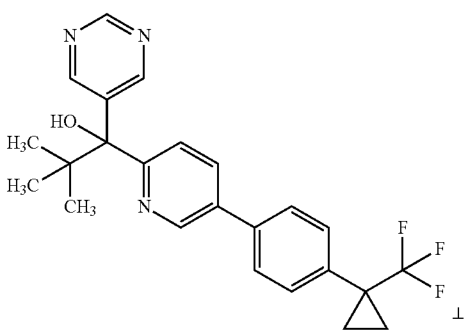 [SMILES: CC(C)(C)C(O)(c1cncnc1)c1ccc(-c2ccc(C3(C(F)(F)F)CC3)cc2)cn1] | Prepared according to Example 16A-16C, using tert-butylmagnesium chloride in 16B and 4,4,5,5-tetramethyl-2-(4-(1-(trifluoromethyl)cyclopropyl)-phenyl)-1,3,2-dioxaborolane in 16C |
| 161 | 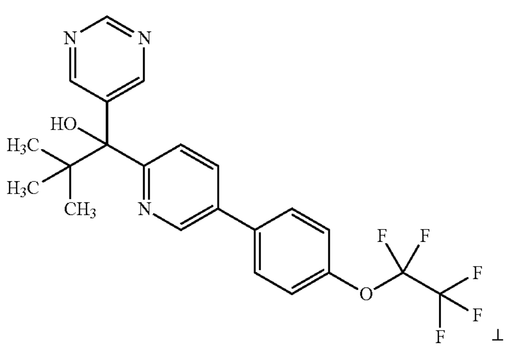 [SMILES: CC(C)(C)C(O)(c1cncnc1)c1ccc(-c2ccc(OC(F)(F)C(F)(F)F)cc2)cn1] | Prepared according to Example 16A-16C, using tert-butylmagnesium chloride in 16B and 4,4,5,5-tetramethyl-2-(4-(perfluoroethoxy)phenyl)-1,3,2-dioxaborolane in 16C |

TABLE 1-continued

Structure and Preparation Method.

| Compound Number | Structure | Prepared According to Example |
|---|---|---|
| 162 | 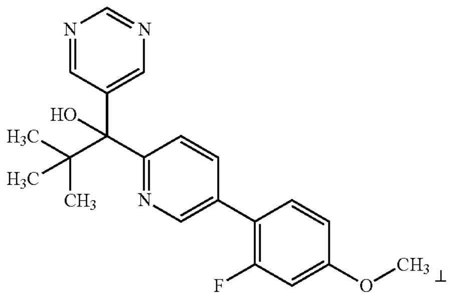 [SMILES: COc1ccc(-c2ccc(C(O)(c3cncnc3)C(C)(C)C)nc2)c(F)c1] | Prepared according to Example 16A-16C, using tert-butylmagnesium chloride in 16B and (2-fluoro-4-methoxyphenyl)boronic acid in 16C |
| 163 | 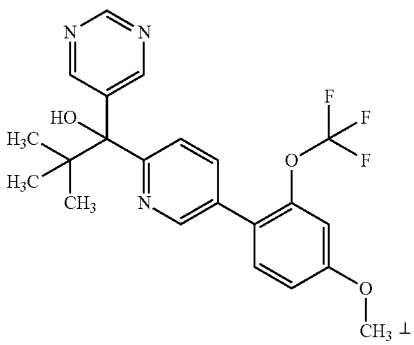 [SMILES: COc1ccc(-c2ccc(C(O)(c3cncnc3)C(C)(C)C)nc2)c(OC(F)(F)F)c1] | Prepared according to Example 16A-16C, using tert-butylmagnesium chloride in 16B and (4-methoxy-2-(trifluoromethoxy)phenyl)boronic acid in 16C |
| 164 | 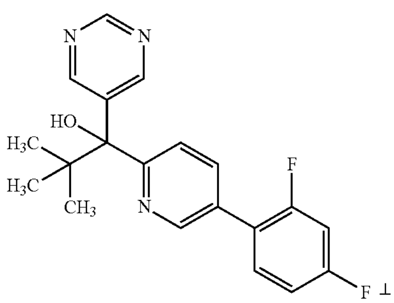 [SMILES: CC(C)(C)C(O)(c1cncnc1)c1ccc(-c2ccc(F)cc2F)cn1] | Prepared according to Example 16A-16C, using tert-butylmagnesium chloride in 16B and (2,4-difluorophenyl)boronic acid in 16C |
| 165 | 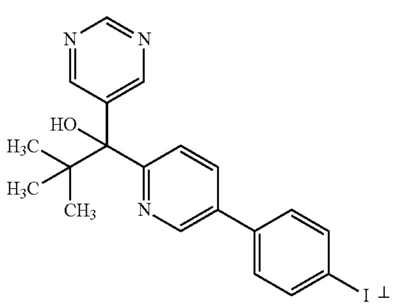 | Example 22 |

TABLE 1-continued

Structure and Preparation Method.

| Compound Number | Structure | Prepared According to Example |
|---|---|---|
| 166 | 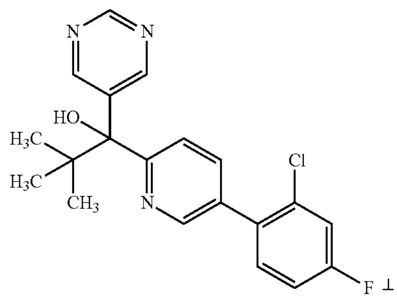 [SMILES: CC(C)(C)C(O)(c1cncnc1)c1ccc(-c2ccc(F)cc2Cl)cn1] | Prepared according to Example 16A-16C, using tert-butylmagnesium chloride in 16B and (2-chloro-4-fluorophenyl)-boronic acid in 16C |
| 167 | 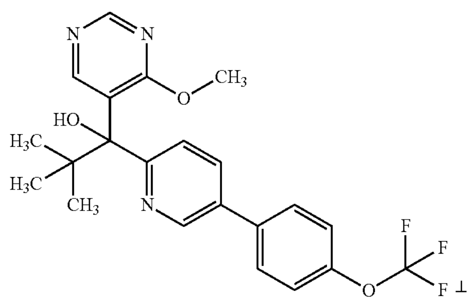 [SMILES: COc1ncncc1C(O)(c1ccc(-c2ccc(OC(F)(F)F)cc2)cn1)C(C)(C)C] | Prepared according to Example 16A-16C, using N,4-dimethoxy-N-methylpyrimidine-5-carboxamide (prepared from 4-methoxypyrimidine-5-carboxylic acid) in 16A, tert-butylmagnesium chloride in 16B, and (4-(trifluoromethoxy)-phenyl)boronic acid in 16C |
| 168 | 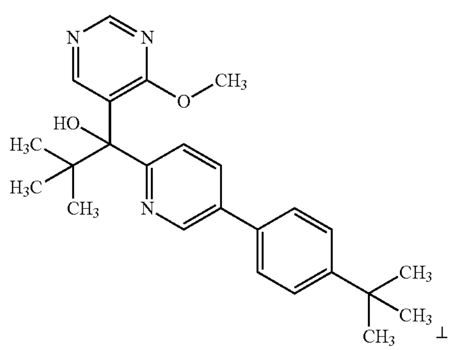 [SMILES: COc1ncncc1C(O)(c1ccc(-c2ccc(C(C)(C)C)cc2)cn1)C(C)(C)C] | Prepared according to Example 16A-16C, using N,4-dimethoxy-N-methylpyrimidine-5-carboxamide (prepared from 4-methoxypyrimidine-5-carboxylic acid) in 16A, tert-butylmagnesium chloride in 16B, and (4-(tert-butyl)phenyl)boronic acid in 16C |
| 169 | 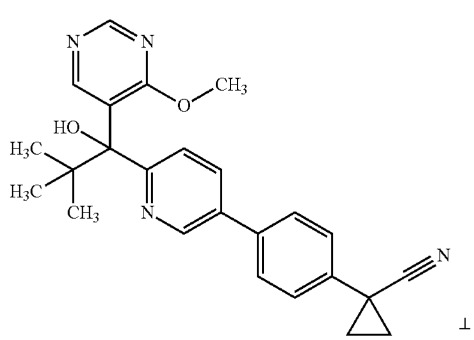 [SMILES: COc1ncncc1C(O)(c1ccc(-c2ccc(C3(C#N)CC3)cc2)cn1)C(C)(C)C] | Prepared according to Example 16A-16C, using N,4-dimethoxy-N-methylpyrimidine-5-carboxamide (prepared from 4-methoxypyrimidine-5-carboxylic acid) in 16A, tert-butylmagnesium chloride in 16B, and (4-(1-cyanocyclopropyl)-phenyl)boronic acid in 16C |

TABLE 1-continued

Structure and Preparation Method.

| Compound Number | Structure | Prepared According to Example |
|---|---|---|
| 170 | 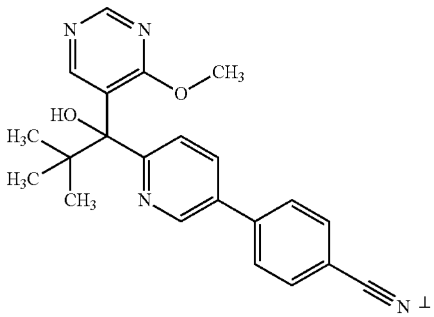 [SMILES: COc1ncncc1C(O)(c1ccc(-c2ccc(C#N)cc2)cn1)C(C)(C)C] | Prepared according to Example 16A-16C, using N,4-dimethoxy-N-methylpyrimidine-5-carboxamide (prepared from 4-methoxypyrimidine-5-carboxylic acid) in 16A, tert-butylmagnesium chloride in 16B, and (4-cyanophenyl)boronic acid in 16C |
| 171 | 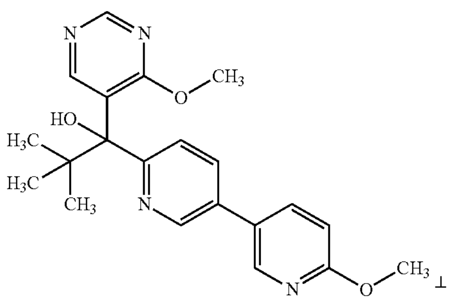 [SMILES: COc1ccc(-c2ccc(C(O)(c3cncnc3OC)C(C)(C)C)nc2)cn1] | Prepared according to Example 16A-16C, using N,4-dimethoxy-N-methylpyrimidine-5-carboxamide (prepared from 4-methoxypyrimidine-5-carboxylic acid) in 16A, tert-butylmagnesium chloride in 16B, and (6-methoxypyridin-3-yl)boronic acid in 16C |
| 172 | 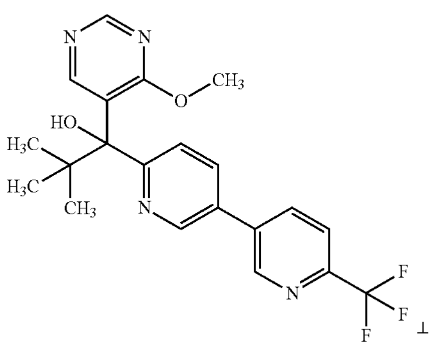 [SMILES: COc1ncncc1C(O)(c1ccc(-c2ccc(C(F)(F)F)nc2)cn1)C(C)(C)C] | Prepared according to Example 16A-16C, using N,4-dimethoxy-N-methylpyrimidine-5-carboxamide (prepared from 4-methoxypyrimidine-5-carboxylic acid) in 16A, tert-butylmagnesium chloride in 16B, and (6-(trifluoromethyl)pyridin-3-yl)boronic acid in 16C |
| 173 | 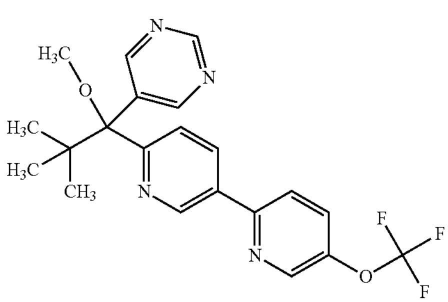 [SMILES: COC(c1cncnc1)(c1ccc(-c2ccc(OC(F)(F)F)cn2)cn1)C(C)(C)C] | Prepared according to Example 23 from 2,2-dimethyl-1-(pyrimidin-5-yl)-1-(5-(trifluoromethoxy)-[2,3'-bipyridin]-6'-yl)propan-1-ol |

TABLE 1-continued

Structure and Preparation Method.

| Compound Number | Structure | Prepared According to Example |
|---|---|---|
| 174 | 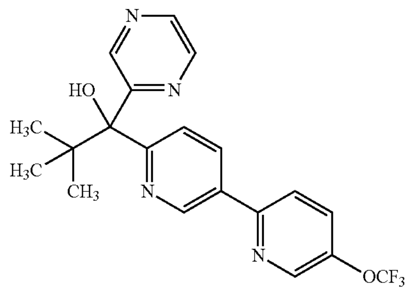 [SMILES: CC(C)(C)C(O)(c1ccc(-c2ccc(OC(F)(F)F)cn2)cn1)c1cnccn1] | Prepared according to Example 16 using N-methoxy-N-methylpyrazine-2-carboxamide in 16A, tert-butylmagnesium chloride in 16B, and 2-(4,4,5,5-tetramethyl-1,3,2-dioxaborolan-2-yl)-5-(trifluoromethoxy)pyridine (prepared as described in 17A from 2-bromo-5-(trifluoromethoxy)pyridine) in 16C |
| 175 | 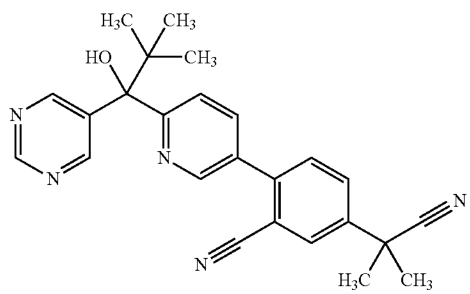 [SMILES: CC(C)(C#N)c1ccc(-c2ccc(C(O)(c3cncnc3)C(C)(C)C)nc2)c(C#N)c1] | Example 25 |
| 176 | 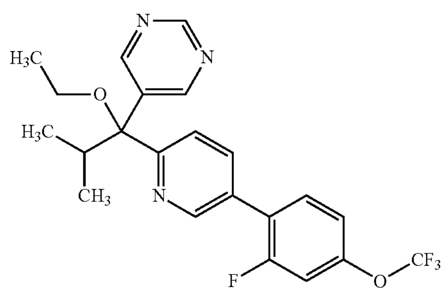 [SMILES: CCOC(c1cncnc1)(c1ccc(-c2ccc(OC(F)(F)F)cc2F)cn1)C(C)C] | Prepared according to Example 23 from 1-(5-(2-fluoro-4-(trifluoromethoxy)phenyl)pyridin-2-yl)-2-methyl-1-(pyrimidin-5-yl)propan-1-ol (163) and iodoethane |
| 177 | 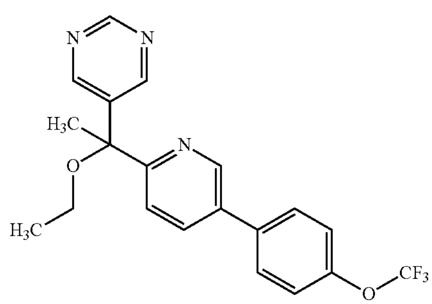 [SMILES: CCOC(C)(c1cncnc1)c1ccc(-c2ccc(OC(F)(F)F)cc2)cn1] | Prepared according to Example 23 from 1-(pyrimidin-5-yl)-1-(5-(4-(trifluoromethoxy)phenyl)pyridin-2-yl)ethanol and iodoethane |
| 178 | 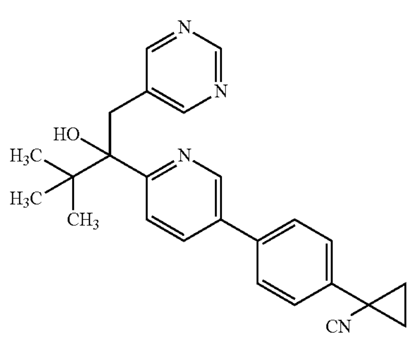 [SMILES: CC(C)(C)C(O)(Cc1cncnc1)c1ccc(-c2ccc(C3(C#N)CC3)cc2)cn1] | Prepared according to Example 6 using (4-(1-cyanocyclopropyl)phenyl)boronic acid in step 6C and tert-butylmagnesium chloride in step 6D. |

TABLE 1-continued

Structure and Preparation Method.

| Compound Number | Structure | Prepared According to Example |
|---|---|---|
| 179 | 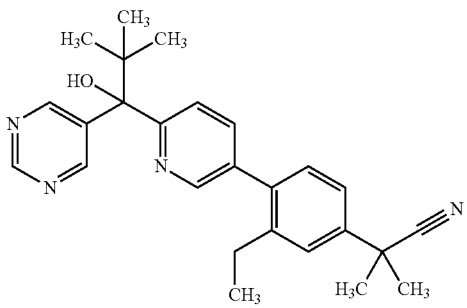 | Example 29 |
| 180 | 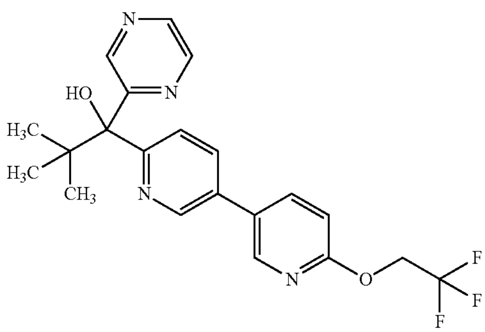 [SMILES: CC(C)(C)C(O)(c1ccc(-c2ccc(OCC(F)(F)F)nc2)cn1)c1cnccn1] | Prepared according to Example 16 using N-methoxy-N-methylpyrazine-2-carboxamide in 16A, tert-butylmagnesium chloride in 16B, and (6-(2,2,2-trifluoroethoxy)pyridin-3-yl)boronic acid in 16C |
| 181 | 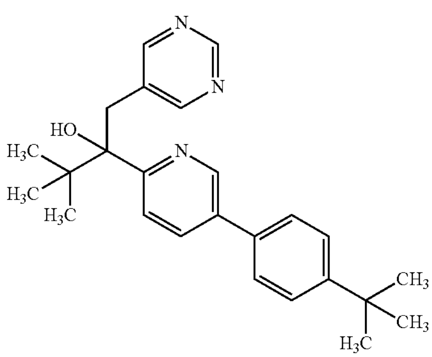 | Prepared according to Example 6 using (4-(tert-butyl)phenyl)boronic acid in step 6C and tert-butylmagnesium chloride in step 6D. |
| 182 | 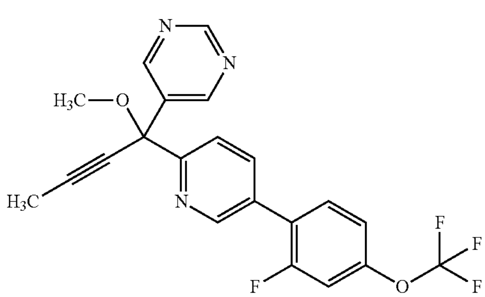 [SMILES: CC#CC(OC)(c1cncnc1)c1ccc(-c2ccc(OC(F)(F)F)cc2F)cn1] | Prepared according to Example 23 from 1-(5-(2-fluoro-4-(trifluoromethoxy)phenyl)pyridin-2-yl)-1-(pyrimidin-5-yl)but-2-yn-1-ol (118) and iodomethane |

TABLE 1-continued

Structure and Preparation Method.

| Compound Number | Structure | Prepared According to Example |
|---|---|---|
| 183 | 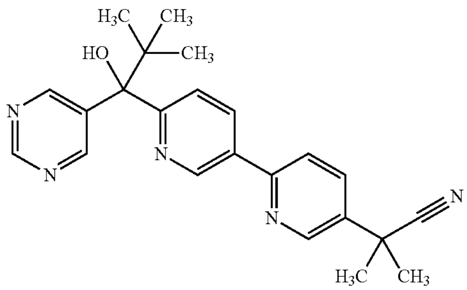 [SMILES: CC(C)(C#N)c1ccc(-c2ccc(C(O)(c3cncnc3)C(C)(C)C)nc2)nc1] | Prepared according to Example 25 using 2-(6-bromopyridin-3-yl)-2-methylpropanenitrile in 25E. 2-(6-bromopyridin-3-yl)-2-methylpropanenitrile was prepared from 6-bromonicotinaldehyde according to conditions described for 25A-25D |
| 184 | 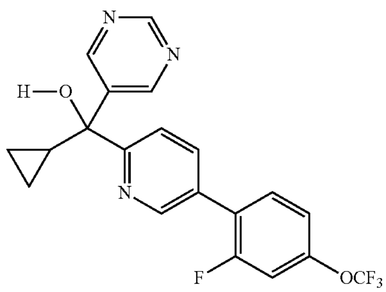 [SMILES: OC(c1cncnc1)(c1ccc(-c2ccc(OC(F)(F)F)cc2F)cn1)C1CC1] | Prepared according to Example 27 using 2-(2-fluoro-4-(trifluoromethoxy)phenyl)-4,4,5,5-tetramethyl-1,3,2-dioxaborolane (prepared as described in 17A) in 27C and cyclopropyl magnesium bromide in 27D |
| 185 | 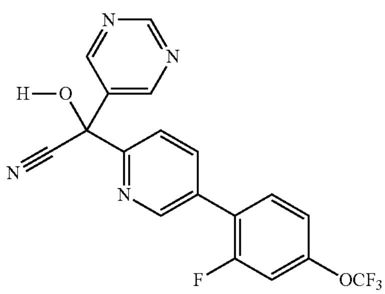 [SMILES: N#CC(O)(c1cncnc1)c1ccc(-c2ccc(OC(F)(F)F)cc2F)cn1] | Prepared according to Example 27 using 2-(2-fluoro-4-(trifluoromethoxy)phenyl)-4,4,5,5-tetramethyl-1,3,2-dioxaborolane (prepared as described in 17A) in 27C |
| 186 | 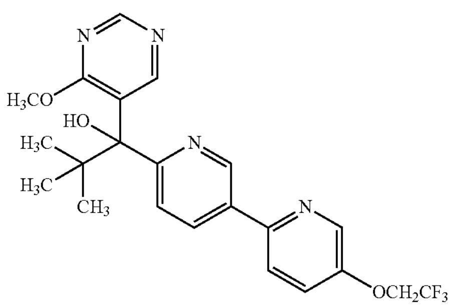 | Prepared according to Example 30 using 2-bromo-5-(2,2,2-trifluoroethoxy)pyridine in step 30F. |
| 187 | 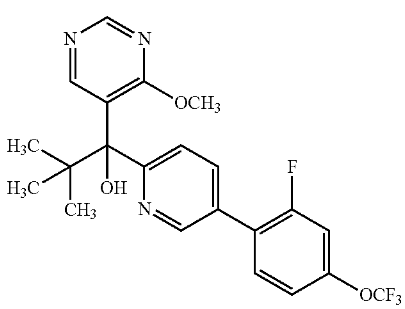 [SMILES: COc1ncncc1C(O)(c1ccc(-c2ccc(OC(F)(F)F)cc2F)cn1)C(C)(C)C] | Prepared according to Example 28 using (2-fluoro-4-(trifluoromethoxy)phenyl)boronic acid in step 28F (skip steps 28D-E) |

TABLE 1-continued

Structure and Preparation Method.

| Compound Number | Structure | Prepared According to Example |
|---|---|---|
| 188 | 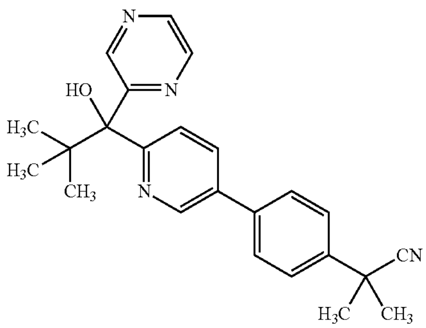 [SMILES: CC(C)(C#N)c1ccc(-c2ccc(C(O)(c3cnccn3)C(C)(C)C)nc2)cc1] | Prepared according to Example 16 using N-methoxy-N-methylpyrazine-2-carboxamide in 16A, tert-butylmagnesium chloride in 16B, and (4-(2-cyanopropan-2-yl)phenyl)boronic acid in 16C |
| 189 | 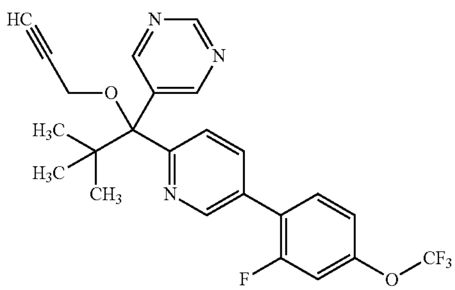 [SMILES: C#CCOC(c1cncnc1)(c1ccc(-c2ccc(OC(F)(F)F)cc2F)cn1)C(C)(C)C] | Prepared according to Example 23 from 1-(5-(2-fluoro-4-(trifluoromethoxy)phenyl)pyridin-2-yl)-2,2-dimethyl-1-(pyrimidin-5-yl)propan-1-ol and propargyl bromide |
| 190 | 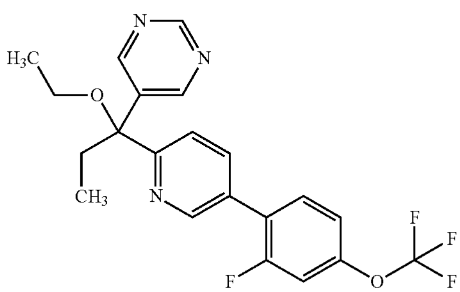 [SMILES: CCOC(CC)(c1cncnc1)c1ccc(-c2ccc(OC(F)(F)F)cc2F)cn1] | Prepared according to Example 23 from 1-(5-(2-fluoro-4-(trifluoromethoxy)phenyl)pyridin-2-yl)-1-(pyrimidin-5-yl)propan-(138) and iodoethane |
| 191 | 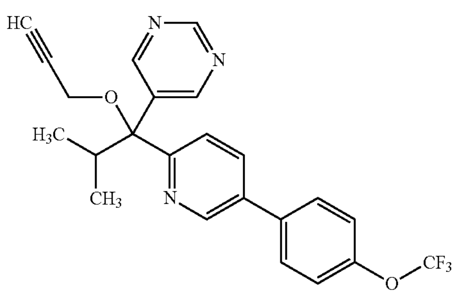 [SMILES: C#CCOC(c1cncnc1)(c1ccc(-c2ccc(OC(F)(F)F)cc2)cn1)C(C)C] | Prepared according to Example 23 from 2-methyl-1-(pyrimidin-5-yl)-1-(5-(4-(trifluoromethoxy)phenyl)pyridin-2-yl)propan-1-ol and propargyl bromide |
| 192 | 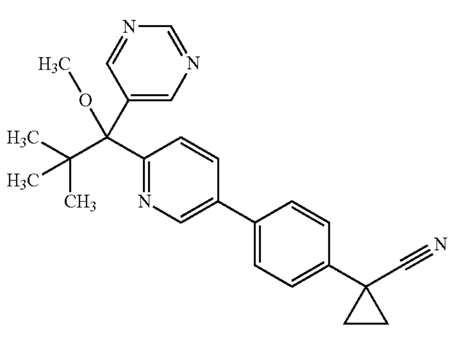 [SMILES: COC(c1cncnc1)(c1ccc(-c2ccc(C3(C#N)CC3)cc2)cn1)C(C)(C)C] | Prepared according to Example 23 from 1-(4-(6-(1-hydroxy-2,2-dimethyl-1-(pyrimidin-5-yl)propyl)pyridin-3-yl)phenyl)cyclopropanecarbonitrile |

TABLE 1-continued

Structure and Preparation Method.

| Compound Number | Structure | Prepared According to Example |
|---|---|---|
| 193 | 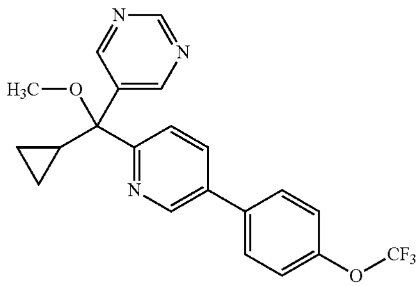 [SMILES: COC(c1cncnc1)(c1ccc(-c2ccc(OC(F)(F)F)cc2)cn1)C1CC1] | Prepared according to Example 23 from cyclopropyl(pyrimidin-5-yl)(5-(4-(trifluoromethoxy)phenyl)pyridin-2-yl)methanol |
| 194 | 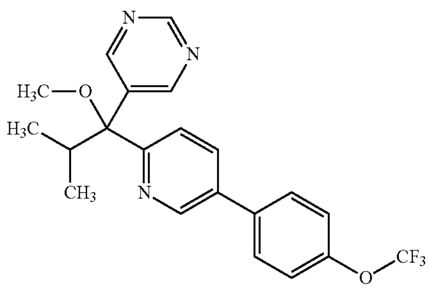 [SMILES: COC(c1cncnc1)(c1ccc(-c2ccc(OC(F)(F)F)cc2)cn1)C(C)C] | Prepared according to Example 23 from 2-methyl-1-(pyrimidin-5-yl)-1-(5-(4-(trifluoromethoxy)phenyl)pyridin-2-yl)propan-1-ol |
| 195 | 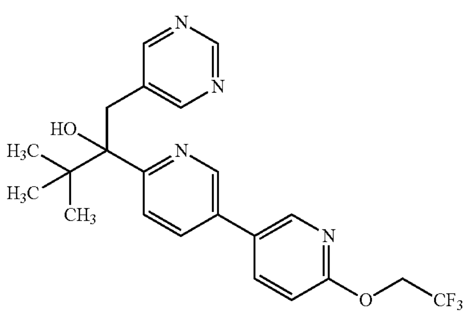 | Prepared according to Example 6 using 5-(4,4,5,5-tetramethyl-1,3,2-dioxaborolan-2-yl)-2-(2,2,2-trifluoroethoxy)pyridine in step 6C and tert-butylmagnesium chloride in step 6D. |
| 196 | 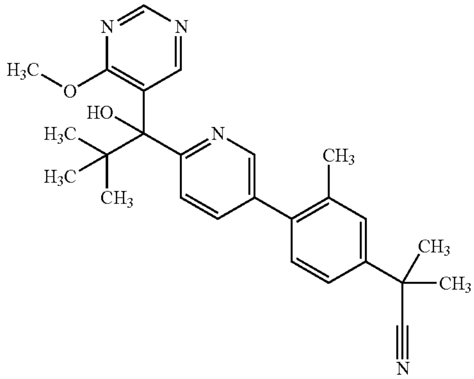 [SMILES: COc1ncncc1C(O)(c1ccc(-c2ccc(C(C)(C)C#N)cc2C)cn1)C(C)(C)C] | Example 28 |

TABLE 1-continued

Structure and Preparation Method.

| Compound Number | Structure | Prepared According to Example |
|---|---|---|
| 197 | 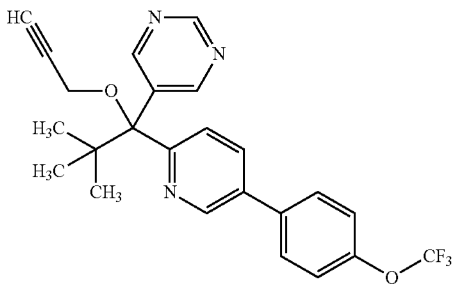 [SMILES: C#CCOC(c1cncnc1)(c1ccc(-c2ccc(OC(F)(F)F)cc2)cn1)C(C)(C)C] | Prepared according to Example 23 using propargyl bromide |
| 198 | 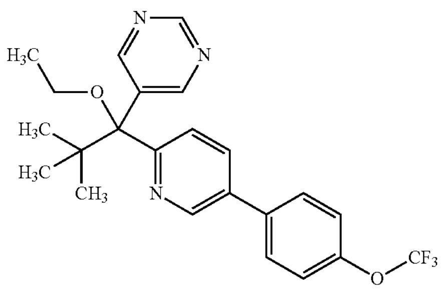 [SMILES: CCOC(c1cncnc1)(c1ccc(-c2ccc(OC(F)(F)F)cc2)cn1)C(C)(C)C] | Prepared according to Example 23 using iodoethane |
| 199 | 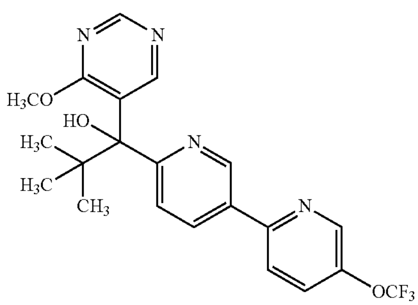 [SMILES: COc1ncncc1C(O)(c1ccc(-c2ccc(OC(F)(F)F)cn2)cn1)C(C)(C)C] | Prepared according to Example 28 using 2-bromo-5-(trifluoromethoxy)pyridine in step 28E |
| 200 | 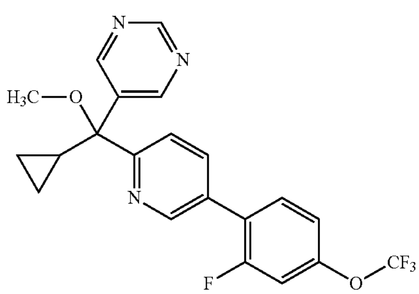 [SMILES: COC(c1cncnc1)(c1ccc(-c2ccc(OC(F)(F)F)cc2F)cn1)C1CC1] | Prepared according to Example 23 from cyclopropyl(5-(2-fluoro-4-(trifluoromethoxy)phenyl)pyridin-2-yl)(pyrimidin-5-yl)methanol (117) and iodomethane |
| 201 | 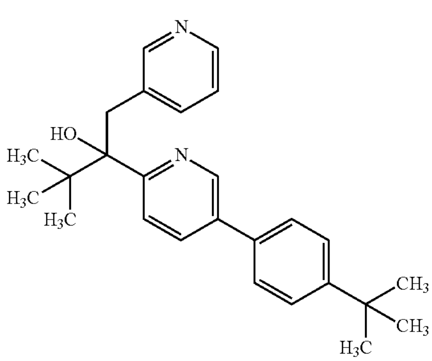 [SMILES: CC(C)(C)c1ccc(-c2ccc(C(O)(Cc3cccnc3)C(C)(C)C)nc2)cc1] | Prepared according to Example 6 using nicotinaldehyde in step 6B, (4-(tert-butyl)phenyl)boronic acid in step 6C and tert-butylmagnesium chloride in step 6D. |

TABLE 1-continued

Structure and Preparation Method.

| Compound Number | Structure | Prepared According to Example |
|---|---|---|
| 202 | 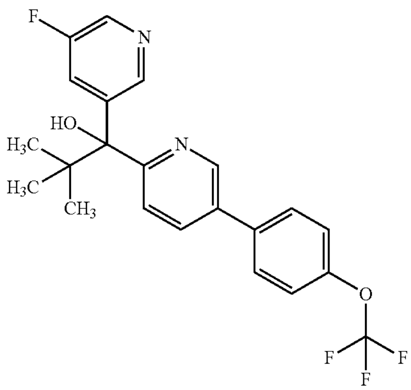 [SMILES: CC(C)(C)C(O)(c1cncc(F)c1)c1ccc(-c2ccc(OC(F)(F)F)cc2)cn1] | Prepared according to Example 16 from 1-(5-bromopyridin-2-yl)-1-(5-fluoropyridin-3-yl)-2,2-dimethylpropan-1-ol (178) and (4-(trifluoromethoxy)phenyl)boronic acid in 16C. |
| 203 | 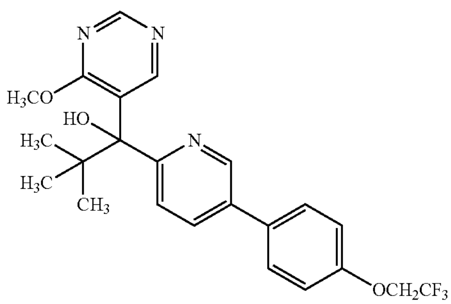 | Prepared according to Example 28 using (4-(2,2,2-trifluoroethoxy)phenyl)boronic acid in step 28F (skip steps 28D-E) |
| 204 | 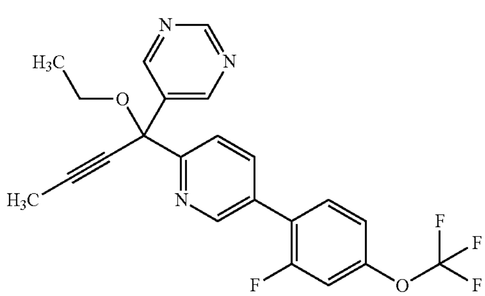 [SMILES: CC#CC(OCC)(c1cncnc1)c1ccc(-c2ccc(OC(F)(F)F)cc2F)cn1] | Prepared according to Example 23 from 1-(5-(2-fluoro-4-(trifluoromethoxy)phenyl)pyridin-2-yl)-1-(pyrimidin-5-yl)but-2-yn-1-ol (118) and iodoethane |
| 205 | 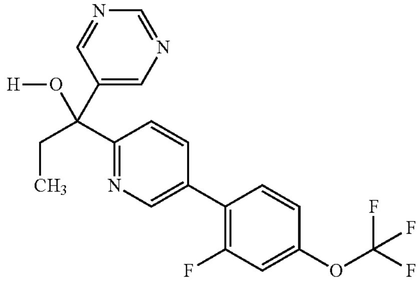 [SMILES: CCC(O)(c1cncnc1)c1ccc(-c2ccc(OC(F)(F)F)cc2F)cn1] | Prepared according to Example 27 using 2-(2-fluoro-4-(trifluoromethoxy)phenyl)-4,4,5,5-tetramethyl-1,3,2-dioxaborolane (prepared as described in 17A) in 27C and ethyl magnesium bromide in 27D |

TABLE 1-continued

Structure and Preparation Method.

| Compound Number | Structure | Prepared According to Example |
|---|---|---|
| 206 | 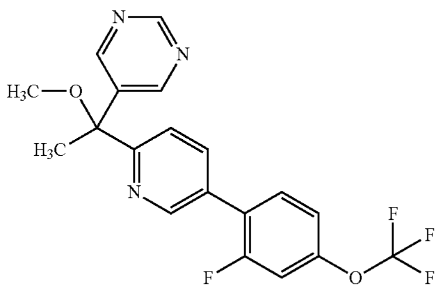 [SMILES: COC(C)(c1cncnc1)c1ccc(-c2ccc(OC(F)(F)F)cc2F)cn1] | Prepared according to Example 23 from 1-(5-(2-fluoro-4-(trifluoromethoxy)phenyl)pyridin-2-yl)-1-(pyrimidin-5-yl)ethanol (154) and iodomethane |
| 207 | 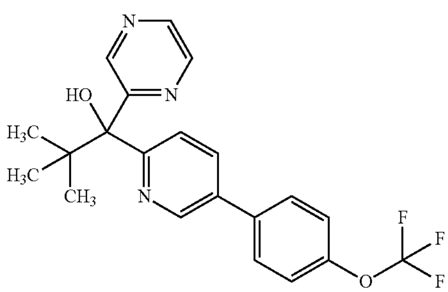 [SMILES: CC(C)(C)C(O)(c1ccc(-c2ccc(OC(F)(F)F)cc2)cn1)c1cnccn1] | Prepared according to Example 16 using N-methoxy-N-methylpyrazine-2-carboxamide in 16A and tert-butylmagnesium chloride in 16B |
| 208 | 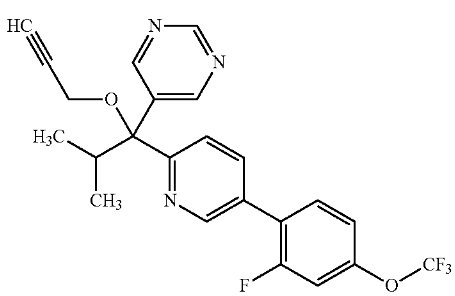 [SMILES: C#CCOC(c1cncnc1)(c1ccc(-c2ccc(OC(F)(F)F)cc2F)cn1)C(C)C] | Prepared according to Example 23 from 1-(5-(2-fluoro-4-(trifluoromethoxy)phenyl)pyridin-2-yl)-2-methyl-1-(pyrimidin-5-yl)propan-1-ol (163) and propargyl bromide |
| 210 | 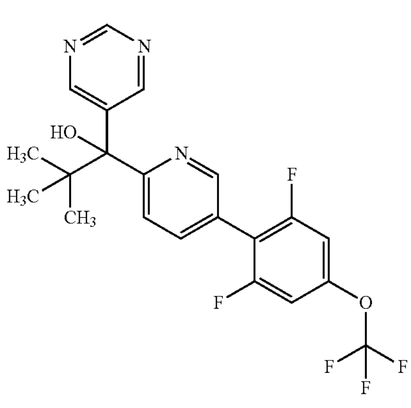 [SMILES: CC(C)(C)C(O)(c1cncnc1)c1ccc(-c2c(F)cc(OC(F)(F)F)cc2F)cn1] | Prepared according to Example 24 using 2-bromo-1,3-difluoro-5-(trifluoromethoxy)benzene in 24C |

TABLE 1-continued

Structure and Preparation Method.

| Compound Number | Structure | Prepared According to Example |
|---|---|---|
| 211 | 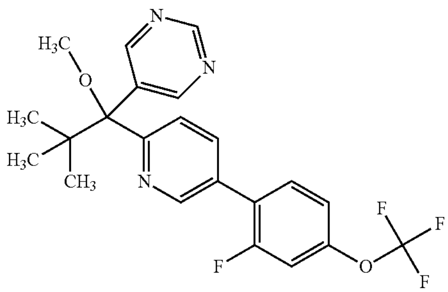 [SMILES: COC(c1cncnc1)(c1ccc(-c2ccc(OC(F)(F)F)cc2F)cn1)C(C)(C)C] | Prepared according to Example 23 from 2,2-dimethyl-1-(5-(2-fluoro-4-(trifluoromethoxy)phenyl)pyridin-2-yl)-1-(pyrimidin-5-yl)propan-1-ol |
| 212 | 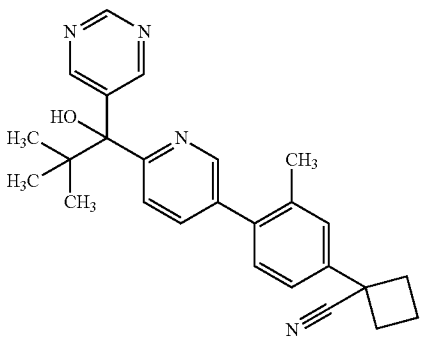 [SMILES: Cc1cc(C2(C#N)CCC2)ccc1-c1ccc(C(O)(c2cncnc2)C(C)(C)C)nc1] | Prepared according to Example 24 using 1-(4-bromo-3-methylphenyl)cyclobutanecarbonitrile in 24C |
| 213 | 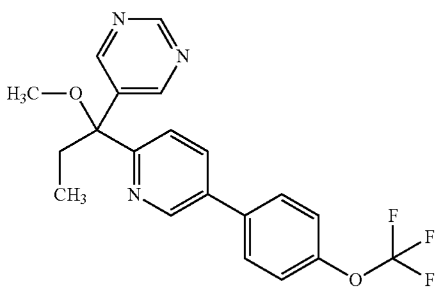 [SMILES: CCC(OC)(c1cncnc1)c1ccc(-c2ccc(OC(F)(F)F)cc2)cn1] | Prepared according to Example 23 from 1-(pyrimidin-5-yl)-1-(5-(4-(trifluoromethoxy)phenyl)pyridin-2-yl)propan-1-ol (191) and iodomethane |
| 214 | 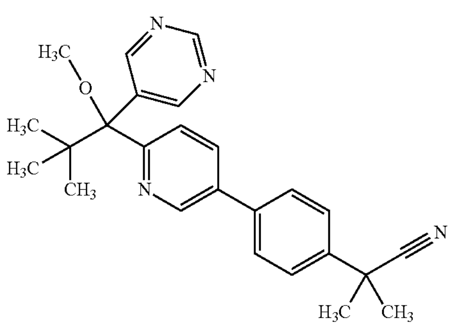 [SMILES: COC(c1cncnc1)(c1ccc(-c2ccc(C(C)(C)C#N)cc2)cn1)C(C)(C)C] | Prepared according to Example 23 from 2-(4-(6-(1-methoxy-2,2-dimethyl-1-(pyrimidin-5-yl)propyl)pyridin-3-yl)phenyl)-2-methylpropanenitrile |
| 215 | 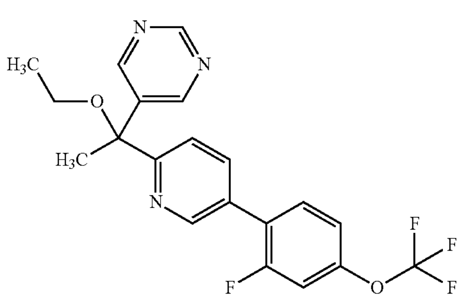 [SMILES: CCOC(C)(c1cncnc1)c1ccc(-c2ccc(OC(F)(F)F)cc2F)cn1] | Prepared according to Example 23 from 1-(5-(2-fluoro-4-(trifluoromethoxy)phenyl)pyridin-2-yl)-1-(pyrimidin-5-yl)ethanol (154) and iodoethane |

TABLE 1-continued

Structure and Preparation Method.

| Compound Number | Structure | Prepared According to Example |
|---|---|---|
| 216 | 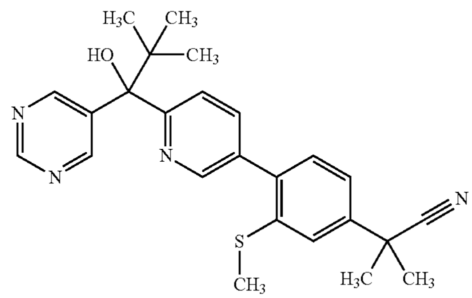 [SMILES: CSc1cc(C(C)(C)C#N)ccc1-c1ccc(C(O)(c2cncnc2)C(C)(C)C)nc1] | Example 26 |
| 217 | 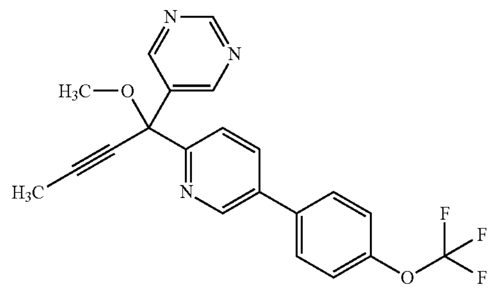 [SMILES: CC#CC(OC)(c1cncnc1)c1ccc(-c2ccc(OC(F)(F)F)cc2)cn1] | Prepared according to Example 23 from 1-(pyrimidin-5-yl)-1-(5-(4-(trifluoromethoxy)phenyl)pyridin-2-yl)but-2-yn-1-ol (199) |
| 218 | 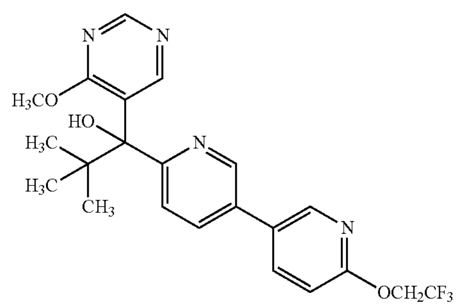 | Prepared according to Example 28 using 5-(4,4,5,5-tetramethyl-1,3,2-dioxaborolan-2-yl)-2-(2,2,2-trifluoroethoxy)pyridine in step 28F (skip steps 28D-E) |
| 219 | 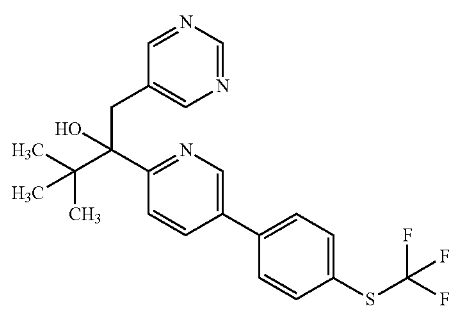 [SMILES: CC(C)(C)C(O)(Cc1cncnc1)c1ccc(-c2ccc(SC(F)(F)F)cc2)cn1] | Prepared according to Example 6 using (4-((trifluoromethyl)thio)phenyl) boronic acid in step 6C and tert-butylmagnesium chloride in step 6D. |
| 220 | 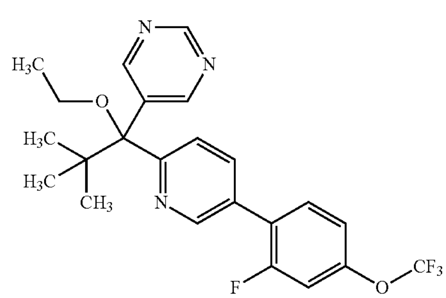 [SMILES: CCOC(c1cncnc1)(c1ccc(-c2ccc(OC(F)(F)F)cc2F)cn1)C(C)(C)C] | Prepared according to Example 23 from 1-(5-(2-fluoro-4-(trifluoromethoxy)phenyl)pyridin-2-yl)-2,2-dimethyl-1-(pyrimidin-5-yl)propan-1-ol and iodoethane |

TABLE 1-continued

Structure and Preparation Method.

| Compound Number | Structure | Prepared According to Example |
|---|---|---|
| 221 | 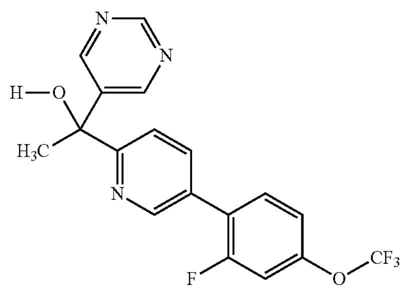 [SMILES: CC(O)(c1cncnc1)c1ccc(-c2ccc(OC(F)(F)F)cc2F)cn1] | Prepared according to Example 27 using 2-(2-fluoro-4-(trifluoromethoxy)phenyl)-4,4,5,5-tetramethyl-1,3,2-dioxaborolane (prepared as described in 17A) in 27C and methyl magnesium bromide in 27D |
| 222 | 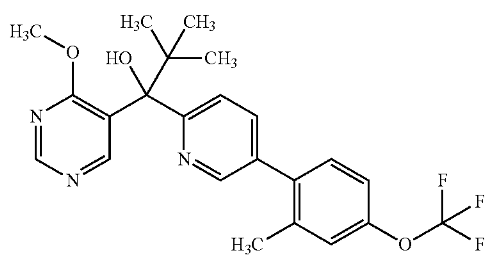 [SMILES: COc1ncncc1C(O)(c1ccc(-c2ccc(OC(F)(F)F)cc2C)cn1)C(C)(C)C] | Prepared according to Example 28 using (2-methyl-4-(trifluoromethoxy)phenyl)boronic acid in step 28F (skip steps 28D-E) |
| 223 | 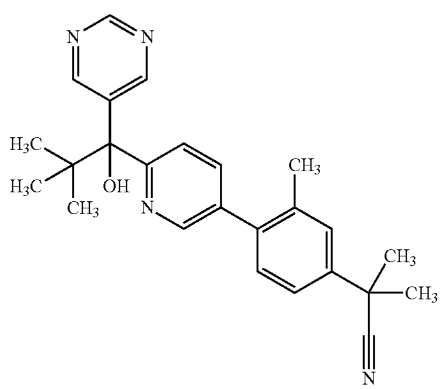 [SMILES: Cc1cc(C(C)(C)C#N)ccc1-c1ccc(C(O)(c2cncnc2)C(C)(C)C)nc1] | Example 24 |
| 224 | 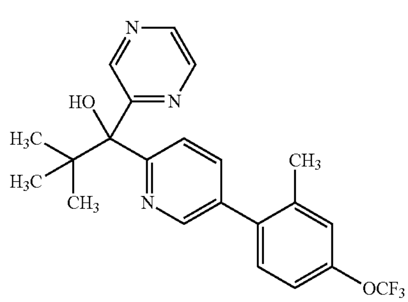 [SMILES: Cc1cc(OC(F)(F)F)ccc1-c1ccc(C(O)(c2cnccn2)C(C)(C)C)nc1] | Prepared according to Example 16 using N-methoxy-N-methylpyrazine-2-carboxamide in 16A, tert-butylmagnesium chloride in 16B, and (2-methyl-4-(trifluoromethoxy)phenyl)boronic acid in 16C |

TABLE 1-continued

Structure and Preparation Method.

| Compound Number | Structure | Prepared According to Example |
|---|---|---|
| 225 | 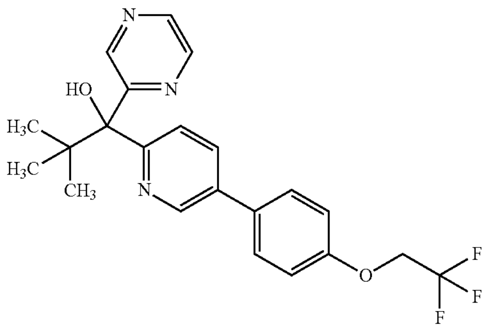 [SMILES: CC(C)(C)C(O)(c1ccc(-c2ccc(OCC(F)(F)F)cc2)cn1)c1cnccn1] | Prepared according to Example 16 using N-methoxy-N-methylpyrazine-2-carboxamide in 16A, tert-butylmagnesium chloride in 16B, and (4-(2,2,2-trifluoroethoxy)phenyl)boronic acid in 16C |
| 226 | 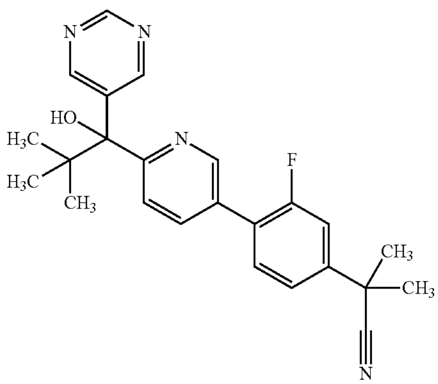 [SMILES: CC(C)(C#N)c1ccc(-c2ccc(C(O)(c3cncnc3)C(C)(C)C)nc2)c(F)c1] | Prepared according to Example 24 using 2-(4-bromo-3-fluorophenyl)-2-methylpropanenitrile. 2-(4-bromo-3-fluorophenyl)-2-methylpropanenitrile was prepared from 2-(4-bromo-3-fluorophenyl)acetonitrile and iodomethane according to conditions described in 24A in 24C |
| 227 | 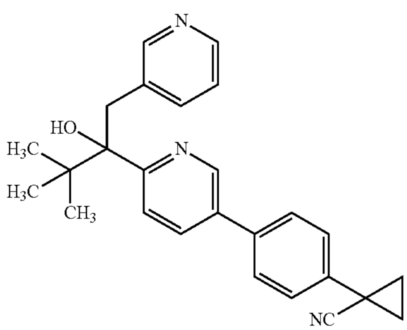 [SMILES: CC(C)(C)C(O)(Cc1cccnc1)c1ccc(-c2ccc(C3(C#N)CC3)cc2)cn1] | Prepared according to Example 6 using nicotinaldehyde in step 6B, (4-(1-cyanocyclopropyl)phenyl)boronic acid in step 6C and tert-butylmagnesium chloride in step 6D. |
| 228 | 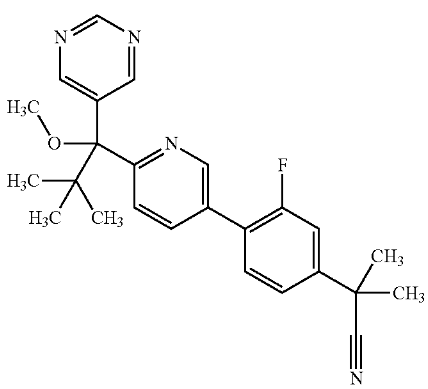 [SMILES: COC(c1cncnc1)(c1ccc(-c2ccc(C(C)(C)C#N)cc2F)cn1)C(C)(C)C] | Prepared according to Example 23 from 2-(3-fluoro-4-(6-(1-hydroxy-2,2-dimethyl-1-(pyrimidin-5-yl)propyl)pyridin-3-yl)phenyl)-2-methylpropanenitrile (159) |

TABLE 1-continued

Structure and Preparation Method.

| Compound Number | Structure | Prepared According to Example |
|---|---|---|
| 229 | 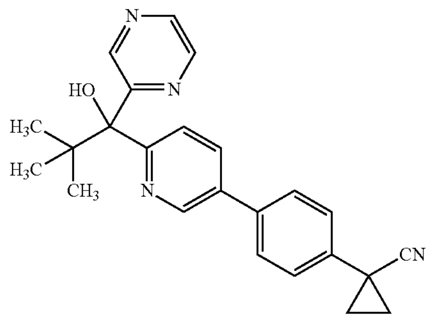 [SMILES: CC(C)(C)C(O)(c1ccc(-c2ccc(C3(C#N)CC3)cc2)cn1)c1cnccn1] | Prepared according to Example 16 using N-methoxy-N-methylpyrazine-2-carboxamide in 16A, tert-butylmagnesium chloride in 16B, and (4-(1-cyanocyclopropyl)phenyl)boronic acid in 16C |
| 230 | 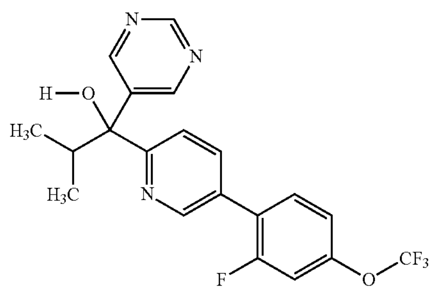 [SMILES: CC(C)C(O)(c1cncnc1)c1ccc(-c2ccc(OC(F)(F)F)cc2F)cn1] | Prepared according to Example 27 using 2-(2-fluoro-4-(trifluoromethoxy)phenyl)-4,4,5,5-tetramethyl-1,3,2-dioxaborolane (prepared as described in 17A) in 27C and isopropyl magnesium chloride in 27D |
| 231 | 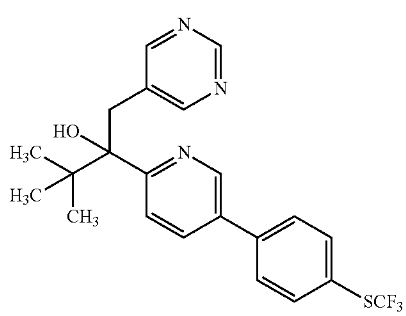 | Prepared according to Example 6 using nicotinaldehyde in step 6B, (4-((trifluoromethyl)thio)phenyl) boronic acid in step 6C and tert-butylmagnesium chloride in step 6D. |
| 232 | 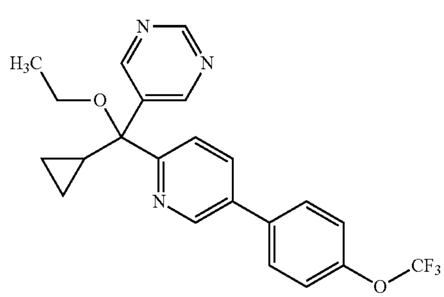 [SMILES: CCOC(c1cncnc1)(c1ccc(-c2ccc(OC(F)(F)F)cc2)cn1)C1CC1] | Prepared according to Example 23 from cyclopropyl(pyrimidin-5-yl)(5-(4-(trifluoromethoxy)phenyl)pyridin-2-yl)methanol and iodoethane |

TABLE 1-continued

Structure and Preparation Method.

| Compound Number | Structure | Prepared According to Example |
|---|---|---|
| 233 | 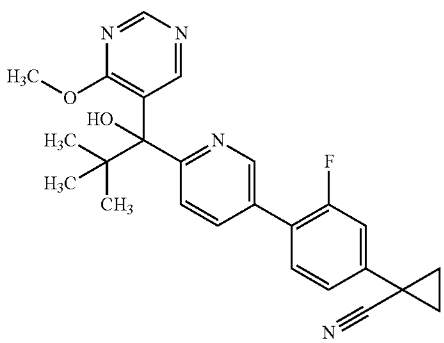 [SMILES: COc1ncncc1C(O)(c1ccc(-c2ccc(C3(C#N)CC3)cc2F)cn1)C(C)(C)C] | Prepared according to Example 28 using 1-(4-bromo-3-fluorophenyl)cyclopropanecarbonitrile in 28E |
| 234 | 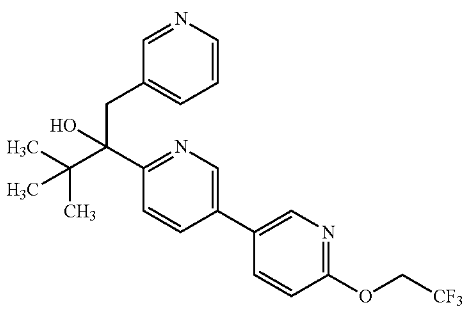 [SMILES: CC(C)(C)C(O)(Cc1cccnc1)c1ccc(-c2ccc(OCC(F)(F)F)nc2)cn1] | Prepared according to Example 6 using nicotinaldehyde in step 6B, 5-(4,4,5,5-tetramethyl-1,3,2-dioxaborolan-2-yl)-2-(2,2,2-trifluoroethoxy)pyridine in step 6C and tert-butylmagnesium chloride in step 6D. |
| 235 | 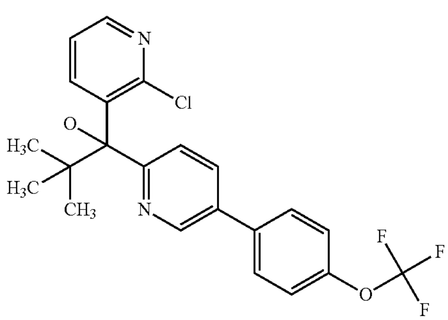 [SMILES: CC(C)(C)C(O)(c1ccc(-c2ccc(OC(F)(F)F)cc2)cn1)c1cccnc1Cl] | Prepared according to Example 16 using 2-chloro-N-methoxy-N-methylnicotinamide in 16A and tert-butylmagnesium chloride in 16B |
| 236 | 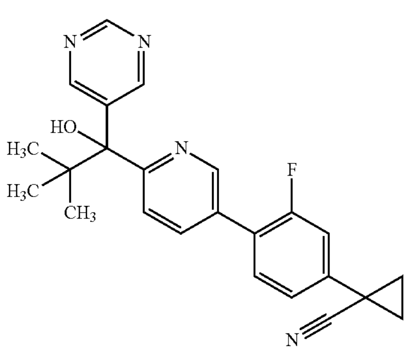 [SMILES: CC(C)(C)C(O)(c1cncnc1)c1ccc(-c2ccc(C3(C#N)CC3)cc2F)cn1] | Prepared according to Example 24 using 1-(4-bromo-3-fluorophenyl)cyclopropanecarbonitrile in 24C |

TABLE 1-continued

Structure and Preparation Method.

| Compound Number | Structure | Prepared According to Example |
|---|---|---|
| 237 | 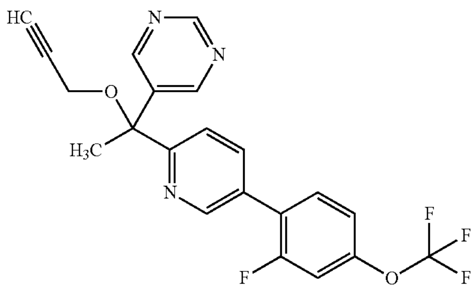 [SMILES: C#CCOC(C)(c1cncnc1)c1ccc(-c2ccc(OC(F)(F)F)cc2F)cn1] | Prepared according to Example 23 from 1-(5-(2-fluoro-4-(trifluoromethoxy)phenyl)pyridin-2-yl)-1-(pyrimidin-5-yl)ethanol (154) and propargyl bromide |
| 238 | 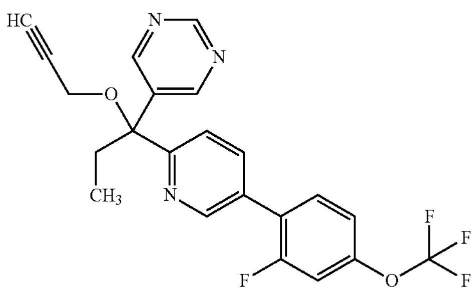 [SMILES: C#CCOC(CC)(c1cncnc1)c1ccc(-c2ccc(OC(F)(F)F)cc2F)cn1] | Prepared according to Example 23 from 1-(5-(2-fluoro-4-(trifluoromethoxy)phenyl)pyridin-2-yl)-1-(pyrimidin-5-yl)propan-1-ol (138) and propargyl bromide |
| 239 | 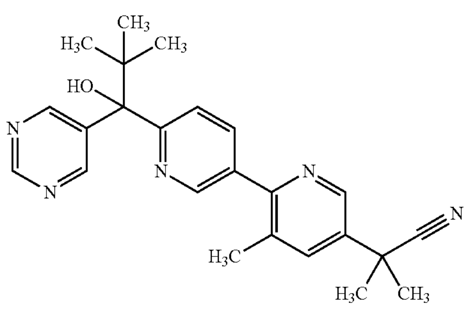 [SMILES: Cc1cc(C(C)(C)C#N)cnc1-c1ccc(C(O)(c2cncnc2)C(C)(C)C)nc1] | Prepared according to Example 29 using 2-(6-bromo-5-methylpyridin-3-yl)-2-methylpropanenitrile in 29F. 2-(6-bromo-5-methylpyridin-3-yl)-2-methylpropanenitrile was prepared from 6-bromo-5-methylnicotinaldehyde according to conditions described for 29B-29E |
| 240 | 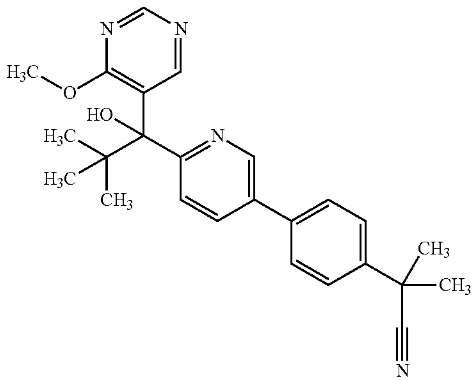 [SMILES: COc1ncncc1C(O)(c1ccc(-c2ccc(C(C)(C)C#N)cc2)cn1)C(C)(C)C] | Prepared according to Example 28 using 2-(4-bromophenyl)-2-methylpropanenitrile in 28E |

TABLE 1-continued

Structure and Preparation Method.

| Compound Number | Structure | Prepared According to Example |
|---|---|---|
| 241 | 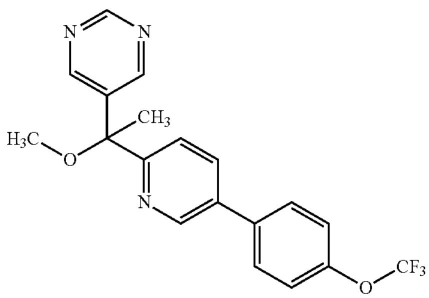 [SMILES: COC(C)(c1cncnc1)c1ccc(-c2ccc(OC(F)(F)F)cc2)cn1] | Prepared according to Example 23 from 1-(pyrimidin-5-yl)-1-(5-(4-(trifluoromethoxy)phenyl)pyridin-2-yl)ethano |
| 242 | 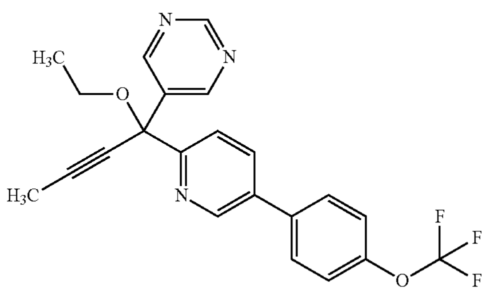 [SMILES: CC#CC(OCC)(c1cncnc1)c1ccc(-c2ccc(OC(F)(F)F)cc2)cn1] | Prepared according to Example 23 from 1-(pyrimidin-5-yl)-1-(5-(4-(trifluoromethoxy)phenyl)pyridin-2-yl)but-2-yn-1-ol (199) and iodoethane |
| 243 | 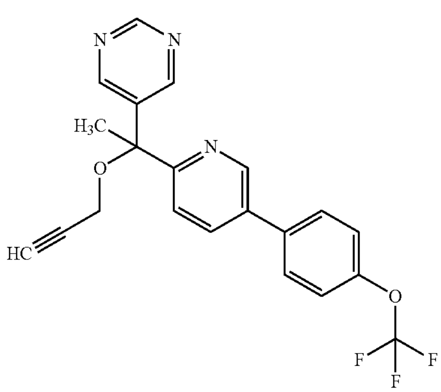 [SMILES: C#CCOC(C)(c1cncnc1)c1ccc(-c2ccc(OC(F)(F)F)cc2)cn1] | Prepared according to Example 23 from 1-(pyrimidin-5-yl)-1-(5-(4-(trifluoromethoxy)phenyl)pyridin-2-yl)ethanol and propargyl bromide |
| 244 | 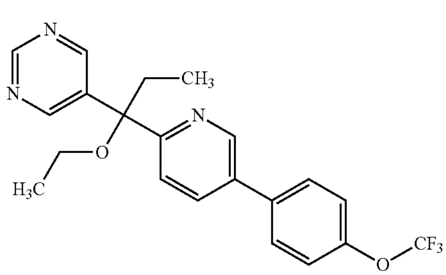 [SMILES: CCOC(CC)(c1cncnc1)c1ccc(-c2ccc(OC(F)(F)F)cc2)cn1] | Prepared according to Example 23 from 1-(pyrimidin-5-yl)-1-(5-(4-(trifluoromethoxy)phenyl)pyridin-2-yl)propan-1-ol (191) and iodoethane |

TABLE 1-continued

Structure and Preparation Method.

| Compound Number | Structure | Prepared According to Example |
|---|---|---|
| 246 | 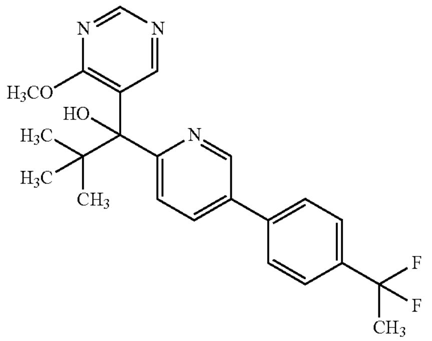 [SMILES: COc1ncncc1C(O)(c1ccc(-c2ccc(C(C)(F)F)cc2)cn1)C(C)(C)C] | Prepared according to Example 28 using 1-bromo-4-(1,1-difluoroethyl)benzene in step 28E |
| 247 | 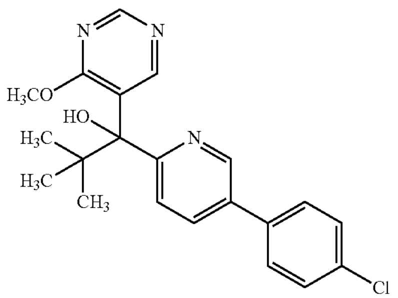 [SMILES: COc1ncncc1C(O)(c1ccc(-c2ccc(Cl)cc2)cn1)C(C)(C)C] | Prepared according to Example 28 using (4-chlorophenyl)boronic acid in step 28F (skip steps 28D-E) |
| 248 | 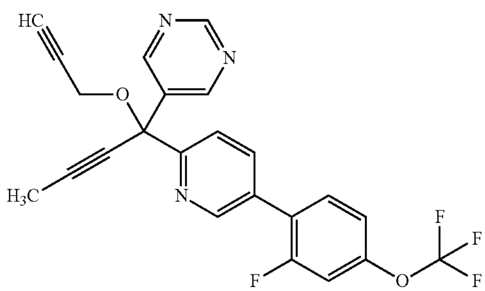 [SMILES: C#CCOC(C#CC)(c1cncnc1)c1ccc(-c2ccc(OC(F)(F)F)cc2F)cn1] | Prepared according to Example 23 from 1-(5-(2-fluoro-4-(trifluoromethoxy)phenyl)pyridin-2-yl)-1-(pyrimidin-5-yl)but-2-yn-1-ol (118) and propargyl bromide |
| 249 | 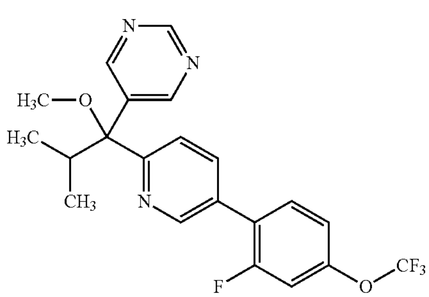 [SMILES: COC(c1cncnc1)(c1ccc(-c2ccc(OC(F)(F)F)cc2F)cn1)C(C)C] | Prepared according to Example 23 from 1-(5-(2-fluoro-4-(trifluoromethoxy)phenyl)pyridin-2-yl)-2-methyl-1-(pyrimidin-5-yl)propan-1-ol (163) and iodomethane |
| 250 | 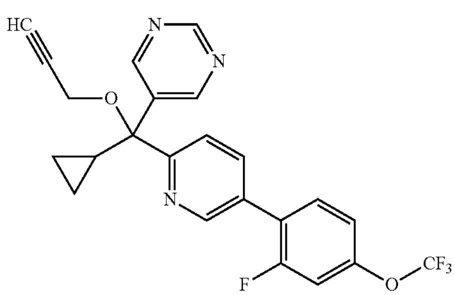 [SMILES: C#CCOC(c1cncnc1)(c1ccc(-c2ccc(OC(F)(F)F)cc2F)cn1)C1CC1] | Prepared according to Example 23 from cyclopropyl(5-(2-fluoro-4-(trifluoromethoxy)phenyl)pyridin-2-yl)(pyrimidin-5-yl)methanol (117) and propargyl bromide |

TABLE 1-continued

Structure and Preparation Method.

| Compound Number | Structure | Prepared According to Example |
|---|---|---|
| 251 | 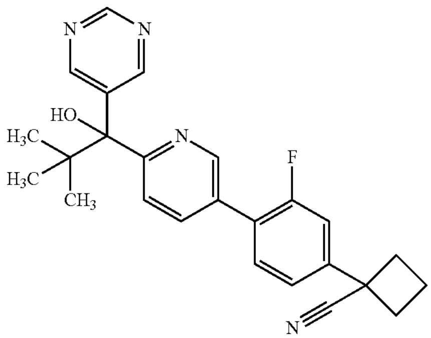 [SMILES: CC(C)(C)C(O)(c1cncnc1)c1ccc(-c2ccc(C3(C#N)CCC3)cc2F)cn1] | Prepared according to Example 24 using 1-(4-bromo-3-fluorophenyl)cyclobutanecarbonitrile in 24C |
| 252 | 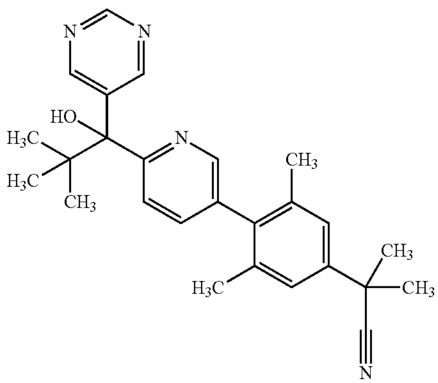 [SMILES: Cc1cc(C(C)(C)C#N)cc(C)c1-c1ccc(C(O)(c2cncnc2)C(C)(C)C)nc1] | Prepared according to Example 24 using 2-(4-bromo-3,5-dimethylphenyl)-2-methylpropanenitrile in 24C. 2-(4-bromo-3,5-dimethylphenyl)-2-methylpropanenitrile was prepared from 4-bromo-3,5-dimethylbenzaldehyde according to conditions described for 25A-25D using methanesulfonyl chloride, triethylamine, and DCM in 25B and potassium cyanide and DMF in 25C |
| 253 | 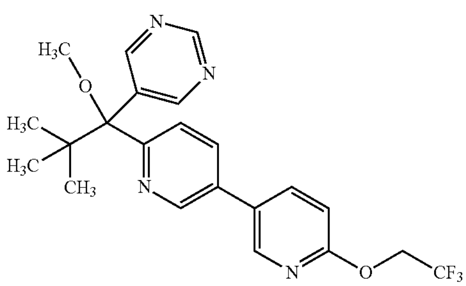 [SMILES: COC(c1cncnc1)(c1ccc(-c2ccc(OCC(F)(F)F)nc2)cn1)C(C)(C)C] | Prepared according to Example 23 from 2,2-dimethyl-1-(pyrimidin-5-yl)-1-(6'-(2,2,2-trifluoroethoxy)-[3,3'-bipyridin]-6-yl)propan-1-ol |
| 254 | 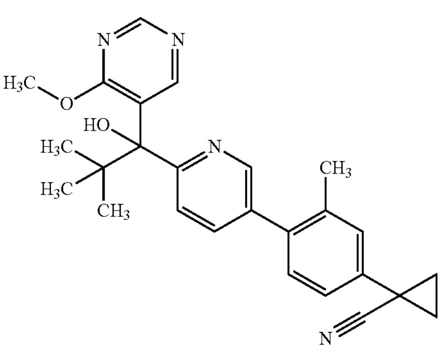 [SMILES: COc1ncncc1C(O)(c1ccc(-c2ccc(C3(C#N)CC3)cc2C)cn1)C(C)(C)C] | Prepared according to Example 28 using 1-(4-bromo-3-methylphenyl)cyclopropanecarbonitrile in 28E |

TABLE 1-continued

Structure and Preparation Method.

| Compound Number | Structure | Prepared According to Example |
|---|---|---|
| 255 | 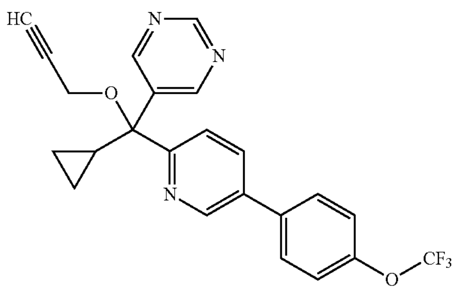 [SMILES: C#CCOC(c1cncnc1)(c1ccc(-c2ccc(OC(F)(F)F)cc2)cn1)C1CC1] | Prepared according to Example 23 from cyclopropyl(pyrimidin-5-yl)(5-(4-(trifluoromethoxy)phenyl)pyridin-2-yl)methanol and propargyl bromide |
| 256 | 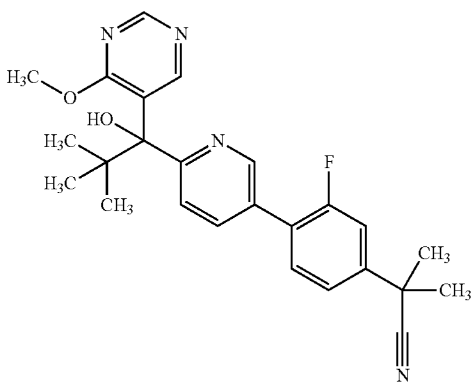 [SMILES: COc1ncncc1C(O)(c1ccc(-c2ccc(C(C)(C)C#N)cc2F)cn1)C(C)(C)C] | Prepared according to Example 28 using 2-(4-bromo-3-fluorophenyl)-2-methylpropanenitrile in 28E |
| 257 | 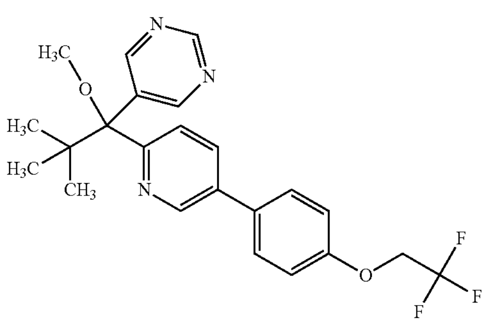 [SMILES: COC(c1cncnc1)(c1ccc(-c2ccc(OCC(F)(F)F)cc2)cn1)C(C)(C)C] | Prepared according to Example 23 from 2,2-dimethyl-1-(pyrimidin-5-yl)-1-(5-(4-(2,2,2-trifluoroethoxy)phenyl)pyridin-2-yl)propan-1-ol |
| 258 | 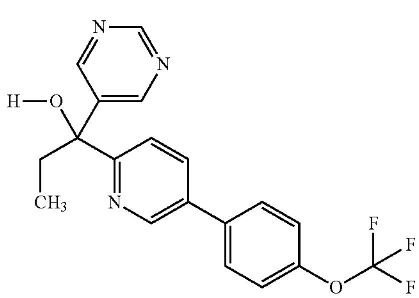 [SMILES: CCC(O)(c1cncnc1)c1ccc(-c2ccc(OC(F)(F)F)cc2)cn1] | Prepared according to Example 27 using ethyl magnesium bromide in 27D |

TABLE 1-continued

Structure and Preparation Method.

| Compound Number | Structure | Prepared According to Example |
|---|---|---|
| 259 | 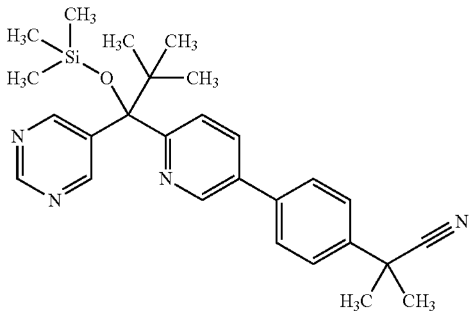 [SMILES: CC(C)(C#N)c1ccc(-c2ccc(C(O[Si](C)(C)C)(c3cncnc3)C(C)(C)C)nc2)cc1] | Prepared according to Example 23 from 2-(4-(6-(1-hydroxy-2,2-dimethyl-1-(pyrimidin-5-yl)propyl)pyridin-3-yl)phenyl)-2-methylpropanenitrile using LHMDS and trimethylsilyl chloride |
| 260 | 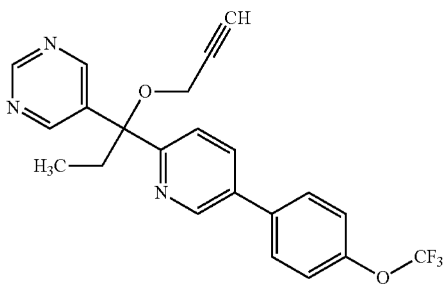 [SMILES: C#CCOC(CC)(c1cncnc1)c1ccc(-c2ccc(OC(F)(F)F)cc2)cn1] | Prepared according to Example 23 from 1-(pyrimidin-5-yl)-1-(5-(4-(trifluoromethoxy)phenyl)pyridin-2-yl)propan-1-ol (191) and propargyl bromide |
| 261 | 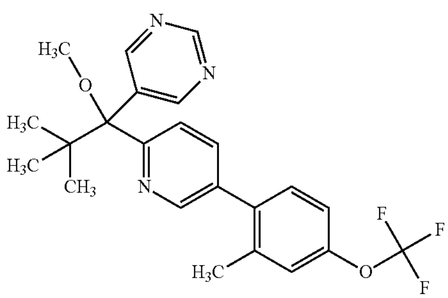 [SMILES: COC(c1cncnc1)(c1ccc(-c2ccc(OC(F)(F)F)cc2C)cn1)C(C)(C)C] | Prepared according to Example 23 from 2,2-dimethyl-1-(5-(2-methyl-4-(trifluoromethoxy)phenyl)pyridin-2-yl)-1-(pyrimidin-5-yl)propan-1-ol |
| 262 | 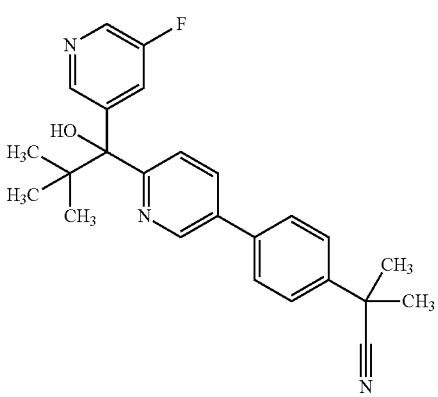 [SMILES: CC(C)(C#N)c1ccc(-c2ccc(C(O)(c3cncc(F)c3)C(C)(C)C)nc2)cc1] | Prepared according to Example 16 from 1-(5-bromopyridin-2-yl)-1-(5-fluoropyridin-3-yl)-2,2-dimethylpropan-1-ol (178) and (4-(2-cyanopropan-2-yl)phenyl)boronic acid in 16C. |

TABLE 1-continued

Structure and Preparation Method.

| Compound Number | Structure | Prepared According to Example |
|---|---|---|
| 263 | 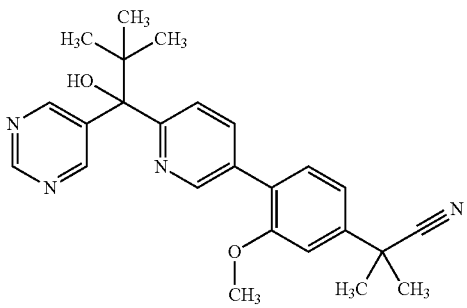 [SMILES: COc1cc(C(C)(C)C#N)ccc1-c1ccc(C(O)(c2cncnc2)C(C)(C)C)nc1] | Prepared according to Example 29 using 2-(4-bromo-3-methoxyphenyl)-2-methylpropanenitrile in 29F. 2-(4-bromo-3-methoxyphenyl)-2-methylpropanenitrile was prepared from 4-bromo-3-methoxybenzaldehyde according to conditions described for 29B-29E using para-toluenesulfonyl chloride in 29C and sodium hydride in 29E |
| 264 | 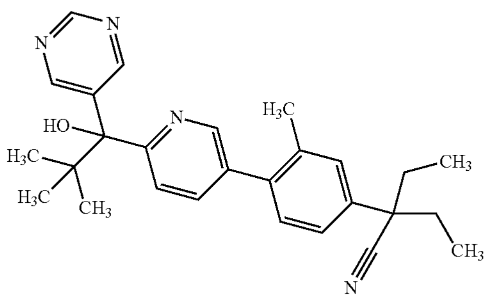 [SMILES: CCC(C#N)(CC)c1ccc(-c2ccc(C(O)(c3cncnc3)C(C)(C)C)nc2)c(C)c1] | Prepared according to Example 24 using 2-(4-bromo-3-methylphenyl)-2-ethylbutanenitrile in 24C. 2-(4-bromo-3-methylphenyl)-2-ethylbutanenitrile was prepared from 2-(4-bromo-3methylphenyl)acetonitrile and iodoethane according to conditions described in 24A |
| 265 | 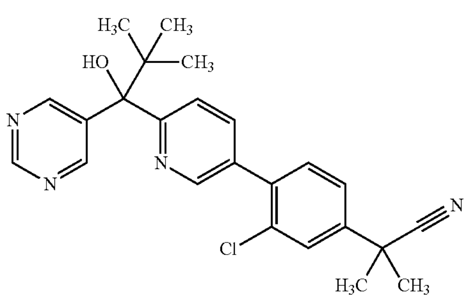 | Prepared according to Example 25 using 2-(4-bromo-3-chlorophenyl)-2-methylpropanenitrile in 25E. 2-(4-bromo-3-chlorophenyl)-2-methylpropanenitrile was prepared from 2-(4-bromo-3-chlorophenyl)acetonitrile according to conditions described for 25D |
| 266 | 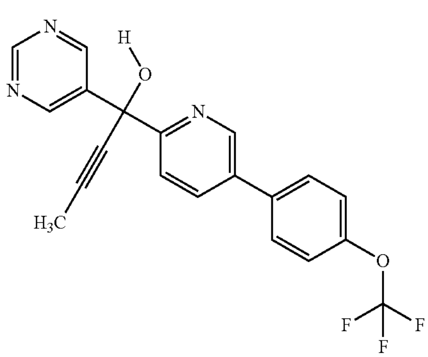 [SMILES: CC#CC(O)(c1cncnc1)c1ccc(-c2ccc(OC(F)(F)F)cc2)cn1] | Example 27 |

TABLE 1-continued

Structure and Preparation Method.

| Compound Number | Structure | Prepared According to Example |
|---|---|---|
| 267 | 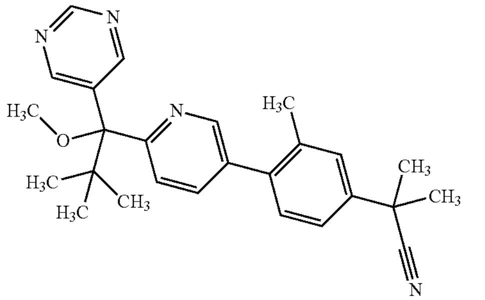 [SMILES: COC(c1cncnc1)(c1ccc(-c2ccc(C(C)(C)C#N)cc2C)cn1)C(C)(C)C] | Prepared according to Example 23 from 2-(4-(6-(1-hydroxy-2,2-dimethyl-1-(pyrimidin-5-yl)propyl)pyridin-3-yl)-3-methylphenyl)-2-methylpropanenitrile (156) |
| 268 | 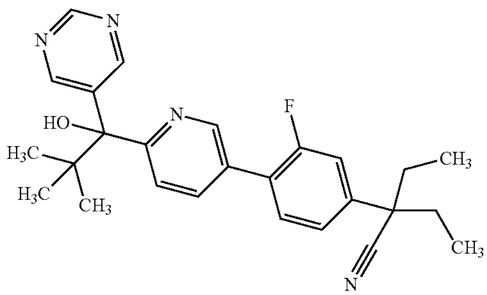 [SMILES: CCC(C#N)(CC)c1ccc(-c2ccc(C(O)(c3cncnc3)C(C)(C)C)nc2)c(F)c1] | Prepared according to Example 24 using 2-(4-bromo-3-fluorophenyl)-2-ethylbutanenitrile in 24C. 2-(4-bromo-3-fluorophenyl)-2-ethylbutanenitrile was prepared from 2-(4-bromo-3-fluorophenyl)acetonitrile and iodoethane according to conditions described in 24A |
| 269 | 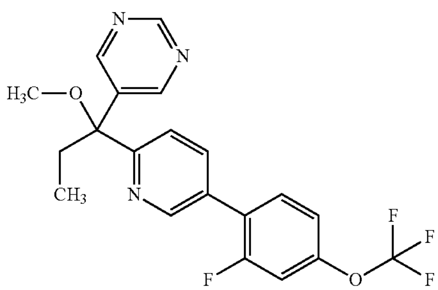 [SMILES: CCC(OC)(c1cncnc1)c1ccc(-c2ccc(OC(F)(F)F)cc2F)cn1] | Prepared according to Example 23 from 1-(5-(2-fluoro-4-(trifluoromethoxy)phenyl)pyridin-2-yl)-1-(pyrimidin-5-yl)propan-1-ol (138) and iodomethane |
| 270 | 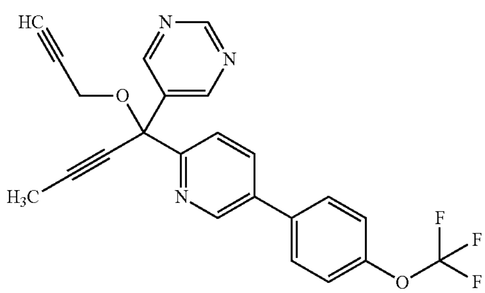 [SMILES: C#CCOC(C#CC)(c1cncnc1)c1ccc(-c2ccc(OC(F)(F)F)cc2)cn1] | Prepared according to Example 23 from 1-(pyrimidin-5-yl)-1-(5-(4-(trifluoromethoxy)phenyl)pyridin-2-yl)but-2-yn-1-ol (199) and propargyl bromide |
| 271 | 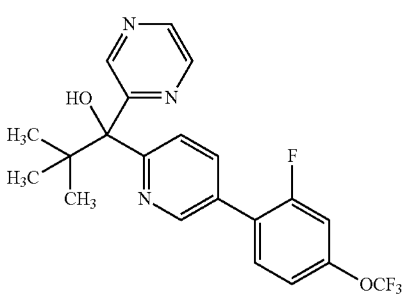 | Prepared according to Example 16 using N-methoxy-N-methylpyrazine-2-carboxamide in 16A, tert-butylmagnesium chloride in 16B, and 2-(2-fluoro-4-(trifluoromethoxy)phenyl)-4,4,5,5-tetramethyl-1,3,2-dioxaborolane (prepared as described in 17A) in 16C |

TABLE 1-continued

Structure and Preparation Method.

| Compound Number | Structure | Prepared According to Example |
|---|---|---|
| 272 | 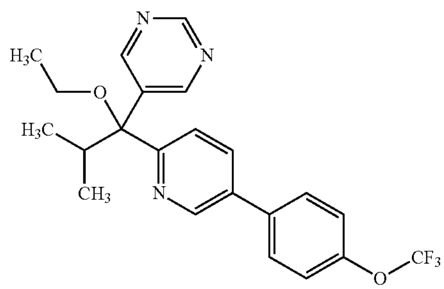 [SMILES: CCOC(c1cncnc1)(c1ccc(-c2ccc(OC(F)(F)F)cc2)cn1)C(C)C] | Prepared according to Example 23 from 2-methyl-1-(pyrimidin-5-yl)-1-(5-(4-(trifluoromethoxy)phenyl)pyridin-2-yl)propan-1-ol and iodoethane |
| 273 | 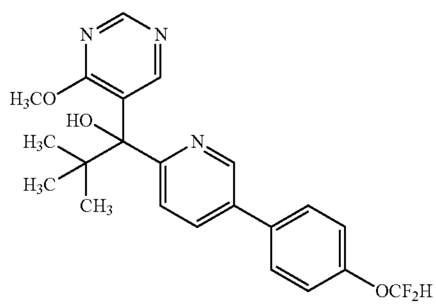 | Prepared according to Example 28 using 2-(4-(difluoromethoxy)phenyl)-4,4,5,5-tetramethyl-1,3,2-dioxaborolane in step 28F (skip steps 28D-E) |
| 274 | 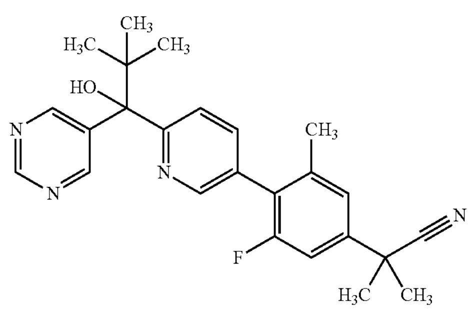 [SMILES: Cc1cc(C(C)(C)C#N)cc(F)c1-c1ccc(C(O)(c2cncnc2)C(C)(C)C)nc1] | Prepared according to Example 29 using 2-(4-bromo-3-fluoro-5-methylphenyl)-2-methylpropanenitrile in 29F. 2-(4-bromo-3-fluoro-5-methylphenyl)-2-methylpropanenitrile was prepared from 2-bromo-1-fluoro-5-iodo-3-methylbenzene according to conditions described for 29A-29E |
| 275 | 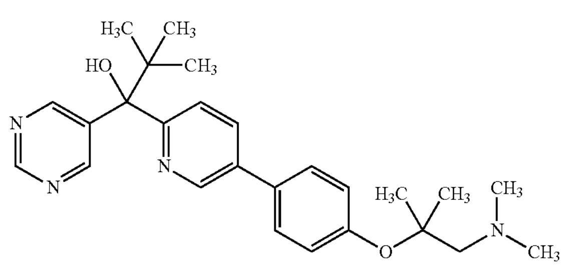 [SMILES: CN(C)CC(C)(C)Oc1ccc(-c2ccc(C(O)(c3cncnc3)C(C)(C)C)nc2)cc1] | Prepared according to Example 25 using 2-(4-bromophenoxy)-N,N,2-trimethylpropan-1-amine in 25E. |
| 277 | 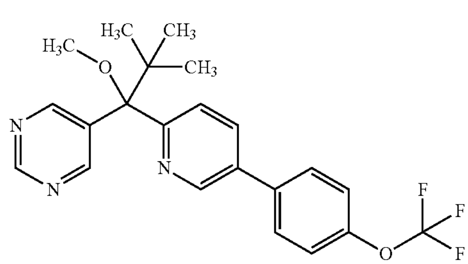 [SMILES: COC(c1cncnc1)(c1ccc(-c2ccc(OC(F)(F)F)cc2)cn1)C(C)(C)C] | Example 23 |

TABLE 1-continued

Structure and Preparation Method.

| Compound Number | Structure | Prepared According to Example |
|---|---|---|
| 278 | 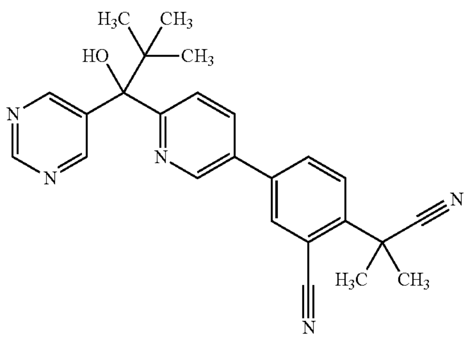 [SMILES: CC(C)(C#N)c1ccc(-c2ccc(C(O)(c3cncnc3)C(C)(C)C)nc2)cc1C#N] | Prepared according to Example 25 using 5-bromo-2-(2-cyanopropan-2-yl)benzonitrile in 25E. 5-bromo-2-(2-cyanopropan-2-yl)benzonitrile was prepared from 5-bromo-2-(cyanomethyl)benzonitrile according to conditions described for 25D |
| 279 | 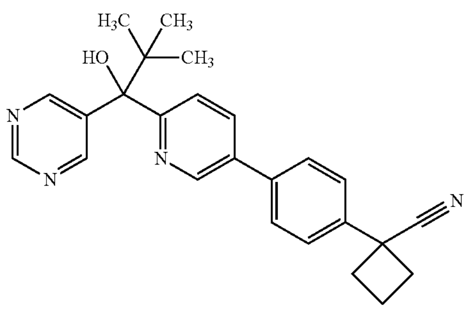 [SMILES: CC(C)(C)C(O)(c1cncnc1)c1ccc(-c2ccc(C3(C#N)CCC3)cc2)cn1] | Prepared according to Example 25 using 1-(4-bromophenyl)cyclobutanecarbonitrile in 25E. |

TABLE 2

Analytical Data.

| Compound Number | Mass Spec | NMR ($^1$H, $^{13}$C, $^{19}$F) IR (Thin Film; cm$^{-1}$) |
|---|---|---|
| 1 | ESIMS m/z 471 [M + H]$^+$ | $^1$H NMR (300 MHz, CDCl$_3$) δ 8.57 (s, 1H), 8.43 (s, 1H), 7.69 (d, J = 8.4 Hz, 2H), 7.57-7.52 (m, 1H), 7.41 (d, J = 8.7 Hz, 1H), 7.32 (dd, J = 8.7, 2.4 Hz, 1H), 7.09 (d, J = 8.4 Hz, 2H), 6.94-6.86 (m, 2H), 5.77 (d, J = 14.7 Hz, 1H), 5.07 (d, J = 14.7 Hz, 1H) |
| 2 | ESIMS m/z 475 [M + H]$^+$ | $^1$H NMR (400 MHz, CDCl$_3$) δ 8.73 (s, 1H), 8.32-8.30 (m, 1H), 8.12-8.09 (m, 1H), 7.72 (dd, J = 8.7, 2.7 Hz, 1H), 7.61 (dd, J = 8.6, 2.6 Hz, 1H), 7.49 (d, J = 8.6 Hz, 1H), 7.05-6.94 (m, 2H), 6.77-6.69 (m, 2H), 5.62 (s, 1H), 4.81 (d, J = 14.0 Hz, 1H), 4.73 (d, J = 14.0 Hz, 1H), 2.74-2.65 (m, 1H), 2.38-2.24 (m, 2H), 2.09 (ddd, J = 13.7, 11.8, 5.0 Hz, 1H) $^{19}$F NMR (376 MHz, CDCl$_3$) δ −113.02 (d, J = 6.6 Hz), −114.47 (d, J = 6.8 Hz) |
| 3 | HRMS-ESI (m/z) [M + H]$^+$ calcd for C$_{20}$H$_{19}$F$_3$N$_3$O$_2$, 390.1424; found, 390.1402 | $^1$H NMR (400 MHz, CDCl$_3$) δ 9.09 (s, 1H), 9.00 (s, 2H), 8.31 (dd, J = 2.7, 0.8 Hz, 1H), 7.68-7.58 (m, 2H), 7.46 (dd, J = 8.7, 0.8 Hz, 1H), 7.40 (dd, J = 8.7, 2.7 Hz, 1H), 7.10-7.04 (m, 2H), 5.56 (s, 1H), 2.79 (hept, J = 6.7 Hz, 1H), 0.96 (d, J = 6.7 Hz, 3H), 0.79 (d, J = 6.6 Hz, 3H) $^{19}$F NMR (376 MHz, CDCl$_3$) δ −62.00 IR 3353, 1323, 1241 |
| 4 | ESIMS m/z 459 [M + H]$^+$ | $^1$H NMR (400 MHz, CDCl$_3$) δ 8.72 (d, J = 1.1 Hz, 1H), 8.31 (d, J = 2.6 Hz, 1H), 8.11 (t, J = 2.2 Hz, 1H), 7.74-7.69 (m, 1H), 7.61 (dt, J = 8.6, 2.5 Hz, 1H), 7.49 (d, J = 8.6 Hz, 1H), 7.02-6.95 (m, 4H), 5.62 (s, 1H), 4.81 (d, J = 14.0 Hz, 1H), 4.73 (dd, J = 14.0, 1.2 Hz, 1H), 2.74-2.64 (m, 1H), 2.37-2.23 (m, 2H), 2.09 (dt, J = 11.0, 6.9 Hz, 1H) $^{19}$F NMR (376 MHz, CDCl$_3$) δ −115.94 (d, J = 4.9 Hz) |

TABLE 2-continued

Analytical Data.

| Compound Number | Mass Spec | NMR ($^1$H, $^{13}$C, $^{19}$F)<br>IR (Thin Film; cm$^{-1}$) |
|---|---|---|
| 5 | ESIMS<br>m/z 493<br>[M + H]$^+$ | $^1$H NMR (400 MHz, CDCl$_3$) δ 8.73 (s, 1H), 8.43 (dd, J = 1.6, 0.8 Hz, 1H), 8.34 (dd, J = 2.6, 0.6 Hz, 1H), 8.00-7.95 (m, 1H), 7.64 (dd, J = 8.6, 2.6 Hz, 1H), 7.53 (dd, J = 8.6, 0.5 Hz, 1H), 7.11 (d, J = 8.6 Hz, 1H), 7.02 (td, J = 8.7, 6.5 Hz, 1H), 6.77-6.69 (m, 2H), 5.60 (s, 1H), 4.84 (d, J = 14.0 Hz, 1H), 4.75 (d, J = 14.0 Hz, 1H), 2.76-2.66 (m, 1H), 2.40-2.26 (m, 2H), 2.12 (ddd, J = 13.7, 11.7, 5.0 Hz, 1H)<br>$^{19}$F NMR (376 MHz, CDCl$_3$) δ −61.77, −112.99 (d, J = 6.8 Hz), −114.48 (d, J = 6.8 Hz) |
| 6 | HRMS-ESI (m/z)<br>[M + H]$^+$<br>calcd for C$_{19}$H$_{19}$ClN$_3$O$_2$, 356.1160;<br>found, 356.1156 | $^1$H NMR (400 MHz, CDCl$_3$) δ 9.08 (s, 1H), 8.99 (s, 2H), 8.25 (dd, J = 2.7, 0.8 Hz, 1H), 7.40 (dd, J = 8.7, 0.8 Hz, 1H), 7.36-7.28 (m, 3H), 6.98-6.92 (m, 2H), 5.63 (s, 1H), 2.77 (p, J = 6.7 Hz, 1H), 0.95 (d, J = 6.7 Hz, 3H), 0.78 (d, J = 6.6 Hz, 3H)<br>IR 3342, 1486, 1473, 1240 |
| 7 | HRMS-ESI (m/z)<br>[M + H]$^+$<br>calcd for C$_{19}$H$_{17}$ClN$_3$O$_2$, 354.1004;<br>found, 354.1003 | $^1$H NMR (400 MHz, CDCl$_3$) δ 9.12 (s, 1H), 8.89 (s, 2H), 8.28 (dd, J = 2.6, 0.9 Hz, 1H), 7.38-7.33 (m, 2H), 7.32 (d, J = 2.6 Hz, 1H), 7.29 (dd, J = 8.7, 0.9 Hz, 1H), 7.03-6.96 (m, 2H), 5.49 (s, 1H), 1.69-1.57 (m, 1H), 0.75-0.61 (m, 2H), 0.62-0.52 (m, 1H), 0.52-0.43 (m, 1H)<br>IR 3336, 1486, 1242 |
| 8 | HRMS-ESI (m/z)<br>[M + H]$^+$<br>calcd for C$_{20}$H$_{17}$F$_3$N$_3$O$_3$, 404.1217;<br>found, 404.1215 | $^1$H NMR (400 MHz, CDCl$_3$) δ 9.12 (s, 1H), 8.90 (s, 2H), 8.30 (dd, J = 2.6, 0.8 Hz, 1H), 7.35 (dd, J = 8.7, 2.6 Hz, 1H), 7.31 (dd, J = 8.7, 0.9 Hz, 1H), 7.29-7.21 (m, 2H), 7.10-7.03 (m, 2H), 5.48 (s, 1H), 1.67-1.60 (m, 1H), 0.74-0.61 (m, 2H), 0.61-0.53 (m, 1H), 0.53-0.45 (m, 1H)<br>$^{19}$F NMR (376 MHz, CDCl$_3$) δ −58.25<br>IR 3324, 1501, 1474, 1242 |
| 9 | HRMS-ESI (m/z)<br>[M + H]$^+$<br>calcd for C$_{20}$H$_{19}$F$_3$N$_3$O$_3$, 406.1373;<br>found, 406.1374 | $^1$H NMR (400 MHz, CDCl$_3$) δ 9.08 (s, 1H), 8.99 (s, 2H), 8.27 (dd, J = 2.8, 0.8 Hz, 1H), 7.42 (dd, J = 8.7, 0.8 Hz, 1H), 7.34 (dd, J = 8.7, 2.7 Hz, 1H), 7.25-7.19 (m, 2H), 7.07-6.97 (m, 2H), 5.61 (s, 1H), 2.78 (p, J = 6.7 Hz, 1H), 0.96 (d, J = 6.7 Hz, 3H), 0.78 (d, J = 6.6 Hz, 3H)<br>$^{19}$F NMR (376 MHz, CDCl$_3$) δ −58.26<br>IR 3346, 1501, 1241 |
| 10 | HRMS-ESI (m/z)<br>[M + H]$^+$<br>calcd for C$_{18}$H$_{18}$ClN$_4$O$_2$, 357.1113;<br>found, 357.1114 | $^1$H NMR (400 MHz, CDCl$_3$) δ 9.09 (s, 1H), 8.99 (s, 2H), 8.30 (dd, J = 2.8, 0.7 Hz, 1H), 8.19 (dd, J = 2.8, 0.8 Hz, 1H), 7.46 (dd, J = 8.8, 0.8 Hz, 1H), 7.39-7.27 (m, 3H), 5.45 (s, 1H), 2.80 (p, J = 6.7 Hz, 1H), 0.96 (d, J = 6.7 Hz, 3H), 0.78 (d, J = 6.6 Hz, 3H)<br>IR 3358, 1567, 1454, 1261 |
| 11 | HRMS-ESI (m/z)<br>[M + H]$^+$<br>calcd for C$_{18}$H$_{16}$ClN$_4$O$_2$, 355.0956;<br>found, 355.0952 | $^1$H NMR (400 MHz, CDCl$_3$) δ 9.13 (s, 1H), 8.90 (s, 2H), 8.33 (dd, J = 2.5, 1.0 Hz, 1H), 8.23 (dd, J = 2.3, 1.3 Hz, 1H), 7.40-7.31 (m, 4H), 5.38 (s, 1H), 1.70-1.55 (m, 1H), 0.73-0.63 (m, 2H), 0.61-0.53 (m, 1H), 0.53-0.45 (m, 1H)<br>IR 3330, 1567, 1454, 1261 |
| 12 | ESIMS<br>m/z 509<br>[M + H]$^+$ | $^1$H NMR (400 MHz, CDCl$_3$) δ 8.73 (s, 1H), 8.43 (d, J = 0.9 Hz, 1H), 8.34 (dd, J = 2.6, 0.6 Hz, 1H), 7.98 (dd, J = 8.6, 2.5 Hz, 1H), 7.65 (dd, J = 8.6, 2.6 Hz, 1H), 7.53 (d, J = 8.6 Hz, 1H), 7.11 (d, J = 8.6 Hz, 1H), 7.04-6.97 (m, 3H), 5.59 (s, 1H), 4.84 (d, J = 14.0 Hz, 1H), 4.74 (d, J = 14.0 Hz, 1H), 2.76-2.66 (m, 1H), 2.32 (tdd, J = 16.3, 11.5, 5.1 Hz, 2H), 2.11 (ddd, J = 14.1, 12.0, 5.3 Hz, 1H)<br>$^{19}$F NMR (376 MHz, CDCl$_3$) δ −61.77, −115.96 |
| 13 | HRMS-ESI (m/z)<br>[M + H]$^+$<br>calcd for C$_{18}$H$_{18}$ClN$_4$O$_2$, 357.1113;<br>found, 357.1102 | $^1$H NMR (400 MHz, CDCl$_3$) δ 9.09 (s, 1H), 9.01 (s, 2H), 8.39 (dd, J = 2.6, 0.8 Hz, 1H), 8.06 (d, J = 2.6, 0.7 Hz, 1H), 7.70 (dd, J = 8.7, 2.6 Hz, 1H), 7.56 (dd, J = 8.7, 2.6 Hz, 1H), 7.46 (dd, J = 8.7, 0.8 Hz, 1H), 6.96 (dd, J = 8.7, 0.7 Hz, 1H), 5.72 (s, 1H), 2.79 (hept, J = 6.7 Hz, 1H), 0.97 (d, J = 6.7 Hz, 3H), 0.80 (d, J = 6.6 Hz, 3H)<br>IR 3349, 1457, 1370, 1269 |

TABLE 2-continued

Analytical Data.

| Compound Number | Mass Spec | NMR ($^1$H, $^{13}$C, $^{19}$F)<br>IR (Thin Film; cm$^{-1}$) |
|---|---|---|
| 14 | HRMS-ESI (m/z) [M + H]$^+$ calcd for C$_{18}$H$_{16}$ClN$_4$O$_2$, 355.0956; found, 355.0946 | $^1$H NMR (400 MHz, CDCl$_3$) δ 9.13 (s, 1H), 8.92 (s, 2H), 8.42 (dd, J = 2.6, 0.7 Hz, 1H), 8.09 (dd, J = 2.7, 0.7 Hz, 1H), 7.71 (dd, J = 8.7, 2.6 Hz, 1H), 7.57 (dd, J = 8.6, 2.6 Hz, 1H), 7.36 (dd, J = 8.6, 0.7 Hz, 1H), 6.99 (dd, J = 8.7, 0.7 Hz, 1H), 5.56 (s, 1H), 1.66 (tt, J = 8.1, 5.3 Hz, 1H), 0.72-0.63 (m, 2H), 0.63-0.54 (m, 1H), 0.54-0.44 (m, 1H)<br>IR 3342, 1457, 1370, 1269 |
| 15 | ESIMS m/z 491 [M + H]$^+$ | $^1$H NMR (400 MHz, CDCl$_3$) δ 8.71 (d, J = 1.1 Hz, 1H), 8.42 (s, 1H), 8.35 (dd, J = 2.6, 0.5 Hz, 1H), 7.97 (dd, J = 8.6, 2.0 Hz, 1H), 7.64 (dt, J = 8.6, 2.4 Hz, 1H), 7.51 (d, J = 8.6, 1H), 7.23-7.17 (m, 2H), 7.11 (d, J = 8.7 Hz, 1H), 7.03-6.98 (m, 2H), 5.54 (s, 1H), 4.86 (d, J = 14.0 Hz, 1H), 4.75 (d, J = 14.0 Hz, 1H), 2.77-2.67 (m, 1H), 2.33-2.23 (m, 2H), 2.15 (dt, J = 13.8, 9.3 Hz, 1H)<br>$^{19}$F NMR (376 MHz, CDCl$_3$) δ -61.76 |
| 16 | HRMS-ESI (m/z) [M + H]$^+$ calcd for C$_{20}$H$_{19}$N$_4$O$_2$, 347.1503; found, 347.1506 | $^1$H NMR (400 MHz, CDCl$_3$) δ 9.10 (s, 1H), 9.01 (s, 2H), 8.33 (dd, J = 2.7, 0.8 Hz, 1H), 7.70-7.61 (m, 2H), 7.50 (dd, J = 8.7, 0.8 Hz, 1H), 7.43 (dd, J = 8.7, 2.7 Hz, 1H), 7.08-6.98 (m, 2H), 5.46 (s, 1H), 2.81 (p, J = 6.6 Hz, 1H), 0.97 (d, J = 6.7 Hz, 3H), 0.79 (d, J = 6.6 Hz, 3H)<br>IR 3356, 2228, 1502, 1472, 1242 |
| 17 | HRMS-ESI (m/z) [M + H]$^+$ calcd for C$_{20}$H$_{17}$F$_3$N$_3$O$_2$, 388.1267; found, 388.1252 | $^1$H NMR (400 MHz, CDCl$_3$) δ 9.13 (s, 1H), 8.91 (s, 2H), 8.34 (dd, J = 2.7, 0.8 Hz, 1H), 7.68-7.59 (m, 2H), 7.41 (dd, J = 8.6, 2.7 Hz, 1H), 7.35 (dd, J = 8.6, 0.8 Hz, 1H), 7.14-7.05 (m, 2H), 5.46 (s, 1H), 1.70-1.60 (m, 1H), 0.76-0.62 (m, 2H), 0.62-0.53 (m, 1H), 0.54-0.41 (m, 1H)<br>$^{19}$F NMR (376 MHz, CDCl$_3$) δ -61.99<br>IR 3333, 1323, 1241 |
| 18 | HRMS-ESI (m/z) [M + H]$^+$ calcd for C$_{20}$H$_{17}$N$_4$O$_2$, 345.1346; found, 345.1334 | $^1$H NMR (400 MHz, CDCl$_3$) δ 9.14 (s, 1H), 8.91 (s, 2H), 8.36 (dd, J = 2.6, 0.8 Hz, 1H), 7.72-7.64 (m, 2H), 7.44 (dd, J = 8.6, 2.6 Hz, 1H), 7.39 (dd, J = 8.6, 0.9 Hz, 1H), 7.13-7.03 (m, 2H), 5.39 (s, 1H), 1.72-1.61 (m, 1H), 0.76-0.63 (m, 2H), 0.65-0.55 (m, 1H), 0.55-0.46 (m, 1H)<br>IR 3350, 2228, 1502, 1473, 1243 |
| 19 | HRMS-ESI (m/z) [M + H]$^+$ calcd for C$_{18}$H$_{17}$N$_6$O$_2$, 349.1408; found, 349.1413 | $^1$H NMR (400 MHz, CDCl$_3$) δ 8.73 (s, 1H), 8.16 (dd, J = 2.7, 0.7 Hz, 1H), 7.72-7.65 (m, 2H), 7.62 (dd, J = 8.6, 0.8 Hz, 1H), 7.47 (dd, J = 8.6, 2.7 Hz, 1H), 7.08-7.00 (m, 2H), 5.08 (s, 1H), 5.01 (d, J = 14.1 Hz, 1H), 4.75 (d, J = 14.1 Hz, 1H), 1.36-1.24 (m, 1H), 0.67-0.56 (m, 1H), 0.52 (dddd, J = 9.3, 8.1, 6.0, 4.3 Hz, 1H), 0.45-0.24 (m, 2H)<br>IR 3362, 2228, 1502, 1477, 1242 |
| 20 | HRMS-ESI (m/z) [M + H]$^+$ calcd for C$_{19}$H$_{17}$ClN$_3$O$_2$, 354.1004; found, 354.1006 | $^1$H NMR (400 MHz, CDCl$_3$) δ 9.10 (s, 1H), 8.93 (s, 2H), 8.31 (dd, J = 2.8, 0.7 Hz, 1H), 7.41 (d, J = 8.7, 0.8 Hz, 1H), 7.37-7.28 (m, 3H), 6.99-6.93 (m, 2H), 5.68 (ddt, J = 17.2, 10.2, 7.0 Hz, 1H), 5.24-5.09 (m, 2H), 4.90 (s, 1H), 3.20-2.97 (m, 2H)<br>IR 3280, 1486, 1473, 1236 |
| 21 | HRMS-ESI (m/z) [M + H]$^+$ calcd for C$_{20}$H$_{19}$ClN$_3$O$_2$, 368.1160; found, 368.1141 | $^1$H NMR (400 MHz, CDCl$_3$) δ 9.10 (s, 1H), 8.91 (s, 2H), 8.29 (dd, J = 2.3, 1.2 Hz, 1H), 7.40-7.30 (m, 4H), 7.06-6.90 (m, 2H), 5.81 (ddt, J = 16.9, 10.2, 6.5 Hz, 1H), 5.61 (s, 1H), 5.07-4.91 (m, 2H), 2.47-2.29 (m, 2H), 2.25-2.08 (m, 1H), 2.05-1.91 (m, 1H)<br>IR 3262, 1486, 1474, 1237 |
| 22 | HRMS-ESI (m/z) [M + H]$^+$ calcd for C$_{21}$H$_{19}$F$_3$N$_3$O$_3$, 418.1373; found, 418.1382 | $^1$H NMR (400 MHz, CDCl$_3$) δ 9.11 (s, 1H), 8.91 (s, 2H), 8.30 (dd, J = 2.2, 1.3 Hz, 1H), 7.37-7.33 (m, 2H), 7.28-7.19 (m, 2H), 7.09-7.01 (m, 2H), 5.81 (ddt, J = 16.8, 10.2, 6.5 Hz, 1H), 5.59 (s, 1H), 5.04-4.91 (m, 2H), 2.47-2.29 (m, 2H), 2.24-2.10 (m, 1H), 2.06-1.89 (m, 1H)<br>$^{19}$F NMR (376 MHz, CDCl$_3$) δ -58.26<br>IR 3274, 1502, 1249, 1187 |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 23 | HRMS-ESI (m/z) [M + H]$^+$ calcd for C$_{19}$H$_{19}$N$_6$O$_2$, 363.1564; found, 363.1568 | $^1$H NMR (400 MHz, CDCl$_3$) δ 8.73 (s, 1H), 8.22 (dd, J = 2.7, 0.7 Hz, 1H), 7.74-7.61 (m, 2H), 7.52 (dd, J = 8.7, 0.8 Hz, 1H), 7.40 (dd, J = 8.6, 2.7 Hz, 1H), 7.04-6.97 (m, 2H), 5.10 (d, J = 0.7 Hz, 1H), 5.01 (dd, J = 14.1, 0.8 Hz, 1H), 4.81 (d, J = 14.0 Hz, 1H), 1.98 (dd, J = 14.2, 6.4 Hz, 1H), 1.77 (dd, J = 14.2, 7.1 Hz, 1H), 0.83-0.63 (m, 1H), 0.52 (ddd, J = 13.5, 9.1, 5.0 Hz, 1H), 0.37 (dddd, J = 9.3, 8.0, 5.6, 4.4 Hz, 1H), 0.28-0.07 (m, 1H), −0.04−−0.22 (m, 1H) IR 3377, 2228, 1502, 1479, 1242 |
| 24 | HRMS-ESI (m/z) [M + H]$^+$ calcd for C$_{18}$H$_{19}$N$_6$O$_2$, 351.1564; found, 351.1569 | $^1$H NMR (400 MHz, CDCl$_3$) δ 8.70 (s, 1H), 8.12 (dd, J = 2.7, 0.8 Hz, 1H), 7.71-7.64 (m, 2H), 7.48 (dd, J = 8.7, 0.8 Hz, 1H), 7.41 (dd, J = 8.6, 2.7 Hz, 1H), 7.05-6.93 (m, 2H), 5.30 (t, J = 1.0 Hz, 1H), 5.00 (d, J = 14.0 Hz, 1H), 4.78 (d, J = 14.0 Hz, 1H), 2.27 (hept, J = 6.8 Hz, 1H), 1.17 (d, J = 6.7 Hz, 3H), 0.76 (d, J = 6.8 Hz, 3H) IR 3363, 2228, 1478, 1242 |
| 25 | ESIMS m/z 326 [M + H]$^+$ | $^1$H NMR (400 MHz, CDCl$_3$) δ 8.99 (s, 1H), 8.61 (dd, J = 2.2, 0.7 Hz, 1H), 8.39 (s, 2H), 7.90 (dd, J = 8.2, 2.2 Hz, 1H), 7.50-7.44 (m, 5H), 5.10 (s, 1H), 3.13 (d, J = 13.7 Hz, 1H), 3.07 (d, J = 13.7 Hz, 1H), 1.67 (s, 3H) $^{13}$C NMR (101 MHz, CDCl$_3$) δ 161.91, 158.03, 156.91, 145.77, 135.53, 135.44, 134.62, 134.38, 130.46, 129.37, 128.35, 119.25, 73.62, 44.28, 28.79 |
| 26 | ESIMS m/z 408 [M + H]$^+$ | $^1$H NMR (400 MHz, CDCl$_3$) δ 8.75 (s, 1H), 8.57 (d, J = 1.6 Hz, 1H), 7.82 (dd, J = 8.2, 2.3 Hz, 1H), 7.57 (d, J = 8.4 Hz, 2H), 7.53 (d, J = 8.4 Hz, 2H), 7.32 (d, J = 8.4 Hz, 2H), 5.82 (brs, 1H), 5.42 (d, J = 14.1 Hz, 1H), 4.77 (d, J = 14.1 Hz, 1H), 1.06 (s, 9H) |
| 27 | HRMS-ESI (m/z) [M + H]$^+$ calcd for C$_{21}$H$_{21}$F$_3$N$_3$O$_2$, 404.1580; found, 404.1582 | $^1$H NMR (400 MHz, Chloroform-d) δ 9.21 (s, 2H), 9.09 (s, 1H), 8.76 (dd, J = 2.4, 0.9 Hz, 1H), 7.94 (dd, J = 8.4, 2.4 Hz, 1H), 7.86 (dd, J = 8.4, 0.9 Hz, 1H), 7.66-7.57 (m, 2H), 7.39-7.32 (m, 2H), 6.16 (s, 1H), 1.09 (s, 9H) $^{19}$F NMR (376 MHz, CDCl$_3$) δ −57.80 IR 3263, 1256, 1210, 1166 |
| 28 | ESIMS m/z 494 [M + H]$^+$ | $^1$H NMR (300 MHz, CDCl$_3$) δ 8.71 (s, 1H), 8.52 (d, J = 2.1 Hz, 1H), 7.90 (dd, J = 8.2, 2.3 Hz, 1H), 7.60-7.50 (m, 3H), 7.32 (d, J = 8.3 Hz, 2H), 7.14 (t, J = 8.1 Hz, 1H), 7.06-6.87 (m, 2H), 5.54 (s, 1H), 5.13 (d, J = 14.1 Hz, 1H), 4.72 (d, J = 14.1 Hz, 1H), 3.23 (s, 2H) |
| 29 | HRMS-ESI (m/z) [M + H]$^+$ calcd for C$_{22}$H$_{21}$ClN$_3$O$_2$, 394.1317; found, 394.1321 | $^1$H NMR (400 MHz, CDCl$_3$) δ 9.13 (s, 1H), 8.96 (s, 2H), 8.27 (dd, J = 2.7, 0.7 Hz, 1H), 7.46 (dd, J = 8.7, 0.7 Hz, 1H), 7.38-7.33 (m, 2H), 7.32 (dd, J = 8.7, 2.7 Hz, 1H), 7.06-6.92 (m, 2H), 6.07 (s, 1H), 1.30 (s, 9H) IR 3246, 1486, 1472, 1237 |
| 30 | HRMS-ESI (m/z) [M + H]$^+$ calcd for C$_{22}$H$_{20}$ClN$_3$O$_2$, 342.1004; found, 342.1010 | $^1$H NMR (400 MHz, CDCl$_3$) δ 9.10 (s, 1H), 8.90 (s, 2H), 8.29 (dd, J = 2.0, 1.5 Hz, 1H), 7.37-7.31 (m, 4H), 6.99-6.94 (m, 2H), 5.55 (s, 1H), 2.31 (hept, J = 7.0 Hz, 2H), 0.90 (t, J = 7.3 Hz, 3H) IR 3308, 1486, 1474, 1238 |
| 31 | HRMS-ESI (m/z) [M + H]$^+$ calcd for C$_{23}$H$_{21}$F$_3$N$_3$O$_3$, 444.1530; found, 444.1523 | $^1$H NMR (400 MHz, CDCl$_3$) δ 9.13 (s, 1H), 8.96 (s, 2H), 8.29 (dd, J = 2.7, 0.7 Hz, 1H), 7.48 (dd, J = 8.7, 0.7 Hz, 1H), 7.34 (dd, J = 8.7, 2.7 Hz, 1H), 7.28-7.20 (m, 2H), 7.10-7.03 (m, 2H), 6.06 (s, 1H), 1.31 (s, 9H) $^{19}$F NMR (376 MHz, CDCl$_3$) δ −58.25 IR 3181, 1501, 1471, 1238, 1185 |
| 32 | HRMS-ESI (m/z) [M + H]$^+$ calcd for C$_{19}$H$_{17}$F$_3$N$_3$O$_3$, 392.1217; found, 392.1213 | $^1$H NMR (400 MHz, CDCl$_3$) δ 9.10 (s, 1H), 8.90 (s, 2H), 8.31 (dd, J = 2.2, 1.3 Hz, 1H), 7.38-7.32 (m, 2H), 7.26-7.20 (m, 2H), 7.09-7.01 (m, 2H), 5.53 (s, 1H), 2.31 (hept, J = 7.0 Hz, 2H), 0.90 (t, J = 7.3 Hz, 3H) $^{19}$F NMR (376 MHz, CDCl$_3$) δ −58.26 IR 3278, 1501, 1473, 1239, 1185 |

TABLE 2-continued

Analytical Data.

| Compound Number | Mass Spec | NMR ($^1$H, $^{13}$C, $^{19}$F)<br>IR (Thin Film; cm$^{-1}$) |
|---|---|---|
| 33 | HRMS-ESI (m/z) [M + H]$^+$ calcd for C$_{23}$H$_{21}$F$_3$N$_3$O$_2$, 428.1580; found, 428.1582 | $^1$H NMR (400 MHz, CDCl$_3$) δ 9.14 (s, 1H), 8.97 (s, 2H), 8.33 (dd, J = 2.8, 0.7 Hz, 1H), 7.69-7.61 (m, 2H), 7.52 (dd, J = 8.7, 0.8 Hz, 1H), 7.39 (dd, J = 8.6, 2.7 Hz, 1H), 7.18-7.06 (m, 2H), 6.02 (s, 1H), 1.31 (s, 9H)<br>$^{19}$F NMR (376 MHz, CDCl$_3$) δ −62.02<br>IR 3191, 1471, 1325, 1240 |
| 34 | HRMS-ESI (m/z) [M + H]$^+$ calcd for C$_{19}$H$_{17}$F$_3$N$_3$O$_2$, 376.1267; found, 376.1268 | $^1$H NMR (400 MHz, CDCl$_3$) δ 9.11 (s, 1H), 8.91 (s, 2H), 8.35 (dd, J = 2.5, 1.0 Hz, 1H), 7.70-7.58 (m, 2H), 7.45-7.34 (m, 2H), 7.12-7.03 (m, 2H), 5.48 (s, 1H), 2.33 (hept, J = 7.0 Hz, 2H), 0.91 (t, J = 7.3 Hz, 3H)<br>$^{19}$F NMR (376 MHz, CDCl$_3$) δ −62.00<br>IR 3289, 1474, 1325, 1241 |
| 35 | HRMS-ESI (m/z) [M + H]$^+$ calcd for C$_{21}$H$_{20}$ClN$_4$O$_2$, 395.1269; found, 395.1260 | $^1$H NMR (400 MHz, CDCl$_3$) δ 9.13 (s, 1H), 8.96 (s, 2H), 8.32 (dd, J = 2.8, 0.7 Hz, 1H), 8.22 (dd, J = 2.5, 1.2 Hz, 1H), 7.52 (dd, J = 8.7, 0.7 Hz, 1H), 7.40-7.32 (m, 3H), 5.94 (s, 1H), 1.31 (s, 9H)<br>IR 3191, 1568, 1454, 1262 |
| 36 | HRMS-ESI (m/z) [M + H]$^+$ calcd for C$_{17}$H$_{16}$ClN$_4$O$_2$, 343.0956; found, 343.0952 | $^1$H NMR (400 MHz, CDCl$_3$) δ 9.11 (s, 1H), 8.90 (s, 2H), 8.33 (dd, J = 2.4, 1.1 Hz, 1H), 8.20 (dd, J = 2.8, 0.9 Hz, 1H), 7.44-7.29 (m, 4H), 5.38 (s, 1H), 2.42-2.22 (m, 2H), 0.90 (t, J = 7.3 Hz, 3H)<br>IR 3325, 1567, 1454, 1261 |
| 37 | HRMS-ESI (m/z) [M + H]$^+$ calcd for C$_{20}$H$_{17}$N$_4$O$_2$, 345.1346; found, 345.1351 | $^1$H NMR (400 MHz, CDCl$_3$) δ 9.12 (s, 1H), 8.96 (s, 2H), 8.38 (dd, J = 2.8, 0.7 Hz, 1H), 7.72-7.61 (m, 2H), 7.53 (dd, J = 8.7, 0.7 Hz, 1H), 7.41 (dd, J = 8.6, 2.7 Hz, 1H), 7.10-6.99 (m, 2H), 5.68 (ddt, J = 17.2, 10.2, 7.1 Hz, 1H), 5.30-5.13 (m, 2H), 4.68 (s, 1H), 3.27-2.97 (m, 2H)<br>IR 3261, 2228, 1502, 1472, 1238 |
| 38 | ESIMS m/z 354 [M + H]$^+$ | $^1$H NMR (400 MHz, CDCl$_3$) δ 8.89 (s, 1H), 8.51 (dd, J = 2.2, 0.7 Hz, 1H), 8.32 (s, 2H), 7.87 (dd, J = 8.2, 2.2 Hz, 1H), 7.48-7.41 (m, 5H), 5.21 (s, 1H), 3.37 (d, J = 13.8 Hz, 1H), 2.98 (d, J = 13.8 Hz, 1H), 2.25 (hept, J = 6.6 Hz, 1H), 1.19 (d, J = 6.7 Hz, 3H), 0.71 (d, J = 6.8 Hz, 3H)<br>$^{13}$C NMR (101 MHz, CDCl$_3$) δ 160.28, 157.95, 156.57, 145.34, 135.33, 135.19, 134.57, 134.03, 130.85, 129.33, 128.30, 119.85, 78.08, 40.21, 38.01, 17.47, 16.89 |
| 39 | ESIMS m/z 352 [M + H]$^+$ | $^1$H NMR (400 MHz, CDCl$_3$) δ 8.97 (s, 1H), 8.56 (d, J = 2.2 Hz, 1H), 8.43 (s, 2H), 7.92 (dd, J = 8.2, 2.2 Hz, 1H), 7.57 (d, J = 8.2 Hz, 1H), 7.47 (q, J = 8.5 Hz, 4H), 5.04 (s, 1H), 3.24 (d, J = 13.8 Hz, 1H), 3.14 (d, J = 13.8 Hz, 1H), 1.34 (tt, J = 8.2, 5.2 Hz, 1H), 0.61 (td, J = 9.9, 5.1 Hz, 1H), 0.53-0.44 (m, 1H), 0.34 (td, J = 9.8, 5.4 Hz, 1H), 0.29-0.21 (m, 1H)<br>$^{13}$C NMR (101 MHz, CDCl$_3$) δ 161.63, 158.18, 156.83, 145.49, 135.62, 135.56, 134.67, 134.47, 130.59, 129.45, 128.43, 119.70, 73.49, 43.33, 20.97, 1.62, 0.00 |
| 40 | HRMS-ESI (m/z) [M + H]$^+$ calcd for C$_{21}$H$_{17}$ClN$_3$O$_2$, 378.1004; found, 378.1004 | $^1$H NMR (400 MHz, CDCl$_3$) δ 9.13 (s, 1H), 8.94 (s, 2H), 8.27 (dd, J = 2.8, 0.8 Hz, 1H), 7.44 (dd, J = 8.6, 0.7 Hz, 1H), 7.38-7.33 (m, 2H), 7.31 (dd, J = 8.7, 2.7 Hz, 1H), 7.02-6.93 (m, 2H), 6.02 (s, 1H), 1.42-1.32 (m, 1H), 0.90-0.81 (m, 2H), 0.82-0.74 (m, 2H)<br>IR 3157, 2239, 1485, 1471, 1238 |
| 41 | HRMS-ESI (m/z) [M + H]$^+$ calcd for C$_{23}$H$_{17}$Cl$_2$FN$_3$O$_2$, 456.0676; found, 456.0678 | $^1$H NMR (400 MHz, Chloroform-d) δ 9.12 (s, 1H), 8.93 (s, 2H), 8.21 (dd, J = 2.7, 0.7 Hz, 1H), 7.49-7.41 (m, 1H), 7.39-7.29 (m, 3H), 7.19 (t, J = 8.1 Hz, 1H), 7.03-6.97 (m, 1H), 6.97-6.89 (m, 3H), 5.40 (d, J = 0.7 Hz, 1H), 3.71-3.52 (m, 2H)<br>$^{19}$F NMR (376 MHz, CDCl$_3$) δ −114.17<br>IR 3220, 1486, 1410, 1239 |

TABLE 2-continued

| | | Analytical Data. | |
|---|---|---|---|
| Compound Number | Mass Spec | NMR ($^1$H, $^{13}$C, $^{19}$F) IR (Thin Film; cm$^{-1}$) | |

| Compound Number | Mass Spec | NMR ($^1$H, $^{13}$C, $^{19}$F) / IR (Thin Film; cm$^{-1}$) |
|---|---|---|
| 42 | ESIMS m/z 460 [M + H]$^+$ | $^1$H NMR (300 MHz, CDCl$_3$) δ 8.68 (s, 1H), 8.05 (d, J = 2.7 Hz, 1H), 7.43 (d, J = 8.4 Hz, 1H), 7.35 (d, J = 8.4 Hz, 2H), 7.29 (dd, J = 9.0, 3.0 Hz, 1H), 7.13 (t, J = 8.1 Hz, 1H), 7.06-6.96 (m, 2H), 6.92 (d, J = 8.4 Hz, 2H), 5.34 (s, 1H), 5.08 (d, J = 14.4 Hz, 1H), 4.68 (d, J = 14.4 Hz, 1H), 3.19 (s, 2H) |
| 43 | ESIMS m/z 374 [M + H]$^+$ | $^1$H NMR (400 MHz, CDCl$_3$) δ 8.71 (s, 1H), 8.10 (d, J = 3.2 Hz, 1H), 7.44 (d, J = 8.8 Hz, 1H), 7.33 (d, J = 8.8 Hz, 2H), 7.22 (dd, J = 8.8, 3.2 Hz, 1H), 6.91 (d, J = 8.8 Hz, 2H), 5.61 (brs, 1H), 5.35 (d, J = 14.0 Hz, 1H), 4.73 (d, J = 14.0 Hz, 1H), 1.03 (s, 9H) |
| 44 | ESIMS m/z 370 [M + H]$^+$ | $^1$H NMR (400 MHz, CDCl$_3$) δ 8.66-8.60 (m, 3H), 8.30 (d, J = 2.8 Hz, 1H), 8.04 (d, J = 8.8 Hz, 1H), 7.40-7.30 (m, 3H), 7.01 (d, J = 8.8 Hz, 2H), 4.73 (s, 1H), 1.07 (s, 9H) |
| 45 | HRMS-ESI (m/z) [M + H]$^+$ calcd for C$_{21}$H$_{19}$F$_3$N$_3$O$_3$, 418.1373; found, 418.1367 | $^1$H NMR (400 MHz, CDCl$_3$) δ 9.10 (s, 1H), 8.94 (s, 2H), 8.32 (dd, J = 2.7, 0.8 Hz, 1H), 7.43 (dd, J = 8.7, 0.8 Hz, 1H), 7.33 (dd, J = 8.7, 2.8 Hz, 1H), 7.22 (s, 2H), 7.08-7.00 (m, 2H), 5.09 (s, 1H), 2.36-2.17 (m, 2H), 0.77-0.62 (m, 1H), 0.52-0.28 (m, 2H), 0.14-0.02 (m, 1H), 0.00--0.02 (m, 1H) $^{19}$F NMR (376 MHz, CDCl$_3$) δ -58.26 IR 3353, 2253, 1502, 1475, 1250 |
| 46 | ESIMS m/z 380 [M + H]$^+$; m/z 378 ([M − H]$^-$) | $^1$H NMR (400 MHz, CDCl$_3$) δ 8.97 (s, 1H), 8.62 (dd, J = 2.2, 0.9 Hz, 1H), 8.46 (s, 2H), 8.00 (dd, J = 8.3, 2.3 Hz, 1H), 7.73 (d, J = 8.3 Hz, 1H), 7.47 (s, 4H), 6.36 (s, 1H), 3.54 (d, J = 14.2 Hz, 1H), 3.33 (d, J = 14.2 Hz, 1H) $^{19}$F NMR (376 MHz, CDCl$_3$) δ -79.12 |
| 47 | HRMS-ESI (m/z) [M + H]$^+$ calcd for C$_{22}$H$_{17}$F$_3$N$_3$O$_2$, 412.1267; found, 412.1271 | $^1$H NMR (400 MHz, CDCl$_3$) δ 9.14 (s, 1H), 8.96 (s, 2H), 8.33 (dd, J = 2.7, 0.7 Hz, 1H), 7.69-7.59 (m, 2H), 7.50 (dd, J = 8.7, 0.8 Hz, 1H), 7.39 (dd, J = 8.6, 2.7 Hz, 1H), 7.16-7.06 (m, 2H), 5.96 (s, 1H), 1.44-1.33 (m, 1H), 0.92-0.82 (m, 2H), 0.83-0.74 (m, 2H) $^{19}$F NMR (376 MHz, CDCl$_3$) δ -62.02 IR 3152, 2237, 1325, 1241 |
| 48 | HRMS-ESI (m/z) [M + H]$^+$ calcd for C$_{22}$H$_{17}$F$_3$N$_3$O$_3$, 428.1217; found, 428.1222 | $^1$H NMR (400 MHz, CDCl$_3$) δ 9.13 (s, 1H), 8.95 (s, 2H), 8.28 (dd, J = 2.7, 0.7 Hz, 1H), 7.46 (dd, J = 8.6, 0.8 Hz, 1H), 7.40-7.28 (m, 1H), 7.29-7.20 (m, 2H), 7.11-7.01 (m, 2H), 6.00 (s, 1H), 1.44-1.31 (m, 1H), 0.90-0.82 (m, 2H), 0.82-0.74 (m, 2H) $^{19}$F NMR (376 MHz, CDCl$_3$) δ -58.25 IR 3167, 2238, 1501, 1471 |
| 49 | HRMS-ESI (m/z) [M + H]$^+$ calcd for C$_{21}$H$_{20}$ClN$_4$O$_2$, 395.1269; found, 395.1278 | $^1$H NMR (400 MHz, CDCl$_3$) δ 9.13 (s, 1H), 8.98 (s, 2H), 8.41 (dd, J = 2.5, 0.9 Hz, 1H), 8.09 (dd, J = 2.7, 0.7 Hz, 1H), 7.72 (dd, J = 8.7, 2.7 Hz, 1H), 7.57 (dd, J = 8.6, 2.5 Hz, 1H), 7.53 (dd, J = 8.6, 0.9 Hz, 1H), 6.99 (dd, J = 8.7, 0.7 Hz, 1H), 6.16 (s, 1H), 1.31 (s, 9H) IR 3167, 2240, 1457, 1370, 1267 |
| 50 | HRMS-ESI (m/z) [M + H]$^+$ calcd for C$_{22}$H$_{23}$N$_4$O$_2$, 375.1816; found, 375.1820 | $^1$H NMR (400 MHz, CDCl$_3$) δ 9.13 (s, 1H), 8.98 (s, 2H), 8.39 (dd, J = 2.6, 0.8 Hz, 1H), 7.97 (dt, J = 2.5, 0.8 Hz, 1H), 7.59-7.53 (m, 2H), 7.49 (dd, J = 8.6, 0.8 Hz, 1H), 6.92 (d, J = 8.3 Hz, 1H), 6.24 (s, 1H), 2.31 (d, J = 0.7 Hz, 3H), 1.31 (s, 9H) IR 3177, 2237, 1466, 1376, 1238 |
| 51 | ESIMS m/z 368 [M + H]$^+$ | $^1$H NMR (400 MHz, CDCl$_3$) δ 8.86 (s, 1H), 8.58 (d, J = 1.6 Hz, 1H), 8.45 (s, 2H), 7.83 (dd, J = 8.3, 2.3 Hz, 1H), 7.50 (dd, J = 8.3, 0.8 Hz, 1H), 7.48-7.42 (m, 4H), 5.61 (s, 1H), 3.31 (q, J = 14.1 Hz, 2H), 1.05 (s, 9H) $^{13}$C NMR (101 MHz, CDCl$_3$) δ 158.40, 156.42, 145.27, 135.28, 134.58, 134.11, 133.94, 131.32, 129.33, 128.27, 121.66, 79.83, 39.56, 35.05, 25.94 |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 52 | ESIMS m/z 394 [M + H]$^+$ | $^1$H NMR (400 MHz, CDCl$_3$) δ 8.88 (s, 1H), 8.53-8.50 (m, 1H), 8.32 (s, 2H), 7.87 (dd, J = 8.2, 2.3 Hz, 1H), 7.48-7.40 (m, 5H), 5.22 (s, 1H), 3.38 (d, J = 13.8 Hz, 1H), 2.97 (d, J = 13.7 Hz, 1H), 2.16-2.09 (m, 1H), 1.88 (s, 2H), 1.67 (s, 4H), 1.14 (s, 4H) $^{13}$C NMR (101 MHz, CDCl$_3$) δ 160.27, 157.99, 156.55, 145.33, 135.35, 135.13, 134.55, 133.97, 130.89, 129.32, 128.29, 119.97, 78.11, 48.12, 39.64, 27.33, 26.76, 26.58, 26.47, 26.26 |
| 53 | HRMS-ESI (m/z) [M + H]$^+$ calcd for C$_{19}$H$_{21}$N$_4$O$_2$, 337.1659; found, 337.1662 | $^1$H NMR (400 MHz, CDCl$_3$) δ 9.08 (s, 1H), 9.00 (s, 2H), 8.37 (dd, J = 2.6, 0.7 Hz, 1H), 7.95 (dt, J = 2.5, 0.8 Hz, 1H), 7.54 (m, 2H), 7.43 (dd, J = 8.7, 0.8 Hz, 1H), 6.89 (d, J = 8.3 Hz, 1H), 5.81 (s, 1H), 2.85-2.69 (m, 1H), 2.29 (s, 3H), 0.96 (d, J = 6.7 Hz, 3H), 0.80 (d, J = 6.6 Hz, 3H) IR 3339, 1470, 1377, 1241 |
| 54 | HRMS-ESI (m/z) [M + H]$^+$ calcd for C$_{17}$H$_{16}$ClN$_4$O$_2$, 343.0956; found, 343.0959 | $^1$H NMR (400 MHz, CDCl$_3$) δ 9.11 (s, 1H), 8.92 (s, 2H), 8.42 (dd, J = 2.6, 0.7 Hz, 1H), 8.08 (dd, J = 2.7, 0.7 Hz, 1H), 7.71 (dd, J = 8.7, 2.6 Hz, 1H), 7.56 (dd, J = 8.6, 2.7 Hz, 1H), 7.39 (dd, J = 8.6, 0.8 Hz, 1H), 6.98 (dd, J = 8.7, 0.7 Hz, 1H), 5.63 (s, 1H), 2.47-2.22 (m, 2H), 0.92 (t, J = 7.3 Hz, 3H) IR 3219, 1463, 1373, 1276 |
| 55 | HRMS-ESI (m/z) [M + H]$^+$ calcd for C$_{18}$H$_{19}$N$_4$O$_2$, 323.1503; found, 323.1508 | $^1$H NMR (400 MHz, CDCl$_3$) δ 9.10 (s, 1H), 8.92 (s, 2H), 8.41 (dd, J = 2.7, 0.7 Hz, 1H), 7.96 (dt, J = 2.5, 0.8 Hz, 1H), 7.62-7.47 (m, 2H), 7.35 (dd, J = 8.6, 0.7 Hz, 1H), 6.90 (d, J = 8.3 Hz, 1H), 5.72 (s, 1H), 2.39-2.25 (m, 5H), 0.92 (t, J = 7.3 Hz, 3H) IR 3251, 1471, 1412, 1380, 1240 |
| 56 | ESIMS m/z 380 [M + H]$^+$ | $^1$H NMR (400 MHz, CDCl$_3$) δ 8.90 (s, 1H), 8.50 (dd, J = 2.2, 0.7 Hz, 1H), 8.29 (s, 2H), 7.88 (dd, J = 8.2, 2.3 Hz, 1H), 7.49-7.42 (m, 5H), 5.25 (s, 1H), 3.30 (d, J = 13.8 Hz, 1H), 3.02 (d, J = 13.8 Hz, 1H), 2.54 (p, J = 8.7 Hz, 1H), 2.01-1.83 (m, 2H), 1.80-1.42 (m, 4H), 1.24-1.07 (m, 2H) $^{13}$C NMR (101 MHz, CDCl$_3$) δ 160.83, 157.91, 156.63, 145.24, 135.36, 135.30, 134.56, 134.02, 130.57, 129.33, 128.30, 119.79, 76.94, 50.03, 41.88, 27.04, 26.95, 26.07, 25.72 |
| 57 | ESIMS m/z 382 [M + H]$^+$ | $^1$H NMR (400 MHz, CDCl$_3$) δ 8.85 (s, 1H), 8.57 (d, J = 2.0 Hz, 1H), 8.43 (s, 2H), 7.83 (dd, J = 8.3, 2.3 Hz, 1H), 7.50 (dd, J = 8.3, 0.5 Hz, 1H), 7.48-7.41 (m, 4H), 5.64 (s, 1H), 3.35 (d, J = 13.9 Hz, 1H), 3.28 (d, J = 13.8 Hz, 1H), 1.54 (dq, J = 14.9, 7.5 Hz, 1H), 1.37-1.28 (m, 1H), 1.01 (s, 3H), 1.00 (s, 3H), 0.85 (t, J = 7.5 Hz, 3H) $^{13}$C NMR (101 MHz, CDCl$_3$) δ 158.45, 156.39, 145.21, 135.28, 134.58, 134.05, 133.90, 131.33, 129.33, 128.26, 121.92, 80.54, 42.31, 35.06, 29.14, 21.34, 8.75 |
| 58 | HRMS-ESI (m/z) [M + H]$^+$ calcd for C$_{19}$H$_{18}$F$_3$N$_4$O$_2$, 391.1376; found, 391.1377 | $^1$H NMR (400 MHz, CDCl$_3$) δ 9.10 (s, 1H), 9.02 (s, 2H), 8.58 (dd, J = 2.5, 0.8 Hz, 1H), 7.86 (dd, J = 8.5, 2.5 Hz, 1H), 7.70 (ddd, J = 2.9, 1.5, 0.8 Hz, 1H), 7.65 (dd, J = 8.5, 0.8 Hz, 1H), 7.55 (dd, J = 9.7, 2.7 Hz, 1H), 6.75 (dt, J = 9.8, 0.8 Hz, 1H), 5.27 (s, 1H), 2.89 (hept, J = 6.7 Hz, 1H), 0.98 (d, J = 6.8 Hz, 3H), 0.82 (d, J = 6.7 Hz, 3H) $^{19}$F NMR (376 MHz, CDCl$_3$) δ −62.80 IR 3384, 1682, 1332 |
| 59 | HRMS-ESI (m/z) [M + H]$^+$ calcd for C$_{21}$H$_{22}$F$_2$N$_3$O$_2$, 386.1675; found, 386.1679 | $^1$H NMR (400 MHz, CDCl$_3$) δ 9.21 (s, 2H), 9.08 (s, 1H), 8.76 (dd, J = 2.4, 0.9 Hz, 1H), 7.94 (dd, J = 8.4, 2.3 Hz, 1H), 7.84 (dd, J = 8.4, 0.9 Hz, 1H), 7.65-7.55 (m, 2H), 7.36-7.20 (m, 2H), 6.57 (t, J = 73.5 Hz, 1H), 6.21 (s, 1H), 1.09 (s, 9H) $^{19}$F NMR (376 MHz, CDCl$_3$) δ −81.09 IR 3276, 1738, 1127 |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 60 | HRMS-ESI (m/z) [M + H]$^+$ calcd for C$_{20}$H$_{18}$F$_2$N$_3$O$_2$, 370.1362; found, 370.1364 | $^1$H NMR (400 MHz, CDCl$_3$) δ 9.13 (s, 1H), 8.94 (s, 2H), 8.73 (dd, J = 2.3, 0.9 Hz, 1H), 7.89 (dd, J = 8.2, 2.3 Hz, 1H), 7.65-7.53 (m, 2H), 7.39 (dd, J = 8.2, 0.9 Hz, 1H), 7.27 (s, 2H), 6.58 (t, J = 73.5 Hz, 1H), 5.75 (s, 1H), 1.68 (tt, J = 8.3, 5.4 Hz, 1H), 0.78-0.64 (m, 2H), 0.64-0.55 (m, 1H), 0.55-0.44 (m, 1H) $^{19}$F NMR (376 MHz, CDCl$_3$) δ −81.09 IR 3326, 1563, 1410, 1124 |
| 61 | ESI-APCI-MS m/z 394 [M + H]$^+$ | $^1$H NMR (300 MHz, CDCl$_3$) δ 8.71 (s, 1H), 8.53 (d, J = 2.2 Hz, 1H), 7.88 (dd, J = 8.2, 2.3 Hz, 1H), 7.54 (d, J = 9.0 Hz, 2H), 7.50 (d, J = 8.4 Hz, 1H), 7.32 (d, J = 8.4 Hz, 2H), 5.56 (s, 1H), 5.06 (d, J = 14.0 Hz, 1H), 4.81 (d, J = 14.0 Hz, 1H), 2.32-2.18 (m, 1H), 1.16 (d, J = 6.7 Hz, 3H), 0.76 (d, J = 6.7 Hz, 3H) |
| 62 | ESI-APCI-MS m/z 409 [M + H]$^+$ | $^1$H NMR (300 MHz, DMSO-d$_6$) δ 8.72 (br s, 1H), 8.50 (s, 1H), 8.28 (d, J = 2.4 Hz, 1H), 7.84 (d, J = 8.1 Hz, 1H), 7.78 (d, J = 8.4 Hz, 1H), 7.51 (d, J = 8.1 Hz, 1H), 6.94 (d, J = 8.4 Hz, 1H), 5.20-4.60 (m, 5H), 2.32-2.18 (m, 1H), 1.12 (d, J = 6.4 Hz, 3H), 0.74 (d, J = 6.5 Hz, 3H) |
| 63 | HRMS-ESI (m/z) [M + H]$^+$ calcd for C$_{20}$H$_{19}$F$_3$N$_3$O$_2$, 390.1424; found, 390.1427 | $^1$H NMR (400 MHz, Chloroform-d) δ 9.09 (s, 1H), 9.03 (s, 2H), 8.70 (dd, J = 2.3, 0.9 Hz, 1H), 7.89 (dd, J = 8.3, 2.3 Hz, 1H), 7.60-7.54 (m, 2H), 7.52 (dd, J = 8.3, 0.9 Hz, 1H), 7.38-7.29 (m, 2H), 5.88 (s, 1H), 2.82 (hept, J = 6.7 Hz, 1H), 0.99 (d, J = 6.7 Hz, 3H), 0.81 (d, J = 6.6 Hz, 3H) $^{19}$F NMR (376 MHz, CDCl$_3$) δ −57.82 IR 3326, 1563, 1410, 1124 |
| 64 | ESI-APCI-MS m/z 405 [M + H]$^+$ | $^1$H NMR (300 MHz, DMSO-d$_6$) δ 9.09 (s, 1H), 9.03 (s, 2H), 8.68 (d, J = 2.2 Hz, 1H), 8.33 (d, J = 2.4 Hz, 1H), 7.87 (dd, J = 8.4, 2.4 Hz, 1H), 7.82 (dd, J = 8.4, 2.4 Hz, 1H), 7.53 (d, J = 8.3 Hz, 1H), 6.99 (d, J = 8.7 Hz, 1H), 5.81 (s, 1H), 4.81 (q, J = 8.5 Hz, 2H), 2.90-2.76 (m, 1H), 0.99 (d, J = 6.7 Hz, 3H), 0.81 (d, J = 6.6 Hz, 3H) |
| 65 | HRMS-ESI (m/z) [M + H]$^+$ calcd for C$_{20}$H$_{21}$ClN$_3$O, 354.1368; found, 354.1368 | $^1$H NMR (400 MHz, CDCl$_3$) δ 9.21 (s, 2H), 9.08 (s, 1H), 8.76 (dd, J = 2.4, 0.9 Hz, 1H), 7.94 (dd, J = 8.4, 2.4 Hz, 1H), 7.84 (dd, J = 8.4, 0.9 Hz, 1H), 7.59-7.41 (m, 4H), 6.19 (s, 1H), 1.08 (s, 9H) IR 3251, 1558, 1469, 1409, 1365 |
| 66 | HRMS-ESI (m/z) [M + H]$^+$ calcd for C$_{19}$H$_{17}$ClN$_3$O, 338.1055; found, 338.1057 | $^1$H NMR (400 MHz, CDCl$_3$) δ 9.13 (s, 1H), 8.93 (s, 2H), 8.73 (dd, J = 2.3, 0.9 Hz, 1H), 7.89 (dd, J = 8.2, 2.3 Hz, 1H), 7.61-7.43 (m, 4H), 7.38 (dd, J = 8.2, 0.9 Hz, 1H), 5.74 (s, 1H), 1.68 (tt, J = 8.1, 5.3 Hz, 1H), 0.78-0.64 (m, 2H), 0.63-0.55 (m, 1H), 0.49 (tdd, J = 9.1, 6.1, 4.4 Hz, 1H) IR 3324, 1562, 1471, 1409 |
| 67 | HRMS-ESI (m/z) [M + H]$^+$ calcd for C$_{19}$H$_{16}$F$_3$N$_4$O$_2$, 389.1220; found, 389.1215 | $^1$H NMR (400 MHz, CDCl$_3$) δ 9.15 (s, 1H), 8.94 (s, 2H), 8.60 (dd, J = 2.5, 0.8 Hz, 1H), 7.87 (dd, J = 8.5, 2.5 Hz, 1H), 7.74 (s, 1H), 7.57 (dd, J = 9.7, 2.7 Hz, 1H), 7.54-7.47 (m, 1H), 6.77 (dt, J = 9.7, 0.8 Hz, 1H), 5.34 (s, 1H), 1.76-1.63 (m, 1H), 0.79-0.67 (m, 2H), 0.62 (dt, J = 9.5, 4.8 Hz, 1H), 0.57-0.46 (m, 1H) $^{19}$F NMR (376 MHz, CDCl$_3$) δ −62.79 IR 3365, 1683, 1332 |
| 68 | ESIMS m/z 400 [M + H]$^+$ | $^1$H NMR (400 MHz, CDCl$_3$) δ 8.86 (s, 1H), 8.58 (d, J = 1.6 Hz, 1H), 8.45 (s, 2H), 7.83 (dd, J = 8.3, 2.3 Hz, 1H), 7.55-7.48 (m, 3H), 7.22 (t, J = 5.8 Hz, 2H), 6.56 (t, J = 73.6 Hz, 1H), 5.61 (s, 1H), 3.31 (q, J = 14.0 Hz, 2H), 1.05 (s, 9H) $^{19}$F NMR (376 MHz, CDCl$_3$) δ −81.02 |
| 69 | HRMS-ESI (m/z) [M + H]$^+$ calcd for C$_{18}$H$_{18}$ClN$_4$O$_2$, 357.1113; found, 357.1114 | $^1$H NMR (400 MHz, CDCl$_3$) δ 9.10 (s, 1H), 9.02 (s, 2H), 8.41 (dd, J = 2.6, 0.7 Hz, 1H), 7.69 (dd, J = 8.1, 7.6 Hz, 1H), 7.61 (dd, J = 8.7, 2.7 Hz, 1H), 7.47 (dd, J = 8.7, 0.8 Hz, 1H), 7.09 (dd, J = 7.6, 0.6 Hz, 1H), 6.89 (dd, J = 8.1, 0.7 Hz, 1H), 5.72 (s, 1H), 2.80 (hept, J = 6.7 Hz, 1H), 0.97 (d, J = 6.7 Hz, 3H), 0.80 (d, J = 6.6 Hz, 3H) IR 3346, 1566, 1427, 1283 |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 70 | HRMS-ESI (m/z) [M + H]$^+$ calcd for C$_{17}$H$_{16}$ClN$_4$O$_2$, 343.0956; found, 343.0957 | $^1$H NMR (400 MHz, CDCl$_3$) δ 9.11 (s, 1H), 8.93 (s, 2H), 8.45 (dd, J = 2.7, 0.7 Hz, 1H), 7.70 (dd, J = 8.1, 7.6 Hz, 1H), 7.61 (dd, J = 8.6, 2.7 Hz, 1H), 7.39 (dd, J = 8.7, 0.8 Hz, 1H), 7.10 (dd, J = 7.6, 0.7 Hz, 1H), 6.91 (dd, J = 8.1, 0.7 Hz, 1H), 5.64 (s, 1H), 2.34 (hept, J = 7.0 Hz, 2H), 0.92 (t, J = 7.3 Hz, 3H) IR 3272, 1566, 1427, 1284 |
| 71 | HRMS-ESI (m/z) [M + H]$^+$ calcd for C$_{21}$H$_{20}$ClN$_4$O$_2$, 395.1269; found, 395.1274 | $^1$H NMR (400 MHz, CDCl$_3$) δ 9.14 (s, 1H), 8.99 (s, 2H), 8.44 (dd, J = 2.6, 0.8 Hz, 1H), 7.71 (dd, J = 8.1, 7.6 Hz, 1H), 7.61 (dd, J = 8.6, 2.6 Hz, 1H), 7.53 (dd, J = 8.6, 0.8 Hz, 1H), 7.11 (dd, J = 7.6, 0.7 Hz, 1H), 6.92 (dd, J = 8.1, 0.7 Hz, 1H), 6.15 (s, 1H), 1.32 (s, 9H) IR 3172, 2243, 1567, 1428 |
| 72 | HRMS-ESI (m/z) [M + H]$^+$ calcd for C$_{18}$H$_{16}$ClN$_4$O$_2$, 355.0956; found, 355.0960 | $^1$H NMR (400 MHz, CDCl$_3$) δ 9.13 (s, 1H), 8.93 (s, 2H), 8.44 (dd, J = 2.6, 0.7 Hz, 1H), 7.71 (dd, J = 8.1, 7.6 Hz, 1H), 7.61 (dd, J = 8.6, 2.6 Hz, 1H), 7.37 (dd, J = 8.6, 0.7 Hz, 1H), 7.11 (dd, J = 7.6, 0.7 Hz, 1H), 6.92 (dd, J = 8.1, 0.7 Hz, 1H), 5.56 (s, 1H), 1.66 (tt, J = 8.1, 5.3 Hz, 1H), 0.74-0.64 (m, 2H), 0.64-0.55 (m, 1H), 0.55-0.46 (m, 1H) IR 3328, 1564, 1427, 1282, 1161 |
| 73 | HRMS-ESI (m/z) [M + H]$^+$ calcd for C$_{20}$H$_{17}$F$_3$N$_3$O$_2$, 388.1267; found, 388.1270 | $^1$H NMR (400 MHz, CDCl$_3$) δ 9.14 (s, 1H), 8.94 (s, 2H), 8.73 (dd, J = 2.3, 0.9 Hz, 1H), 7.90 (dd, J = 8.2, 2.3 Hz, 1H), 7.65-7.56 (m, 2H), 7.40 (dd, J = 8.2, 0.9 Hz, 1H), 7.38-7.32 (m, 2H), 5.72 (s, 1H), 1.68 (tt, J = 8.2, 5.3 Hz, 1H), 0.71 (dddd, J = 13.4, 12.3, 9.5, 4.2 Hz, 2H), 0.64-0.55 (m, 1H), 0.55-0.45 (m, 1H) $^{19}$F NMR (376 MHz, CDCl$_3$) δ −57.80 IR 3332, 1257, 1211, 1165 |
| 74 | ESIMS m/z 418 [M + H]$^+$ | $^1$H NMR (400 MHz, CDCl$_3$) δ 8.86 (s, 1H), 8.58 (d, J = 1.6 Hz, 1H), 8.45 (s, 2H), 7.84 (dd, J = 8.3, 2.3 Hz, 1H), 7.57-7.53 (m, 2H), 7.51 (dd, J = 8.3, 0.8 Hz, 1H), 7.34-7.29 (m, 2H), 5.58 (s, 1H), 3.38-3.25 (m, 2H), 1.05 (s, 9H) $^{19}$F NMR (376 MHz, CDCl$_3$) δ −57.82 |
| 75 | HRMS-ESI (m/z) [M + H]$^+$ calcd for C$_{21}$H$_{20}$F$_3$N$_2$O$_2$, 389.1471; found, 389.1479 | $^1$H NMR (400 MHz, CDCl$_3$) δ 8.88 (dd, J = 2.5, 0.9 Hz, 1H), 8.47 (dd, J = 4.8, 1.6 Hz, 1H), 8.28 (dd, J = 2.7, 0.8 Hz, 1H), 7.98 (ddd, J = 8.0, 2.4, 1.6 Hz, 1H), 7.66-7.56 (m, 2H), 7.47 (dd, J = 8.7, 0.8 Hz, 1H), 7.36 (dd, J = 8.7, 2.7 Hz, 1H), 7.30-7.21 (m, 1H), 7.09-7.02 (m, 2H), 5.67 (s, 1H), 2.90-2.75 (m, 1H), 0.95 (d, J = 6.7 Hz, 3H), 0.79 (d, J = 6.6 Hz, 3H) $^{19}$F NMR (376 MHz, CDCl$_3$) δ −61.97 IR 1472, 1325, 1242 |
| 76 | HRMS-ESI (m/z) [M + H]$^+$ calcd for C$_{21}$H$_{18}$F$_3$N$_2$O$_2$, 387.1315; found, 387.1320 | $^1$H NMR (400 MHz, CDCl$_3$) δ 8.80 (dd, J = 2.4, 0.9 Hz, 1H), 8.51 (dd, J = 4.8, 1.6 Hz, 1H), 8.32 (dd, J = 2.6, 0.9 Hz, 1H), 7.88 (ddd, J = 8.0, 2.4, 1.6 Hz, 1H), 7.69-7.57 (m, 2H), 7.37 (dd, J = 8.6, 2.6 Hz, 1H), 7.33 (dd, J = 8.6, 0.9 Hz, 1H), 7.31-7.23 (m, 1H), 7.17-7.04 (m, 2H), 5.44 (s, 1H), 1.66 (tt, J = 8.1, 5.3 Hz, 1H), 0.75-0.60 (m, 2H), 0.58-0.50 (m, 1H), 0.50-0.41 (m, 1H) $^{19}$F NMR (376 MHz, CDCl$_3$) δ −61.96 IR 1473, 1323, 1242, 1065 |
| 77 | HRMS-ESI (m/z) [M + H]$^+$ calcd for C$_{19}$H$_{19}$ClN$_3$O$_2$, 356.1160; found, 356.1165 | $^1$H NMR (400 MHz, CDCl$_3$) δ 8.90 (dd, J = 2.5, 0.9 Hz, 1H), 8.46 (dd, J = 4.8, 1.6 Hz, 1H), 8.36 (dd, J = 2.5, 0.9 Hz, 1H), 8.06 (dd, J = 2.7, 0.7 Hz, 1H), 7.99 (ddd, J = 8.0, 2.4, 1.6 Hz, 1H), 7.68 (dd, J = 8.7, 2.7 Hz, 1H), 7.33-7.15 (m, 1H), 7.57-7.41 (m, 2H), 6.94 (dd, J = 8.7, 0.7 Hz, 1H), 5.80 (s, 1H), 2.83 (hept, J = 6.9 Hz, 1H), 0.95 (d, J = 6.7 Hz, 3H), 0.79 (d, J = 6.6 Hz, 3H) IR 3344, 1457, 1370, 1270 |
| 78 | HRMS-ESI (m/z) [M + H]$^+$ calcd for C$_{21}$H$_{18}$F$_3$N$_2$O$_2$, 387.1315; found, 387.1324 | $^1$H NMR (400 MHz, CDCl$_3$) δ 8.85 (dd, J = 2.3, 0.9 Hz, 1H), 8.71 (dd, J = 2.3, 0.9 Hz, 1H), 8.52 (dd, J = 4.8, 1.7 Hz, 1H), 7.89 (ddd, J = 8.0, 2.4, 1.7 Hz, 1H), 7.85 (dd, J = 8.2, 2.3 Hz, 1H), 7.63-7.54 (m, 2H), 7.38 (dd, J = 8.2, 0.9 Hz, 1H), 7.31-7.22 (m, 1H), 7.34 (dq, J = 8.8, 0.9 Hz, 2H), 5.70 (s, 1H), 1.70 (tt, J = 8.2, 5.3 Hz, 1H), 0.76-0.62 (m, 2H), 0.56 (dtd, J = 9.6, 5.5, 4.3 Hz, 1H), 0.46 (dddd, J = 9.1, 8.2, 6.1, 4.3 Hz, 1H) $^{19}$F NMR (376 MHz, CDCl$_3$) δ −57.81 IR 1257, 1210, 1165 |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 79 | HRMS-ESI (m/z) [M + H]$^+$ calcd for C$_{19}$H$_{17}$ClN$_3$O$_2$, 354.1004; found, 354.1004 | $^1$H NMR (400 MHz, CDCl$_3$) δ 8.84 (dd, J = 2.4, 0.9 Hz, 1H), 8.51 (dd, J = 4.8, 1.7 Hz, 1H), 8.39 (dd, J = 2.6, 0.7 Hz, 1H), 8.09 (dd, J = 2.7, 0.7 Hz, 1H), 7.87 (ddd, J = 8.0, 2.4, 1.6 Hz, 1H), 7.70 (dd, J = 8.7, 2.7 Hz, 1H), 7.52 (dd, J = 8.6, 2.6 Hz, 1H), 7.31-7.22 (m, 1H), 7.34 (dd, J = 8.6, 0.8 Hz, 1H), 6.98 (dd, J = 8.7, 0.7 Hz, 1H) 5.55 (s, 1H), 1.67 (tt, J = 8.2, 5.3 Hz, 1H), 0.73-0.60 (m, 2H), 0.60-0.51 (m, 1H), 0.50-0.40 (m, 1H) IR 1457, 1370, 1269 |
| 80 | HRMS-ESI (m/z) [M + H]$^+$ calcd for C$_{22}$H$_{22}$F$_3$N$_2$O$_2$, 403.1628; found, 403.1632 | $^1$H NMR (400 MHz, CDCl$_3$) δ 9.03 (d, J = 2.4 Hz, 1H), 8.73 (dd, J = 2.2, 1.1 Hz, 1H), 8.46 (dd, J = 4.8, 1.6 Hz, 1H), 8.17 (ddd, J = 8.1, 2.5, 1.6 Hz, 1H), 7.99-7.84 (m, 2H), 7.67-7.56 (m, 2H), 7.40-7.30 (m, 2H), 7.31-7.17 (m, 1H), 6.26 (s, 1H), 1.10 (s, 9H) $^{19}$F NMR (376 MHz, CDCl$_3$) δ −57.81 IR3197, 1256, 1210,1166 |
| 81 | HRMS-ESI (m/z) [M + H]$^+$ calcd for C$_{21}$H$^{19}$F$_2$N$_2$O$_2$, 369.1409; found, 369.1414 | $^1$H NMR (400 MHz, CDCl$_3$) δ 8.90-8.80 (m, 1H), 8.71 (dd, J = 2.3, 0.9 Hz, 1H), 8.51 (dd, J = 4.7, 1.7 Hz, 1H), 7.89 (ddd, J = 8.0, 2.4, 1.6 Hz, 1H), 7.84 (dd, J = 8.2, 2.3 Hz, 1H), 7.63-7.53 (m, 2H), 7.36 (dd, J = 8.3, 0.9 Hz, 1H), 7.31-7.19 (m, 3H), 6.57 (t, J = 73.5 Hz, 1H), 5.72 (s, 1H), 1.70 (tt, J = 8.3, 5.3 Hz, 1H), 0.76-0.61 (m, 2H), 0.61-0.50 (m, 1H), 0.50-0.40 (m, 1H) $^{19}$F NMR (376 MHz, CDCl$_3$) δ −81.04 IR 3335, 1475, 1220, 1124, 1043 |
| 82 | HRMS-ESI (m/z) [M + H]$^+$ calcd for C$_{22}$H$_{23}$F$_2$N$_2$O$_2$, 385.1722; found, 385.1734 | $^1$H NMR (400 MHz, CDCl$_3$) δ 9.03 (dd, J = 2.5, 0.9 Hz, 1H), 8.73 (dd, J = 2.2, 1.1 Hz, 1H), 8.46 (dd, J = 4.7, 1.6 Hz, 1H), 8.17 (ddd, J = 8.1, 2.4, 1.6 Hz, 1H), 7.95-7.84 (m, 2H), 7.64-7.53 (m, 2H), 7.34-7.19 (m, 3H), 6.57 (t, J = 73.6 Hz, 1H), 6.31 (s, 1H), 1.10 (s, 9H) $^{19}$F NMR (376 MHz, CDCl$_3$) δ −81.03 IR 3255, 1475, 1219, 1126, 1049 |
| 83 | HRMS-ESI (m/z) [M + H]$^+$ calcd for C$_{22}$H$_{23}$F$_3$N$_3$O$_2$, 418.1737; found, 418.1741 | $^1$H NMR (400 MHz, CDCl$_3$) δ 9.09 (s, 2H), 8.75 (dd, J = 2.3, 0.9 Hz, 1H), 7.92 (dd, J = 8.4, 2.4 Hz, 1H), 7.82 (dd, J = 8.4, 1.0 Hz, 1H), 7.65-7.56 (m, 2H), 7.39-7.31 (m, 2H), 6.14 (s, 1H), 2.71 (s, 3H), 1.08 (s, 9H) $^{19}$F NMR (376 MHz, CDCl$_3$) δ −57.81 IR 3279, 1257, 1211, 1167 |
| 84 | ESIMS m/z 409 [M + H]$^+$ | $^1$H NMR (400 MHz, CDCl$_3$) δ 8.73 (dd, J = 2.3, 0.9 Hz, 1H), 8.70 (s, 1H), 8.13 (d, J = 0.7 Hz, 1H), 7.89 (dd, J = 8.3, 2.3 Hz, 1H), 7.74 (dd, J = 8.4, 0.9 Hz, 1H), 7.64-7.54 (m, 2H), 7.38-7.31 (m, 2H), 6.66 (s, 1H), 1.06 (s, 9H) $^{19}$F NMR (376 MHz, CDCl$_3$) δ −57.81 |
| 85 | ESIMS m/z 377 [M + H]$^+$ | $^1$H NMR (400 MHz, CDCl$_3$) δ 8.68 (dd, J = 2.3, 0.9 Hz, 1H), 8.67 (d, J = 0.7 Hz, 1H), 7.92 (d, J = 0.7 Hz, 1H), 7.88 (dd, J = 8.3, 2.3 Hz, 1H), 7.59-7.51 (m, 3H), 7.25-7.21 (m, 2H), 6.59 (t, J = 72 Hz, 1H), 6.49 (s, 1H), 2.64 (hept, J = 6.7 Hz, 1H), 1.08 (d, J = 6.7 Hz, 3H), 0.72 (d, J = 6.6 Hz, 3H) $^{19}$F NMR (376 MHz, CDCl$_3$) δ −81.05; |
| 86 | ESIMS m/z 391 [M + H]$^+$ | $^1$H NMR (400 MHz, CDCl$_3$) δ 8.72 (dd, J = 2.3, 0.9 Hz, 1H), 8.69 (d, J = 0.6 Hz, 1H), 8.12 (d, J = 0.7 Hz, 1H), 7.88 (dd, J = 8.3, 2.3 Hz, 1H), 7.73 (dd, J = 8.4, 0.9 Hz, 1H), 7.61-7.54 (m, 2H), 7.26-7.21 (m, 2H), 6.71 (s, 1H), 6.57 (t, J = 72 Hz, 1H), 1.06 (s, 9H) $^{19}$F NMR (376 MHz, CDCl$_3$) δ −81.0 |
| 87 | ESIMS m/z 395 [M + H]$^+$ | $^1$H NMR (400 MHz, CDCl$_3$) δ 8.69 (dd, J = 2.3, 0.9 Hz, 1H), 8.67 (d, J = 0.7 Hz, 1H), 7.92 (d, J = 0.7 Hz, 1H), 7.89 (dd, J = 8.3, 2.3 Hz, 1H), 7.61-7.54 (m, 3H), 7.33 (ddt, J = 7.8, 2.1, 1.1 Hz, 2H), 6.38 (s, 1H), 2.65 (hept., J = 6.7 Hz, 1H), 1.08 (d, J = 6.6 Hz, 3H), 0.72 (d, J = 6.6 Hz, 3H) $^{19}$F NMR (376 MHz, CDCl$_3$) δ −57.81 |

TABLE 2-continued

| | | Analytical Data. | |
|---|---|---|---|
| Compound Number | Mass Spec | NMR ($^1$H, $^{13}$C, $^{19}$F) IR (Thin Film; cm$^{-1}$) | |

| Compound Number | Mass Spec | NMR ($^1$H, $^{13}$C, $^{19}$F) / IR (Thin Film; cm$^{-1}$) |
|---|---|---|
| 88 | HRMS-ESI (m/z) [M + H]$^+$ calcd for C$_{21}$H$_{21}$N$_4$O, 345.1710; found, 345.1713 | $^1$H NMR (400 MHz, CDCl$_3$) δ 9.22 (s, 2H), 9.09 (s, 1H), 8.81 (dd, J = 2.4, 0.9 Hz, 1H), 7.98 (dd, J = 8.4, 2.4 Hz, 1H), 7.90 (dd, J = 8.4, 1.0 Hz, 1H), 7.84-7.75 (m, 2H), 7.74-7.66 (m, 2H), 5.94 (s, 1H), 1.09 (s, 9H) IR 3246, 2228, 1410 |
| 89 | ESIMS m/z 393 [M + H]$^+$ | $^1$H NMR (400 MHz, CDCl$_3$) δ 8.74 (d, J = 0.7 Hz, 1H), 8.72 (dd, J = 2.3, 0.9 Hz, 1H), 7.92-7.88 (m, 2H), 7.63-7.58 (m, 2H), 7.50 (dd, J = 8.2, 0.9 Hz, 1H), 7.34 (dq, J = 7.7, 1.1 Hz, 2H), 5.98 (s, 1H), 1.77-1.65 (m, 1H), 0.83 (dddd, J = 9.5, 6.0, 5.2, 4.3 Hz, 1H), 0.71-0.62 (m, 1H), 0.56 (dddd, J = 9.6, 5.9, 5.1, 4.3 Hz, 1H), 0.48-0.38 (m, 1H) $^{19}$F NMR (376 MHz, CDCl$_3$) δ −57.80 |
| 90 | HRMS-ESI (m/z) [M + H]$^+$ calcd for C$_{24}$H$_{17}$ClF$_4$N$_3$O$_2$, 490.0940; found, 490.0939 | $^1$H NMR (400 MHz, CDCl$_3$) δ 9.12 (s, 1H), 8.97 (s, 2H), 8.67 (dd, J = 2.3, 0.9 Hz, 1H), 7.91 (dd, J = 8.3, 2.3 Hz, 1H), 7.65-7.55 (m, 3H), 7.39-7.29 (m, 2H), 7.23 (t, J = 8.1 Hz, 1H), 7.04-6.96 (m, 1H), 6.92 (dd, J = 9.8, 2.1 Hz, 1H), 5.66 (d, J = 0.6 Hz, 1H), 3.80-3.52 (m, 2H) $^{19}$F NMR (376 MHz, CDCl$_3$) δ −57.82, −114.06 IR 3242, 1489, 1410, 1257 |
| 91 | HRMS-ESI (m/z) [M + H]$^+$ calcd for C$_{22}$H$_{15}$F$_5$N$_3$O$_2$, 460.1079; found, 460.1080 | $^1$H NMR (400 MHz, CDCl$_3$) δ 9.18 (s, 1H), 8.81 (dd, J = 2.4, 0.9 Hz, 1H), 8.71 (d, J = 0.5 Hz, 2H), 7.91 (dd, J = 8.2, 2.3 Hz, 1H), 7.69-7.57 (m, 2H), 7.48-7.32 (m, 4H), 6.92 (tdd, J = 8.8, 2.6, 1.0 Hz, 1H), 6.85 (ddd, J = 11.2, 8.5, 2.5 Hz, 1H), 6.21 (d, J = 0.6 Hz, 1H) $^{19}$F NMR (376 MHz, CDCl$_3$) δ −57.80, −103.26 (d, J = 8.9 Hz), −108.91 (d, J = 9.0 Hz) IR 3159, 1256, 1211, 1167 |
| 92 | ESIMS m/z 419 [M + H]$^+$; m/z 417 [M − H]$^−$ | $^1$H NMR (400 MHz, CDCl$_3$) δ 9.21 (s, 2H), 9.09 (s, 1H), 8.74 (dd, J = 2.3, 0.9 Hz, 1H), 8.37 (dd, J = 2.5, 0.7 Hz, 1H), 7.92 (dd, J = 8.4, 2.3 Hz, 1H), 7.86 (dt, J = 8.6, 1.7 Hz, 2H), 7.00 (dd, J = 8.6, 0.7 Hz, 1H), 6.09 (s, 1H), 4.82 (q, J = 8.5 Hz, 2H), 1.09 (s, 9H) $^{19}$F NMR (376 MHz, CDCl$_3$) δ −73.79 |
| 93 | HRMS-ESI (m/z) [M + H]$^+$ calcd for C$_{22}$H$_{23}$F$_3$N$_3$O$_2$, 418.1737; found, 418.1738 | $^1$H NMR (400 MHz, CDCl$_3$) δ 9.21 (s, 2H), 9.08 (s, 1H), 8.76 (dd, J = 2.4, 0.9 Hz, 1H), 7.94 (dd, J = 8.4, 2.3 Hz, 1H), 7.86 (dd, J = 8.4, 1.0 Hz, 1H), 7.66-7.56 (m, 2H), 7.35 (dd, J = 8.4, 1.3 Hz, 2H), 6.20 (s, 1H), 1.59-1.45 (m, 1H), 1.45-1.32 (m, 1H), 1.04 (s, 6H), 0.82 (t, J = 7.5 Hz, 3H) $^{19}$F NMR (376 MHz, CDCl$_3$) δ −57.80 |
| 94 | HRMS-ESI (m/z) [M + H]$^+$ calcd for C$_{22}$H$_{14}$F$_5$N$_2$O$_2$S, 465.0691; found, 465.0688 | $^1$H NMR (400 MHz, CDCl$_3$) δ 8.83 (d, J = 0.7 Hz, 1H), 8.77 (dd, J = 2.3, 0.9 Hz, 1H), 7.90 (dd, J = 8.2, 2.3 Hz, 1H), 7.66-7.56 (m, 3H), 7.45-7.38 (m, 2H), 7.38-7.32 (m, 2H), 6.92-6.85 (m, 1H), 6.81 (ddd, J = 11.2, 8.6, 2.6 Hz, 1H), 6.46 (d, J = 0.6 Hz, 1H) $^{19}$F NMR (376 MHz, CDCl$_3$) δ −57.80, −103.95 (d, J = 9.1 Hz), −109.30 (d, J = 9.0 Hz) |
| 95 | HRMS-ESI (m/z) [M + H]$^+$ calcd for C$_{21}$H$_{24}$N$_3$O$_2$, 350.1863; found, 350.1869 | $^1$H NMR (400 MHz, CDCl$_3$) δ 9.20 (s, 2H), 9.08 (s, 1H), 8.74 (dd, J = 2.4, 0.9 Hz, 1H), 7.92 (dd, J = 8.4, 2.4 Hz, 1H), 7.81 (dd, J = 8.4, 0.9 Hz, 1H), 7.60-7.46 (m, 2H), 7.10-6.98 (m, 2H), 6.40 (s, 1H), 3.87 (s, 3H), 1.08 (s, 9H) |
| 96 | HRMS-ESI (m/z) [M + H]$^+$ calcd for C$_{21}$H$_{21}$F$_3$N$_3$O, 388.1631; found, 388.1636 | $^1$H NMR (400 MHz, CDCl$_3$) δ 9.22 (s, 2H), 9.09 (s, 1H), 8.81 (dd, J = 2.4, 0.9 Hz, 1H), 7.98 (dd, J = 8.4, 2.3 Hz, 1H), 7.88 (dd, J = 8.3, 0.9 Hz, 1H), 7.78-7.74 (m, 2H), 7.72-7.65 (m, 2H), 6.07 (s, 1H), 1.09 (s, 9H) $^{19}$F NMR (376 MHz, CDCl$_3$) δ −62.63 |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 97 | HRMS-ESI (m/z) [M + H]$^+$ calcd for C$_{24}$H$_{30}$N$_3$O, 376.2383; found, 376.2382 | $^1$H NMR (400 MHz, CDCl$_3$) δ 9.21 (s, 2H), 9.08 (s, 1H), 8.77 (dd, J = 2.3, 0.9 Hz, 1H), 7.96 (dd, J = 8.4, 2.3 Hz, 1H), 7.82 (dd, J = 8.4, 0.9 Hz, 1H), 7.52 (s, 4H), 6.39 (s, 1H), 1.37 (s, 9H), 1.08 (s, 9H) |
| 98 | HRMS-ESI (m/z) [M + H]$^+$ calcd for C$_{21}$H$_{24}$N$_3$OS, 366.1635; found, 366.1637 | $^1$H NMR (400 MHz, CDCl$_3$) δ 9.21 (s, 2H), 9.08 (s, 1H), 8.76 (dd, J = 2.3, 0.9 Hz, 1H), 7.94 (dd, J = 8.4, 2.4 Hz, 1H), 7.82 (dd, J = 8.3, 0.9 Hz, 1H), 7.59-7.46 (m, 2H), 7.41-7.31 (m, 2H), 6.30 (s, 1H), 2.54 (s, 3H), 1.08 (s, 9H) |
| 99 | HRMS-ESI (m/z) [M + H]$^+$ calcd for C$_{18}$H$_{15}$F$_3$N$_3$O$_2$, 362.1111; found, 362.1114 | $^1$H NMR (400 MHz, CDCl$_3$) δ 9.12 (s, 1H), 8.90 (s, 2H), 8.75 (dd, J = 2.4, 0.9 Hz, 1H), 7.89 (dd, J = 8.2, 2.3 Hz, 1H), 7.64-7.54 (m, 2H), 7.43 (dd, J = 8.2, 0.9 Hz, 1H), 7.38-7.30 (m, 2H), 5.72 (s, 1H), 2.01 (s, 3H) $^{19}$F NMR (376 MHz, CDCl$_3$) δ −57.81 |
| 100 | HRMS-ESI (m/z) [M + H]$^+$ calcd for C$_{22}$H$_{27}$N$_4$O, 363.2179; found, 363.2182 | $^1$H NMR (400 MHz, CDCl$_3$) δ 9.20 (s, 2H), 9.07 (s, 1H), 8.73 (dd, J = 2.4, 0.9 Hz, 1H), 7.91 (dd, J = 8.4, 2.4 Hz, 1H), 7.77 (dd, J = 8.4, 0.9 Hz, 1H), 7.59-7.45 (m, 2H), 6.88-6.76 (m, 2H), 6.53 (s, 1H), 3.02 (s, 6H), 1.07 (s, 9H) |
| 101 | HRMS-ESI (m/z) [M + H]$^+$ calcd for C$_{22}$H$_{24}$N$_3$O$_2$, 362.1863; found, 362.1866 | $^1$H NMR (400 MHz, CDCl$_3$) δ 9.22 (s, 2H), 9.09 (s, 1H), 8.83 (dd, J = 2.3, 0.9 Hz, 1H), 8.15-8.04 (m, 2H), 8.01 (dd, J = 8.4, 2.4 Hz, 1H), 7.88 (dd, J = 8.4, 0.9 Hz, 1H), 7.77-7.63 (m, 2H), 6.11 (s, 1H), 2.66 (s, 3H), 1.09 (s, 9H) |
| 102 | HRMS-ESI (m/z) [M + H]$^+$ calcd for C$_{23}$H$_{26}$N$_3$O$_2$, 376.2020; found, 376.2019 | $^1$H NMR (400 MHz, CDCl$_3$) δ 9.20 (s, 2H), 9.08 (s, 1H), 8.74 (dd, J = 2.4, 0.9 Hz, 1H), 7.92 (dd, J = 8.4, 2.4 Hz, 1H), 7.81 (dd, J = 8.4, 0.9 Hz, 1H), 7.56-7.47 (m, 2H), 7.20-7.13 (m, 2H), 6.40 (s, 1H), 3.88-3.58 (m, 1H), 1.08 (s, 9H), 0.91-0.73 (m, 4H) |
| 103 | HRMS-ESI (m/z) [M + H]$^+$ calcd for C$_{21}$H$_{21}$F$_3$N$_3$O$_2$, 404.1580; found, 404.1583 | $^1$H NMR (400 MHz, CDCl$_3$) δ 9.22 (s, 2H), 9.09 (s, 1H), 8.78 (dd, J = 2.4, 0.9 Hz, 1H), 7.96 (dd, J = 8.4, 2.4 Hz, 1H), 7.87 (dd, J = 8.4, 0.9 Hz, 1H), 7.58-7.48 (m, 2H), 7.43 (td, J = 1.9, 1.0 Hz, 1H), 7.29 (ddd, J = 6.5, 2.4, 1.3 Hz, 1H), 6.11 (s, 1H), 1.09 (s, 9H) $^{19}$F NMR (376 MHz, CDCl$_3$) δ −57.74 |
| 104 | HRMS-ESI (m/z) [M + H]$^+$ calcd for C$_{21}$H$_{21}$F$_3$N$_3$O$_2$, 404.1580; found, 404.1582 | $^1$H NMR (400 MHz, CDCl$_3$) δ 9.23 (s, 2H), 9.10 (s, 1H), 8.66 (dd, J = 2.3, 1.0 Hz, 1H), 7.90 (dd, J = 8.4, 2.2 Hz, 1H), 7.85 (dd, J = 8.3, 1.0 Hz, 1H), 7.53-7.36 (m, 4H), 6.22 (s, 1H), 1.08 (s, 9H) $^{19}$F NMR (376 MHz, CDCl$_3$) δ −57.20 |
| 105 | HRMS-ESI (m/z) [M + H]$^+$ calcd for C$_{24}$H$_{25}$N$_4$O, 385.2023; found, 385.2026 | $^1$H NMR (400 MHz, CDCl$_3$) δ 9.21 (s, 2H), 9.08 (s, 1H), 8.76 (dd, J = 2.4, 0.9 Hz, 1H), 7.95 (dd, J = 8.4, 2.4 Hz, 1H), 7.85 (dd, J = 8.4, 0.9 Hz, 1H), 7.61-7.54 (m, 2H), 7.46-7.38 (m, 2H), 6.21 (s, 1H), 1.85-1.76 (m, 2H), 1.50-1.43 (m, 2H), 1.08 (s, 9H) |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 106 | HRMS-ESI (m/z) [M + H]$^+$ calcd for C$_{21}$H$_{20}$F$_4$N$_3$O$_2$, 422.1486; found, 422.1490 | $^1$H NMR (400 MHz, CDCl$_3$) δ 9.22 (s, 2H), 9.09 (s, 1H), 8.76 (dd, J = 2.3, 0.9 Hz, 1H), 7.93 (dd, J = 8.4, 2.4 Hz, 1H), 7.87 (dd, J = 8.4, 1.0 Hz, 1H), 7.49-7.34 (m, 3H), 5.99 (s, 1H), 1.08 (s, 9H) $^{19}$F NMR (376 MHz, CDCl$_3$) δ −58.71 (d, J = 4.8 Hz), −127.10 (q, J = 4.8 Hz) |
| 107 | HRMS-ESI (m/z) [M + H]$^+$ calcd for C$_{20}$H$_{20}$F$_3$N$_4$O, 389.1584; found, 389.1592 | $^1$H NMR (400 MHz, CDCl$_3$) δ 9.23 (s, 2H), 9.10 (s, 1H), 8.97 (d, J = 2.3 Hz, 1H), 8.84 (dd, J = 2.4, 1.0 Hz, 1H), 8.07 (dd, J = 7.9, 2.3 Hz, 1H), 8.01 (dd, J = 8.4, 2.4 Hz, 1H), 7.94 (dd, J = 8.4, 1.0 Hz, 1H), 7.86-7.81 (m, 1H), 5.78 (s, 1H), 1.10 (s, 9H) $^{19}$F NMR (376 MHz, CDCl$_3$) δ −67.88 |
| 108 | HRMS-ESI (m/z) [M + H]$^+$ calcd for C$_{20}$H$_{20}$N$_5$O, 346.1662; found, 346.1664 | $^1$H NMR (400 MHz, CDCl$_3$) δ 9.23 (s, 2H), 9.10 (s, 1H), 8.97 (dd, J = 2.3, 0.9 Hz, 1H), 8.84 (dd, J = 2.4, 1.0 Hz, 1H), 8.03 (dd, J = 13.6, 2.4 Hz, 1H), 8.01 (dd, J = 14.0, 2.3 Hz, 1H), 7.95 (dd, J = 8.4, 1.0 Hz, 1H), 7.84 (dd, J = 8.1, 0.9 Hz, 1H), 5.64 (s, 1H), 1.10 (s, 9H) |
| 109 | HRMS-ESI (m/z) [M + H]$^+$ calcd for C$_{22}$H$_{24}$N$_3$O, 346.1914; found, 346.1917 | $^1$H NMR (400 MHz, CDCl$_3$) δ 9.21 (s, 2H), 9.08 (s, 1H), 8.79 (dd, J = 2.4, 0.9 Hz, 1H), 7.97 (dd, J = 8.4, 2.3 Hz, 1H), 7.84 (dd, J = 8.4, 0.9 Hz, 1H), 7.66-7.45 (m, 4H), 6.77 (dd, J = 17.6, 10.9 Hz, 1H), 6.31 (s, 1H), 5.83 (dd, J = 17.6, 0.8 Hz, 1H), 5.33 (dd, J = 10.9, 0.8 Hz, 1H), 1.09 (s, 9H) |
| 110 | HRMS-ESI (m/z) [M + H]$^+$ calcd for C$_{18}$H$_{20}$N$_3$OS, 326.1322; found, 326.1328 | $^1$H NMR (400 MHz, CDCl$_3$) δ 9.20 (s, 2H), 9.08 (s, 1H), 8.80 (dd, J = 2.3, 0.9 Hz, 1H), 7.96 (dd, J = 8.4, 2.3 Hz, 1H), 7.80 (dd, J = 8.4, 0.9 Hz, 1H), 7.55 (dd, J = 2.9, 1.3 Hz, 1H), 7.47 (dd, J = 5.0, 2.9 Hz, 1H), 7.40 (dd, J = 5.0, 1.4 Hz, 1H), 6.26 (s, 1H), 1.07 (s, 9H) |
| 111 | HRMS-ESI (m/z) [M + H]$^+$ calcd for C$_{22}$H$_{26}$N$_3$O$_2$, 364.2020; found, 364.2024 | $^1$H NMR (400 MHz, CDCl$_3$) δ 9.21 (s, 2H), 9.08 (s, 1H), 8.78 (dd, J = 2.4, 0.9 Hz, 1H), 7.97 (dd, J = 8.4, 2.3 Hz, 1H), 7.84 (dd, J = 8.4, 0.9 Hz, 1H), 7.62-7.55 (m, 2H), 7.50-7.42 (m, 2H), 6.32 (s, 1H), 4.52 (s, 2H), 3.44 (s, 3H), 1.08 (s, 9H) |
| 112 | HRMS-ESI (m/z) [M + H]$^+$ calcd for C$_{19}$H$_{20}$FN$_4$O, 339.1616; found, 339.1616 | $^1$H NMR (400 MHz, CDCl$_3$) δ 9.22 (s, 2H), 9.09 (s, 1H), 8.78 (dt, J = 2.3, 1.1 Hz, 1H), 8.29 (ddd, J = 4.9, 2.0, 1.2 Hz, 1H), 8.01 (ddd, J = 8.4, 2.3, 1.6 Hz, 1H), 7.98-7.85 (m, 2H), 7.36 (ddd, J = 7.4, 4.9, 1.7 Hz, 1H), 5.99 (s, 1H), 1.09 (s, 9H) $^{19}$F NMR (376 MHz, CDCl$_3$) δ −70.55 |
| 113 | HRMS-ESI (m/z) [M + H]$^+$ calcd for C$_{18}$H$_{20}$N$_5$O, 322.1662; found, 322.1663 | $^1$H NMR (400 MHz, CDCl$_3$) δ 9.30 (s, 1H), 9.23 (s, 2H), 9.10 (s, 1H), 8.99 (s, 2H), 8.83 (dd, J = 2.3, 1.0 Hz, 1H), 7.99 (dd, J = 8.4, 2.3 Hz, 1H), 7.95 (dd, J = 8.4, 1.0 Hz, 1H), 5.73 (s, 1H), 1.10 (s, 9H) |
| 114 | HRMS-ESI (m/z) [M + H]$^+$ calcd for C$_{20}$H$_{22}$N$_3$O, 320.1757; found, 320.1755 | $^1$H NMR (400 MHz, CDCl$_3$) δ 9.21 (s, 2H), 9.08 (s, 1H), 8.78 (dd, J = 2.4, 0.9 Hz, 1H), 7.97 (dd, J = 8.4, 2.4 Hz, 1H), 7.84 (dd, J = 8.4, 0.9 Hz, 1H), 7.62-7.55 (m, 2H), 7.53-7.46 (m, 2H), 7.46-7.40 (m, 1H), 6.33 (s, 1H), 1.09 (s, 9H) |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 115 | HRMS-ESI (m/z) [M + H]$^+$ calcd for C$_{20}$H$_{21}$FN$_3$O, 338.1663; found, 338.1668 | $^1$H NMR (400 MHz, CDCl$_3$) δ 9.21 (s, 2H), 9.08 (s, 1H), 8.74 (dd, J = 2.4, 0.9 Hz, 1H), 7.92 (dd, J = 8.4, 2.4 Hz, 1H), 7.84 (dd, J = 8.4, 1.0 Hz, 1H), 7.61-7.48 (m, 2H), 7.23-7.13 (m, 2H), 6.23 (s, 1H), 1.08 (s, 9H) $^{19}$F NMR (376 MHz, CDCl$_3$) δ −113.43 |
| 116 | HRMS-ESI (m/z) [M + H]$^+$ calcd for C$_{22}$H$_{23}$F$_3$N$_3$O$_2$, 418.1737; found, 418.1742 | $^1$H NMR (400 MHz, CDCl$_3$) δ 9.21 (s, 2H), 9.08 (s, 1H), 8.75 (dd, J = 2.3, 0.9 Hz, 1H), 7.93 (dd, J = 8.4, 2.3 Hz, 1H), 7.84 (dd, J = 8.4, 0.9 Hz, 1H), 7.46 (dd, J = 1.9, 1.2 Hz, 1H), 7.41 (ddd, J = 8.5, 2.3, 0.7 Hz, 1H), 7.35-7.29 (m, 1H), 6.20 (s, 1H), 2.40 (s, 3H), 1.08 (s, 9H) $^{19}$F NMR (376 MHz, CDCl$_3$) δ −57.42 |
| 117 | HRMS-ESI (m/z) [M + H]$^+$ calcd for C$_{22}$H$_{23}$F$_3$N$_3$O$_2$, 418.1737; found, 418.1740 | $^1$H NMR (400 MHz, CDCl$_3$) δ 9.23 (s, 2H), 9.10 (s, 1H), 8.52 (dd, J = 2.3, 0.9 Hz, 1H), 7.85 (dd, J = 8.3, 1.0 Hz, 1H), 7.73 (dd, J = 8.3, 2.3 Hz, 1H), 7.23 (d, J = 8.3 Hz, 1H), 7.20-7.10 (m, 2H), 6.24 (s, 1H), 2.27 (s, 3H), 1.09 (s, 9H) $^{19}$F NMR (376 MHz, CDCl$_3$) δ −57.69 |
| 118 | HRMS-ESI (m/z) [M + H]$^+$ calcd for C$_{22}$H$_{23}$F$_3$N$_3$O$_2$, 418.1737; found, 418.1737 | $^1$H NMR (400 MHz, CDCl$_3$) δ 9.25 (s, 1H), 8.96 (s, 1H), 8.81 (dd, J = 2.3, 0.9 Hz, 1H), 7.80 (dd, J = 8.3, 2.4 Hz, 1H), 7.66-7.58 (m, 2H), 7.41-7.31 (m, 2H), 7.10 (dd, J = 8.2, 0.9 Hz, 1H), 5.92 (s, 1H), 2.13 (s, 3H), 1.23 (s, 9H) $^{19}$F NMR (376 MHz, CDCl$_3$) δ −57.82 |
| 119 | HRMS-ESI (m/z) [M + H]$^+$ calcd for C$_{22}$H$_{23}$F$_3$N$_3$O$_2$, 418.1737; found, 418.1739 | $^1$H NMR (400 MHz, CDCl$_3$) δ 9.21 (s, 2H), 9.09 (s, 1H), 8.36 (s, 1H), 7.70-7.63 (m, 1H), 7.40-7.28 (m, 4H), 6.31 (s, 1H), 2.36 (d, J = 0.6 Hz, 3H), 1.09 (s, 9H) $^{19}$F NMR (376 MHz, CDCl$_3$) δ −57.78 |
| 120 | HRMS-ESI (m/z) [M + H]$^+$ calcd for C$_{22}$H$_{23}$F$_3$N$_3$O$_2$, 418.1737; found, 418.1736 | $^1$H NMR (400 MHz, CDCl$_3$) δ 9.21 (s, 2H), 9.08 (s, 1H), 8.74 (dd, J = 2.4, 0.9 Hz, 1H), 7.92 (dd, J = 8.4, 2.4 Hz, 1H), 7.82 (dd, J = 8.3, 0.9 Hz, 1H), 7.60-7.49 (m, 2H), 7.14-7.03 (m, 2H), 6.28 (s, 1H), 4.41 (q, J = 8.1 Hz, 2H), 1.08 (s, 9H) $^{19}$F NMR (376 MHz, CDCl$_3$) δ −73.87 |
| 121 | HRMS-ESI (m/z) [M + H]$^+$ calcd for C$_{23}$H$_{30}$N$_3$OSi, 392.2153; found, 392.2155 | $^1$H NMR (400 MHz, CDCl$_3$) δ 9.21 (s, 2H), 9.08 (s, 1H), 8.78 (dd, J = 2.3, 0.9 Hz, 1H), 7.97 (dd, J = 8.4, 2.3 Hz, 1H), 7.84 (dd, J = 8.4, 1.0 Hz, 1H), 7.68-7.62 (m, 2H), 7.61-7.53 (m, 2H), 6.33 (s, 1H), 1.09 (s, 9H), 0.31 (s, 9H) |
| 122 | HRMS-ESI (m/z) [M + H]$^+$ calcd for C$_{18}$H$_{22}$N$_5$O, 324.1819; found, 324.1823 | $^1$H NMR (400 MHz, CDCl$_3$) δ 9.19 (s, 2H), 9.07 (s, 1H), 8.68 (dd, J = 2.3, 0.9 Hz, 1H), 7.82 (dd, J = 8.3, 2.3 Hz, 1H), 7.79 (d, J = 0.8 Hz, 1H), 7.75 (dd, J = 8.4, 1.0 Hz, 1H), 7.68 (d, J = 0.8 Hz, 1H), 6.27 (s, 1H), 3.98 (s, 3H), 1.06 (s, 9H) |
| 123 | HRMS-ESI (m/z) [M + H]$^+$ calcd for C$_{18}$H$_{20}$N$_3$O$_2$, 310.1550; found, 310.1549 | $^1$H NMR (400 MHz, CDCl$_3$) δ 9.19 (s, 2H), 9.08 (s, 1H), 8.70 (dd, J = 2.3, 1.0 Hz, 1H), 7.85 (dd, J = 8.4, 2.3 Hz, 1H), 7.80 (dd, J = 1.5, 0.9 Hz, 1H), 7.77 (dd, J = 8.4, 1.0 Hz, 1H), 7.56-7.52 (m, 1H), 6.72 (dd, J = 1.9, 0.9 Hz, 1H), 6.22 (s, 1H), 1.06 (s, 9H) |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 124 | HRMS-ESI (m/z) [M + H]$^+$ calcd for C$_{21}$H$_{20}$F$_4$N$_3$O$_2$, 422.1486; found, 422.1486 | $^1$H NMR (400 MHz, CDCl$_3$) δ 9.22 (s, 2H), 9.09 (s, 1H), 8.72 (ddd, J = 2.3, 1.4, 0.9 Hz, 1H), 7.95 (ddd, J = 8.4, 2.3, 1.5 Hz, 1H), 7.87 (dd, J = 8.4, 1.0 Hz, 1H), 7.48 (t, J = 8.5 Hz, 1H), 7.24-7.07 (m, 2H), 6.09 (s, 1H), 1.09 (s, 9H) $^{19}$F NMR (376 MHz, CDCl$_3$) δ −57.97, −113.27 |
| 125 | HRMS-ESI (m/z) [M + H]$^+$ calcd for C$_{21}$H$_{21}$F$_3$N$_3$OS, 420.1352; found, 420.1355 | $^1$H NMR (400 MHz, CDCl$_3$) δ 9.22 (s, 2H), 9.09 (s, 1H), 8.80 (dd, J = 2.4, 1.0 Hz, 1H), 7.98 (dd, J = 8.4, 2.4 Hz, 1H), 7.87 (dd, J = 8.4, 1.0 Hz, 1H), 7.82-7.75 (m, 2H), 7.70-7.58 (m, 2H), 6.09 (s, 1H), 1.09 (s, 9H) $^{19}$F NMR (376 MHz, CDCl$_3$) δ −42.46 |
| 126 | HRMS-ESI (m/z) [M + H]$^+$ calcd for C$_{19}$H$_{21}$N$_4$O, 321.1710; found, 321.1710 | $^1$H NMR (400 MHz, CDCl$_3$) δ 9.22 (s, 2H), 9.09 (s, 1H), 8.87 (dd, J = 2.4, 0.9 Hz, 1H), 8.80 (dd, J = 2.4, 1.0 Hz, 1H), 8.69 (dd, J = 4.8, 1.6 Hz, 1H), 7.98 (dd, J = 8.4, 2.3 Hz, 1H), 7.92-7.87 (m, 2H), 7.44 (ddd, J = 7.9, 4.8, 0.9 Hz, 1H), 6.05 (s, 1H), 1.09 (s, 9H) |
| 127 | HRMS-ESI (m/z) [M + H]$^+$ calcd for C$_{23}$H$_{23}$N$_4$O, 371.1866; found, 371.1861 | $^1$H NMR (400 MHz, CDCl$_3$) δ 9.24 (s, 2H), 9.17 (d, J = 2.3 Hz, 1H), 9.10 (s, 1H), 8.94 (dd, J = 2.4, 0.9 Hz, 1H), 8.41-8.30 (m, 1H), 8.25-8.14 (m, 1H), 8.12 (dd, J = 8.3, 2.4 Hz, 1H), 8.03-7.85 (m, 2H), 7.79 (ddd, J = 8.5, 6.9, 1.5 Hz, 1H), 7.64 (ddd, J = 8.2, 6.9, 1.2 Hz, 1H), 6.07 (s, 1H), 1.11 (s, 9H) |
| 128 | HRMS-ESI (m/z) [M + H]$^+$ calcd for C$_{22}$H$_{20}$F$_6$N$_3$O, 456.1505; found, 456.1509 | $^1$H NMR (400 MHz, CDCl$_3$) δ 9.24 (s, 2H), 9.11 (s, 1H), 8.54 (d, J = 2.2 Hz, 1H), 8.06 (s, 1H), 7.90 (d, J = 8.2 Hz, 1H), 7.87 (dd, J = 8.3, 1.0 Hz, 1H), 7.81-7.71 (m, 1H), 7.50 (d, J = 8.0 Hz, 1H), 5.93 (s, 1H), 1.08 (s, 9H) $^{19}$F NMR (376 MHz, CDCl$_3$) δ −57.27, −62.92 |
| 130 | HRMS-ESI (m/z) [M + H]$^+$ calcd for C$_{23}$H$_{27}$N$_4$O$_2$, 391.2129; found, 391.2132 | $^1$H NMR (400 MHz, CDCl$_3$) δ 9.21 (s, 2H), 9.08 (s, 1H), 8.80 (dd, J = 2.4, 0.9 Hz, 1H), 7.98 (dd, J = 8.4, 2.3 Hz, 1H), 7.84 (dd, J = 8.4, 1.0 Hz, 1H), 7.82-7.73 (m, 2H), 7.65-7.55 (m, 2H), 6.27 (s, 1H), 4.03 (s, 3H), 2.26 (s, 3H), 1.09 (s, 9H) |
| 131 | HRMS-ESI (m/z) [M + H]$^+$ calcd for C$_{22}$H$_{23}$F$_3$N$_3$O$_2$, 418.1737; found, 418.1743 | $^1$H NMR (400 MHz, CDCl$_3$) δ 9.10 (s, 1H), 8.81 (s, 2H), 8.65 (dd, J = 2.4, 0.7 Hz, 1H), 7.65-7.57 (m, 2H), 7.56 (dd, J = 2.4, 0.7 Hz, 1H), 7.34 (dq, J = 8.8, 1.0 Hz, 2H), 4.38 (s, 1H), 1.98 (d, J = 0.6 Hz, 3H), 1.26 (s, 9H) $^{19}$F NMR (376 MHz, CDCl$_3$) δ −57.80 |
| 132 | HRMS-ESI (m/z) [M + H]$^+$ calcd for C$_{23}$H$_{27}$N$_4$O$_2$, 391.2129; found, 391.2128 | $^1$H NMR (400 MHz, CDCl$_3$) δ 9.21 (s, 2H), 9.08 (s, 1H), 8.79 (dd, J = 2.4, 0.9 Hz, 1H), 7.97 (dd, J = 8.4, 2.4 Hz, 1H), 7.85 (dd, J = 8.4, 1.0 Hz, 1H), 7.67-7.56 (m, 4H), 6.24 (s, 1H), 3.89 (s, 3H), 2.25 (s, 3H), 1.09 (s, 9H) |
| 133 | HRMS-ESI (m/z) [M + H]$^+$ calcd for C$_{19}$H$_{21}$N$_4$O$_2$S, 369.1380; found, 369.1377 | $^1$H NMR (400 MHz, CDCl$_3$) δ 9.21 (s, 2H), 9.09 (s, 1H), 8.84 (dd, J = 2.4, 0.9 Hz, 1H), 7.97 (dd, J = 8.4, 2.4 Hz, 1H), 7.83 (dd, J = 8.4, 0.9 Hz, 1H), 7.52 (d, J = 3.9 Hz, 1H), 7.36 (d, J = 3.9 Hz, 1H), 5.85 (s, 1H), 5.73 (s, 2H), 1.08 (s, 9H) $^{13}$C NMR (126 MHz, CDCl$_3$) δ 163.02, 160.48, 156.92, 156.39, 144.69, 144.33, 138.23, 136.88, 133.96, 130.07, 128.68, 124.98, 122.40, 79.63, 40.18, 26.25 |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 134 | HRMS-ESI (m/z) [M + H]$^+$ calcd for C$_{18}$H$_{20}$N$_3$OS, 326.1322; found, 326.1327 | $^1$H NMR (400 MHz, CDCl$_3$) δ 9.20 (s, 2H), 9.08 (s, 1H), 8.82 (dd, J = 2.4, 0.9 Hz, 1H), 7.95 (dd, J = 8.4, 2.3 Hz, 1H), 7.78 (dd, J = 8.4, 0.9 Hz, 1H), 7.46-7.35 (m, 2H), 7.23-7.09 (m, 1H), 6.11 (s, 1H), 1.07 (s, 9H) |
| 135 | HRMS-ESI (m/z) [M + H]$^+$ calcd for C$_{24}$H$_{19}$F$_3$N$_3$O$_2$, 438.1424; found, 438.1425 | $^1$H NMR (400 MHz, CDCl$_3$) δ 9.11 (s, 1H), 9.01 (s, 2H), 8.71 (dd, J = 2.3, 0.9 Hz, 1H), 7.88 (dd, J = 8.2, 2.3 Hz, 1H), 7.63-7.54 (m, 3H), 7.38-7.30 (m, 2H), 7.21-7.15 (m, 3H), 7.06-7.00 (m, 2H), 4.99 (s, 1H), 3.79 (d, J = 13.6 Hz, 1H), 3.58 (d, J = 13.5 Hz, 1H) $^{19}$F NMR (376 MHz, CDCl$_3$) δ -57.82 |
| 136 | HRMS-ESI (m/z) [M + H]$^+$ calcd for C$_{24}$H$_{18}$F$_4$N$_3$O$_2$, 456.1330; found, 456.1332 | $^1$H NMR (400 MHz, CDCl$_3$) δ 9.12 (s, 1H), 8.98 (s, 2H), 8.69 (dd, J = 2.3, 0.9 Hz, 1H), 7.90 (dd, J = 8.2, 2.3 Hz, 1H), 7.60-7.56 (m, 2H), 7.54 (dd, J = 8.2, 0.9 Hz, 1H), 7.38-7.31 (m, 2H), 7.06-6.97 (m, 2H), 6.91-6.81 (m, 2H), 5.24 (s, 1H), 3.73 (d, J = 13.7 Hz, 1H), 3.55 (d, J = 13.7 Hz, 1H) $^{19}$F NMR (376 MHz, CDCl$_3$) δ -57.82, -115.64 |
| 137 | HRMS-ESI (m/z) [M + H]$^+$ calcd for C$_{23}$H$_{26}$N$_3$O$_2$, 376.2020; found, 376.2020 | $^1$H NMR (400 MHz, CDCl$_3$) δ 9.20 (s, 2H), 9.07 (s, 1H), 8.72 (dd, J = 2.4, 0.9 Hz, 1H), 7.90 (dd, J = 8.4, 2.3 Hz, 1H), 7.79 (dd, J = 8.4, 0.9 Hz, 1H), 7.31 (dd, J = 8.4, 2.4 Hz, 1H), 7.29-7.23 (m, 1H), 6.90 (d, J = 8.4 Hz, 1H), 6.42 (s, 1H), 4.41-4.06 (m, 2H), 2.86 (t, J = 6.5 Hz, 2H), 2.17-1.88 (m, 2H), 1.07 (s, 9H) |
| 138 | HRMS-ESI (m/z) [M + H]$^+$ calcd for C$_{24}$H$_{17}$F$_5$N$_3$O$_2$, 474.1235; found, 474.1237 | $^1$H NMR (400 MHz, CDCl$_3$) δ 9.12 (s, 1H), 8.97 (s, 2H), 8.67 (dd, J = 2.3, 0.9 Hz, 1H), 7.91 (dd, J = 8.3, 2.3 Hz, 1H), 7.63-7.54 (m, 3H), 7.34 (dq, J = 8.6, 0.9 Hz, 2H), 7.25 (s, 1H), 6.78-6.70 (m, 1H), 6.64 (ddd, J = 10.2, 8.9, 2.6 Hz, 1H), 5.63 (d, J = 0.6 Hz, 1H), 3.85-3.45 (m, 2H) $^{19}$F NMR (376 MHz, CDCl$_3$) δ -57.82, -111.42 (d, J = 7.5 Hz), -112.47 (d, J = 7.5 Hz) |
| 139 | HRMS-ESI (m/z) [M + H]$^+$ calcd for C$_{24}$H$_{18}$F$_4$N$_3$O$_2$, 456.1330; found, 456.1329 | $^1$H NMR (400 MHz, CDCl$_3$) δ 9.12 (s, 1H), 8.99 (s, 2H), 8.70 (dd, J = 2.3, 0.9 Hz, 1H), 7.90 (dd, J = 8.2, 2.3 Hz, 1H), 7.59-7.56 (m, 2H), 7.55 (dd, J = 8.3, 0.9 Hz, 1H), 7.39-7.31 (m, 2H), 7.13 (td, J = 8.1, 6.1 Hz, 1H), 6.91-6.84 (m, 1H), 6.84-6.78 (m, 2H), 5.29 (s, 1H), 3.75 (d, J = 13.7 Hz, 1H), 3.57 (d, J = 13.6 Hz, 1H) $^{19}$F NMR (376 MHz, CDCl$_3$) δ -57.82, -113.32 |
| 140 | HRMS-ESI (m/z) [M + H]$^+$ calcd for C$_{24}$H$_{18}$ClF$_3$N$_3$O$_2$, 472.1034; found, 472.1009 | $^1$H NMR (400 MHz, CDCl$_3$) δ 9.12 (s, 1H), 8.98 (s, 2H), 8.69 (dd, J = 2.3, 0.9 Hz, 1H), 7.90 (dd, J = 8.2, 2.3 Hz, 1H), 7.61-7.55 (m, 2H), 7.54 (dd, J = 8.2, 0.9 Hz, 1H), 7.38-7.31 (m, 2H), 7.17-7.10 (m, 2H), 7.03-6.94 (m, 2H), 5.30 (s, 1H), 3.72 (d, J = 13.6 Hz, 1H), 3.54 (d, J = 13.7 Hz, 1H) $^{19}$F NMR (376 MHz, CDCl$_3$) δ -57.82 |
| 141 | HRMS-ESI (m/z) [M + H]$^+$ calcd for C$_{24}$H$_{18}$ClF$_3$N$_3$O$_2$, 472.1034; found, 472.1013 | $^1$H NMR (400 MHz, CDCl$_3$) δ 9.13 (s, 1H), 8.99 (s, 2H), 8.68 (dd, J = 2.3, 0.9 Hz, 1H), 7.90 (dd, J = 8.2, 2.3 Hz, 1H), 7.59-7.55 (m, 2H), 7.53 (dd, J = 8.2, 0.9 Hz, 1H), 7.34 (dq, J = 8.8, 1.0 Hz, 2H), 7.15 (ddd, J = 8.0, 2.1, 1.2 Hz, 1H), 7.09 (t, J = 7.8 Hz, 1H), 7.05 (t, J = 1.9 Hz, 1H), 6.92 (dt, J = 7.6, 1.4 Hz, 1H), 5.34 (s, 1H), 3.71 (d, J = 13.6 Hz, 1H), 3.54 (d, J = 13.6 Hz, 1H) $^{19}$F NMR (376 MHz, CDCl$_3$) δ -57.82 |
| 142 | HRMS-ESI (m/z) [M + H]$^+$ calcd for C$_{24}$H$_{17}$Cl$_2$F$_3$N$_3$O$_2$, 506.0644; found, 506.0643 | $^1$H NMR (400 MHz, CDCl$_3$) δ 9.12 (s, 1H), 8.92 (s, 2H), 8.70 (dd, J = 2.3, 0.9 Hz, 1H), 7.91 (dd, J = 8.2, 2.3 Hz, 1H), 7.65-7.54 (m, 3H), 7.37-7.31 (m, 2H), 7.31-7.26 (m, 2H), 7.09 (dd, J = 8.4, 2.2 Hz, 1H), 5.58 (s, 1H), 3.87-3.76 (m, 2H) $^{19}$F NMR (376 MHz, CDCl$_3$) δ -57.82 |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 143 | HRMS-ESI (m/z) [M + H]$^+$ calcd for C$_{25}$H$_{31}$N$_2$O, 375.2431; found, 375.2435 | $^1$H NMR (400 MHz, CDCl$_3$) δ 9.09-9.01 (m, 1H), 8.74 (dd, J = 2.3, 1.0 Hz, 1H), 8.46 (dd, J = 4.8, 1.6 Hz, 1H), 8.18 (ddd, J = 8.2, 2.5, 1.6 Hz, 1H), 7.92 (dd, J = 8.4, 2.3 Hz, 1H), 7.28-7.20 (m, 1H), 7.86 (dd, J = 8.4, 1.0 Hz, 1H), 7.51 (d, J = 0.7 Hz, 4H), 6.46 (s, 1H), 1.37 (s, 9H), 1.09 (s, 9H) |
| 144 | HRMS-ESI (m/z) [M + H]$^+$ calcd for C$_{23}$H$_{24}$F$_3$N$_2$O$_2$, 417.1784; found, 417.1787 | $^1$H NMR (400 MHz, CDCl$_3$) δ 8.82 (d, J = 2.3 Hz, 1H), 8.73 (dd, J = 2.2, 1.1 Hz, 1H), 8.29 (dd, J = 2.1, 0.8 Hz, 1H), 7.98 (td, J = 2.2, 0.8 Hz, 1H), 7.90 (dd, J = 8.4, 2.2 Hz, 1H), 7.87 (dd, J = 8.4, 1.1 Hz, 1H), 7.64-7.55 (m, 2H), 7.41-7.29 (m, 2H), 6.30 (s, 1H), 2.33 (q, J = 0.7 Hz, 3H), 1.10 (s, 9H)<br>$^{19}$F NMR (376 MHz, CDCl$_3$) δ -57.81 |
| 145 | HRMS-ESI (m/z) [M + H]$^+$ calcd for C$_{25}$H$_{26}$N$_3$O, 384.2070; found, 384.2072 | $^1$H NMR (400 MHz, CDCl$_3$) δ 9.02 (dd, J = 2.5, 0.9 Hz, 1H), 8.74 (dd, J = 2.3, 1.0 Hz, 1H), 8.46 (dd, J = 4.8, 1.6 Hz, 1H), 8.17 (ddd, J = 8.1, 2.4, 1.6 Hz, 1H), 7.92 (dd, J = 8.4, 2.3 Hz, 1H), 7.88 (dd, J = 8.4, 1.0 Hz, 1H), 7.61-7.54 (m, 2H), 7.46-7.37 (m, 2H), 7.26-7.20 (m, 1H), 6.30 (s, 1H), 1.88-1.73 (m, 2H), 1.50-1.40 (m, 2H), 1.10 (s, 9H) |
| 146 | HRMS-ESI (m/z) [M + H]$^+$ calcd for C$_{23}$H$_{24}$F$_3$N$_2$O$_2$, 417.1784; found, 417.1788 | $^1$H NMR (400 MHz, CDCl$_3$) δ 9.04 (dd, J = 2.5, 0.9 Hz, 1H), 8.52-8.44 (m, 2H), 8.21 (ddd, J = 8.1, 2.4, 1.6 Hz, 1H), 7.88 (dd, J = 8.3, 1.0 Hz, 1H), 7.31-7.23 (m, 1H), 7.69 (dd, J = 8.3, 2.3 Hz, 1H), 7.23 (d, J = 8.3 Hz, 1H), 7.18-7.10 (m, 2H), 6.34 (s, 1H), 2.27 (s, 3H), 1.10 (s, 9H)<br>$^{19}$F NMR (376 MHz, CDCl$_3$) δ -57.69 |
| 147 | HRMS-ESI (m/z) [M + H]$^+$ calcd for C$_{22}$H$_{21}$F$_4$N$_2$O$_2$, 421.1534; found, 421.1531 | $^1$H NMR (400 MHz, CDCl$_3$) δ 9.11-8.98 (m, 1H), 8.69 (q, J = 1.5 Hz, 1H), 8.46 (dd, J = 4.7, 1.7 Hz, 1H), 8.17 (ddd, J = 8.1, 2.5, 1.6 Hz, 1H), 7.91 (t, J = 1.5 Hz, 2H), 7.48 (t, J = 8.5 Hz, 1H), 7.30-7.21 (m, 1H), 7.22-7.04 (m, 2H), 6.21 (s, 1H), 1.10 (s, 9H)<br>$^{19}$F NMR (376 MHz, CDCl$_3$) δ -57.97, -113.28 |
| 148 | HRMS-ESI (m/z) [M + H]$^+$ calcd for C$_{23}$H$_{24}$F$_3$N$_2$O$_2$, 417.1784; found, 417.1784 | $^1$H NMR (400 MHz, CDCl$_3$) δ 8.90 (d, J = 2.4 Hz, 1H), 8.72 (dd, J = 2.3, 1.0 Hz, 1H), 8.04 (dd, J = 8.3, 2.5 Hz, 1H), 7.93-7.79 (m, 2H), 7.69-7.54 (m, 2H), 7.40-7.29 (m, 2H), 7.10 (d, J = 8.2 Hz, 1H), 6.22 (s, 1H), 2.52 (s, 3H), 1.09 (s, 9H)<br>$^{19}$F NMR (376 MHz, CDCl$_3$) δ -57.81 |
| 149 | HRMS-ESI (m/z) [M + H]$^+$ calcd for C$_{23}$H$_{24}$F$_3$N$_2$O$_2$, 417.1784; found, 417.1787 | $^1$H NMR (400 MHz, CDCl$_3$) δ 9.18 (s, 1H), 8.78 (dd, J = 2.4, 0.9 Hz, 1H), 8.33 (d, J = 4.9 Hz, 1H), 7.76 (dd, J = 8.3, 2.4 Hz, 1H), 7.66-7.56 (m, 2H), 7.38-7.31 (m, 2H), 7.09 (dd, J = 8.3, 0.9 Hz, 1H), 7.00 (d, J = 4.9 Hz, 1H), 5.89 (s, 1H), 1.91 (d, J = 0.6 Hz, 3H), 1.25 (s, 9H)<br>$^{19}$F NMR (376 MHz, CDCl$_3$) δ -57.82 |
| 150 | HRMS-ESI (m/z) [M + H]$^+$ calcd for C$_{20}$H$_{20}$F$_3$N$_4$O$_2$, 405.1533; found, 405.1529 | $^1$H NMR (400 MHz, CDCl$_3$) δ 9.22 (s, 2H), 9.13 (dd, J = 2.3, 0.9 Hz, 1H), 9.09 (s, 1H), 8.66 (d, J = 2.7 Hz, 1H), 8.40 (dd, J = 8.5, 2.3 Hz, 1H), 7.89 (dd, J = 8.5, 0.9 Hz, 1H), 7.82 (dd, J = 8.7, 0.7 Hz, 1H), 7.73-7.65 (m, 1H), 6.12 (s, 1H), 1.08 (s, 9H)<br>$^{19}$F NMR (376 MHz, CDCl$_3$) δ -58.11 |
| 151 | HRMS-ESI (m/z) [M + H]$^+$ calcd for C$_{23}$H$_{24}$F$_3$N$_2$O$_2$, 417.1784; found, 417.1786 | $^1$H NMR (400 MHz, CDCl$_3$) δ 8.79 (dd, J = 2.4, 0.9 Hz, 1H), 8.40 (dd, J = 4.8, 1.6 Hz, 1H), 8.29 (dd, J = 8.2, 1.7 Hz, 1H), 7.74 (dd, J = 8.2, 2.3 Hz, 1H), 7.68-7.57 (m, 2H), 7.41-7.29 (m, 2H), 7.13 (dd, J = 8.1, 4.7 Hz, 1H), 7.03 (dd, J = 8.3, 0.9 Hz, 1H), 5.79 (s, 1H), 2.09 (s, 3H), 1.23 (s, 9H)<br>$^{19}$F NMR (376 MHz, CDCl$_3$) δ -57.82 |

TABLE 2-continued

| | | Analytical Data. | |
|---|---|---|---|
| Compound Number | Mass Spec | NMR ($^1$H, $^{13}$C, $^{19}$F) IR (Thin Film; cm$^{-1}$) | |

| Compound Number | Mass Spec | NMR ($^1$H, $^{13}$C, $^{19}$F) / IR (Thin Film; cm$^{-1}$) |
|---|---|---|
| 152 | HRMS-ESI (m/z) [M + H]$^+$ calcd for C$_{24}$H$_{27}$N$_4$O, 387.2179; found, 387.2179 | $^1$H NMR (400 MHz, CDCl$_3$) δ 9.21 (s, 2H), 9.08 (s, 1H), 8.78 (dd, J = 2.3, 1.0 Hz, 1H), 7.96 (dd, J = 8.4, 2.3 Hz, 1H), 7.85 (dd, J = 8.4, 0.9 Hz, 1H), 7.61 (s, 4H), 6.22 (s, 1H), 1.78 (s, 6H), 1.09 (s, 9H) |
| 153 | HRMS-ESI (m/z) [M + H]$^+$ calcd for C$_{22}$H$_{23}$N$_4$O, 359.1866; found, 359.1866 | $^1$H NMR (400 MHz, CDCl$_3$) δ 9.21 (s, 2H), 9.08 (s, 1H), 8.78 (dd, J = 2.4, 0.9 Hz, 1H), 7.96 (dd, J = 8.4, 2.4 Hz, 1H), 7.86 (dd, J = 8.4, 0.9 Hz, 1H), 7.64-7.55 (m, 2H), 7.50-7.41 (m, 2H), 6.20 (s, 1H), 3.83 (s, 2H), 1.09 (s, 9H) |
| 154 | HRMS-ESI (m/z) [M + H]$^+$ calcd for C$_{23}$H$_{24}$F$_3$N$_2$O$_2$, 417.1782; found, 417.1784. | $^1$H NMR (400 MHz, CDCl$_3$) δ 9.05 (dd, J = 2.4, 0.9 Hz, 1H), 8.73 (t, J = 1.6 Hz, 1H), 8.47 (dd, J = 4.8, 1.6 Hz, 1H), 8.19 (ddd, J = 8.2, 2.5, 1.6 Hz, 1H), 7.93-7.84 (m, 2H), 7.30-7.21 (m, 1H), 7.62-7.55 (m, 2H), 7.34 (dq, J = 8.8, 1.0 Hz, 2H), 6.30 (s, 1H), 1.62-1.47 (m, 1H), 1.47-1.34 (m, 1H), 1.05 (s, 6H), 0.81 (t, J = 7.5 Hz, 3H) $^{19}$F NMR (376 MHz, CDCl$_3$) δ −57.81 |
| 155 | HRMS-ESI (m/z) [M + H]$^+$ calcd for C$_{22}$H$_{24}$F$_2$N$_3$O, 384.1879; found, 384.1882 | $^1$H NMR (400 MHz, CDCl$_3$) δ 9.22 (s, 2H), 9.09 (s, 1H), 8.79 (dd, J = 2.4, 0.9 Hz, 1H), 7.97 (dd, J = 8.4, 2.4 Hz, 1H), 7.86 (dd, J = 8.4, 0.9 Hz, 1H), 7.64 (s, 4H), 6.19 (s, 1H), 1.97 (t, J = 18.1 Hz, 3H), 1.09 (s, 9H) $^{19}$F NMR (376 MHz, CDCl$_3$) δ −87.73 |
| 156 | HRMS-ESI (m/z) [M + H]$^+$ calcd for C$_{23}$H$_{25}$F$_3$N$_3$O$_2$, 432.1893; found, 432.1897 | $^1$H NMR (400 MHz, CDCl$_3$) δ 9.25 (s, 1H), 8.95 (s, 1H), 8.55 (dd, J = 2.2, 0.9 Hz, 1H), 7.57 (dd, J = 8.1, 2.2 Hz, 1H), 7.26 (d, J = 8.6 Hz, 1H), 7.20-7.12 (m, 2H), 7.10 (dd, J = 8.1, 0.9 Hz, 1H), 5.96 (s, 1H), 2.26 (s, 3H), 2.14 (s, 3H), 1.24 (s, 9H) $^{19}$F NMR (376 MHz, CDCl$_3$) δ −57.69 |
| 157 | HRMS-ESI (m/z) [M + H]$^+$ calcd for C$_{22}$H$_{22}$F$_4$N$_3$O$_2$, 436.1643; found, 436.1645 | $^1$H NMR (400 MHz, CDCl$_3$) δ 9.24 (s, 1H), 8.95 (s, 1H), 8.76 (ddd, J = 2.3, 1.4, 0.9 Hz, 1H), 7.80 (ddd, J = 8.3, 2.3, 1.5 Hz, 1H), 7.51 (t, J = 8.5 Hz, 1H), 7.17 (ddd, J = 9.5, 2.1, 1.0 Hz, 1H), 7.15-7.08 (m, 2H), 5.89 (s, 1H), 2.14 (s, 3H), 1.23 (s, 9H) $^{19}$F NMR (376 MHz, CDCl$_3$) δ −57.98, −113.16 |
| 158 | HRMS-ESI (m/z) [M + H]$^+$ calcd for C$_{25}$H$_{27}$N$_4$O, 399.2179; found, 399.2183 | $^1$H NMR (300 MHz, CDCl$_3$) δ 9.22 (s, 2H), 9.09 (s, 1H), 8.51 (dd, J = 2.3, 0.9 Hz, 1H), 7.84 (dd, J = 8.3, 1.0 Hz, 1H), 7.72 (dd, J = 8.3, 2.2 Hz, 1H), 7.30-7.24 (m, 1H), 7.24-7.12 (m, 2H), 6.29 (s, 1H), 2.27 (s, 3H), 1.84-1.72 (m, 2H), 1.50-1.41 (m, 2H), 1.09 (s, 9H) |
| 159 | HRMS-ESI (m/z) [M + H]$^+$ calcd for C$_{23}$H$_{26}$N$_3$O, 360.2070; found, 360.2077 | $^1$H NMR (300 MHz, CDCl$_3$) δ 9.20 (s, 2H), 9.08 (s, 1H), 8.75 (dd, J = 2.3, 0.9 Hz, 1H), 7.94 (dd, J = 8.4, 2.3 Hz, 1H), 7.81 (dd, J = 8.4, 1.0 Hz, 1H), 7.52-7.42 (m, 2H), 7.22-7.14 (m, 2H), 6.39 (s, 1H), 2.03-1.87 (m, 1H), 1.08 (s, 9H), 1.06-0.97 (m, 2H), 0.75 (dt, J = 6.8, 4.7 Hz, 2H) |
| 160 | HRMS-ESI (m/z) [M + H]$^+$ calcd for C$_{24}$H$_{25}$F$_3$N$_3$O, 428.1944; found, 428.1949 | $^1$H NMR (400 MHz, CDCl$_3$) δ 9.21 (s, 2H), 9.08 (s, 1H), 8.77 (dd, J = 2.4, 0.8 Hz, 1H), 7.95 (dd, J = 8.4, 2.4 Hz, 1H), 7.91-7.73 (m, 1H), 7.64-7.48 (m, 4H), 6.26 (s, 1H), 1.44-1.37 (m, 2H), 1.13-1.03 (m, 11H) $^{19}$F NMR (376 MHz, CDCl$_3$) δ −70.00 |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 161 | HRMS-ESI (m/z) [M + H]$^+$ calcd for C$_{22}$H$_{21}$F$_5$N$_3$O$_2$, 454.1548; found, 454.1553 | $^1$H NMR (400 MHz, CDCl$_3$) δ 9.21 (s, 2H), 9.09 (s, 1H), 8.81-8.73 (m, 1H), 7.95 (dd, J = 8.3, 2.4 Hz, 1H), 7.89-7.81 (m, 1H), 7.65-7.56 (m, 2H), 7.40-7.31 (m, 2H), 6.15 (s, 1H), 1.09 (s, 9H) $^{19}$F NMR (376 MHz, CDCl$_3$) δ −85.95, −87.71 |
| 162 | HRMS-ESI (m/z) [M + H]$^+$ calcd for C$_{21}$H$_{23}$FN$_3$O$_2$, 368.1769; found, 368.1773 | $^1$H NMR (400 MHz, CDCl$_3$) δ 9.21 (s, 2H), 9.08 (s, 1H), 8.70 (s, 1H), 7.93 (dt, J = 8.5, 1.8 Hz, 1H), 7.82 (dd, J = 8.4, 0.9 Hz, 1H), 7.36 (t, J = 8.7 Hz, 1H), 6.82 (dd, J = 8.6, 2.6 Hz, 1H), 6.76 (dd, J = 12.5, 2.5 Hz, 1H), 6.34 (s, 1H), 3.86 (s, 3H), 1.08 (s, 9H) $^{19}$F NMR (376 MHz, CDCl$_3$) δ −115.26 |
| 163 | HRMS-ESI (m/z) [M + H]$^+$ calcd for C$_{22}$H$_{23}$F$_3$N$_3$O$_3$, 434.1686; found, 434.1695 | $^1$H NMR (400 MHz, CDCl$_3$) δ 9.22 (s, 2H), 9.09 (s, 1H), 8.62 (dd, J = 2.3, 1.0 Hz, 1H), 7.86 (dd, J = 8.4, 2.2 Hz, 1H), 7.82 (dd, J = 8.3, 1.1 Hz, 1H), 7.35 (d, J = 8.4 Hz, 1H), 7.00-6.90 (m, 2H), 6.28 (s, 1H), 3.88 (s, 3H), 1.07 (s, 9H) $^{19}$F NMR (376 MHz, CDCl$_3$) δ −57.13 |
| 164 | HRMS-ESI (m/z) [M + H]$^+$ calcd for C$_{20}$H$_{20}$F$_2$N$_3$O, 356.1569; found, 356.1572 | $^1$H NMR (400 MHz, CDCl$_3$) δ 9.21 (s, 2H), 9.09 (s, 1H), 8.70 (s, 1H), 7.98-7.89 (m, 1H), 7.85 (dd, J = 8.4, 1.0 Hz, 1H), 7.43 (td, J = 8.6, 6.3 Hz, 1H), 7.08-6.91 (m, 2H), 6.17 (s, 1H), 1.09 (s, 9H) $^{19}$F NMR (376 MHz, CDCl$_3$) δ −108.87 (d, J = 8.1 Hz), −113.11 (d, J = 8.1 Hz) |
| 165 | HRMS-ESI (m/z) [M + H]$^+$ calcd for C$_{20}$H$_{21}$IN$_3$O, 446.0724; found, 446.0727 | $^1$H NMR (400 MHz, CDCl$_3$) δ 9.20 (s, 2H), 9.08 (s, 1H), 8.75 (dd, J = 2.4, 0.9 Hz, 1H), 7.93 (dd, J = 8.4, 2.4 Hz, 1H), 7.87-7.78 (m, 3H), 7.35-7.28 (m, 2H), 6.17 (s, 1H), 1.08 (s, 9H) |
| 166 | HRMS-ESI (m/z) [M + H]$^+$ calcd for C$_{20}$H$_{20}$ClFN$_3$O, 372.1273; found, 372.1275 | $^1$H NMR (400 MHz, CDCl$_3$) δ 9.22 (s, 2H), 9.09 (s, 1H), 8.60 (t, J = 1.6 Hz, 1H), 7.85 (t, J = 1.7 Hz, 2H), 7.37-7.25 (m, 2H), 7.11 (td, J = 8.2, 2.6 Hz, 1H), 6.18 (s, 1H), 1.09 (s, 9H) $^{19}$F NMR (376 MHz, CDCl$_3$) δ −111.02 |
| 167 | ESIMS m/z 434 [M + H]$^+$ | $^1$H NMR (400 MHz, CDCl$_3$) δ 9.19 (s, 1H), 8.74 (dd, J = 2.4, 0.8 Hz, 1H), 8.67 (s, 1H), 7.82 (dd, J = 8.4, 2.4 Hz, 1H), 7.77 (dd, J = 8.4, 0.8 Hz, 1H), 7.64-7.59 (m, 2H), 7.33 (d, J = 7.9 Hz, 2H), 5.71 (s, 1H), 3.82 (s, 3H), 1.17 (s, 9H) $^{19}$F NMR (376 MHz, CDCl$_3$) δ −57.82 (s) |
| 168 | ESIMS m/z 406 [M + H]$^+$ | $^1$H NMR (400 MHz, CDCl$_3$) δ 9.19 (s, 1H), 8.75 (dd, J = 2.3, 0.6 Hz, 1H), 8.66 (s, 1H), 7.84 (dd, J = 8.4, 2.4 Hz, 1H), 7.70 (dd, J = 8.4, 0.7 Hz, 1H), 7.56-7.53 (m, 2H), 7.53-7.49 (m, 2H), 5.78 (s, 1H), 3.78 (s, 3H), 1.37 (s, 9H), 1.17 (s, 9H) $^{13}$C NMR (101 MHz, CDCl$_3$) δ 166.48, 160.91, 157.47, 156.62, 151.29, 144.93, 134.55, 134.42, 133.66, 126.65, 126.07, 124.38, 122.89, 80.20, 53.39, 40.20, 34.64, 31.31, 26.82 |
| 169 | ESIMS m/z 415 [M + H]$^+$ | $^1$H NMR (400 MHz, CDCl$_3$) δ 9.19 (s, 1H), 8.74 (d, J = 2.2 Hz, 1H), 8.66 (s, 1H), 7.83 (dd, J = 8.4, 2.4 Hz, 1H), 7.76 (dd, J = 8.4, 0.7 Hz, 1H), 7.61-7.57 (m, 2H), 7.43-7.38 (m, 2H), 5.73 (s, 1H), 3.82 (s, 3H), 1.79 (q, J = 5.1 Hz, 2H), 1.46 (q, J = 5.2 Hz, 2H), 1.17 (s, 9H) $^{13}$C NMR (101 MHz, CDCl$_3$) δ 166.40, 161.79, 157.61, 156.62, 144.95, 136.84, 136.09, 133.77, 127.49, 126.43, 124.12, 123.04, 122.28, 80.36, 53.46, 40.35, 26.78, 18.40, 13.66 |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 170 | ESIMS m/z 375 [M + H]$^+$ | $^1$H NMR (400 MHz, CDCl$_3$) δ 9.19 (s, 1H), 8.78 (dd, J = 2.3, 0.8 Hz, 1H), 8.67 (s, 1H), 7.87 (dd, J = 8.4, 2.3 Hz, 1H), 7.83 (dd, J = 8.4, 0.9 Hz, 1H), 7.81-7.77 (m, 2H), 7.73-7.69 (m, 2H), 5.66 (s, 1H), 3.85 (s, 3H), 1.16 (s, 9H) $^{13}$C NMR (101 MHz, CDCl$_3$) δ 166.33, 163.18, 157.72, 156.67, 145.15, 141.96, 134.07, 132.89, 132.82, 127.64, 123.73, 123.22, 118.56, 111.90, 80.52, 53.60, 40.51, 26.72 |
| 171 | ESIMS m/z 381 [M + H]$^+$ | $^1$H NMR (400 MHz, CDCl$_3$) δ 9.19 (s, 1H), 8.76 (dd, J = 2.3, 0.8 Hz, 1H), 8.67 (s, 1H), 8.47 (d, J = 1.8 Hz, 1H), 8.36 (d, J = 2.8 Hz, 1H), 7.86 (dd, J = 8.4, 2.3 Hz, 1H), 7.81 (dd, J = 8.4, 0.9 Hz, 1H), 7.38 (dd, J = 2.7, 1.9 Hz, 1H), 5.70 (s, 1H), 3.94 (s, 3H), 3.84 (s, 3H), 1.17 (s, 9H) $^{13}$C NMR (101 MHz, CDCl$_3$) δ 166.36, 162.61, 157.64, 156.65, 155.85, 145.12, 140.42, 136.99, 134.09, 133.73, 131.48, 123.90, 123.18, 118.87, 80.42, 55.71, 53.56, 40.42, 26.75 |
| 172 | ESIMS m/z 419 [M + H]$^+$ | $^1$H NMR (400 MHz, CDCl$_3$) δ 9.20 (s, 1H), 8.97 (d, J = 1.5 Hz, 1H), 8.80 (d, J = 1.5 Hz, 1H), 8.68 (s, 1H), 8.08 (dd, J = 8.1, 2.1 Hz, 1H), 7.90 (d, J = 1.6 Hz, 2H), 7.82 (d, J = 8.2 Hz, 1H), 5.63 (s, 1H), 3.87 (s, 3H), 1.17 (s, 9H) $^{19}$F NMR (376 MHz, CDCl$_3$) δ −67.83 (s) |
| 173 | ESIMS m/z 419.5 [M + H]$^+$ | $^1$H NMR (400 MHz, CDCl$_3$) δ 9.70 (s, 2H), 9.21 (d, J = 1.8 Hz, 1H), 9.14 (s, 1H), 8.67 (d, J = 2.8 Hz, 1H), 8.37 (dd, J = 8.4, 2.4 Hz, 1H), 7.85 (d, J = 8.7 Hz, 1H), 7.72 (d, J = 8.4 Hz, 2H), 3.18 (d, J = 15.4 Hz, 3H), 0.87 (d, J = 13.6 Hz, 9H). $^{19}$F NMR (376 MHz, CDCl$_3$) δ −58.12 (s). |
| 174 | ESIMS m/z 405.46 [M + H]$^+$ | $^1$H NMR (400 MHz, CDCl$_3$) δ 9.47 (s, 1H), 9.10 (d, J = 1.6 Hz, 1H), 8.64 (d, J = 2.4 Hz, 1H), 8.52-8.47 (m, 2H), 8.38 (d, J = 8.4 Hz, 1H), 8.29 (dd, J = 8.8, 2.4 Hz, 1H), 7.80-7.87 (m, 1H), 7.67-7.64 (m, 1H), 6.76 (s, 1H), 1.01 (s, 9H). $^{13}$C NMR (100 MHz, CDCl$_3$) δ 160.73, 157.84, 153.18, 145.86, 145.43, 144.72, 143.07, 142.53, 141.084, 134.17, 132.26, 129.21, 124.04, 121.69, 120.98, 80.25, 41.08, 26.01. |
| 175 | ESIMS m/z 412.5 [M + H]$^+$ | $^1$H NMR (400 MHz, CDCl$_3$) δ 9.24 (s, 2H), 9.10 (s, 1H), 8.75 (d, J = 1.6 Hz, 1H), 8.02 (dd, J = 8.3, 2.3 Hz, 1H), 7.95-7.91 (m, 1H), 7.90 (d, J = 2.0 Hz, 1H), 7.86 (dd, J = 8.3, 2.1 Hz, 1H), 7.58 (d, J = 8.2 Hz, 1H), 5.81 (s, 1H), 1.80 (s, 6H), 1.10 (s, 9H). $^{13}$C NMR (126 MHz, CDCl$_3$) δ 161.16, 157.01, 156.41, 146.60, 142.76, 140.39, 136.75, 136.73, 132.24, 130.71, 130.63, 130.44, 123.12, 122.12, 122.08, 117.50, 112.30, 40.25, 36.95, 28.90, 26.30. |
| 176 | ESIMS m/z 436.45 [M + H]$^+$ | $^1$H NMR (300 MHz, CDCl$_3$) δ 9.14 (s, 1H), 8.84 (s, 2H), 8.74 (s, 1H), 7.90 (td, J = 1.9, 8.3 Hz, 1H), 7.59 (d, J = 8.4 Hz, 1H), 7.55-7.45 (m, 1H), 7.14 (br t, J = 10.3 Hz, 2H), 3.26-2.97 (m, 3H), 1.18 (t, J = 7.0 Hz, 3H), 0.88 (t, J = 7.3 Hz, 6H). $^{19}$F NMR (282.2 MHz, CDCl$_3$) δ −57.96 −113.18. |
| 177 | ESIMS m/z 390.44 [M + H]$^+$ | $^1$H NMR (400 MHz, CDCl$_3$) δ 9.09 (s, 1H), 8.83 (s, 2H), 8.73 (d, J = 2.0 Hz, 1H), 7.85 (dd, J = 2.2, 8.1 Hz, 1H), 7.72 (d, J = 7.8 Hz, 1H), 7.60-7.53 (m, 2H), 7.32 (d, J = 8.3 Hz, 2H), 3.47 (dquin, J = 1.7, 6.8 Hz, 2H), 2.05 (s, 3H), 1.33 (t, J = 6.8 Hz, 3H). $^{13}$C NMR (101 MHz, CDCl$_3$): δ 162.44, 157.24, 155.16, 149.27, 147.16, 138.99, 136.15, 135.24, 121.99, 121.54, 120.43, 119.17, 79.62, 58.71, 24.03, 15.62. |
| 178 | ESIMS m/z 399 [M + H]$^+$ | $^1$H NMR (400 MHz, CDCl$_3$) δ 8.85 (s, 1H), 8.58 (s, 1H), 8.43 (s, 2H), 7.82 (dd, J = 8.0, 2.0 Hz, 1H), 7.53-7.47 (m, 3H), 7.37 (d, J = 8.0 Hz, 2H), 5.29 (bs, 1H), 3.33 (d, J = 14.4 Hz, 1H) 3.27 (d, J = 14.0 Hz, 1H), 1.78 (dd, J = 7.6, 3.2 Hz, 2H), 1.47 (dd, J = 7.2, 4.8 Hz, 2H), 1.05 (s, 9H). |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 179 | HRMS-ESI (m/z) [M + H]$^+$ calcd for C$_{26}$H$_{30}$N$_4$O, 414.2420; found, 414.2425 | $^1$H NMR (300 MHz, DMSO-d6) d 9.46 (s, 2H), 9.06 (s, 1H), 8.62 (dd, J = 2.3, 0.8 Hz, 1H), 7.91 (dd, J = 8.3, 0.9 Hz, 1H), 7.84 (dd, J = 8.3, 2.3 Hz, 1H), 7.51 (d, J = 2.1 Hz, 1H), 7.44 (dd, J = 8.0, 2.1 Hz, 1H), 7.30 (d, J = 8.0 Hz, 1H), 6.26 (s, 1H), 2.58 (q, J = 7.5 Hz, 2H), 1.73 (s, 6H), 1.03 (t, J = 7.5 Hz, 3H), 0.94 (s, 9H). $^{13}$C NMR (126 MHz, DMSO) d 162.42, 157.08, 156.90, 147.06, 142.58, 141.92, 137.10, 134.83, 131.03, 126.05, 125.09, 123.32, 122.48, 79.36, 37.06, 28.79, 26.26, 26.24, 15.79. |
| 180 | ESIMS m/z 419 [M + H]$^+$ | $^1$H NMR (400 MHz, CDCl$_3$) δ 9.80 (bs, 1H), 8.71 (d, J = 2.0 Hz, 1H), 8.58 (bs, 2H), 8.37-8.35 (m, 2H), 7.84 (dt, J = 8.8, 2.4 Hz, 2H), 6.96 (d, J = 8.8 Hz, 1H), 6.73 (s, 1H), 4.82 (q, J = 8.4 Hz, 2H), 1.01 (s, 9H). $^{13}$C NMR (100 MHz, CDCl$_3$) δ 161.64, 159.27, 145.79, 144.70, 144.17, 142.48, 137.97, 133.90, 131.70, 128.08, 124.98, 124.18, 122.22, 111.44, 80.20, 62.44, 41.02, 26.02. |
| 181 | ESIMS m/z 390.42 [M + H]$^+$ | $^1$H NMR (300 MHz, CDCl$_3$) δ 8.84 (s, 1H), 8.59 (d, J = 2.1 Hz, 1H), 8.45 (s, 1H), 8.44 (s, 2H), 7.85 (d, J = 8.4, 2.1 Hz, 1H), 7.49-7.46 (m, 4H), 5.72 (bs, 1H), 3.30 (d, J = 13.8 Hz, 1H); 3.26 (d, J = 13.8 Hz, 1H), 1.35 (s, 9H), 1.02 (s, 9H). |
| 182 | ESIMS m/z 418.4 [M + H]$^+$ | $^1$H NMR (400 MHz, CDCl$_3$) δ 9.14 (s, 1H), 8.99 (s, 2H), 8.69 (s, 1H), 7.91 (s, 2H), 7.44 (t, J = 8.6 Hz, 1H), 7.18-7.07 (m, 2H), 3.45 (s, 3H), 2.08 (s, 3H). $^{13}$C NMR (75 MHz, CDCl$_3$): δ 161.01, 159.65, 158.51, 157.97, 155.95, 149.77, 149.13, 149.10, 137.21, 137.18, 135.64, 131.16, 131.12, 129.71, 123.88, 123.75, 121.58, 120.41, 119.04, 117.04, 109.79, 109.52, 88.24, 79.10, 75.84, 52.70. NMR (376 MHz, CDCl$_3$): δ −57.99, −113.26. |
| 183 | ESIMS m/z 388.5 [M + H]$^+$ | $^1$H NMR (400 MHz, CDCl$_3$) δ 9.22 (s, 2H), 9.15 (d, J = 1.5 Hz, 1H), 9.09 (s, 1H), 8.86 (d, J = 1.9 Hz, 1H), 8.42 (dd, J = 8.5, 2.3 Hz, 1H), 7.97-7.86 (m, 2H), 7.79 (dd, J = 8.3, 0.7 Hz, 1H), 6.18 (s, 1H), 1.82 (s, 6H), 1.08 (s, 9H). $^{13}$C NMR (126 MHz, CDCl$_3$) δ 160.82, 156.93, 156.41, 153.53, 147.15, 145.52, 137.00, 136.57, 135.09, 134.27, 133.32, 123.23, 122.24, 120.32, 40.18, 35.54, 28.88, 26.31. |
| 184 | ESIMS m/z 406.38 [M + H]$^+$ | $^1$H NMR (300 MHz, DMSO-d6) δ 9.07 (s, 1H), 8.95 (s, 2H), 8.68 (s, 1H), 8.09-8.02 (m, 1H), 7.90 (d, J = 8.4 Hz, 1H), 7.77 (t, J = 8.6 Hz, 1H), 7.57 (d, J = 11.0 Hz, 1H), 7.38 (d, J = 8.4 Hz, 1H), 5.99 (s, 1H), 2.06-1.93 (m, 1H), 0.66-0.49 (m, 3H), 0.48-0.34 (m, 1H). $^{19}$F NMR (282.2 MHz, DMSO-d6) δ −56.96-113.68. |
| 185 | ESIMS m/z 404.31 [M + H]$^+$ | $^1$H NMR (400 MHz, CDCl$_3$) δ 9.15 (s, 1H), 9.01 (s, 2H), 8.70 (s, 1H), 7.90 (d, J = 8.4 Hz, 1H), 7.59 (d, J = 8.4 Hz, 1H), 7.46 (t, J = 8.4 Hz, 1H), 7.20-7.08 (m, 2H), 6.24 (s, 1H), 2.01 (s, 3H). $^{13}$C NMR (101 MHz, CDCl$_3$) δ 160.99, 159.21, 158.48, 158.02, 149.89, 147.30, 147.27, 138.16, 138.12, 137.76, 131.18, 131.14, 130.40, 123.46, 123.32, 121.58, 121.00, 119.01, 117.17, 109.85, 109.59, 85.30, 79.16, 70.75, 3.83. $^{19}$F NMR (376 MHz, CDCl$_3$): δ −57.98, −113.28. |
| 186 | ESIMS m/z 449 [M + H]$^+$ | $^1$H NMR (400 MHz, CDCl$_3$) δ 9.19 (s, 1H) 9.04 (d, J = 2.0 Hz, 1H), 8.66 (s, 1H), 8.46 (d, J = 2.4 Hz, 1H) 8.23 (dd, J = 8.0, 2.4 Hz, 1H)7.74 (dd, J = 8.8, 5.2 Hz, 2H), 7.40-7.35 (m, 1H) 5.76 (s, 1H), 4.47 (q, J = 8.0 Hz, 2H) 3.82 (s, 3H), 1.16 (s, 9H). $^{13}$C NMR (75 MHz, CDCl$_3$) δ 166.47, 162.47, 157.33, 156.61, 153.20, 149.00, 144.76, 138.19, 133.48, 132.36, 124.32, 124.18, 121.91, 122.79, 121.55, 120.90, 80.26, 66.13, 53.46, 40.18, 26.75. $^{19}$F NMR (282 MHz, CDCl$_3$) δ −73.80 (t). |
| 187 | ESIMS m/z 451 [M + H]$^+$ | $^1$H NMR (400 MHz, CDCl$_3$) δ 9.19 (s, 1H), 8.67 (d, J = 4.0 Hz, 2H), 7.85-7.76 (m, 2H), 7.49 (t, J = 17.2 Hz, 1H), 7.13 (q, J = 9.2 Hz, 2H), 5.69 (bs, 1H) 3.82 (s, 3H), 1.17 (s, 9H). $^{13}$C NMR (101 MHz, CDCl$_3$) δ 166.42, 162.27, 161.00, 158.50, 157.48, 156.60, 149.57, 149.46, 146.39, 146.36, 135.75, 135.71, 131.12, 131.10, 128.59, 124.16, 124.02, 122.79, 121.59, 119.02, 117.07, 117.04, 109.81, 109.54, 80.37, 53.51, 40.33, 26.73. $^{19}$F NMR (282 MHz, CDCl$_3$) δ −57.9, −113.2 (t). |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 188 | ESIMS m/z 387.51 [M + H]$^+$ | $^1$H NMR (300 MHz, CDCl$_3$) δ 9.47 (s, 1H), 8.75 (d, J = 2.4 Hz, 1H), 8.53-8.46 (m, 2H), 8.35 (d, J = 8.4 Hz, 1H), 7.87 (dd, J = 8.1, 2.1 Hz, 1H), 7.62-7.56 (m, 4H), 6.78 (s, 1H), 1.77 (s, 6H), 1.01 (s, 9H). $^{13}$C NMR (75 MHz, CDCl$_3$) δ 158.94, 158.11, 145.76, 144.48, 144.46, 141.36, 141.09, 137.02, 134.32, 134.17, 127.56, 125.881, 124.26, 124.04, 80.09, 40.99, 36.97, 29.08, 26.03. |
| 189 | ESIMS m/z 460.47 [M + H]$^+$ | $^1$H NMR (400 MHz, CDCl$_3$) δ 9.74 (s, 2H), 9.15 (s, 1H), 8.82 (s, 1H), 7.94 (d, J = 8.3 Hz, 1H), 7.82 (d, J = 8.3 Hz, 1H), 7.52 (t, J = 8.6 Hz, 1H), 7.20-7.07 (m, 2H), 3.89 (t, J = 2.4 Hz, 2H), 2.55 (t, J = 2.4 Hz, 1H), 0.93 (s, 9H). $^{19}$F NMR (376 MHz, CDCl$_3$) δ −57.96-113.17. |
| 190 | ESIMS m/z 422.46 [M + H]$^+$ | $^1$H NMR (400 MHz, CDCl$_3$) δ 9.08 (s, 1H), 8.82 (s, 2H), 8.67 (s, 1H), 7.84 (td, J = 1.8, 8.2 Hz, 1H), 7.73 (d, J = 8.3 Hz, 1H), 7.45 (t, J = 8.3 Hz, 1H), 7.12 (br dd, J = 10.0, 14.9 Hz, 2H), 3.36 (dq, J = 2.0, 7.0 Hz, 2H), 2.69 (qd, J = 7.3, 14.7 Hz, 1H), 2.50 (qd, J = 7.3, 14.7 Hz, 1H), 1.33 (t, J = 6.8 Hz, 3H), 0.77 (t, J = 7.1 Hz, 3H). $^{13}$C NMR (101 MHz, CDCl$_3$) δ 162.18, 160.99, 158.48, 157.17, 155.52, 149.60, 148.54, 148.51, 137.66, 136.82, 136.79, 131.15, 131.10, 128.85, 124.15, 121.59, 121.00, 119.02, 117.06, 109.79, 109.52, 81.92, 57.87, 26.92, 6.89. $^{19}$F NMR (376 MHz, CDCl$_3$): δ −57.98, −113.30. |
| 191 | ESIMS m/z 428.4 [M + H]$^+$ | $^1$H NMR (300 MHz, CDCl$_3$) δ 9.17 (s, 1H), 8.89 (s, 2H), 8.81 (d, J = 2.2 Hz, 1H), 7.93 (dd, J = 2.4, 8.3 Hz, 1H), 7.67-7.59 (m, 3H), 7.35 (d, J = 8.1 Hz, 2H), 3.84 (dd, J = 2.6, 4.8 Hz, 2H), 3.07 (hept, J = 6.8 Hz, 1H), 2.35 (t, J = 2.4 Hz, 1H), 0.89 (dd, J = 6.6, 17.2 Hz, 6H). $^{19}$F NMR (282.2 MHz, CDCl$_3$) δ −57.8. |
| 192 | ESIMS m/z 399.6 [M + H]$^+$ | $^1$H NMR (400 MHz, CDCl$_3$) δ 9.69 (s, 2H), 9.13 (s, 1H), 8.87 (d, J = 1.8 Hz, 1H), 7.91 (dd, J = 8.4, 2.4 Hz, 1H), 7.66 (d, J = 8.4 Hz, 1H), 7.62 (d, J = 8.4 Hz, 2H), 7.42 (d, J = 8.4 Hz, 2H), 3.19 (s, 3H), 1.80 (q, J = 5.0 Hz, 2H), 1.48 (q, J = 5.3 Hz, 2H), 0.90 (s, 9H). IR (ATR) 2961, 2234, 1411, 1071 cm$^{-1}$. |
| 193 | ESIMS m/z 402.42 [M + H]$^+$ | $^1$H NMR (300 MHz, CDCl$_3$) δ 9.13 (s, 2H), 8.84 (s, 2H), 8.73 (d, J = 1.8 Hz, 1H), 7.92-7.83 (m, 1H), 7.75 (d, J = 8.4 Hz, 1H), 7.63-7.51 (m, 2H), 7.33 (d, J = 8.1 Hz, 2H), 3.33 (s, 3H), 1.76-1.66 (m, 1H), 0.73 (m, 2H), 0.55-0.43 (m, 1H), 0.40-0.29 (m, 1H). $^{19}$F NMR (282.2 MHz, CDCl$_3$) δ −57.8. |
| 194 | ESIMS m/z 404.40 [M + H]$^+$ | $^1$H NMR (300 MHz, CDCl$_3$) δ 9.15 (s, 1H), 8.85 (s, 2H), 8.81 (d, J = 2.2 Hz, 1H), 7.91 (dd, J = 2.4, 8.3 Hz, 1H), 7.63 (d, J = 8.8 Hz, 2H), 7.57 (d, J = 8.1 Hz, 1H), 7.35 (d, J = 8.4 Hz, 2H), 3.05 (s, 4H), 0.88 (t, J = 7.2 Hz, 6H). $^{19}$F NMR (282.2 MHz, CDCl$_3$) δ −57.8. |
| 195 | ESIMS m/z 433 [M + H]$^+$ | $^1$H NMR (300 MHz, CDCl$_3$) δ 8.86 (s, 1H), 8.56 (d, J = 1.8 Hz, 1H), 8.44 (s, 2H), 8.31(d, J = 1.8 Hz, 1H), 7.84-7.77 (m, 2H), 7.51(d, J = 7.8 Hz, 1H), 6.96 (d, J = 8.4 Hz, 1H), 5.53 (bs, 1H), 4.83 (d, J = 8.7 Hz, 1H), 4.78 (d, J = 8.4 Hz, 1H), 3.34 (d, J = 13.8 Hz, 1H), 3.28 (d, J = 13.8 Hz, 1H), 1.02 (s, 9H). |
| 196 | ESIMS m/z 431.6 [M + H]$^+$ | $^1$H NMR (400 MHz, CDCl$_3$) δ 9.20 (s, 1H), 8.67 (s, 1H), 8.48 (d, J = 1.9 Hz, 1H), 7.73 (d, J = 8.3 Hz, 1H), 7.60 (dd, J = 8.3, 2.3 Hz, 1H), 7.41 (s, 1H), 7.37 (dd, J = 8.1, 1.9 Hz, 1H), 7.24 (s, 1H), 5.74 (s, 1H), 3.81 (s, 3H), 2.30 (s, 3H), 1.77 (s, 6H), 1.18 (s, 9H). IR (ATR) 2957, 2236, 1470, 1005 cm$^{-1}$. |
| 197 | ESIMS m/z 442.42 [M + H]$^+$ | $^1$H NMR (300 MHz, CDCl$_3$) δ 9.74 (s, 2H), 9.15 (s, 1H), 8.87 (d, J = 2.2 Hz, 1H), 7.94 (dd, J = 2.6, 8.4 Hz, 1H), 7.81 (d, J = 8.4 Hz, 1H), 7.70-7.58 (m, 2H), 7.36 (d, J = 8.1 Hz, 2H), 3.89 (d, J = 1.1 Hz, 2H), 2.55 (, J = 2.4 Hz, 1H), 0.93 (s, 9H). $^{19}$F NMR (282.2 MHz, CDCl$_3$) δ −57.8. |
| 198 | ESIMS m/z 432.46 [M + H]$^+$ | $^1$H NMR (300 MHz, CDCl$_3$) δ 9.65 (s, 2H), 9.12 (s, 1H), 8.86 (d, J = 2.2 Hz, 1H), 7.89 (dd, J = 2.2, 8.4 Hz, 1H), 7.68-7.59 (m, 3H), 7.35 (d, J = 8.1 Hz, 2H), 3.32-3.14 (m, 2H), 1.33 (t, J = 7.0 Hz, 3H), 0.91 (s, 9H). $^{19}$F NMR (282.2 MHz, CDCl$_3$) δ −57.8. |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 199 | ESIMS m/z 434 [M + H]$^+$ | $^1$H NMR (400 MHz, CDCl$_3$) δ 9.20 (s, 1H) 9.09 (d, J = 2.0 Hz, 1H), 8.67-8.63 (m, 2H) 8.27 (dd, J = 8.8, 2.0 Hz, 1H), 7.83-7.65 (m, 3H), 5.71 (s, 1H), 3.79 (s, 3H), 1.16 (s, 9H). $^{13}$C NMR (101 MHz, CDCl$_3$) δ 166.46, 163.45, 157.41, 156.67, 153.12, 145.44, 145.15, 143.08, 133.91, 131.80, 129.24, 124.01, 123.00, 121.70, 120.95, 119.12, 80.38, 53.51, 40.26, 26.75. $^{19}$F NMR (282 MHz, CDCl$_3$) δ −58.13 |
| 200 | ESIMS m/z 420.13 [M + H]$^+$ | $^1$H NMR (400 MHz, CDCl$_3$) δ 9.13 (s, 1H), 8.85 (s, 2H), 8.68 (s, 1H), 7.89 (td, J = 2.0, 8.3 Hz, 1H), 7.76 (d, J = 8.8 Hz, 1H), 7.47 (t, J = 8.3 Hz, 1H), 7.19-7.03 (m, 2H), 3.34 (s, 3H), 1.72 (tt, J = 5.4, 8.5 Hz, 1H), 0.78-0.67 (m, 2H), 0.50 (td, J = 4.6, 9.3 Hz, 1H), 0.41-0.28 (m, 1H). $^{19}$F NMR (376 MHz, CDCl$_3$) δ −57.95 −113.26. |
| 201 | ESIMS m/z 389 [M + H]$^+$ | $^1$H NMR (300 MHz, CDCl$_3$) δ 8.59 (d, J = 1.2 Hz, 1H), 8.23 (d, J = 7.5 Hz, 2H), 7.81 (dd, J = 8.1, 2.1 Hz, 1H), 7.55-7.47 (m, 6H), 7.00-6.90 (m, 1H), 3.33 (s, 2H), 1.35 (s, 9H), 1.04 (s, 9H). |
| 202 | ESIMS m/z 421.5 [M + H]$^+$ | $^1$H NMR (400 MHz, CDCl$_3$) δ 8.85 (s, 1H), 8.76-8.72 (m, 1H), 8.33 (d, J = 2.8 Hz, 1H), 8.01-7.95 (m, 1H), 7.93 (dd, J = 8.4, 2.3 Hz, 1H), 7.89 (d, J = 7.7 Hz, 1H), 7.63-7.57 (m, 2H), 7.34 (d, J = 8.0 Hz, 2H), 6.28 (s, 1H), 1.09 (s, 9H). $^{19}$F NMR (376 MHz, CDCl$_3$) δ −57.81 (s), −127.51 (s). |
| 203 | ESIMS m/z 448 [M + H]$^+$ | $^1$H NMR (400 MHz, CDCl$_3$) δ 9.19 (s, 1H), 8.71 (d, J = 2.0 Hz, 1H), 8.67 (s, 1H), 7.80 (dd, J = 8.4, 2.8 Hz, 1H), 7.72 (d, J = 8.0, Hz, 1H) 7.56 (d, J = 8.8 Hz, 2H), 7.05 (d, J = 8.8 Hz, 2H), 5.70 (bs, 1H) 4.41 (q, J = 8.0 Hz, 2H), 3.82 (s, 3H), 1.17 (s, 9H). $^{13}$C NMR (101 MHz, CDCl$_3$) δ 166.50, 166.99, 157.45, 157.29, 156.49, 144.74, 133.91, 133.52, 131.73, 128.35, 124.62, 124.29, 122.94, 121.86, 115.55, 80.23, 65.87, 53.49, 40.25, 26.75. $^{19}$F NMR (276 MHz, CDCl$_3$) δ −73.88 (t). |
| 204 | ESIMS m/z 432.42 [M + H]$^+$ | $^1$H NMR (400 MHz, CDCl$_3$) δ 9.13 (s, 1H), 8.99 (s, 2H), 8.68 (s, 1H), 7.96-7.85 (m, 2H), 7.44 (t, J = 8.3 Hz, 1H), 7.17-7.06 (m, 2H), 3.78-3.68 (m, 1H), 3.62-3.51 (m, 1H), 2.06 (s, 3H), 1.33 (t, J = 7.1 Hz, 3H). $^{13}$C NMR (101 MHz, CDCl$_3$) δ 161.06, 160.14, 158.51, 157.87, 155.90, 149.72, 149.63, 149.04, 149.01, 137.19, 137.16, 131.15, 131.10, 129.60, 123.95, 123.81, 121.59, 120.23, 119.04, 117.06, 109.78, 109.52, 87.67, 78.36, 60.85, 15.25. $^{19}$F NMR (376 MHz, CDCl$_3$): δ −57.99, −113.27. |
| 205 | ESIMS m/z 394.4 [M + H]$^+$ | $^1$H NMR (400 MHz, CDCl$_3$) δ 9.11 (s, 1H), 8.95 (s, 2H), 8.70 (s, 1H), 7.90 (td, J = 2.0, 8.3 Hz, 1H), 7.50-7.42 (m, 2H), 7.19-7.09 (m, 2H), 5.77 (s, 1H), 2.42-2.31 (m, 2H), 0.93 (t, J = 7.1 Hz, 3H). $^{13}$C NMR (101 MHz, CDCl$_3$) δ 160.94, 158.45, 157.36, 155.04, 149.80, 147.47, 139.13, 137.75, 131.12, 129.64, 123.50, 121.57, 119.72, 109.84, 109.58, 75.59, 33.78, 7.64. |
| 206 | ESIMS m/z 394.2 [M + H]$^+$ | $^1$H NMR (300 MHz, CDCl$_3$) δ 9.10 (s, 1H), 8.83 (s, 2H), 8.68 (s, 1H), 7.86 (td, J = 1.9, 8.3 Hz, 1H), 7.71 (d, J = 8.4 Hz, 1H), 7.49-7.38 (m, 1H), 7.17-7.07 (m, 2H), 3.34 (s, 3H), 2.04 (s, 3H). $^{13}$C NMR (75 MHz, CDCl$_3$): δ 162.39, 161.03, 158.51, 157.33, 149.67, 149.58, 148.57, 148.54, 138.48, 137.08, 137.05, 131.16, 129.13, 124.10, 123.96, 121.60, 120.24,, 119.03, 117.04, 117.06, 109.79, 109.52, 80.05, 51.06, 23.31. |
| 207 | ESIMS m/z 404.2 [M + H]$^+$ | $^1$H NMR (300 MHz, CDCl$_3$) δ 9.47 (s, 1H), 8.37 (s, 1H), 8.52 (s, 1H), 8.48-8.47 (m, 1H), 8.35 (d, J = 8.4 Hz, 1H), 7.85 (dd, J = 8.7, 2.4 Hz, 1H), 7.60 (d, J = 8.7 Hz, 2H), 7.32 (d, J = 9.0 Hz, 2H), 6.75 (s, 1H), 0.95 (s, 9H). $^{13}$C NMR (75 MHz, CDCl$_3$) δ 159.18, 158.04, 149.27, 145.82, 144.52, 142.49, 141.09, 136.17, 134.21, 133.94 128.49, 124.05, 122.53, 80.13, 41.02, 26.05. |
| 208 | ESIMS m/z 446.45 [M + H]$^+$ | $^1$H NMR (300 MHz, CDCl$_3$) δ 9.17 (s, 1H), 8.90 (s, 2H), 8.75 (s, 1H), 7.97-7.86 (m, 1H), 7.66 (d, J = 8.4 Hz, 1H), 7.51 (t, J = 8.6 Hz, 1H), 7.15 (t, J = 10.8 Hz, 2H), 3.86 (dd, J = 2.6, 4.0 Hz, 2H), 3.07 (td, J = 6.8, 13.6 Hz, 1H), 2.35 (t, J = 2.4 Hz, 1H), 0.90 (dd, J = 6.8, 15.6 Hz, 6H). $^{19}$F NMR (282.2 MHz, CDCl$_3$) δ −57.96 −113.15. |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 210 | ESIMS m/z 440.5 [M + H]$^+$ | $^1$H NMR (500 MHz, CDCl$_3$) δ 9.23 (s, 2H), 9.09 (s, 1H), 8.67 (s, 1H), 7.89 (s, 2H), 6.97 (d, J = 7.8 Hz, 2H), 6.01 (s, 1H), 1.09 (s, 9H). IR (ATR) 2958, 1410, 1213, 1035 cm$^{-1}$. |
| 211 | ESIMS m/z 436.4 [M + H]$^+$ | $^1$H NMR (400 MHz, CDCl$_3$) δ 9.69 (s, 2H), 9.13 (s, 1H), 8.82 (s, 1H), 7.91 (td, J = 2.0, 8.3 Hz, 1H), 7.69 (d, J = 7.8 Hz, 1H), 7.52 (t, J = 8.3 Hz, 1H), 7.20-7.08 (m, 2H), 3.20 (s, 1H), 0.90 (s, 9H). $^{19}$F NMR (376 MHz, CDCl$_3$): δ −57.97, −113.22 (t). |
| 212 | ESIMS m/z 413.4 [M + H]$^+$ | $^1$H NMR (300 MHz, CDCl$_3$) δ 9.23 (s, 2H), 9.09 (s, 1H), 8.53 (d, J = 1.4 Hz, 1H), 7.85 (d, J = 8.3 Hz, 1H), 7.74 (dd, J = 8.2, 2.1 Hz, 1H), 7.34 (d, J = 7.5 Hz, 2H), 7.25 (d, J = 8.5 Hz, 1H), 6.31 (s, 1H), 2.93-2.78 (m, 2H), 2.75-2.58 (m, 2H), 2.56-2.39 (m, 1H), 2.30 (s, 3H), 2.20-2.03 (m, 1H), 1.09 (s, 9H). IR (ATR) 2955, 2230, 1409, 909 cm$^{-1}$. |
| 213 | ESIMS m/z 390.38 [M + H]$^+$ | $^1$H NMR (400 MHz, CDCl$_3$) δ 9.08 (s, 1H), 8.81 (s, 2H), 8.75-8.68 (m, 1H), 7.84 (dd, J = 2.4, 8.3 Hz, 1H), 7.68 (d, J = 8.3 Hz, 1H), 7.59-7.53 (m, 2H), 7.32 (d, J = 8.3 Hz, 2H), 3.32 (s, 3H), 2.69 (qd, J = 7.3, 14.7 Hz, 1H), 2.50 (qd, J = 7.3, 14.7 Hz, 1H), 0.78 (t, J = 7.3 Hz, 3H). $^{13}$C NMR (101 MHz, CDCl$_3$): δ 161.41, 157.22, 155.60, 149.30, 147.30, 137.38, 136.15, 134.99, 133.86, 128.51, 121.52, 121.38, 82.34, 50.43, 26.40; 7.64. |
| 214 | ESIMS m/z 401.6 [M + H]$^+$ | $^1$H NMR (400 MHz, CDCl$_3$) δ 9.69 (s, 2H), 9.13 (s, 1H), 8.89 (d, J = 1.6 Hz, 1H), 7.93 (dd, J = 8.4, 2.5 Hz, 1H), 7.65 (dt, J = 18.9, 7.2 Hz, 5H), 3.20 (s, 3H), 1.79 (s, 6H), 0.90 (s, 9H). IR (ATR) 2978, 2236, 1411, 1069 cm$^{-1}$. |
| 215 | ESIMS m/z 408.2 [M + H]$^+$ | $^1$H NMR (300 MHz, CDCl$_3$) δ 9.09 (s, 2H), 8.84 (s, 2H), 8.67 (s, 1H), 7.90-7.79 (m, 1H), 7.77-7.66 (m, 1H), 7.48-7.40 (m, 1H), 7.18-7.06 (m, 2H), 3.48 (q, J = 7.0 Hz, 2H), 2.05 (s, 3H), 1.33 (t, J = 7.0 Hz, 3H). $^{13}$C NMR (75 MHz, CDCl$_3$) δ 162.39, 161.03, 158.51, 157.33, 149.67, 149.58, 148.57, 148.54, 138.48, 137.08, 137.05, 131.16, 129.13, 124.10, 123.96, 121.60, 120.24,, 119.03, 117.04, 117.06, 109.79, 109.52, 80.05, 51.06, 23.31. |
| 216 | ESIMS m/z 433.5 [M + H]$^+$ | $^1$H NMR (300 MHz, CDCl$_3$) δ 9.23 (s, 2H), 9.09 (s, 1H), 8.59 (dd, J = 2.0, 1.0 Hz, 1H), 7.86 (d, J = 2.1 Hz, 1H), 7.84 (d, J = 1.0 Hz, 1H), 7.44 (d, J = 1.9 Hz, 1H), 7.31 (dd, J = 8.0, 2.0 Hz, 1H), 7.22 (d, J = 8.0 Hz, 1H), 6.30 (s, 1H), 2.42 (s, 3H), 1.79 (s, 6H), 1.09 (s, 9H). $^{13}$C NMR (126 MHz, CDCl$_3$) δ 159.25, 158.68, 156.90, 156.43, 147.21, 142.40, 138.62, 137.54, 137.11, 135.79, 134.67, 130.58, 124.07, 122.80, 121.73, 121.49, 40.14, 37.26, 29.11, 26.35, 15.97. |
| 217 | ESIMS m/z 400.44 [M + H]$^+$ | $^1$H NMR (300 MHz, CDCl$_3$) δ 9.14 (s, 1H), 8.99 (s, 2H), 8.75 (t, J = 1.5 Hz, 1H), 7.93-7.84 (m, 2H), 7.62-7.48 (m, 2H), 7.32 (d, J = 7.7 Hz, 2H), 3.44 (s, 3H), 2.08 (s, 3H). $^{13}$C NMR (75 MHz, CDCl$_3$) δ 159.26, 157.95, 149.38, 147.89, 135.89, 135.72, 135.33, 134.65, 128.58, 121.54, 120.64, 88.19, 79.05, 75.85, 52.68, 3.93. |
| 218 | ESIMS m/z 449 [M + H]$^+$ | $^1$H NMR (300 MHz, CDCl$_3$) δ 9.19 (s, 1H), 8.71 (s, 1H), 8.66 (s, 1H), 8.38 (d, J = 2.4 Hz, 1H), 7.88 (d, J = 2.4 Hz, 1H), 7.85 (d, J = 2.4 Hz, 1H), 7.80 (d, J = 1.5 Hz, 1H), 6.98 (d, J = 8.7 Hz, 1H) 5.70 (s, 1H), 4.82 (q, J = 8.4 Hz, 2H), 3.82 (s, 3H), 1.17 (s, 9H). $^{13}$C NMR (101 MHz, CDCl$_3$) δ 166.3, 162.0, 161.5, 157.5, 156.5, 144.6, 137.87, 133.50, 131.16, 128.02, 125.42, 123.93, 123.15, 121.74, 111.36, 80.34, 62.20, 53.44, 40.34, 26.68 20.4. $^{19}$F NMR (276 MHz, CDCl$_3$) δ −73.7 (t). |
| 219 | ESIMS m/z 434 [M + H]$^+$ | $^1$H NMR (400 MHz, CDCl$_3$) δ 8.85 (s, 1H), 8.62 (d, J = 1.6 Hz, 1H), 8.45 (s, 2H), 7.87 (dd, J = 10.8, 6.0 Hz, 1H), 7.74 (d, J = 8.0 Hz, 2H), 7.58 (d, J = 8.4 Hz, 2H), 7.52 (d, J = 8.4 Hz, 2H), 3.34 (t, J = 21.6 Hz, 2H), 1.02 (s, 9H). |
| 220 | ESIMS m/z 450.47 [M + H]$^+$ | $^1$H NMR (400 MHz, CDCl$_3$) δ 9.65 (s, 2H), 9.12 (s, 1H), 8.80 (s, 1H), 7.89 (td, J = 1.8, 8.6 Hz, 1H), 7.66 (d, J = 8.3 Hz, 1H), 7.52 (t, J = 8.6 Hz, 1H), 7.19-7.07 (m, 2H), 3.35-3.16 (m, 2H), 1.33 (t, J = 6.8 Hz, 3H), 0.91 (s, 9H). $^{19}$F NMR (376 MHz, CDCl$_3$) δ −57.96 −113.22. |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 221 | ESIMS m/z 380.38 [M + H]$^+$ | $^1$H NMR (300 MHz, DMSO-d6) δ 9.05 (s, 1H), 8.94 (s, 2H), 8.69 (s, 1H), 8.03 (td, J = 1.7, 8.3 Hz, 1H), 7.90 (d, J = 8.4 Hz, 1H), 7.75 (t, J = 8.8 Hz, 1H), 7.56 (d, J = 11.0 Hz, 1H), 7.38 (d, J = 8.4 Hz, 1H), 6.47 (s, 1H), 1.96 (s, 3H). |
| 222 | ESIMS m/z 448 [M + H]$^+$ | $^1$H NMR (300 MHz, CDCl$_3$) δ 9.20 (s, 1H), 8.67 (s, 1H), 8.46 (d, J = 1.5 Hz, 1H), 7.74 (d, J = 8.1 Hz, 1H), 7.58 (dd, J = 8.1, 2.1 Hz, 1H), 7.24 (d, J = 9.6 Hz, 1H), 7.13 (d, J = 11.4 Hz, 2H) 5.72 (bs, 1H). 82 (s, 3H), 2.27 (s, 3H) 1.17 (s, 9H). $^{13}$C NMR (101 MHz, CDCl$_3$) δ 166.47,, 161.48, 157.45, 156.57, 148.90, 146.67, 137.85, 136.44, 136.06, 134.36, 131.12, 124.22, 122.71, 122.45, 122.19, 118.77, 118.40, 80.32, 53.42, 40.27, 26.76, 20.49. $^{19}$F NMR (282 MHz, CDCl$_3$) δ −57.9. |
| 223 | ESIMS m/z 401.6 [M + H]$^+$ | $^1$H NMR (400 MHz, CDCl$_3$) δ 9.23 (s, 2H), 9.09 (s, 1H), 8.53 (d, J = 1.5 Hz, 1H), 7.85 (d, J = 8.3 Hz, 1H), 7.74 (dd, J = 8.3, 2.1 Hz, 1H), 7.45-7.34 (m, 2H), 7.24 (d, J = 8.0 Hz, 3H), 6.30 (s, 1H), 2.30 (s, 3H), 1.77 (s, 6H), 1.09 (s, 9H). IR (ATR) 2979, 2238, 1409, 1071 cm$^{-1}$. |
| 224 | ESIMS m/z 418.43 [M + H]$^+$ | $^1$H NMR (300 MHz, CDCl$_3$) δ 9.47 (s, 1H), 8.53-8.47 (m, 3H), 8.33 (d, J = 8.1 Hz, 1H), 7.63 (dd, J = 8.4, 2.1 Hz, 1H), 7.26-7.21 (m, 1H), 7.15-7.10 (m, 2H), 6.78 (s, 1H), 2.26 (s, 3H), 1.01 (s, 9H). $^{13}$C NMR (75 MHz, CDCl$_3$) δ 158.63, 158.14, 148.88, 146.13, 145.80, 142.49, 141.13, 137.91, 136.42, 136.32, 134.82, 131.16, 123.52, 122.71, 118.38, 80.11, 41.022, 26.055, 20.54. |
| 225 | ESIMS m/z 418.43 [M + H]$^+$ | $^1$H NMR (400 MHz, CDCl$_3$) δ 9.45 (s, 1H), 8.72 (d, J = 2.0 Hz, 1H), 8.51 (s, 1H), 8.46 (d, J = 2.0 Hz, 1H), 8.31 (d, J = 8.4 Hz, 1H), 7.83 (dd, J = 8.4, 2.4 Hz, 1H), 7.54 (d, J = 8.8 Hz, 2H), 7.04 (d, J = 8.8 Hz, 2H), 6.79 (s, 1H), 4.43-4.37 (m, 2H), 1.01 (s, 9H). $^{13}$C NMR (75 MHz, CDCl$_3$) δ 158.31, 158.26, 157.45, 145.75, 144.25, 142.43, 141.10, 134.41, 133.90, 131.79, 128.42, 123.97, 115.54, 80.07, 66.12, 40.98, 26.04. |
| 226 | ESIMS m/z 405.6 [M + H]$^+$ | $^1$H NMR (400 MHz, CDCl$_3$) δ 9.22 (s, 2H), 9.09 (s, 1H), 8.77-8.71 (m, 1H), 7.97 (ddd, J = 8.4, 2.2, 1.6 Hz, 1H), 7.87 (dd, J = 8.4, 0.8 Hz, 1H), 7.54-7.37 (m, 2H), 7.32 (dd, J = 11.7, 1.9 Hz, 1H), 6.15 (s, 1H), 1.78 (s, 6H), 1.09 (s, 9H). IR (ATR) 2982, 2361, 1419, 1071 cm$^{-1}$. |
| 227 | ESIMS m/z 398 [M + H]$^+$ | $^1$H NMR (400 MHz, CDCl$_3$) δ 8.58 (d, J = 1.8 Hz, 1H), 8.23 (dd, J = 4.8, 1.8 Hz, 2H), 7.81 (dd, J = 8.1, 2.4 Hz, 1H), 7.54-7.48 (m, 4H), 7.37 (d, J = 8.4 Hz, 2H), 6.99 (dd, J = 7.5, 4.8 Hz, 1H), 3.34 (s, 2H), 1.78 (dd, J = 7.5, 5.1 Hz, 2H), 1.44 (dd, J = 7.8, 4.8 Hz, 2H), 1.04 (s, 9H). |
| 228 | ESIMS m/z 419.5 [M + H]$^+$ | $^1$H NMR (300 MHz, CDCl$_3$) δ 9.69 (s, 2H), 9.13 (s, 1H), 8.83 (s, 1H), 7.98-7.88 (m, 1H), 7.68 (dd, J = 8.4, 0.8 Hz, 1H), 7.53 (t, J = 8.0 Hz, 1H), 7.41 (dd, J = 8.1, 2.0 Hz, 1H), 7.33 (dd, J = 11.7, 1.9 Hz, 1H), 3.20 (s, 3H), 1.78 (s, 6H), 0.90 (s, 9H). IR (ATR) 2924, 2238, 1418, 1069 cm$^{-1}$. |
| 229 | ESIMS m/z 385.46 [M + H]$^+$ | $^1$H NMR (300 MHz, CDCl$_3$) δ 9.47 (s, 1H), 8.74 (d, J = 2.4 Hz, 1H), 8.51-8.47 (m, 2H), 8.34 (d, J = 8.4 Hz, 1H), 7.86 (dd, J = 8.4, 2.4 Hz, 1H), 7.56 (d, J = 8.4 Hz, 2H), 7.40 (d, J = 8.7 Hz, 2H), 6.90 (bs, 1H), 1.80-1.76 (m, 2H), 1.47-1.43 (m, 2H), 1.01 (s, 9H). $^{13}$C NMR (75 MHz, CDCl$_3$) δ 158.96, 158.11, 145.76, 144.42, 142.45, 141.08, 136.82, 136.06, 134.28, 134.11, 127.51, 126.32, 124.04, 122.26, 80.10, 40.99, 26.03, 18.40, 13.62. |
| 230 | ESIMS m/z 408.40 [M + H]$^+$ | $^1$H NMR (300 MHz, DMSO-d6) δ 9.08 (s, 2H), 9.03 (s, 1H), 8.75 (s, 1H), 8.02 (d, J = 8.4 Hz, 1H), 7.90 (d, J = 8.4 Hz, 1H), 7.76 (t, J = 8.8 Hz, 1H), 7.56 (d, J = 11.0 Hz, 1H), 7.37 (d, J = 8.4 Hz, 1H), 6.06 (s, 1H), 3.08 (td, J = 6.8, 13.6 Hz, 1H), 0.80 (d, J = 7.0 Hz, 3H), 0.73 (d, J = 7.0 Hz, 3H). $^{19}$F NMR (282.2 MHz, DMSO-d6) δ −56.96 −113.68. |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 231 | ESIMS m/z 433 [M + H]$^+$ | $^1$H NMR (400 MHz, CDCl$_3$) δ 8.61 (s, 1H), 8.24 (d, J = 6.0 Hz, 2H), 7.84 (dd, J = 6.3, 1.8 Hz, 1H), 7.73 (d, J = 6.3 Hz, 2H), 7.60-7.49 (m, 4H), 6.99 (dd, J = 5.7, 3.6 Hz, 1H), 2.61 (s, 2H), 1.05 (s, 9H). $^{13}$C NMR (75 MHz, CDCl$_3$): δ 160.0, 151.3, 147.1, 145.1, 139.6, 138.4, 136.8, 134.0, 133.4, 133.2, 127.9, 124.3, 122.1, 80.2, 39.5, 37.1, 29.6, 25.9 |
| 232 | ESIMS m/z 416.42 [M + H]$^+$ | $^1$H NMR (300 MHz, CDCl$_3$) δ 9.12 (s, 1H), 8.85 (s, 2H), 8.72 (d, J = 2.2 Hz, 1H), 7.92-7.85 (m, 1H), 7.81-7.74 (m, 1H), 7.59 (d, J = 8.4 Hz, 2H), 7.33 (d, J = 8.1 Hz, 2H), 3.55-3.40 (m, 2H), 1.70 (tt, J = 5.5, 8.3 Hz, 1H), 1.27 (t, J = 7.0 Hz, 3H), 0.75-0.62 (m, 2H), 0.56-0.45 (m, 1H), 0.41-0.31 (m, 1H). $^{19}$F NMR (282.2 MHz, CDCl$_3$) δ -57.8. |
| 233 | ESIMS m/z 433.6 [M + H]$^+$ | $^1$H NMR (400 MHz, CDCl$_3$) δ 9.19 (s, 1H), 8.68 (s, 1H), 8.67 (s, 1H), 7.85-7.80 (m, 1H), 7.77 (dd, J = 8.4, 0.8 Hz, 1H), 7.46 (t, J = 8.0 Hz, 1H), 7.21 (dd, J = 8.1, 1.9 Hz, 1H), 7.11 (dd, J = 11.4, 1.9 Hz, 1H), 5.71 (s, 1H), 3.82 (s, 3H), 1.82 (q, J = 5.1 Hz, 2H), 1.47 (q, J = 5.5 Hz, 2H), 1.17 (s, 9H). IR (ATR) 2969, 2237, 1738, 1471 cm$^{-1}$. |
| 234 | ESIMS m/z 432 [M + H]$^+$ | 8.53 (s, 1H), 8.29 (d, J = 2.0 Hz, 1H), 8.21 (d, J = 11.2 Hz, 2H), 7.77 (td, J = 8.8, 2.8 Hz, 2H), 7.54-7.47 (m, 2H), 7.10 (m, 2H ), 4.78 (q, J = 16.8 Hz, 1H), 3.34 (s, 2H), 3.28 (s, 2H), 1.07 (s, 9H). $^{13}$C NMR (75 MHz, CDCl$_3$) δ 161.6, 159.5, 151.3, 147.1, 144.6, 138.4, 137.8, 133.5, 133.4, 131.1, 127.7, 122.5, 122.2, 111.3, 80.2, , 62.0, 39.5, 37.1, 25.9. |
| 235 | ESIMS m/z 437.5 [M + H]$^+$ | $^1$H NMR (400 MHz, CDCl$_3$) δ 8.77 (d, J = 1.5 Hz, 1H), 8.52 (dd, J = 8.0, 1.8 Hz, 1H), 8.30 (dd, J = 4.6, 1.8 Hz, 1H), 7.77 (dd, J = 8.3, 2.3 Hz, 1H), 7.66-7.59 (m, 2H), 7.34 (d, J = 7.9 Hz, 2H), 7.30-7.26 (m, 2H), 5.59 (s, 1H), 1.26 (s, 9H). $^{19}$F NMR (376 MHz, CDCl$_3$) δ -57.82 (s). |
| 236 | ESIMS m/z 403.6 [M + H]$^+$ | $^1$H NMR (400 MHz, CDCl$_3$) δ 9.22 (s, 2H), 9.08 (s, 1H), 8.72 (d, J = 1.0 Hz, 1H), 7.98-7.92 (m, 1H), 7.86 (dd, J = 8.4, 0.8 Hz, 1H), 7.44 (d, J = 8.0 Hz, 1H), 7.22 (dd, J = 8.1, 1.9 Hz, 1H), 7.12 (dd, J = 11.5, 1.9 Hz, 1H), 6.14 (s, 1H), 1.83 (q, J = 5.1 Hz, 2H), 1.48 (q, J = 5.5 Hz, 2H), 1.09 (s, 9H). IR (ATR) 2969, 2238, 1421, 1205 cm$^{-1}$. |
| 237 | ESIMS m/z 418.18 [M + H]$^+$ | $^1$H NMR (400 MHz, CDCl$_3$) δ 9.11 (s, 1H), 8.85 (s, 2H), 8.69 (s, 1H), 7.87 (td, J = 2.0, 8.3 Hz, 1H), 7.76 (d, J = 8.3 Hz, 1H), 7.45 (t, J = 8.6 Hz, 1H), 7.18-7.06 (m, 2H), 4.17 (t, J = 2.7 Hz, 2H), 2.44 (t, J = 2.4 Hz, 1H), 2.11 (s, 3H). $^{13}$C NMR (101 MHz, CDCl$_3$) δ 161.64, 161.06, 158.51, 157.53, 155.18, 149.74, 149.63, 148.62, 148.59, 138.114, 137.24, 137.22, 131.16, 131.12, 129.44, 123.98, 123.84, 121.60, 119.02, 117.06, 109.80, 109.54, 81.04, 79.85, 74.46, 52.29, 24.07. |
| 238 | ESIMS m/z 432.46 [M + H]$^+$ | $^1$H NMR (300 MHz, CDCl$_3$) δ 9.11 (s, 1H), 8.85 (s, 2H), 8.68 (s, 1H), 7.91-7.82 (m, 1H), 7.79-7.72 (m, 1H), 7.50-7.39 (m, 1H), 7.18-7.04 (m, 2H), 4.06 (d, J = 2.2 Hz, 2H), 2.76-2.62 (m, 1H), 2.61-2.48 (m, 1H), 2.45 (t, J = 2.4 Hz, 3H). $^{13}$C NMR (75 MHz, CDCl$_3$) δ 161.39, 160.91, 158.06, 157.45, 155.54, 149.72, 149.58, 148.62, 137.04, 136.99, 136.72, 131.16, 131.10, 129.28, 123.99, 123.80, 122.01, 121.26, 118.58, 117.05, 109.84, 109.84, 109.49, 83.36, 79.43, 74.40, 51.69, 27.16, 7.08. $^{19}$F NMR (282 MHz, CDCl$_3$): δ -57.98, -113.30. |
| 239 | HRMS-ESI (m/z) [M + H]$^+$ calcd for C$_{24}$H$_{27}$N$_5$O, 401.2216; found, 401.2221 | $^1$H NMR (300 MHz, DMSO-d6) d 9.46 (s, 2H), 9.06 (s, 1H), 8.86 (dd, J = 2.3, 0.8 Hz, 1H), 8.70 (dd, J = 2.4, 0.7 Hz, 1H), 8.07 (dd, J = 8.4, 2.3 Hz, 1H), 7.99-7.90 (m, 2H), 6.29 (s, 1H), 2.41 (d, J = 0.7 Hz, 3H), 1.78 (s, 6H), 0.95 (s, 9H). $^{13}$C NMR (126 MHz, DMSO) d 163.24, 157.08, 156.91, 154.68, 147.50, 144.55, 137.06, 137.03, 136.61, 136.37, 133.92, 131.88, 124.39, 122.36, 79.44, 35.28, 28.34, 26.26, 20.04, 15.64. |
| 240 | ESIMS m/z 417.6 [M + H]$^+$ | $^1$H NMR (400 MHz, CDCl$_3$) δ 9.19 (s, 1H), 8.80-8.73 (m, 1H), 8.67 (s, 1H), 7.85 (dd, J = 8.4, 2.4 Hz, 1H), 7.80-7.73 (m, 1H), 7.65-7.56 (m, 4H), 5.73 (s, 1H), 3.81 (s, 3H), 1.78 (s, 6H), 1.17 (s, 9H). IR (ATR) 2959, 1558, 1471, 1011 cm$^{-1}$. |

TABLE 2-continued

| Compound Number | Mass Spec | NMR ($^1$H, $^{13}$C, $^{19}$F) IR (Thin Film; cm$^{-1}$) |
|---|---|---|
| 241 | ESIMS m/z 376.42 [M + H]$^+$ | $^1$H NMR (400 MHz, CDCl$_3$) δ 9.10 (s, 1H), 8.83 (s, 2H), 8.74 (d, J = 2.0 Hz, 1H), 7.86 (dd, J = 2.4, 8.3 Hz, 1H), 7.69 (d, J = 8.3 Hz, 1H), 7.60-7.54 (m, 2H), 7.32 (d, J = 8.3 Hz, 2H), 3.33 (s, 3H), 2.04 (s, 3H). $^{13}$C NMR (101 MHz, CDCl$_3$) δ 161.96, 157.29, 155.22, 149.27, 147.23, 138.58, 136.10, 135.24, 134.07, 128.51, 124.27, 121.53, 120.51, 79.99, 51.029, 23.32. |
| 242 | ESIMS m/z 414.47 [M + H]$^+$ | $^1$H NMR (300 MHz, CDCl$_3$) δ = 9.13 (s, 1H), 8.98 (s, 2H), 8.79-8.67 (m, 1H), 7.98-7.83 (m, 2H), 7.61-7.51 (m, 2H), 7.32 (br d, J = 8.4 Hz, 2H), 3.79-3.65 (m, 1H), 3.63-3.47 (m, 1H), 2.06 (s, 3H), 1.33 (t, J = 7.0 Hz, 3H). $^{13}$C NMR (75 MHz, CDCl$_3$): δ 159.76, 157.87, 155.88, 147.81, 136.27, 135.97, 135.32, 128.57, 121.54, 120.47, 109.97, 87.62, 78.33, 60.81, 15.26, 3.95. |
| 243 | ESIMS m/z 400.4 [M + H]$^+$ | $^1$H NMR (300 MHz, CDCl$_3$) δ 9.12 (s, 1H), 8.85 (s, 2H), 8.74 (d, J = 1.8 Hz, 1H), 7.90-7.85 (m, 1H), 7.78-7.72 (m, 1H), 7.60-7.55 (m, 2H), 7.33 (d, J = 8.1 Hz, 2H), 4.16 (t, J = 2.4 Hz, 2H), 2.45 (t, J = 2.4 Hz, 1H), 2.11 (s, 3H). $^{13}$C NMR (75 MHz, CDCl$_3$) δ 161.17, 149.34, 147.27, 138.24, 135.94, 135.44, 134.38, 128.55, 122.14, 121.56, 120.74, 118.73, 109.97, 80.98, 79.84, 74.46, 52.26, 20.62. |
| 244 | ESIMS m/z 404.37 [M + H]$^+$ | $^1$H NMR (300 MHz, CDCl$_3$) δ 9.08 (s, 1H), 8.82 (s, 2H), 8.74-8.69 (m, 1H), 7.83 (dd, J = 2.4, 8.3 Hz, 1H), 7.71 (d, J = 8.1 Hz, 1H), 7.57 (d, J = 8.8 Hz, 2H), 7.32 (br d, J = 8.1 Hz, 2H), 3.36 (q, J = 7.0 Hz, 2H), 2.68 (qd, J = 7.3, 14.7 Hz, 1H), 2.50 (qd, J = 7.2, 14.6 Hz, 1H), 1.32 (t, J = 7.0 Hz, 3H), 0.77 (t, J = 7.2 Hz, 3H). $^{13}$C NMR (75 MHz, CDCl$_3$) δ 161.81, 157.15, 155.51, 149.24, 147.21, 137.76, 136.18, 134.97, 133.77, 128.50, 121.53, 121.27, 81.90, 57.84, 26.93, 15.39, 6.89. |
| 246 | ESIMS m/z 414 [M + H]$^+$ | $^1$H NMR (300 MHz, CDCl$_3$) δ 9.19 (s, 1H) 8.76 (d, J = 2.0 Hz, 1H ), 8.66 (s, 1H), 7.88-7.83 (m, 1H), 7.77 (d, J = 8.4 Hz, 1H), 7.68-7.59 (m, 4H), 5.72 (bs, 1H), 3.82 (s, 3H), 1.96 (—F2CH3, t, J = 18,36.3 Hz, 3H), 1.16 (s, 9H). $^{13}$C NMR (75 MHz, CDCl$_3$) δ 166.42, 161.94, 157.51, 156.60, 145.10, 138.86, 138.27, 137.92, 133.96, 133.84, 127.11, 125.44, 125.37, 124.11, 123.04, 121.66, 80.34, 53.51, 40.32, 26.13. $^{19}$F NMR (282 MHz, CDCl$_3$) δ −87.59 (dd). |
| 247 | ESIMS m/z 384 [M + H]$^+$ | $^1$H NMR (400 MHz, CDCl$_3$) δ 9.18 (s, 1H) 8.72 (d, J = 2.4 Hz, 1H ), 8.66 (s, 1H), 7.83-7.73 (m, 2H), 7.52 (d, J = 8.4 Hz, 2H), 7.45 (d. J = 8.4 Hz, 2H), 5.71 (s, 1H), 3.82 (s, 3H), 1.16 (s, 9H). $^{13}$C NMR (101 MHz, CDCl$_3$) δ 171.04, 166.35, 161.75, 157.51, 156.55, 144.84, 135.79, 134.30, 133.67, 133.50, 129.24, 128.18, 124.05, 122.99, 80.28, 60.31, 53.43, 40.28, 26.70. |
| 248 | ESIMS m/z 442.42 [M + H]$^+$ | $^1$H NMR (300 MHz, CDCl$_3$) δ 9.16 (s, 1H), 9.01 (s, 2H), 8.68 (s, 1H), 7.94 (q, J = 8.3 Hz, 2H), 7.44 (t, J = 8.4 Hz, 1H), 7.17-7.03 (m, 2H), 4.47-4.38 (m, 1H), 4.35-4.24 (m, 1H), 2.44-2.32 (m, 1H), 2.08 (s, 3H). $^{13}$C NMR (75 MHz, CDCl$_3$) δ 160.99, 159.12, 158.42, 158.12, 156.02, 149.79, 149.68, 149.66, 149.11, 149.02, 137.34, 135.31, 131.16, 131.12, 129.94, 123.80, 121.57, 120.41, 118.99, 117.08, 109.80, 89.34, 79.02, 75.27, 74.73, 53.73. $^{19}$F NMR (282 MHz, CDCl$_3$): δ −57.97, −113.23. |
| 249 | ESIMS m/z 422.46 [M + H]$^+$ | $^1$H NMR (300 MHz, CDCl$_3$) δ 9.15 (s, 1H), 8.86 (s, 2H), 8.76 (s, 1H), 7.95-7.85 (m, 1H), 7.63-7.45 (m, 2H), 7.15 (br t, J = 10.6 Hz, 2H), 3.06 (m, 4H), 0.88 (t, J = 6.6 Hz, 6H). $^{19}$F NMR (282.2 MHz, CDCl$_3$) δ −57.96 −113.17. |
| 250 | ESIMS m/z 444.43 [M + H]$^+$ | $^1$H NMR (400 MHz, CDCl$_3$) δ 9.14 (s, 1H), 8.87 (s, 2H), 8.67 (s, 1H), 7.94-7.88 (m, 1H), 7.86-7.81 (m, 1H), 7.47 (t, J = 8.6 Hz, 1H), 7.20-7.06 (m, 2H), 4.23 (d, J = 2.0 Hz, 2H), 2.39 (t, J = 2.4 Hz, 1H), 1.72 (tt, J = 5.4, 8.3 Hz, 1H), 0.76 (d, J = 8.3 Hz, 2H), 0.62-0.53 (m, 1H), 0.44-0.36 (m, 1H). $^{19}$F NMR (376 MHz, CDCl$_3$) δ −57.95 −113.28. |
| 251 | ESIMS m/z 417.6 [M + H]$^+$ | $^1$H NMR (300 MHz, CDCl$_3$) δ 9.22 (s, 2H), 9.09 (s, 1H), 8.74 (s, 1H), 8.01-7.94 (m, 1H), 7.87 (dd, J = 8.4, 0.9 Hz, 1H), 7.50 (t, J = 8.0 Hz, 1H), 7.36 (d, J = 1.9 Hz, 1H), 7.32 (dd, J = 8.5, 1.9 Hz, 1H), 6.16 (s, 1H), 2.94-2.83 (m, 2H), 2.65 (dt, J = 9.5, 5.9 Hz, 2H), 2.57-2.40 (m, 1H), 2.21-2.06 (m, 1H), 1.09 (s, 9H). |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 252 | ESIMS m/z 415.6 [M + H]$^+$ | $^1$H NMR (400 MHz, CDCl$_3$) δ 9.25 (s, 2H), 9.10 (s, 1H), 8.37 (d, J = 1.4 Hz, 1H), 7.91-7.84 (m, 1H), 7.60 (dd, J = 8.2, 2.2 Hz, 1H), 7.23 (d, J = 9.2 Hz, 2H), 6.35 (s, 1H), 2.04 (d, J = 18.9 Hz, 6H), 1.76 (s, 6H), 1.08 (s, 9H). |
| 253 | ESIMS m/z 433.6 [M + H]$^+$ | $^1$H NMR (400 MHz, CDCl$_3$) δ 9.68 (s, 2H), 9.13 (s, 1H), 8.84 (d, J = 1.9 Hz, 1H), 8.41 (d, J = 2.0 Hz, 1H), 7.89 (ddd, J = 8.8, 6.5, 2.6 Hz, 2H), 7.68 (d, J = 8.4 Hz, 1H), 7.01 (d, J = 8.5 Hz, 1H), 4.83 (q, J = 8.5 Hz, 2H), 3.19 (s, 3H), 0.90 (s, 9H). $^{19}$F NMR (376 MHz, CDCl$_3$) δ -73.79 (s). |
| 254 | ESIMS m/z 429.6 [M + H]$^+$ | $^1$H NMR (400 MHz, CDCl$_3$) δ 9.19 (s, 1H), 8.67 (s, 1H), 8.46 (dd, J = 2.3, 0.8 Hz, 1H), 7.73 (dd, J = 8.3, 0.8 Hz, 1H), 7.58 (dd, J = 8.3, 2.3 Hz, 1H), 7.26-7.12 (m, 3H), 5.73 (s, 1H), 3.81 (s, 3H), 2.27 (s, 3H), 1.76 (q, J = 5.0 Hz, 2H), 1.45 (q, J = 5.3 Hz, 2H), 1.18 (s, 9H). IR (ATR) 2958, 2237, 1559, 1470 cm$^{-1}$. |
| 255 | ESIMS m/z 426.42 [M + H]$^+$ | $^1$H NMR (300 MHz, CDCl$_3$) δ 9.14 (s, 1H), 8.86 (s, 2H), 8.76-8.70 (m, 1H), 7.92-7.87 (m, 1H), 7.86-7.78 (m, 1H), 7.64-7.53 (m, 2H), 7.33 (d, J = 7.8 Hz, 2H), 4.22 (d, J = 2.2 Hz, 2H), 2.39 (t, J = 2.4 Hz, 1H), 1.72 (tt, J = 5.5, 8.3 Hz, 1H), 0.76 (d, J = 8.4 Hz, 2H), 0.63-0.51 (m, 1H), 0.44-0.34 (m, 1H). $^{19}$F NMR (282.2 MHz, CDCl$_3$) δ -57.8. |
| 256 | ESIMS m/z 435.6 [M + H]$^+$ | $^1$H NMR (400 MHz, CDCl$_3$) δ 9.19 (s, 1H), 8.70 (s, 1H), 8.67 (s, 1H), 7.87-7.81 (m, 1H), 7.77 (dd, J = 8.4, 0.8 Hz, 1H), 7.50 (t, J = 8.1 Hz, 1H), 7.39 (dd, J = 8.2, 2.0 Hz, 1H), 7.31 (dd, J = 11.7, 1.9 Hz, 1H), 5.72 (s, 1H), 3.82 (s, 3H), 1.77 (s, 6H), 1.17 (s, 9H). IR (ATR) 2959, 2361, 1471, 1011 cm$^{-1}$. |
| 257 | ESIMS m/z 432.6 [M + H]$^+$ | $^1$H NMR (400 MHz, CDCl$_3$) δ 9.69 (s, 2H), 9.13 (s, 1H), 8.88-8.82 (m, 1H), 7.89 (dd, J = 8.4, 2.5 Hz, 1H), 7.64 (dd, J = 8.4, 0.8 Hz, 1H), 7.62-7.56 (m, 2H), 7.08 (d, J = 8.8 Hz, 2H), 4.42 (q, J = 8.1 Hz, 2H), 3.19 (s, 3H), 0.89 (s, 9H). IR (ATR) 2959, 1476, 1239, 1163 cm$^{-1}$. |
| 258 | ESIMS m/z 376.35 [M + H]$^+$ | $^1$H NMR (400 MHz, CDCl$_3$) δ 9.10 (s, 1H), 8.94 (s, 2H), 8.74 (d, J = 1.5 Hz, 1H), 7.89 (dd, J = 2.4, 8.4 Hz, 1H), 7.61-7.53 (m, 2H), 7.44 (d, J = 8.4 Hz, 1H), 7.34 (d, J = 7.8 Hz, 2H), 5.77 (s, 1H), 2.43-2.30 (m, 2H), 0.93 (t, J = 7.3 Hz, 3H). $^{13}$C NMR (101 MHz, CDCl$_3$): δ 160.61, 157.35, 155.036, 149.50, 146.14, 139.26, 135.98, 135.61, 134.64, 128.59, 121.75, 121.61, 120.06, 75.56, 33.80, 7.64. |
| 259 | ESIMS m/z 459.4 [M + H]$^+$ | $^1$H NMR (400 MHz, CDCl$_3$) δ 9.09 (s, 1H), 9.05 (s, 2H), 8.84-8.78 (m, 1H), 7.87 (dd, J = 8.4, 2.5 Hz, 1H), 7.68-7.55 (m, 5H), 1.78 (s, 6H), 1.10 (s, 9H), 0.00 (s, 9H). IR (ATR) 2959, 1412, 1252, 1096 cm$^{-1}$. |
| 260 | ESIMS m/z 414.4 [M + H]$^+$ | $^1$H NMR (300 MHz, CDCl$_3$) δ 9.11 (s, 1H), 8.84 (s, 2H), 8.74 (d, J = 1.5 Hz, 1H), 7.90-7.82 (m, 1H), 7.77-7.71 (m, 1H), 7.58 (d, J = 8.4 Hz, 2H), 7.33 (br d, J = 8.4 Hz, 2H), 4.05 (d, J = 2.2 Hz, 2H), 2.76-2.61 (m, 1H), 2.60-2.47 (m, 1H), 2.47-2.42 (m, 1H), 0.83 (t, J = 7.3 Hz, 3H). $^{13}$C NMR (75 MHz, CDCl$_3$): δ 160.53, 157.40, 155.52, 149.34, 147.32, 136.82, 135.97, 135.19, 131.17, 128.52, 121.53, 83.34, 79.46, 74.37, 51.65, 27.17, 7.08. |
| 261 | ESIMS m/z 432.5 [M + H]$^+$ | $^1$H NMR (400 MHz, CDCl$_3$) δ 9.70 (s, 2H), 9.13 (s, 1H), 8.61 (d, J = 1.1 Hz, 1H), 7.75-7.63 (m, 3H), 7.19-7.12 (m, 2H), 3.21 (s, 3H), 2.31 (s, 3H), 0.90 (s, 9H). IR (ATR) 2961, 2360, 1411, 1211 cm$^{-1}$. |
| 262 | ESIMS m/z 404.5 [M + H]$^+$ | $^1$H NMR (400 MHz, CDCl$_3$) δ 8.85 (t, J = 1.8 Hz, 1H), 8.76 (d, J = 1.5 Hz, 1H), 8.33 (d, J = 2.8 Hz, 1H), 8.01-7.92 (m, 2H), 7.89 (dd, J = 8.3, 0.7 Hz, 1H), 7.61 (s, 4H), 6.33 (s, 1H), 1.78 (s, 6H), 1.09 (s, 9H). $^{19}$F NMR (376 MHz, CDCl$_3$) δ -127.55 (s). |
| 263 | HRMS-ESI (m/z) [M + H]+ calcd for C$_{25}$H$_{28}$N$_4$O$_2$, 416.2212; found, 416.2204 | $^1$H NMR (400 MHz, DMSO-d6) d 9.43 (s, 2H), 9.06 (s, 1H), 8.76 (dd, J = 2.3, 0.7 Hz, 1H), 7.97 (dd, J = 8.4, 2.3 Hz, 1H), 7.88 (dd, J = 8.4, 0.9 Hz, 1H), 7.52-7.41 (m, 1H), 7.22 (d, J = 6.9 Hz, 2H), 6.22 (s, 1H), 3.85 (s, 3H), 1.76 (s, 6H), 0.95 (s, 9H). $^{13}$C NMR (126 MHz, DMSO) d 161.07, 155.98, 155.80, 146.29, 142.57, 136.10, 130.68, 130.17, 124.87, 123.94, 121.33, 117.09, 108.17, 78.32, 55.19, 36.29, 27.64, 25.24. |

TABLE 2-continued

Analytical Data.

| Compound Number | Mass Spec | NMR ($^1$H, $^{13}$C, $^{19}$F)<br>IR (Thin Film; cm$^{-1}$) |
|---|---|---|
| 264 | ESIMS<br>m/z 429.4<br>[M + H]$^+$ | $^1$H NMR (300 MHz, CDCl$_3$) δ 9.24 (s, 2H), 9.09 (s, 1H), 8.59-8.51 (m, 1H), 7.85 (dd, J = 8.2, 0.7 Hz, 1H), 7.76 (dd, J = 8.3, 2.2 Hz, 1H), 7.34-7.27 (m, 2H), 7.23 (d, J = 8.0 Hz, 1H), 6.34 (s, 1H), 2.30 (s, 3H), 2.08 (dd, J = 13.9, 7.3 Hz, 2H), 1.95 (dd, J = 13.9, 7.3 Hz, 2H), 1.09 (s, 9H), 0.96 (t, J = 7.4 Hz, 6H).<br>IR (ATR) 2970, 2234, 1409, 908 cm$^{-1}$. |
| 265 | ESIMS<br>m/z 421.5<br>[M + H]$^+$ | $^1$H NMR (400 MHz, CDCl$_3$) δ 9.23 (s, 2H), 9.09 (s, 1H), 8.63 (dd, J = 2.1, 0.9 Hz, 1H), 7.95-7.82 (m, 2H), 7.62 (d, J = 2.0 Hz, 1H), 7.50 (dd, J = 8.0, 2.0 Hz, 1H), 7.38 (d, J = 8.0 Hz, 1H), 6.16 (s, 1H), 1.78 (s, 6H), 1.10 (s, 9H).<br>$^{13}$C NMR (126 MHz, CDCl$_3$) δ 159.58, 156.93, 156.42, 147.20, 143.49, 137.54, 137.02, 135.60, 133.54, 133.40, 131.67, 127.10, 124.25, 123.64, 121.53, 40.15, 36.90, 28.98, 26.34. |
| 266 | ESIMS<br>m/z 386.42<br>[M + H]$^+$ | $^1$H NMR (400 MHz, CDCl$_3$) δ 9.14 (s, 1H), 9.01 (s, 2H), 8.74 (d, J = 2.0 Hz, 1H), 7.90 (dd, J = 2.0, 8.3 Hz, 1H), 7.60-7.54 (m, 3H), 7.37-7.31 (m, 2H), 6.06 (bs, 1H), 2.01 (s, 3H).<br>$^{13}$C NMR (101 MHz, CDCl$_3$): δ 158.79, 157.97, 155.29, 149.54, 145.90, 137.83, 136.38, 135.46, 135.42, 128.65, 121.63, 121.20, 85.22, 79.17, 70.67, 3.85. |
| 267 | ESIMS<br>m/z 415.6<br>[M + H]$^+$ | $^1$H NMR (400 MHz, CDCl$_3$) δ 9.70 (s, 2H), 9.13 (s, 1H), 8.65-8.59 (m, 1H), 7.70 (dd, J = 8.3, 2.3 Hz, 1H), 7.65 (d, J = 8.3 Hz, 1H), 7.43 (d, J = 2.0 Hz, 1H), 7.38 (dd, J = 8.0, 1.9 Hz, 1H), 7.28 (d, J = 8.2 Hz, 1H), 3.22 (s, 3H), 2.33 (s, 3H), 1.78 (s, 6H), 0.91 (s, 9H).<br>IR (ATR) 2978, 2234, 1410, 1069 cm$^{-1}$. |
| 268 | ESIMS<br>m/z 433.6<br>[M + H]$^+$ | $^1$H NMR (300 MHz, CDCl$_3$) δ 9.22 (s, 2H), 9.09 (s, 1H), 8.76 (d, J = 0.9 Hz, 1H), 8.05-7.94 (m, 2H), 7.87 (dd, J = 8.5, 0.8 Hz, 1H), 7.49 (t, J = 8.1 Hz, 1H), 7.33 (dd, J = 8.1, 2.0 Hz, 1H), 7.27-7.19 (m, 1H), 6.19 (s, 1H), 2.21-2.03 (m, 2H), 1.94 (dd, J = 14.0, 7.3 Hz, 2H), 1.09 (s, 9H), 0.97 (t, J = 7.4 Hz, 6H).<br>IR (ATR) 2971, 2235, 1411, 909 cm$^{-1}$. |
| 269 | ESIMS<br>m/z 408.35<br>[M + H]$^+$ | $^1$H NMR (400 MHz, CDCl$_3$) δ = 9.08 (s, 1H), 8.82 (s, 2H), 8.67 (s, 1H), 7.84 (td, J = 1.8, 8.2 Hz, 1H), 7.73 (d, J = 8.3 Hz, 1H), 7.45 (t, J = 8.3 Hz, 1H), 7.12 (dd, J = 10.0, 14.9 Hz, 2H), 3.26 (s, 3H), 2.71-2.64 (m, 1H), 2.53-2.43 (s, 1H), 0.78 (t, J = 7.1 Hz, 3H).<br>$^{13}$C NMR (101 MHz, CDCl$_3$) δ 161.75, 160.97, 158.47, 157.21, 155.59, 149.61, 149.50, 148.61, 148.18, 137.27, 136.83, 136.80, 128.94, 128.92, 124.09, 121.57, 121.04, 119.01, 117.06, 117.03, 109.77, 109.51, 82.32, 50.44, 26.35.<br>$^{19}$F NMR (376 MHz, CDCl$_3$) δ −57.98, −113.30. |
| 270 | ESIMS<br>m/z 424.4<br>[M + H]$^+$ | $^1$H NMR (400 MHz, CDCl$_3$) δ 9.15 (s, 1H), 9.00 (s, 2H), 8.74 (d, J = 1.5 Hz, 1H), 7.96-7.87 (m, 2H), 7.59-7.48 (m, 2H), 7.32 (d, J = 8.3 Hz, 2H), 4.44-4.38 (m, 1H), 4.33-4.25 (m, 1H), 2.41 (t, J = 2.4 Hz, 1H), 2.08 (s, 3H).<br>$^{13}$C NMR (101 MHz, CDCl$_3$) δ 158.77, 158.10, 155.99, 149.42, 147.85, 135.83, 135.41, 128.59, 121.57, 120.65, 89.27, 79.27, 75.34, 74.71, 74.67, 53.71, 4.02. |
| 271 | ESIMS<br>m/z 422.2<br>[M + H]$^+$ | $^1$H NMR (300 MHz, CDCl$_3$) δ 9.47 (s, 1H), 8.69 (s, 1H), 8.52-8.47 (m, 2H), 8.36 (d, J = 8.4 Hz, 1H), 7.85 (d, J = 8.7 Hz, 1H), 7.50-7.44 (m, 1H), 7.15-7.08 (m, 2H), 6.73 (s, 1H), 1.01 (s, 9H).<br>$^{13}$C NMR (75 MHz, CDCl$_3$) δ 161.41, 159.58, 157.94, 145.84, 142.51, 141.10, 136.00, 131.18, 129.07, 124.01, 123.83, 117.07, 109.84, 109.49, 80.18, 41.04, 26.03. |
| 272 | ESIMS<br>m/z 418.43<br>[M + H]$^+$ | $^1$H NMR (300 MHz, CDCl$_3$) δ 9.14 (s, 1H), 8.83 (s, 2H), 8.80 (d, J = 2.2 Hz, 1H), 7.90 (dd, J = 2.4, 8.3 Hz, 1H), 7.66-7.53 (m, 2H), 7.57 (d, J = 8.4 Hz, 1H), 7.35 (d, J = 8.1 Hz, 2H), 3.23-2.99 (m, 3H), 1.17 (t, J = 7.0 Hz, 3H), 0.88 (dd, J = 7.0, 8.4 Hz, 6H).<br>$^{19}$F NMR (282.2 MHz, CDCl$_3$) δ −57.8. |

TABLE 2-continued

Analytical Data.

| Compound Number | Mass Spec | NMR ($^1$H, $^{13}$C, $^{19}$F) IR (Thin Film; cm$^{-1}$) |
|---|---|---|
| 273 | ESIMS m/z 415 [M + H]$^+$ | $^1$H NMR (300 MHz, CDCl$_3$) δ 9.19 (s, 1H), 8.72 (d, J = 2.4 Hz, 1H), 8.66 (s, 1H), 7.84-7.73 (m, 2H), 7.06 (s, 1H), 7.57 (d, J = 7.8 Hz, 1H), 7.25 (d, J = 2.7 Hz, 1H), 7.22 (s, 1H), 6.56 (t, J = 147.3 Hz, 1H), 3.82 (s, 3H), 1.16 (s, 9H). $^{13}$C NMR (101 MHz, CDCl$_3$) δ 166.45, 161.58, 157.45, 156.55, 144.91, 134.69, 133.75, 133.65, 128.43, 124.15, 123.01, 120.19, 115.73, 112.27, 80.32, 53.49, 40.31, 26.75. $^{19}$F NMR (282 MHz, CDCl$_3$) δ −80.98 (d) |
| 274 | ESIMS m/z 419 [M + H]$^+$ | $^1$H NMR (400 MHz, DMSO-d6) δ 9.47 (s, 2H), 9.07 (s, 1H), 8.62 (d, J = 2.3 Hz, 1H), 7.95 (dd, J = 8.4, 0.8 Hz, 1H), 7.85 (dd, J = 8.3, 2.3 Hz, 1H), 7.40 (d, J = 2.0 Hz, 1H), 7.34 (dd, J = 10.6, 1.8 Hz, 1H), 6.28 (s, 1H), 2.19 (s, 3H), 1.74 (s, 6H), 0.94 (s, 9H). $^{13}$C NMR (126 MHz, DMSO-d6) δ 162.05, 159.89, 159.16-156.54 (m), 155.94 (d, J = 21.5 Hz), 146.78, 142.66 (d, J = 8.3 Hz), 142.05 (d, J = 7.7 Hz), 140.16-134.58 (m), 127.08, 124.22-121.42 (m), 110.52 (d, J = 24.7 Hz), 109.82-108.93 (m), 35.87 (dd, J = 17.1, 1.9 Hz), 27.36 (d, J = 13.9 Hz), 25.16, 21.69 (d, J = 2.8 Hz), 19.36 (d, J = 3.0 Hz). |
| 275 | ESIMS m/z 435.3 [M + H]$^+$ | $^1$H NMR (400 MHz, CDCl$_3$) δ 9.20 (s, 2H), 9.08 (s, 1H), 8.75 (d, J = 1.6 Hz, 1H), 7.93 (dd, J = 8.3, 2.3 Hz, 1H), 7.81 (d, J = 8.2 Hz, 1H), 7.48 (d, J = 8.7 Hz, 2H), 7.11 (d, J = 8.5 Hz, 2H), 6.36 (s, 1H), 2.54 (s, 2H), 2.41 (s, 6H), 1.35 (s, 6H), 1.08 (s, 9H). IR (ATR) 2970, 1472, 1408, 119 cm$^{-1}$. |
| 276 | ESIMS m/z 449.4 [M + H]$^+$ | $^1$H NMR (400 MHz, CDCl$_3$) δ 9.20 (s, 2H), 9.08 (s, 1H), 8.73 (d, J = 1.6 Hz, 1H), 7.91 (dd, J = 8.3, 2.3 Hz, 1H), 7.80 (d, J = 8.3 Hz, 1H), 7.46 (d, J = 8.8 Hz, 2H), 6.93 (d, J = 8.8 Hz, 2H), 6.34 (s, 1H), 3.18 (s, 3H), 2.98 (s, 3H), 1.68 (s, 6H), 1.07 (s, 9H). IR (ATR) 2955, 1624, 1408, 1154 cm$^{-1}$. |
| 277 | ESIMS m/z 418 [M + H]$^+$ | $^1$H NMR (400 MHz, CDCl$_3$) d 9.69 (s, 2H), 9.13 (s, 1H), 8.87 (d, J = 1.9 Hz, 1H), 7.91 (dd, J = 8.4, 2.5 Hz, 1H), 7.66 (ddd, J = 9.5, 6.9, 1.7 Hz, 1H), 7.35 (d, J = 8.0 Hz, 2H), 3.20 (s, 3H), 0.90 (s, 9H). $^{19}$F NMR (376 MHz, CDCl$_3$) d −57.80 (s, 3F). |
| 278 | ESIMS m/z 412.2 [M + H]$^+$ | $^1$H NMR (400 MHz, CDCl$_3$) d 9.23 (s, 2H), 9.08 (s, 1H), 8.80 (dd, J = 2.2, 0.8 Hz, 1H), 8.00-7.94 (m, 2H), 7.91 (d, J = 8.3 Hz, 2H), 7.84 (dd, J = 8.3, 2.1 Hz, 1H), 5.84 (s, 1H), 2.02 (s, 6H), 1.09 (s, 9H). $^{13}$C NMR (101 MHz, CDCl$_3$) d 161.02, 156.98, 156.39, 145.35, 143.28, 137.59, 136.80, 134.98, 134.13, 132.58, 131.71, 128.27, 122.58, 122.49, 117.50, 111.13, 79.67, 40.19, 37.88, 27.47, 26.28. |
| 279 | ESIMS m/z 399.2 [M + H]$^+$ | $^1$H NMR (400 MHz, CDCl$_3$) d 9.22 (s, 2H), 9.08 (s, 1H), 8.78 (d, J = 1.6 Hz, 1H), 7.96 (dd, J = 8.4, 2.4 Hz, 1H), 7.86 (d, J = 8.4 Hz, 1H), 7.67-7.60 (m, 2H), 7.60-7.52 (m, 2H), 6.21 (s, 1H), 2.95-2.81 (m, 2H), 2.75-2.58 (m, 2H), 2.49 (ddd, J = 17.6, 11.5, 8.7 Hz, 1H), 2.25-2.06 (m, 1H), 1.09 (s, 9H). $^{13}$C NMR (101 MHz, CDCl$_3$) d 159.39, 156.88, 156.40, 145.40, 140.12, 137.13, 136.45, 135.04, 135.01, 127.64, 126.52, 124.06, 122.20, 79.47, 40.12, 39.99, 34.71, 26.33, 17.10. |

TABLE 3

Rating Scale For Disease Control in Wheat Leaf Bloth Assay (SEPTTR).

| % Disease Control | Rating |
|---|---|
| 80-100 | A |
| 60-79 | B |
| 40-59 | C |
| <40 | D |
| Not tested | E |

TABLE 4

Biological Activity - Disease Control in High and Low Volume Assays.

| | SI SEPTTR Type A Assay (50 ppm) | | SI SEPTTR Type B Assay (100 g/ha) | | FI SEPTTR Type B Assay (100 g/ha) | |
|---|---|---|---|---|---|---|
| Compound Number | 1 DP | 3 DC | 3 DC | 3 DP | 3 DC | 3 DP |
| 1 | D | C | E | E | E | E |
| 2 | A | D | E | E | E | E |
| 3 | D | A | A | A | B | C |

TABLE 4-continued

Biological Activity - Disease Control in High and Low Volume Assays.

| Compound Number | SI SEPTTR Type A Assay (50 ppm) | | SI SEPTTR Type B Assay (100 g/ha) | | FI SEPTTR Type B Assay (100 g/ha) | |
|---|---|---|---|---|---|---|
| | 1 DP | 3 DC | 3 DC | 3 DP | 3 DC | 3 DP |
| 4 | B | D | E | E | E | E |
| 5 | D | C | E | E | E | E |
| 6 | A | A | E | E | E | E |
| 7 | A | A | E | E | E | E |
| 8 | A | A | E | E | E | E |
| 9 | A | A | E | E | E | E |
| 10 | A | A | E | E | E | E |
| 11 | C | C | E | E | E | E |
| 12 | A | D | E | E | E | E |
| 13 | A | A | B | A | C | B |
| 14 | A | A | B | B | C | B |
| 15 | B | C | E | E | E | E |
| 16 | A | A | E | E | E | E |
| 17 | A | A | A | A | B | B |
| 18 | D | D | E | E | E | E |
| 19 | D | C | E | E | E | E |
| 20 | E | E | E | E | E | E |
| 21 | A | A | E | E | E | E |
| 22 | A | A | E | E | E | E |
| 23 | D | B | E | E | E | E |
| 24 | D | D | E | E | E | E |
| 25 | C | A | E | E | E | E |
| 26 | D | C | E | E | E | E |
| 27 | A | A | A | A | A | A |
| 28 | B | C | E | E | E | E |
| 29 | A | A | E | E | E | E |
| 30 | E | E | E | E | E | E |
| 31 | D | B | E | E | E | E |
| 32 | A | A | E | E | E | E |
| 33 | A | B | E | E | E | E |
| 34 | A | B | E | E | E | E |
| 35 | D | B | E | E | E | E |
| 36 | D | B | E | E | E | E |
| 37 | E | E | E | E | E | E |
| 38 | A | A | A | A | A | C |
| 39 | A | A | A | A | B | C |
| 40 | A | B | E | E | E | E |
| 41 | A | A | A | A | D | B |
| 42 | A | A | E | E | E | E |
| 43 | B | A | E | E | E | E |
| 44 | D | D | E | E | E | E |
| 45 | E | E | E | E | E | E |
| 46 | A | A | E | E | E | E |
| 47 | C | A | E | E | E | E |
| 48 | D | D | E | E | E | E |
| 49 | B | A | E | E | E | E |
| 50 | D | B | E | E | E | E |
| 51 | A | A | C | B | B | B |
| 52 | B | B | E | E | E | E |
| 53 | C | D | E | E | E | E |
| 54 | D | C | E | E | E | E |
| 55 | D | D | E | E | E | E |
| 56 | A | A | E | E | E | E |
| 57 | A | A | A | A | D | D |
| 58 | B | A | E | E | E | E |
| 59 | A | A | A | A | A | A |
| 60 | A | A | A | A | D | B |
| 61 | C | B | E | E | E | E |
| 62 | C | C | E | E | E | E |
| 63 | A | A | A | A | C | B |
| 64 | A | A | A | A | B | A |
| 65 | A | E | A | A | B | B |
| 66 | A | E | E | E | E | E |
| 67 | D | E | E | E | E | E |
| 68 | A | E | E | E | E | E |
| 69 | A | E | E | E | E | E |
| 70 | C | E | E | E | E | E |
| 71 | E | E | E | E | E | E |
| 72 | D | E | E | E | E | E |
| 73 | A | E | A | A | B | B |
| 74 | A | E | A | A | C | D |
| 75 | A | E | E | E | E | E |
| 76 | A | E | E | E | E | E |
| 77 | A | E | E | E | E | E |
| 78 | A | E | A | A | B | B |
| 79 | A | E | E | E | E | E |
| 80 | A | E | A | A | A | A |
| 81 | A | E | A | B | D | A |
| 82 | A | E | A | A | A | A |
| 83 | C | E | D | C | A | C |
| 84 | A | E | A | A | B | B |
| 85 | A | E | E | E | E | E |
| 86 | B | E | A | A | A | A |
| 87 | A | E | E | E | E | E |
| 88 | A | E | A | A | A | A |
| 89 | A | E | A | A | C | B |
| 90 | A | E | A | A | A | A |
| 91 | A | E | B | A | C | A |
| 92 | A | E | A | A | A | A |
| 93 | A | E | A | A | B | A |
| 94 | B | E | E | E | E | E |
| 95 | A | E | A | A | A | A |
| 96 | A | E | A | A | A | A |
| 97 | A | E | A | A | A | A |
| 98 | A | E | A | A | A | A |
| 99 | A | E | E | E | D | C |
| 100 | A | E | E | E | E | E |
| 101 | A | E | A | A | A | A |
| 102 | A | E | A | A | A | A |
| 103 | A | E | B | A | D | A |
| 104 | A | E | A | A | D | A |
| 105 | A | E | A | A | A | A |
| 106 | A | E | A | A | A | A |
| 107 | A | E | A | B | A | B |
| 108 | B | E | E | E | E | E |
| 109 | B | E | E | E | E | E |
| 110 | A | E | E | E | E | E |
| 111 | B | E | E | E | E | E |
| 112 | A | E | A | A | A | A |
| 113 | B | E | E | E | E | E |
| 114 | B | E | A | A | A | B |
| 115 | A | E | A | A | A | A |
| 116 | B | E | A | A | A | B |
| 117 | A | E | A | A | A | A |
| 118 | A | E | A | A | A | A |
| 119 | A | E | A | A | B | C |
| 120 | A | E | A | A | A | B |
| 121 | A | E | A | A | A | B |
| 122 | A | E | A | A | B | B |
| 123 | B | E | E | E | E | E |
| 124 | A | E | A | A | A | A |
| 125 | A | E | A | A | A | B |
| 126 | B | E | E | E | E | E |
| 127 | A | E | E | E | E | E |
| 128 | A | E | E | E | E | E |
| 129 | B | E | E | E | E | E |
| 130 | A | E | A | A | A | A |
| 131 | A | E | A | B | B | B |
| 132 | E | E | E | E | A | A |
| 133 | E | E | E | E | E | E |
| 134 | E | E | E | E | E | E |
| 135 | E | E | E | E | E | E |
| 136 | A | E | E | E | E | E |
| 137 | A | E | E | E | E | E |
| 138 | A | E | E | E | E | E |
| 139 | A | E | E | E | E | E |
| 140 | A | E | E | E | E | E |
| 141 | B | E | E | E | E | E |
| 142 | A | E | E | E | E | E |
| 143 | A | E | A | B | A | A |
| 144 | A | E | E | E | E | E |
| 145 | A | E | A | B | A | A |

TABLE 4-continued

Biological Activity - Disease Control in High and Low Volume Assays.

| Compound Number | SI SEPTTR Type A Assay (50 ppm) | | SI SEPTTR Type B Assay (100 g/ha) | | FI SEPTTR Type B Assay (100 g/ha) | |
|---|---|---|---|---|---|---|
| | 1 DP | 3 DC | 3 DC | 3 DP | 3 DC | 3 DP |
| 146 | A | E | A | A | A | B |
| 147 | A | E | E | E | E | E |
| 148 | E | E | B | D | B | D |
| 149 | E | E | A | B | A | B |
| 150 | A | E | E | E | A | A |
| 151 | A | E | A | A | E | E |
| 152 | A | E | A | A | A | A |
| 153 | A | E | E | E | E | E |
| 154 | A | E | E | E | E | E |
| 155 | A | E | E | E | B | B |
| 156 | A | E | A | A | A | A |
| 157 | A | E | A | A | A | A |
| 158 | A | E | A | A | A | A |
| 159 | A | E | E | E | E | E |
| 160 | A | E | E | E | A | A |
| 161 | A | E | E | E | A | A |
| 162 | A | E | E | E | A | A |
| 163 | A | E | E | E | A | A |
| 164 | E | E | E | E | A | A |
| 165 | E | E | E | E | A | A |
| 166 | E | E | E | E | A | A |
| 167 | A | E | A | B | A | A |
| 168 | B | E | E | E | E | E |
| 169 | A | E | A | B | A | A |
| 170 | A | E | E | E | E | E |
| 171 | A | E | E | E | E | E |
| 172 | A | E | E | E | E | E |
| 173 | E | E | E | E | A | A |
| 174 | E | E | E | E | B | A |
| 175 | E | E | E | E | A | A |
| 176 | E | E | E | E | D | B |
| 177 | E | E | E | E | D | B |
| 178 | E | E | E | E | D | B |
| 179 | E | E | E | E | A | A |
| 180 | E | E | E | E | B | C |
| 181 | E | E | E | E | D | B |
| 182 | E | E | E | E | D | B |
| 183 | E | E | E | E | A | A |
| 184 | E | E | E | E | D | C |
| 185 | E | E | E | E | D | A |
| 186 | E | E | E | E | C | A |
| 187 | E | E | E | E | A | A |
| 188 | E | E | E | E | B | A |
| 189 | E | E | E | E | C | A |
| 190 | E | E | E | E | B | C |
| 191 | E | E | E | E | D | A |
| 192 | E | E | E | E | A | A |
| 193 | E | E | E | E | D | B |
| 194 | E | E | E | E | D | A |
| 195 | E | E | E | E | D | C |
| 196 | E | E | E | E | E | E |
| 197 | E | E | E | E | D | A |
| 198 | E | E | E | E | D | A |
| 199 | E | E | E | E | C | A |
| 200 | E | E | E | E | D | A |
| 201 | E | E | E | E | B | A |
| 202 | E | E | E | E | B | B |
| 203 | E | E | E | E | C | A |
| 204 | E | E | E | E | D | B |
| 205 | E | E | E | E | C | A |
| 206 | E | E | E | E | D | C |
| 207 | E | E | E | E | C | B |
| 208 | E | E | E | E | D | A |
| 210 | E | E | E | E | A | A |
| 211 | E | E | E | E | A | A |
| 212 | E | E | E | E | A | A |
| 213 | E | E | E | E | B | B |
| 214 | E | E | E | E | D | A |
| 215 | E | E | E | E | D | D |
| 216 | E | E | E | E | A | A |
| 217 | E | E | E | E | D | D |
| 218 | E | E | E | E | D | A |
| 219 | E | E | E | E | C | B |
| 220 | E | E | E | E | D | A |
| 221 | E | E | E | E | D | C |
| 222 | E | E | E | E | C | B |
| 223 | E | E | E | E | A | A |
| 224 | E | E | E | E | C | B |
| 225 | E | E | E | E | A | B |
| 226 | E | E | E | E | A | A |
| 227 | E | E | E | E | D | C |
| 228 | E | E | E | E | A | A |
| 229 | E | E | E | E | B | B |
| 230 | E | E | E | E | D | A |
| 231 | E | E | E | E | D | B |
| 232 | E | E | E | E | D | B |
| 233 | E | E | E | E | A | A |
| 234 | E | E | E | E | C | B |
| 235 | E | E | E | E | B | A |
| 236 | E | E | E | E | A | A |
| 237 | E | E | E | E | D | C |
| 238 | E | E | E | E | B | D |
| 239 | E | E | E | E | A | A |
| 240 | E | E | E | E | A | A |
| 241 | E | E | E | E | D | C |
| 242 | E | E | E | E | D | C |
| 243 | E | E | E | E | D | A |
| 244 | E | E | E | E | D | C |
| 246 | E | E | E | E | B | A |
| 247 | E | E | E | E | D | A |
| 248 | E | E | E | E | D | C |
| 249 | E | E | E | E | B | A |
| 250 | E | E | E | E | D | A |
| 251 | E | E | E | E | A | A |
| 252 | E | E | E | E | A | A |
| 253 | E | E | E | E | A | A |
| 254 | E | E | E | E | E | E |
| 255 | E | E | E | E | D | B |
| 256 | E | E | E | E | A | A |
| 257 | E | E | E | E | B | B |
| 258 | E | E | E | E | D | B |
| 259 | E | E | E | E | B | A |
| 260 | E | E | E | E | D | C |
| 261 | E | E | E | E | A | A |
| 262 | E | E | E | E | A | A |
| 263 | E | E | E | E | A | A |
| 264 | E | E | E | E | A | A |
| 265 | E | E | E | E | A | A |
| 266 | E | E | E | E | D | B |
| 267 | E | E | E | E | B | A |
| 268 | E | E | E | E | A | A |
| 269 | E | E | E | E | C | A |
| 270 | E | E | E | E | D | C |
| 271 | E | E | E | E | D | A |
| 272 | E | E | E | E | D | B |
| 273 | E | E | E | E | D | A |
| 274 | E | E | E | E | E | E |
| 275 | E | E | E | E | E | E |
| 276 | E | E | E | E | E | E |
| 277 | E | E | A | A | A | A |
| 278 | E | E | E | E | E | E |
| 279 | E | E | E | E | E | E |

\* SI—SEPTTR standard laboratory isolate
\* FI—SEPTTR field isolate
\*SEPTTR—Wheat Leaf Blotch (*Septoria tritici*)
\*ppm—Parts per million
\*g/ha—Grams per hectare
\*1 DP—1 Day Protectant
\*3 DC—3 Day Curative
*3 DP—3 Day Protectant

What is claimed is:

1. A compound of Formula I, or salt thereof, wherein:

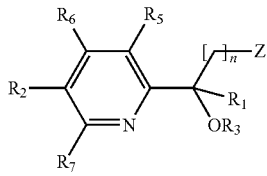

Z is optionally substituted 5-pyrimidinyl, optionally substituted 4-pyrimidinyl, optionally substituted oxazolyl, optionally substituted 3-pyridinyl, or optionally substituted 4-pyridinyl;

n is 0 or 1;

$R_1$ is alkyl, haloalkyl, aryl, or heteroaryl, each optionally substituted with 0, 1, 2 or 3 independent $R_4$;

$R_2$ is aryl, heteroaryl aryloxy, heteroaryloxy, arylalkynyl, heteroarylalkynyl, arylalkyl, heteroarylalkyl, arylalkoxy, heteroarylalkoxy, aryloxyalkyl, or heteroaryloxyalkyl wherein each aryl or heteroaryl is optionally substituted with 0, 1, 2 or 3 independent $R_4$;

$R_3$ is independently H, alkyl, aryl, substituted aryl, heteroaryl, arylalkyl, or heteroarylalkyl, —C(O)alkyl, —C(O)aryl, —Si(alkyl)$_3$, each optionally substituted with 0, 1, 2 or 3 independent $R_4$;

$R_4$ is independently aryl, heteroaryl, alkyl, thioalkyl, cyano, haloalkyl, cyanoalkyl, hydroxy, alkoxy, halo, haloalkoxy, —C(O)alkyl, —C(O)OH, —C(O)Oalkyl, —SCF$_3$, —SF$_5$, —SCN, or SO$_2$(alkyl); and $R_5$ - $R_7$ are independently selected from the group consisting of H, alkyl, alkoxy, halo, and haloalkyl;

with the proviso that when n=1, Z is 1-tetrazolyl or 5-pyrimidinyl.

2. The compound of claim 1 wherein $R_2$ is aryl or heteroaryl optionally substituted with 1, 2 or 3 independent $R_4$.

3. The compound of claim 2 wherein $R_1$ is alkyl, haloalkyl, cycloalkyl, aryl, or heteroarylaryl optionally substituted with 1, 2 or 3 independent $R_4$.

4. The compound of claim 3 wherein $R_1$ is methyl, ethyl, tent-butyl, iso-propyl, cyclopropyl, trifluoromethyl, 2,4-difluorophenyl, 2-fluoro-4-chlorophenyl, —CF$_2$-(2,4-difluorophenyl), —CF$_2$-(2-fluoro-4-chlorophenyl), —CH$_2$-(2,4-difluorophenyl), or —CH$_2$-(2-fluoro-4-chlorophenyl).

5. The compound of claim 2 wherein Z is optionally substituted 5-pyrimidinyl, optionally substituted 4-pyrimidinyl, optionally substituted 3-pyridinyl, optionally substituted 4-pyridinyl; or when n=1,1-tetrazolyl.

6. The compound of claim 5 wherein Z is 5-pyrimidinyl or 3-pyridinyl and n =0.

7. The compound of claim 5 wherein Z is 5-pyrimidinyl, 3-pyridinyl or 1-tetrazolyl and n=1.

8. The compound of claim 2 wherein $R_2$ is phenyl, 2-pyridinyl, 3-pyridinyl, or 5-pyrimidinyl optionally substituted with 1, 2 or 3 independent $R_4$.

9. The compound of claim 8 wherein $R_4$ is halo, haloalkyl, cyanoalkyl, haloalkoxy, or cyano.

10. The compound of claim 8 wherein $R_2$ is phenyl substituted at the 4 position with a halo, haloalkyl, cyanoalkyl, haloalkoxy, or cyano substituent.

11. The compound of claim 8 wherein $R_2$ is 2-pyridinyl substituted at the 5 position with a halo, haloalkyl, cyanoalkyl, haloalkoxy, or cyano substituent.

12. The compound of claim 8 wherein $R_2$ is 3-pyridinyl substituted at the 6 position with a halo, haloalkyl, cyanoalkyl, haloalkoxy, or cyano substituent.

13. The compound of claim 1 wherein $R_2$ is aryloxy or heteroaryloxy optionally substituted with 1, 2 or 3 independent $R_4$.

14. The compound of claim 13 wherein $R_1$ is alkyl, haloalkyl, cycloalkyl, aryl, or heteroarylaryl optionally substituted with 1, 2 or 3 independent $R_4$.

15. The compound of claim 14 wherein R1 is methyl, ethyl, tent-butyl, iso-propyl, cyclopropyl, trifluoromethyl, 2,4-difluorophenyl, 2-fluoro-4-chlorophenyl, —CF$_2$-(2,4-difluorophenyl), —CF$_2$-(2-fluoro-4-chlorophenyl), —CH$_2$-(2,4-difluorophenyl), or —CH$_2$-(2-fluoro-4-chlorophenyl).

16. The compound of claim 13 wherein Z is optionally substituted 5-pyrimidinyl, optionally substituted 4-pyrimidinyl, optionally substituted 3-pyridinyl, optionally substituted 4-pyridinyl; or when n=1,1-tetrazolyl.

17. The compound of claim 16 wherein Z is 5-pyrimidinyl or 3-pyridinyl and n =0.

18. The compound of claim 16 wherein Z is 5-pyrimidinyl, 3-pyridinyl or 1-tetrazolyl and n=1.

19. The compound of claim 13 wherein $R_2$ is phenoxy, (2-pyridinyl)oxy, (3-pyridinyl)oxy, or (5-pyrimidinyl)oxy optionally substituted with 1, 2 or 3 independent $R_4$.

20. The compound of claim 19 wherein $R_4$ is halo, haloalkyl, cyanoalkyl, haloalkoxy, or cyano.

21. The compound of claim 19 wherein $R_2$ is phenoxy substituted at the 4 position with a halo, haloalkyl, cyanoalkyl, haloalkoxy, or cyano substituent.

22. The compound of claim 19 wherein $R_2$ is (2-pyridinyl)oxy substituted at the 5 position with a halo, haloalkyl, cyanoalkyl, haloalkoxy, or cyano substituent.

23. The compound of claim 19 wherein $R_2$ is (3-pyridinyl)oxy substituted at the 6 position with a halo, haloalkyl, cyanoalkyl, haloalkoxy, or cyano substituent.

24. The compound of claim 19 wherein $R_2$ is (3-pyrimidinyl)oxy substituted at the 6 position with a halo, haloalkyl, cyanoalkyl, haloalkoxy, or cyano substituent.

25. The compound of any one of claims 1, wherein the compound inhibits an enzyme selected from 4-hydroxyphenyl pyruvate dioxygenase, 5-lipoxygenase, adenosine deaminase, alcohol dehydrogenase, aminopeptidase P, angiotensin converting enzyme, aromatase (CYP19), calcineurin, carbamoyl phosphate synthetase, carbonic anhydrase family, catechol o-methyl transferase, cyclooxygenase family, dihydropyrimidine dehydrogenase-1, DNA polymerase, farnesyl diphosphate synthase, farnesyl transferase, fumarate reductase, GABA aminotransferase, HIF-prolyl hydroxylase, histone deacetylase family, HIV integrase, HIV-1 reverse transcriptase, isoleucine tRNA ligase, lanosterol demethylase (CYP51), matrix metalloprotease family, methionine aminopeptidase, neutral endopeptidase, nitric oxide synthase family, phosphodiesterase III, phosphodiesterase IV, phosphodiesterase V, pyruvate ferredoxin oxidoreductase, renal peptidase, ribonucleoside diphosphate reductase, thromboxane synthase (CYP5a), thyroid peroxidase, tyrosinase, urease, and xanthine oxidase.

26. The compound of any one of claims 1, wherein the compound inhibits an enzyme selected from 1-deoxy-d-xylulose-5-phosphate reductoisomerase (DXR), 17-alpha hydroxylase/17,20-lyase (CYP17), aldosterone synthase (CYP11B2), aminopeptidase P, anthrax lethal factor, arginase, beta-lactamase, cytochrome P450 2A6, d-ala d-ala ligase, dopamine beta-hydroxylase, endothelin converting enzyme-1, glutamate carboxypeptidase II, glutaminyl cyclase, glyoxalase, heme oxygenase, HPV/HSV E1 helicase, indoleamine 2,3-dioxygenase, leukotriene A4 hydrolase, methionine aminopeptidase 2, peptide deformylase, phosphodiesterase VII, relaxase, retinoic acid hydroxylase (CYP26), TNF-alpha converting enzyme (TACE), UDP-(3-O-(R-3-hydroxymyristoyl))-N-acetylglucosamine deacetylase (LpxC), vascular adhesion protein-1 (VAP-1), and vitamin D hydroxylase (CYP24).

27. The compound of any one of claims 1, wherein the compound inhibits (or is identified to inhibit) lanosterol demethylase (CYP51).

28. The compound of any one of claims 1, wherein the compound is identified as having an activity range against a target organism.

29. A method of treating a subject suffering from or susceptible to a metalloenzyme-related disorder or disease, wherein the disease or disorder is cancer, cardiovascular disease, endocrinologic disease, inflammatory disease, infectious disease, aynecoloaic disease, metabolic disease, opthalmologic disease, central nervous system (CNS) disease, urologic disease, or gastrointestinal disease, wherein the subject has been identified as in need of treatment for a metalloenzyme-related disorder or disease, comprising administering to said subject in need thereof, an effective amount of a compound of claim 1, such that said subject is treated for said disorder.

30. A method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound of claim 1, such that metalloenzyme activity in said subject is modulated down regulated, or inhibited.

31. The method of claim 30, wherein the disease or disorder is systemic fungal infection, or onychomycosis.

32. A method of treating a metalloenzyme-mediated disease or disorder in or on a plant comprising contacting a compound of claim 1 with the plant or seeds.

33. A method of inhibiting metalloenzyme activity in a microorganism on a plant comprising contacting a compound of claim 1 with the plant or seeds.

34. A method of treating a fungal disease or disorder in or on a plant comprising contacting a compound of claim 1 with the plant or seeds.

35. A method of treating fungal growth in or on a plant comprising contacting a compound of claim 1 with the plant or seeds.

36. A method of inhibiting microorganisms in or on a plant comprising contacting a compound of claim 1 with the plant or seeds.

37. A composition comprising a compound of claim 1 and an agriculturally acceptable carrier.

38. A composition for the control of a fungal pathogen including mixtures of at least one of the compounds of claim 1 or one of the compositions of claim 37 with other pesticides including fungicides, insecticides, nematocides, miticides, arthropodicides, bactericides and combinations thereof.

39. The composition according to claim 38, further comprising an azole fungicide selected from the group consisting of epoxiconazole, tebuconazole, fluquinconazole, flutriafol, metconazole, myclobutanil, cycproconazole, prothioconazole and propiconazole.

40. The composition according to claim 38, further comprising a strobilurin fungicide selected from the group consisting of trifloxystrobin, pyraclostrobin, orysastrobin, fluoxastrobin and azoxystrobin.

41. The composition according to claim 38, further comprising a succinate dehydrogenase inhibiting (SDHI) fungicide selected from the group consisting of fluxapyroxad, boscalid, penthiopyrad, benzovindiflupyr, bixafen, flupyram, and isopyrazam.

42. A composition comprising a compound of claim 1 and a pharmaceutically acceptable carrier.

43. The composition of claim 42 further comprising an additional therapeutic agent.

44. The composition of claim 42 further comprising an additional therapeutic agent that is an anti-cancer agent, antifungal agent, cardiovascular agent, antiinflammatory agent, chemotherapeutic agent, an anti-angiogenesis agent, cytotoxic agent, an anti-proliferation agent, metabolic disease agent, opthalmologic disease agent, central nervous system (CNS) disease agent, urologic disease agent, or gastrointestinal disease agent.

45. The compositions according to claim 37 wherein the fungal pathogen is one of Leaf Blotch of Wheat (*Mycosphaerella graminicola*; anamorph: *Septaria tritici*), Wheat Brown Rust (*Puccinia triticina*), Stripe Rust (*Puccinia striiformis*), Scab of Apple (*Venturia inaequalis*), Blister Smut of Maize (*Ustilago maydis*), Powdery Mildew of Grapevine (*Uncinula necator*), Barley Scald (*Rhynchosporium secalis*), Blast of Rice (*Magnaporthe grisea*), Rust of Soybean (*Phakopsora pachyrhizi*), Glume Blotch of Wheat (*Leptosphaeria nodorum*), Powdery Mildew of Wheat (*Blumeria graminis f sp. Tritici*), Powdery Mildew of Barley (*Blumeria graminis f sp. hordei*), Powdery Mildew of Cucurbits (*Erysiphe cichoracearum*), Anthracnose of Cucurbits (*Glomerella lagenarium*), Leaf Spot of Beet (*Cercospora beticola*), Early Blight of Tomato (*Alternaria solani*), and Net Blotch of Barley (*Pyrenophora teres*).

46. The composition according to claim 45 wherein the fungal pathogen is one of Leaf Blotch of Wheat (*Septoria tritici*), Wheat Brown Rust (*Puccinia triticina*), and Rust of Soybean (*Phakopsora pachyrhizi*).

47. A method for the control and prevention of fungal attack on a plant, the method including the step of: Applying a fungicidally effective amount of at least one of the compounds of claim 1 or at least one of the compositions according to claim 37 to at least one of the plant, an area adjacent to the plant, soil adapted to support growth of the plant, a root of the plant, a seed of the plant, and foliage of the plant.

48. A method of treating a subject suffering from or susceptible to a disorder or disease, wherein the subject has been identified as in need of treatment for the disorder or disease, comprising administering to said subject in need thereof, an effective amount of a compound of formula (I), or salt thereof, wherein the disorder or disease is selected from one or more of the group consisting of superficial fungal infection, mucosal fungal infection, systemic fungal infection, Aspergillosis, Blastomycosis, Candidiasis, Chromomycosis, Coccidioidomycosis, Cryptococcosis, Dermatophytosis, Histoplasmosis, Keratomycosis, Lobomycosis, *Malassezia* infection, Mucormycosis, Onychomycosis, Paracoccidioidomycosis, *Penicillium marneffei* infection, Phaeohyphomycosis, Pneumocyctis pneumonia, and tinea (unguium, capitis, corporis, pedis, tonsurans, versicolor).

* * * * *